(12) United States Patent
Carr et al.

(10) Patent No.: US 10,689,648 B2
(45) Date of Patent: Jun. 23, 2020

(54) SHORT INTERFERING NUCLEIC ACID (SINA) COMPOSITIONS

(71) Applicant: SIRNA THERAPEUTICS, INC., Cambridge, MA (US)

(72) Inventors: Brian Allen Carr, West Point, PA (US); Vasant R. Jadhav, Sharon, MA (US); Denise M. Kenski, San Francisco, CA (US); David M. Tellers, West Point, PA (US); Aarron T. Willingham, San Francisco, CA (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/684,902

(22) Filed: Aug. 23, 2017

(65) Prior Publication Data

US 2018/0105812 A1 Apr. 19, 2018

Related U.S. Application Data

(63) Continuation of application No. 14/398,300, filed as application No. PCT/US2013/038305 on Apr. 26, 2013, now abandoned.

(60) Provisional application No. 61/641,626, filed on May 2, 2012.

(51) Int. Cl.
   C07H 21/04 (2006.01)
   C12N 15/113 (2010.01)
   C12N 15/11 (2006.01)

(52) U.S. Cl.
   CPC .......... *C12N 15/113* (2013.01); *C12N 15/111* (2013.01); *C12N 2310/14* (2013.01); *C12N 2310/315* (2013.01); *C12N 2310/321* (2013.01); *C12N 2310/3231* (2013.01); *C12N 2310/344* (2013.01); *C12N 2310/346* (2013.01); *C12N 2310/351* (2013.01); *C12N 2320/32* (2013.01); *C12N 2320/51* (2013.01)

(58) Field of Classification Search
   None
   See application file for complete search history.

(56) References Cited

U.S. PATENT DOCUMENTS

| | | | |
|---|---|---|---|
| 4,751,180 A | 6/1988 | Cousens et al. |
| 4,935,233 A | 6/1990 | Bell et al. |
| 5,138,045 A | 8/1992 | Cook et al. |
| 5,214,136 A | 5/1993 | Lin et al. |
| 5,998,203 A | 12/1999 | Matulic-Adamic et al. |
| 6,001,311 A | 12/1999 | Brennan |
| 6,153,737 A | 11/2000 | Manoharan et al. |
| 6,235,886 B1 | 5/2001 | Manoharan et al. |
| 6,335,434 B1 | 1/2002 | Guzaev et al. |
| 6,506,559 B1 | 1/2003 | Fire et al. |
| 6,528,631 B1 | 3/2003 | Cook et al. |
| 7,491,805 B2 | 2/2009 | Vargeese et al. |
| 7,923,547 B2 | 4/2011 | McSwiggen et al. |
| 8,273,866 B2 | 9/2012 | McSwiggen et al. |
| 8,648,185 B2 | 2/2014 | McSwigen et al. |
| 8,877,439 B2 | 11/2014 | Butora et al. |
| 8,933,044 B2 | 1/2015 | Tuschl et al. |
| 9,096,850 B2 | 8/2015 | Chorn et al. |
| 9,181,551 B2 | 11/2015 | McSwiggen et al. |
| 9,193,753 B2 | 11/2015 | Tuschl et al. |
| 9,243,246 B2 | 1/2016 | Lim et al. |
| 9,260,471 B2 | 2/2016 | Cancilla et al. |
| 2004/0162260 A1 | 8/2004 | Rozema et al. |
| 2004/0192626 A1 | 9/2004 | McSwiggen et al. |
| 2007/0042983 A1 | 2/2007 | Haeberli et al. |
| 2008/0020058 A1 | 1/2008 | Chen et al. |
| 2008/0152661 A1 | 6/2008 | Rozema et al. |
| 2009/0176725 A1* | 7/2009 | Morrissey ............... A61K 31/70 514/44 R |
| 2010/0120895 A1 | 5/2010 | Jadhav et al. |
| 2014/0088937 A1 | 3/2014 | Brown et al. |

FOREIGN PATENT DOCUMENTS

| | | |
|---|---|---|
| EP | 2287305 A1 | 2/2011 |
| WO | 9932619 A1 | 7/1999 |
| WO | 9954459 A2 | 10/1999 |
| WO | 0129058 A1 | 4/2001 |
| WO | 2001075164 A2 | 10/2001 |
| WO | 2002044321 A2 | 6/2002 |
| WO | 2003074654 A2 | 9/2003 |
| WO | 2007095152 A2 | 8/2007 |

(Continued)

OTHER PUBLICATIONS

Allerson et al., "Fully 2'-modified oligonucleotide duplexes with improved in vitro potency and stability compared to unmodified small interfering RNA", J. Med. Chem., 2005, vol. 48, pp. 901-904.
Bongartz et al., "Improved biological activity of antisense oligonucleotides conjugated to a fusogenic peptide," Nucleic Acids Research 22:4681-4688 (1994).
Dowler et al., "Improvements in siRNA Properties Mediated by 2'-Deoxy-2'Fluoro-Beta-D-Arabinonucleic Acid (FANA)", Nucleic Acids Research, vol. 34, No. 6, pp. 1669-1675, (2006).
Elbashir et al. "Functional anatomy of siRNAs for mediating efficient RNAi in *Drosophila melanogaster* embryo lysate," EMBO J. 20(23):6877-6888 (2001).
Filion and Phillips, "Toxicity and immunomodulatory activity of liposomal vectors formulated with cationic lipids toward immune effector cells," Biochimica et Biophysica Acta 1329:345-356 (1997).

(Continued)

*Primary Examiner* — Kimberly Chong
(74) *Attorney, Agent, or Firm* — Lando & Anastasi, LLP

(57) ABSTRACT

The present invention relates to compounds, compositions, and methods for the study, diagnosis, and treatment of traits, diseases and conditions that respond to the modulation of gene expression and/or activity, and/or modulate a gene expression pathway. Specifically, the invention relates to double-stranded nucleic acid molecules including small nucleic acid molecules, such as short interfering nucleic acid (siNA) molecules that are capable of mediating or that mediate RNA interference (RNAi) against target gene expression.

19 Claims, 15 Drawing Sheets

Specification includes a Sequence Listing.

(56) References Cited

FOREIGN PATENT DOCUMENTS

| WO | 2008008476 A2 | 1/2008 |
|---|---|---|
| WO | 2009002944 A1 | 12/2008 |
| WO | 2009134487 A2 | 11/2009 |
| WO | 2012018754 A2 | 2/2012 |
| WO | 2012027206 A1 | 3/2012 |

OTHER PUBLICATIONS

Fire et al., "Potent and Specific Genetic Interference by Double-Stranded RNA in Caenorhabditis Elegans," Nature 391 :806-811(1998).
Hartmann et al., "Spontaneous and Cationic Lipid-Mediated Uptake of Antisense Oligonucleotides in Human Monocytes and Lymphocytes," The Journal of Pharmacology and Experimental Therapeutics 285:920-928 (1998).
Herrmann et al., "Comparative analysis of adenoviral transgene delivery via tail or portal vein into rat liver," Arch Virol 149:1611-1617 (2004).
Hong et al., "pH-sensivite, serum-stable and long-circulating liposomes as a new drug delivery system," Journal of Pharmacy and Pharmacology, 54:51-58 (2002).
International Preliminary Report on Patentability for International Application No. PCTUS2013038305 dated Nov. 4, 2014.
International Search Report for International Application No. PCT/US2013/038305 dated Nov. 15, 2013.
Koller et al. "Competition for RISC binding predicts in vitro potency of siRNA" Nucleic Acids Research (2006) vol. 34, No. 16, pp. 4467-4476.
Kronenwett et al., "Oligodeoxyribonucleotide Uptake in Primary Human Hematopoietic Cells is Enhanced by Cationic Lipids and Depends on the Hematopoietic Cell Subset," Blood 91:852-862 (1998).
Liu et al., "Poly( cationic lipid)-mediated in vivo gene delivery to mouse liver," Gene Therapy, 10:180-187 (2003).
Ma and Wei, "Enhanced Delivery of Synthetic Oligonucleotides to Human Leukaemic Cells by Liposomes and Immunoliposomes," Leukemia Research 20:925-930 (1996).
Martinez et al., "Single-Stranded Antisense siRNAs Guide Target RNA Cleavage in RNAi," Cell 110:563-574 (2002).
Matsuno et al., "Hepatocyte growth factor gene transfer into the liver via the portal vein using electroporation attenuates rat liver cirrhosis," Gene Therapy 10:1559-1566 (2003).
Murao et al., "Targeting Efficiency of Galactosylated Liposomes to Hepatocytes in Vivo: Effect of Lipid Composition," Pharmaceutical Research, 19(12):1808-1814 (2002).
Prakash et al., "Positional Effect of Chemical Modifications on Short Interference RNA Activity in Mammalian Cells", J. Med. Chem., vol. 48, No. 13, pp. 4247-4253, (2005).
Schwarz et al., "Evidence that siRNA's Function as Guides, Not Primers, in the *Drosophila* and Human RNAi Pathways," Molecular Cell 10: 537-548 (2002).
Supplementary European Search Report for European Application No. 13785089.7 dated Nov. 27, 2015.
Wen et al., "Preparation and property analysis of a hepatocyte targeting pH-sensitive liposome," World J Gastroenterology, 10(2):244-249 (2004).
Written Opinion for International Application No. PCT/US2013/038305 dated Nov. 15, 2013.
Zamore et al., "RNAi: Double-Stranded Rna Directs the ATP-Dependent Cleavage of mRNA at 21 to 23 Nucleotide Intervals," Cell 101:25-33 (2000).
European Search Report for European Application No. EP17002009 dated Jul. 4, 2018.
Extended European Search Report issued in European Application No. 18200575.1, dated Feb. 5, 2019.

* cited by examiner

SHORT INTERFERING NUCLEIC ACID (SINA) COMPOSITIONS

CROSS-REFERENCE TO RELATED APPLICATIONS

This application is a continuation of U.S. application Ser. No. 14/398,300, filed Oct. 31, 2014, which is a U.S. national stage under 35 U.S.C. § 371 of International Application No. PCT/US2013/038305, filed Apr. 26, 2013, which claims priority to U.S. Application Ser. No. 61/641,626, filed May 2, 2012, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Feb. 5, 2015, is named A2038-7211US_S-L.txt.txt and is 218,111 bytes in size.

FIELD OF THE INVENTION

The present invention relates to compounds, compositions, and methods for the study, diagnosis, and treatment of traits, diseases and conditions that may respond to the modulation of gene expression and/or activity. The present invention is also directed to compounds, compositions, and methods relating to traits, diseases and conditions that may respond to the modulation of expression and/or activity of genes involved in gene expression pathways or other cellular processes that mediate the maintenance or development of such traits, diseases and conditions. Specifically, the invention relates to chemically modified short interfering nucleic acid (siNA) molecules that may be capable of mediating RNA interference (RNAi) against gene expression, including cocktails of such siNA molecules and formulations of such siNA molecules. Such siNA molecules are useful, for example, in providing compositions that may prevent, inhibit, or reduce various diseases, traits and conditions that are associated with gene expression or activity in a subject or organism.

BACKGROUND OF THE INVENTION

The following is a discussion of relevant art pertaining to RNAi. The discussion is provided only for understanding of the invention that follows. The summary is not an admission that any of the work described below is prior art to the claimed invention.

RNA interference refers to the process of sequence-specific post-transcriptional gene silencing in animals mediated by short interfering RNAs (siRNAs) (Zamore et al., 2000, Cell, 101, 25-33; Bass, 2000, Cell, 101, 235; Fire et al., 1998, Nature, 391, 806; Hamilton et al., 1999, Science, 286, 950-951; Lin et al., 1999, Nature, 402, 128-129; Sharp, 1999, genes & Dev., 13:139-141; and Strauss, 1999, Science, 286, 886). The corresponding process in plants (Heifetz et al., International PCT Publication No. WO 99/61631) is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., 1999, Trends genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The therapeutic potential of RNAi lies in the ability to modulate gene expression in a sequence specific manner by harnessing a highly conserved, robust endogenous mechanism of action. This endogenous mechanism of action vastly expands upon the number of available targets for disease modification when compared to existing small molecule and biologic modalities. Nevertheless, a opposed to exogenously supplied small molecule and biologic modalities, the RNA molecules that serve as triggers for RNAi are not well suited for administration due to their inherent instability, especially in biologic systems. This problem has been addressed through innovation, both in terms of chemical modification of RNA triggers (see U.S. Ser. No. 10/444,853, published as US US.S Patent Appl. Publ. No. 20040192626) and various delivery approaches (see U.S. Ser. No. 11/586,102, published as US US-.S. Patent Appl. Publ. No. 20080020058)), which have provided compounds and compositions that may be available for clinical development. Nevertheless there remains a need for additional RNA triggers that are available to expand the repertoire of available compounds and compositions for use in RNAi based therapeutics, and especially compounds and compositions that are compatible with different delivery systems and/or routes of administration.

SUMMARY OF THE INVENTION

The invention provides a solution to the problem of having a sufficient repertoire of available compounds and compositions for use in RNAi based therapeutics that may be compatible with different delivery modalities and/or routes of administration by providing additional forms of chemically modified short interfering nucleic acid (siNA) molecules.

The present invention provides compounds, compositions, and methods useful for modulating the expression of target genes and for treating diseases and conditions that may respond to such modulation by RNA interference (RNAi). Specially, the present invention provides certain chemically modified short interfering nucleic acid (siNA) molecules having any of Formula A, B, C, D, E, F, G, H, I, J, K, L, M, N, O, or P or as otherwise provided in the description and claims herein. These siNA molecules may be used, inter alia, as RNAi based therapeutic compounds and compositions.

These and other aspects of the invention will be apparent upon reference to the following detailed description and attached figures. Moreover, it is contemplated that any method or composition described herein can be implemented with respect to any other method or composition described herein and that different embodiments may be combined.

Additionally, patents, patent applications, and other documents are cited throughout the specification to describe and more specifically set forth various aspects of this invention. Each of these references cited herein is hereby incorporated by reference in its entirety, including the drawings.

Double-stranded RNA (dsRNA), which is generated by RNA-dependent RNA polymerase (RdRP) from foreign single-stranded RNA, for example viral, transposon, or other exogenous RNA, activates the DICER enzyme that in turn generates siNA duplexes. Alternately, synthetic or expressed siNA can be introduced directly into a cell by appropriate means. An active siNA complex forms that recognizes a target RNA, resulting in degradation of the target RNA by the RISC endonuclease complex or in the synthesis of additional RNA by RNA-dependent RNA polymerase (RdRP), which can activate DICER and result in additional siNA molecules, thereby amplifying the RNAi response.

Figure 1:
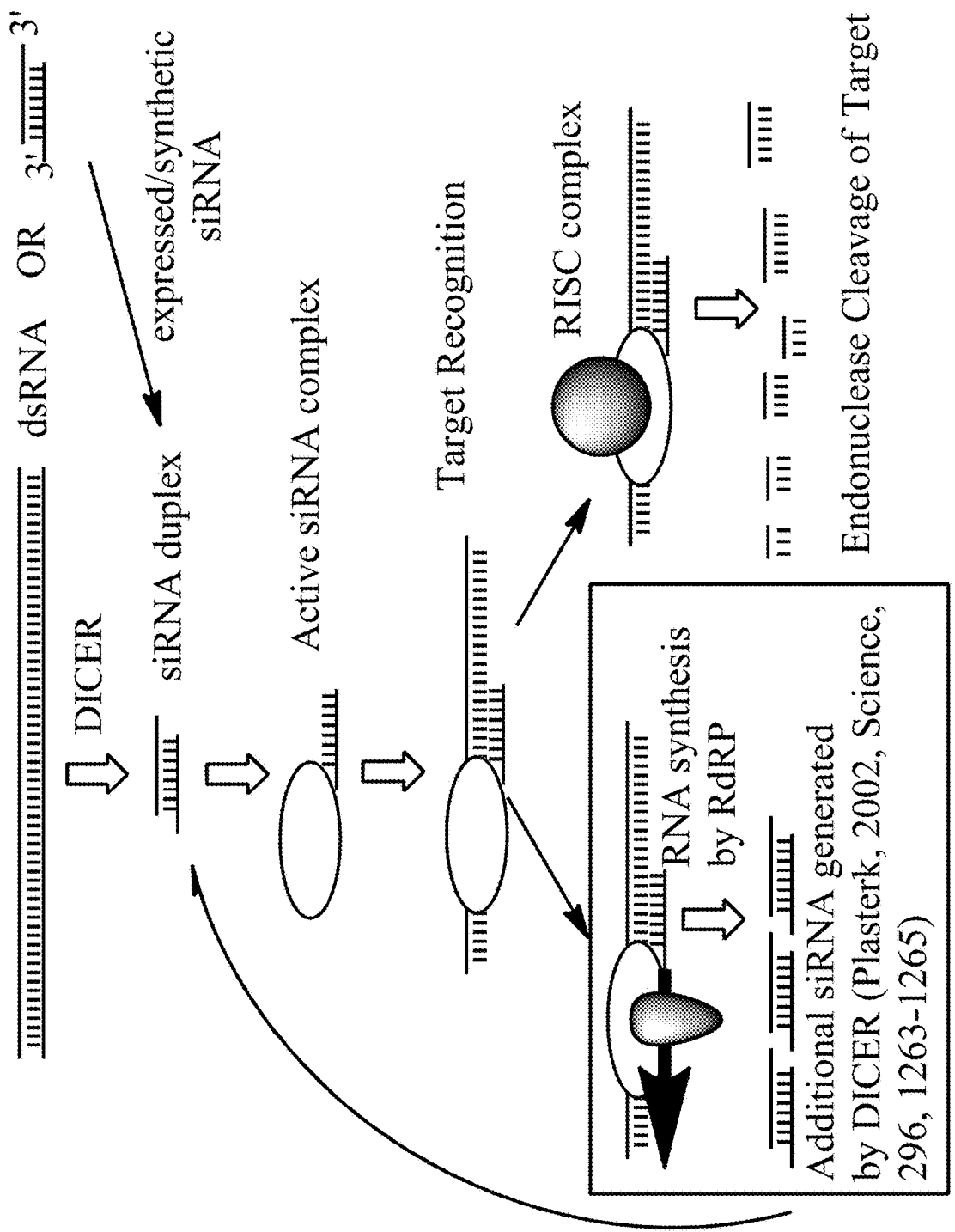
FIG. 1 shows a non-limiting proposed mechanistic representation of target RNA degradation involved in RNAi.
Figure 2:
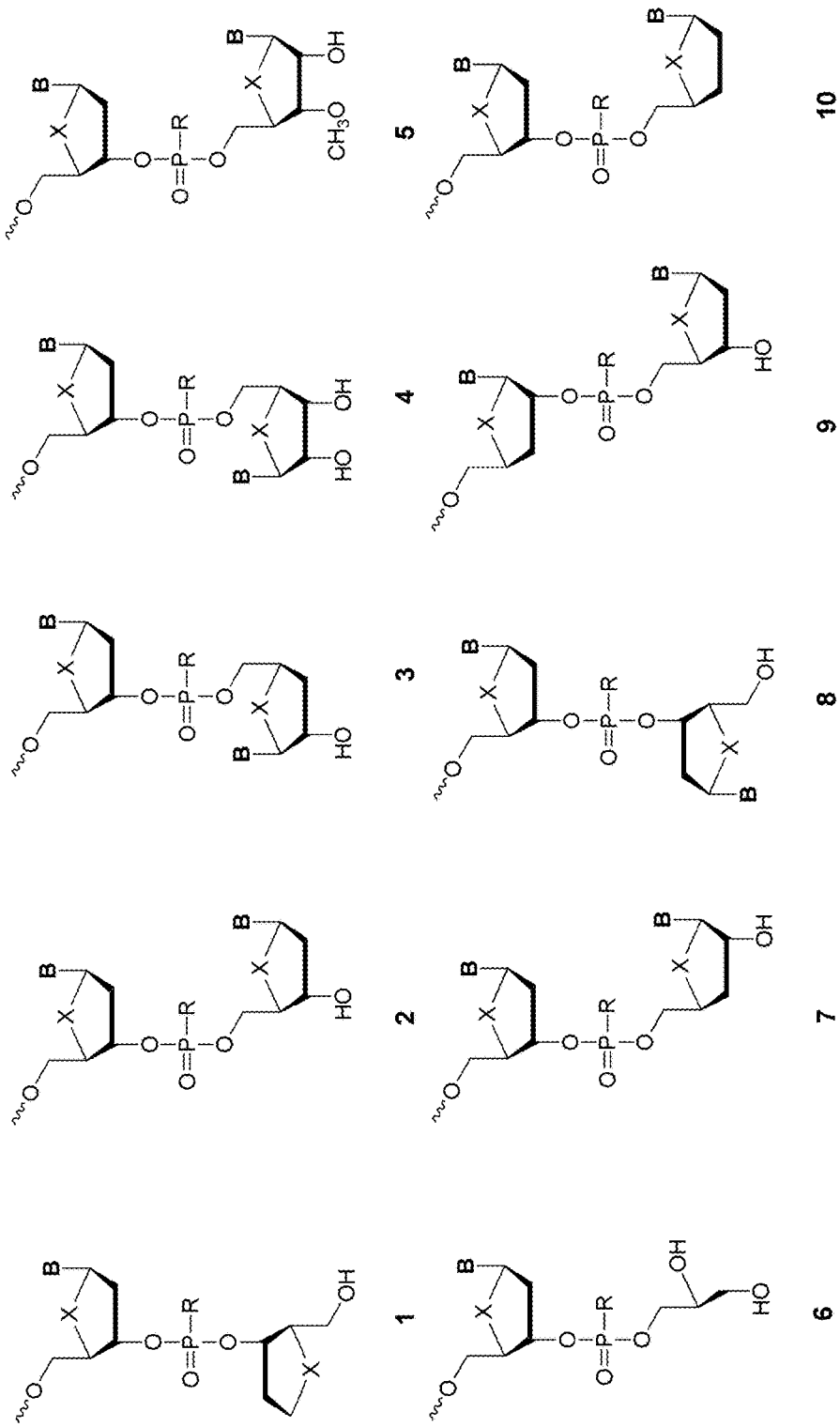

FIG. 2 shows non-limiting examples of different stabilization chemistries (1-10) that can be used, for example, to stabilize the 5 and/or 3-ends of siNA sequences of the invention (e.g., B or a portion thereof with respect to a siNA molecule having any of Formula A, B, C, D, E, F, G, H, I, J, K, L, M, N, O, or P); including (1) [3-3]-inverted deoxyribose; (2) deoxyribonucleotide; (3) [5-3]-3-deoxyribonucleotide; (4) [5-3]-ribonucleotide; (5) [5-3]-3-O-methyl ribonucleotide; (6) 3-glyceryl; (7) [3-5]-3-deoxyribonucleotide; (8) [3-3]-deoxyribonucleotide; (9) [5-2]-deoxyribonucleotide; and (10) [5-3]-dideoxyribonucleotide (when X=O). In addition to modified and unmodified backbone chemistries indicated in the figure, these chemistries can be combined with different sugar and base nucleotide modifications as described herein.

Figure 3:
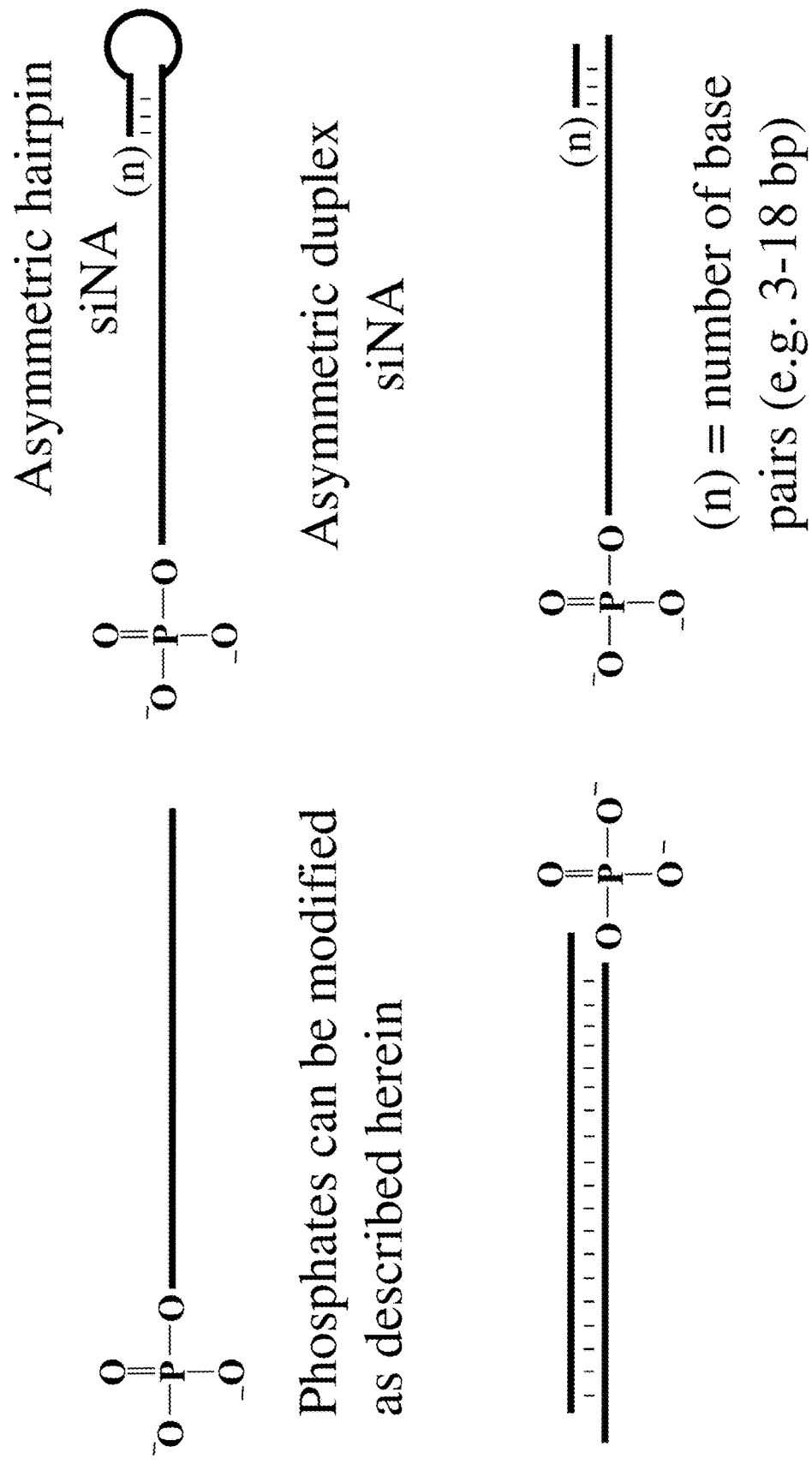

FIG. 3 shows non-limiting examples of phosphorylated siNA molecules of the invention, including linear and duplex constructs and asymmetric derivatives thereof.

Figure 4:
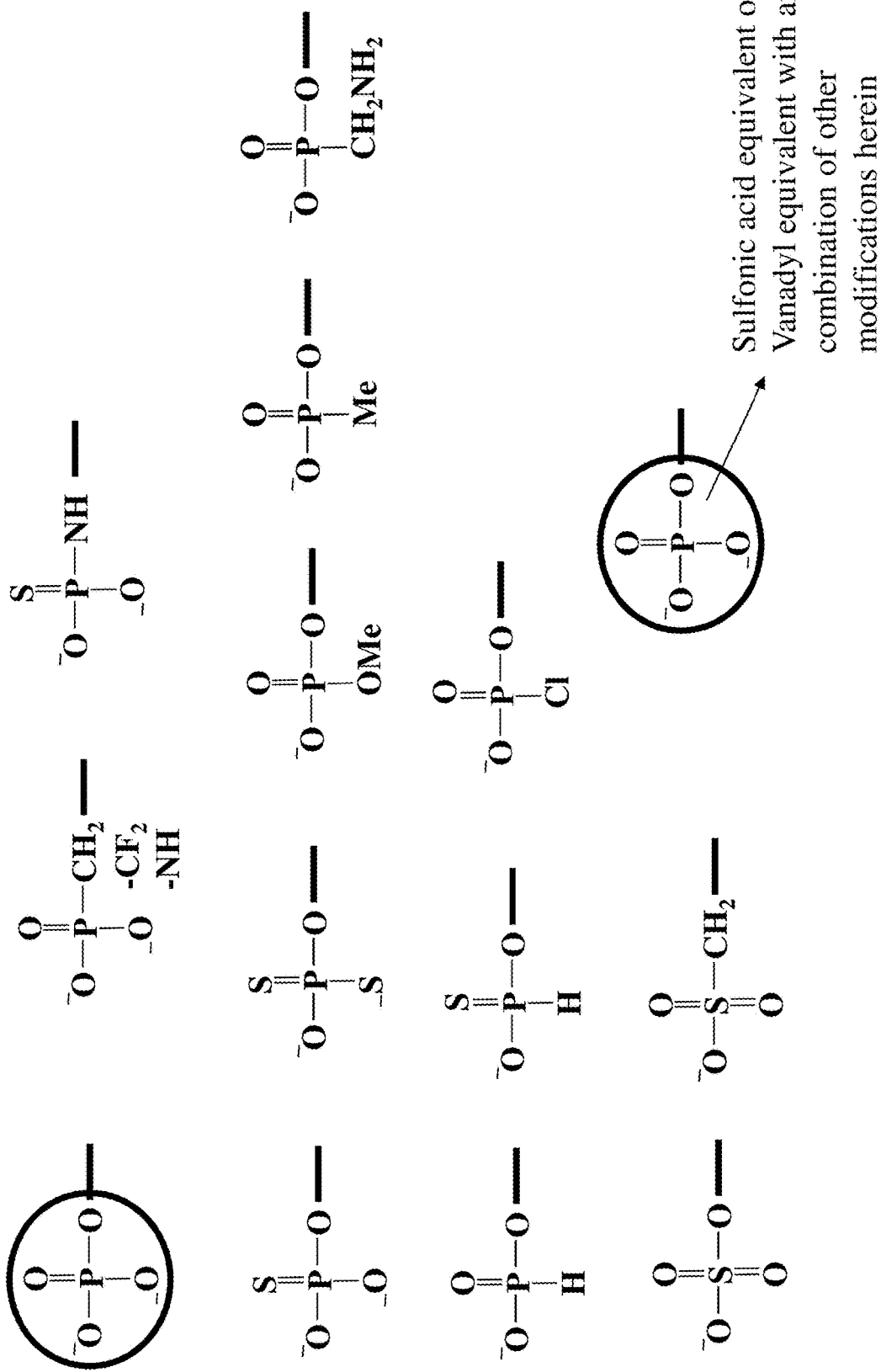

FIG. 4 shows non-limiting examples of chemically modified terminal phosphate groups of the invention. These terminal phosphate groups can be included at the 5-end of the guide strand of any siNA molecule of the invention (e.g., any of Formula A, B, C, D, E, F, G, H, I, J, K, L, M, N, O, or P).

Figure 5:
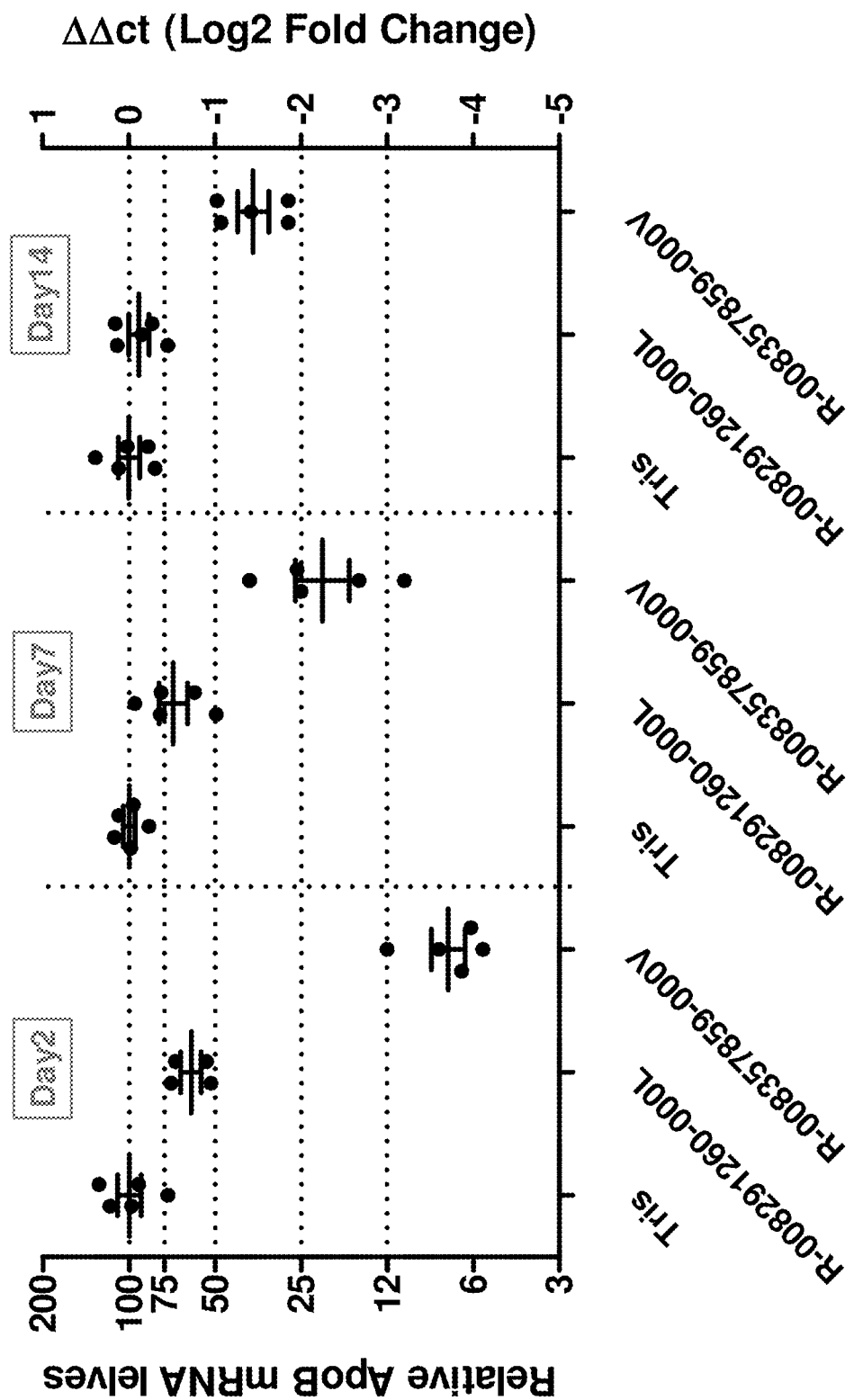

FIG. 5 shows representative data indicating that 2-deoxy-2-fluoro content on the guide strand is important for effective knockdown of ApoB mRNA in vivo. A PVE polymer conjugate delivery vehicle was used to administer the siNAs. mRNA expression in liver tissue was measured at 2 days, 7 days and 14 days post dosing with 3 mpk of siNA. Details on modification motifs and siNA sequences are provided in Table 1.

Figure 6:
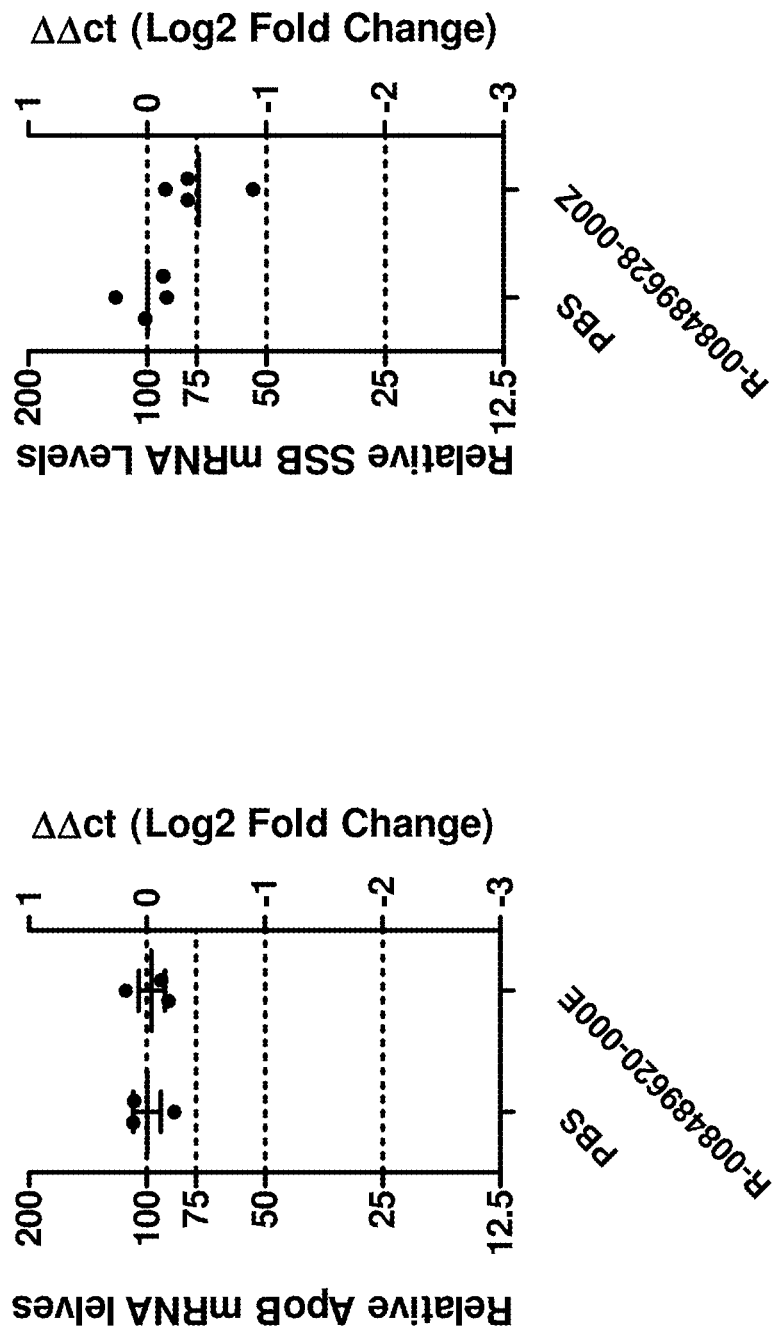

FIG. 6 shows representative data indicating that tetraGalNAc (single chemical entity, SCE) siNA conjugates containing alternating 2-deoxy-2-fluoro and 2-O-methyl modification patterns on the guide strands have little impact on ApoB or SSB mRNA expression in vivo. siNA conjugates were administered subcutaneously (30 mpk for ApoB and 50 mpk for SSB) and mRNA expression in liver tissue was measured 72 hours after dosing. Details on modification motifs and siNA sequences are provided in Table 1.

Figure 7:
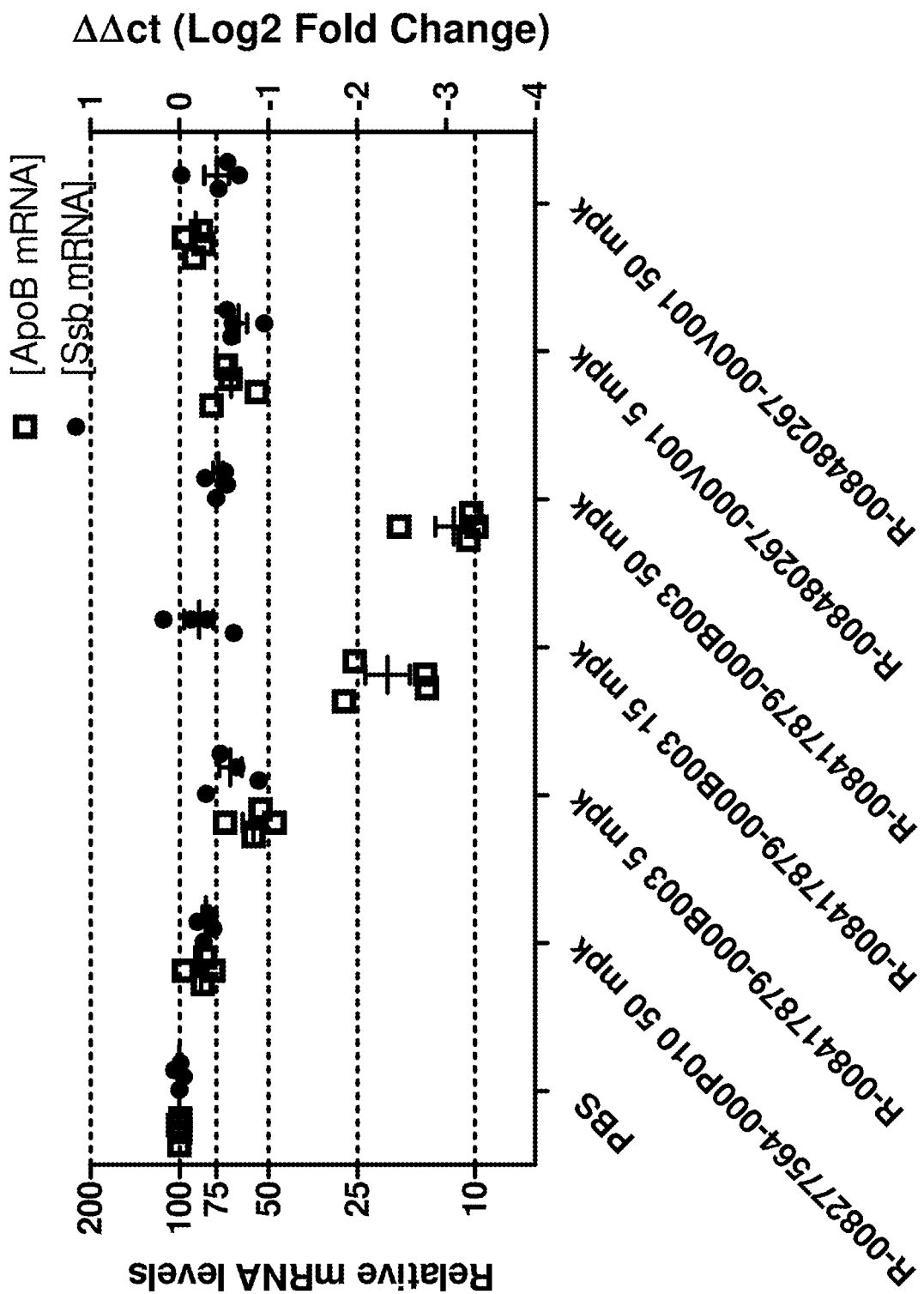

FIG. 7 shows representative data indicating the in vivo activity of subcutaneously delivered tetraGalNAc SCE siNA conjugates in mouse liver 72 hr post dosing. The SSB sequences lacking phosphorothioate linkages at the 5' end of the guide strand showed little to no activity while the ApoB sequence with 5-terminal guide strand phosphorothioate linkages showed dose dependent knockdown. Details on modification motifs and siNA sequences are provided in Table 1.

Figure 8:
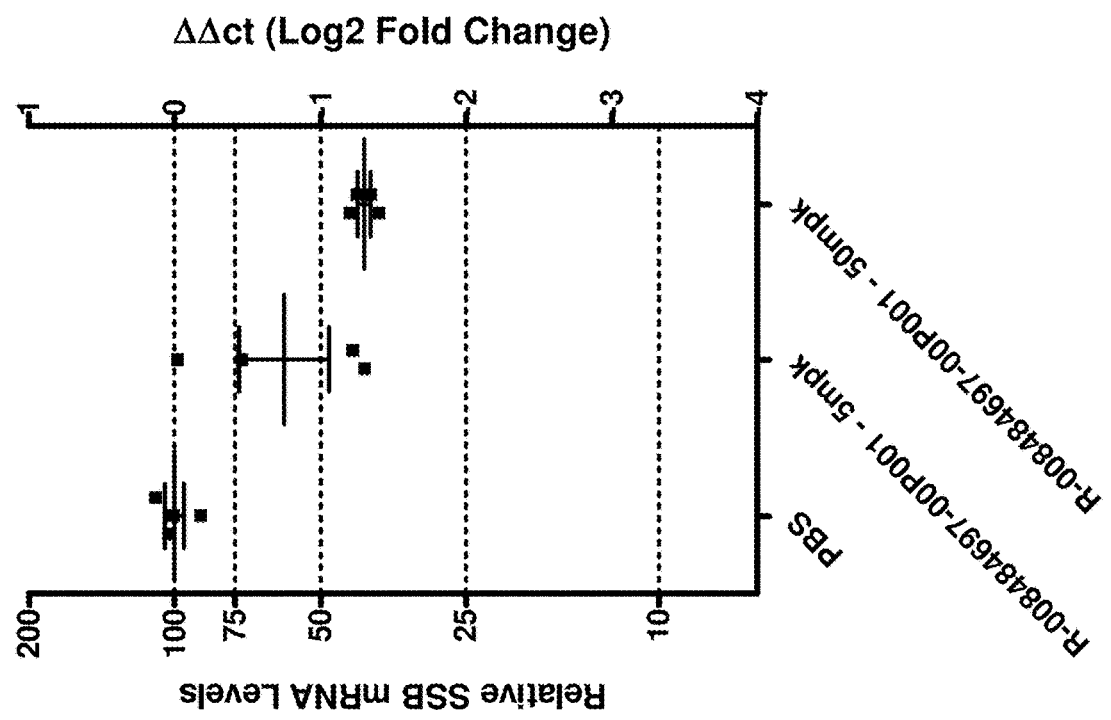

FIG. 8 shows representative data indicating the in vivo activity of subcutaneously delivered tetraGalNAc SCE siNA conjugates in mouse liver 24 hr post dosing. The SSB sequences containing phosphorothioate linkages at the 5' end of the guide strand (pos 1-3) showed dose dependent knockdown. Details on modification motifs and siNA sequences are provided in Table 1.

Figure 9:
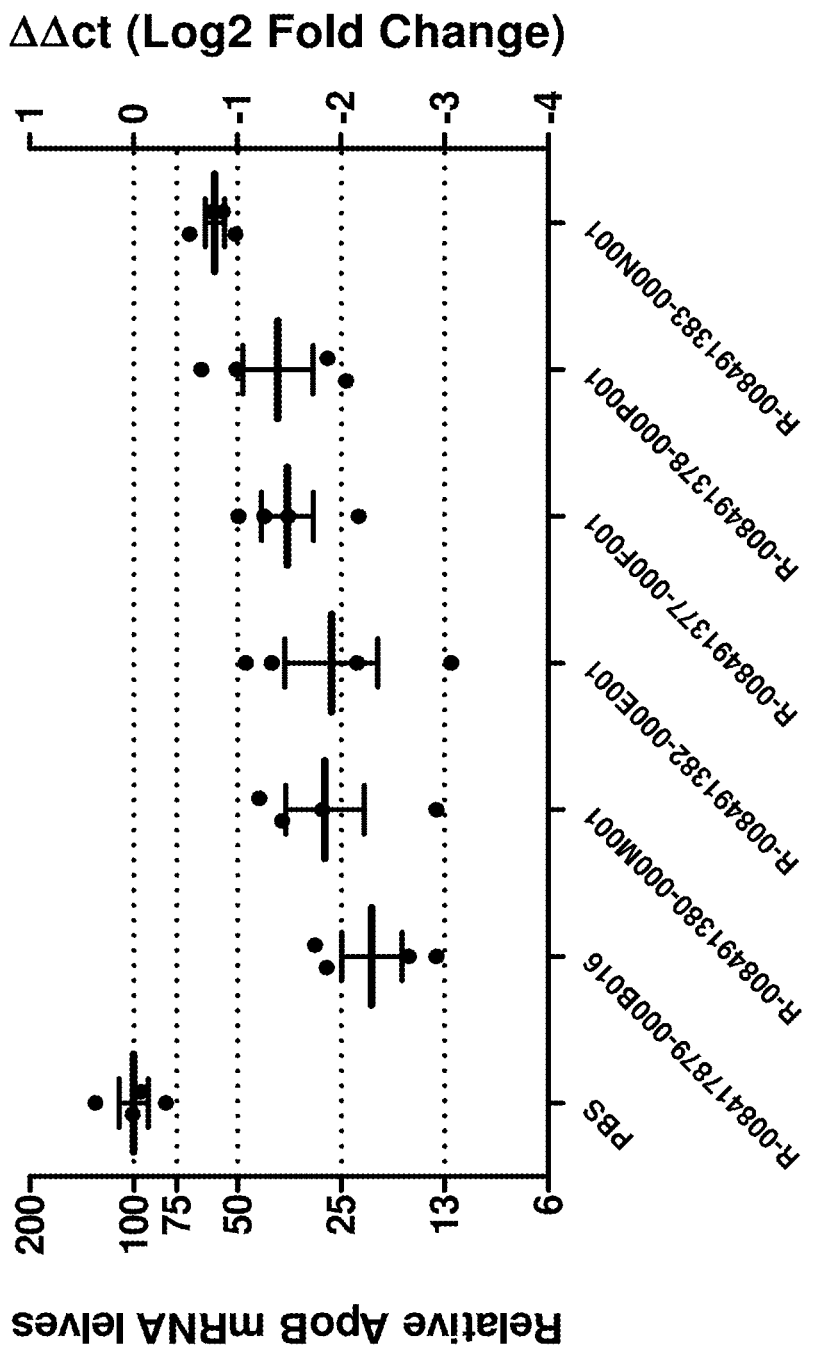

FIG. 9 shows representative data indicating the in vivo activity of subcutaneously delivered tetraGalNAc SCE siNA conjugates in mouse liver 72 hr post dosing. Addition of greater than 3-fold more phosphorothioate content does not appear to improve the activity of the siNA conjugates. Note that all these sequence had three phosphorothioate linkages at 5' end of the guide strand. Details on modification motifs and siNA sequences are provided in Table 1.

Figure 10:
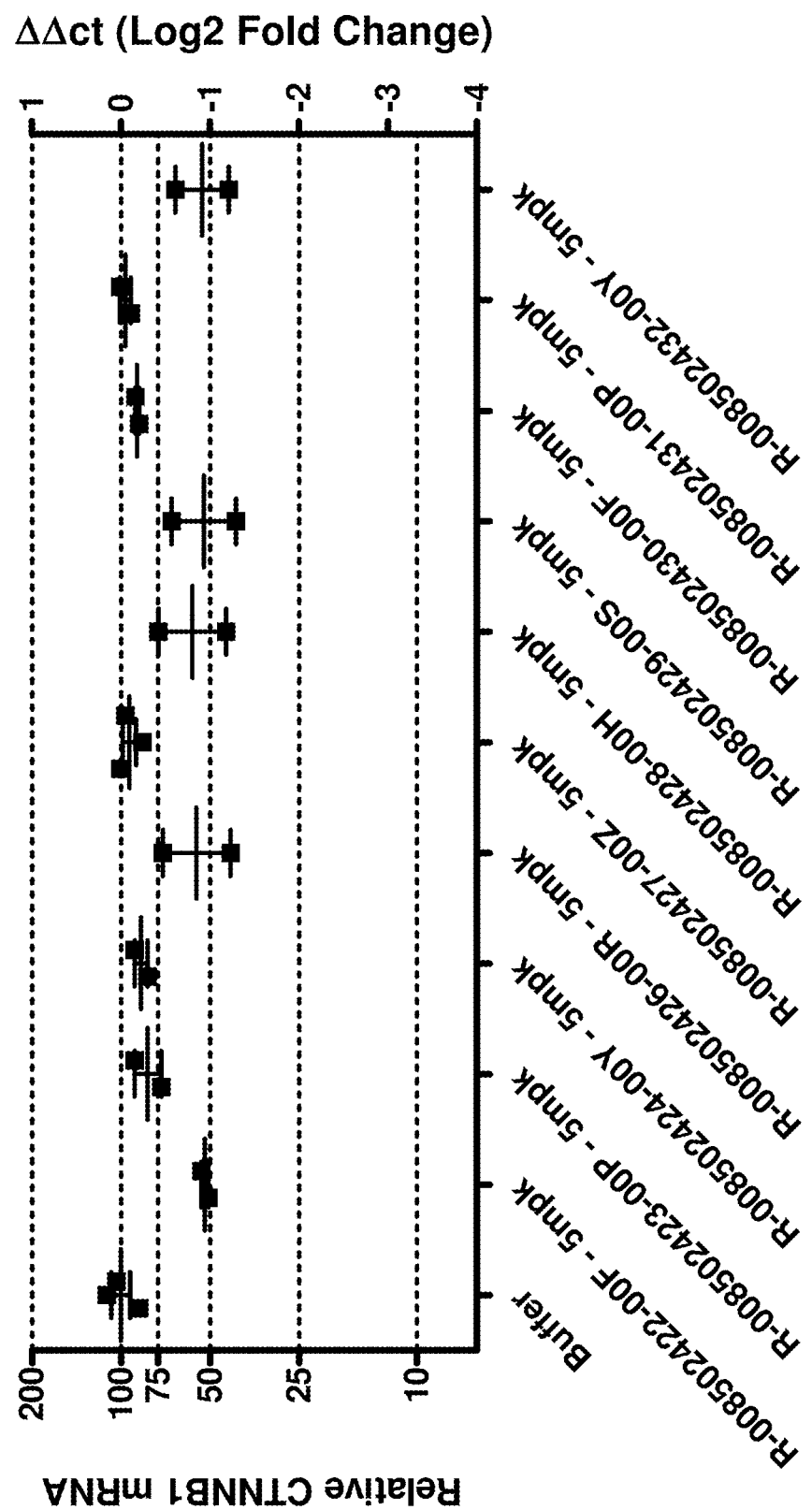

FIG. 10 shows representative data indicating the in vivo activity of subcutaneously delivered tetraGalNAc SCE siNA conjugates in mouse liver 72 hr post dosing. The presence of a single phosphorothioate linkage at the first position at the 5' end of the guide strand is important for in vivo activity. Sequences with phosphorothioate linkages at other positions in the siNA but not at the first position of the 5' end of the guide strand showed poor activity. Details on modification motifs and siNA sequences are provided in Table 1.

Figure 11:
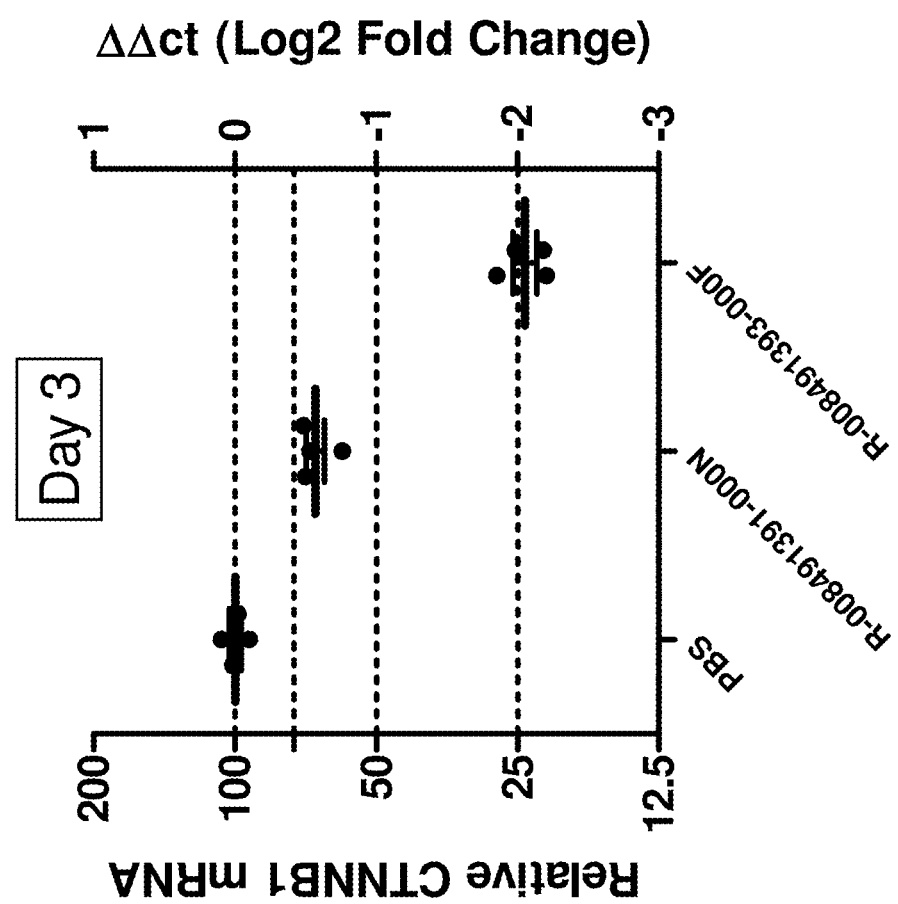

FIG. 11 shows representative data indicating that addition of three phosphorothioate modifications to the 5 end of the guide strand (positions 1-3) significantly improves the knockdown of CTNNB1 mRNA in mice. A 50 mpk dose of siNA was administered as a tetraGalNAc SCE conjugate that was injected subcutaneously. Details on modification motifs and siNA sequences are provided in Table 1.

Figure 12:
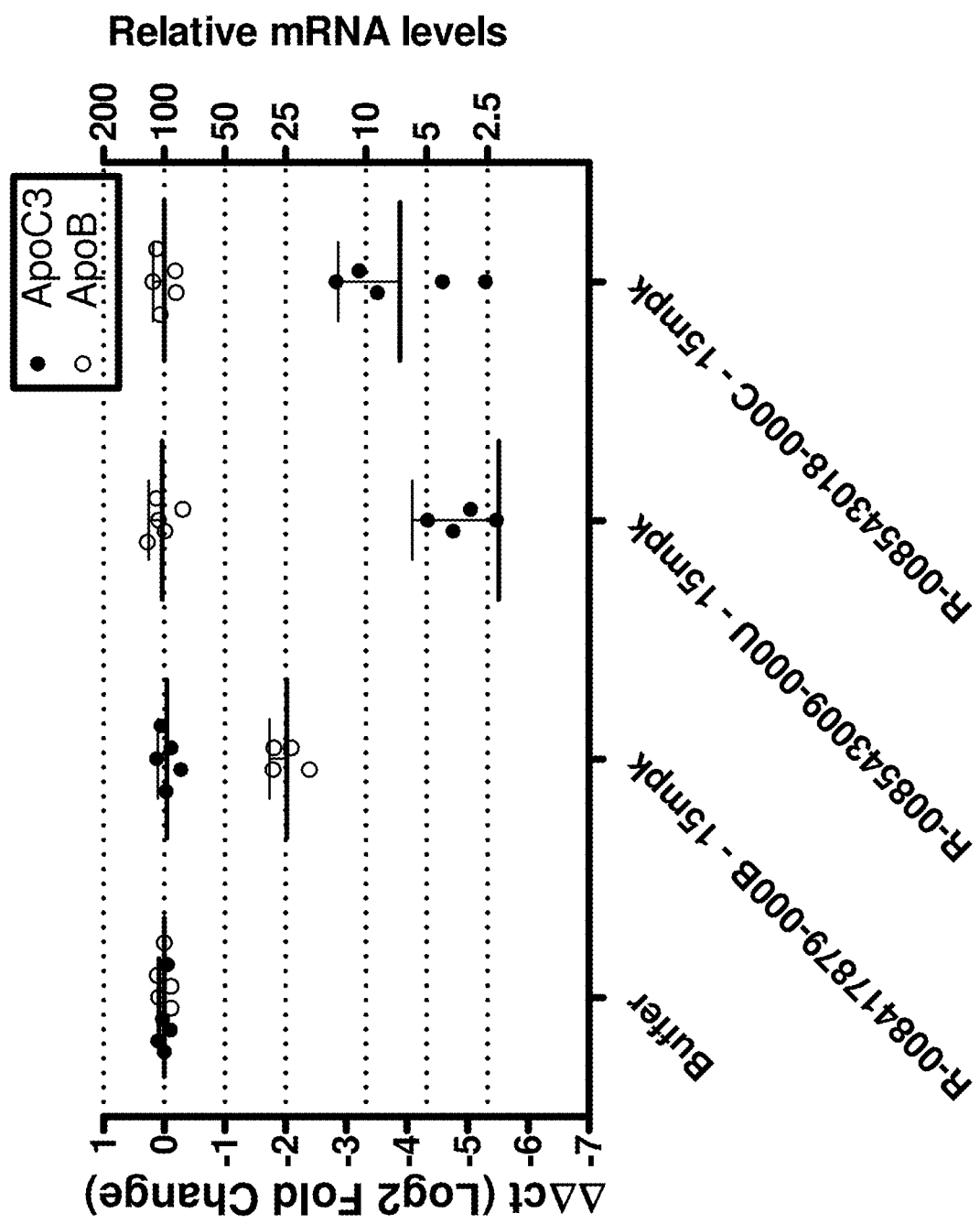

FIG. 12 shows representative data indicating the in vivo activity of subcutaneously delivered tetraGalNAc ApoC3 siNA conjugates in mouse liver 72 hr post dosing. Details on modification motifs and siNA sequences are provided in Table 1.

Figure 13:
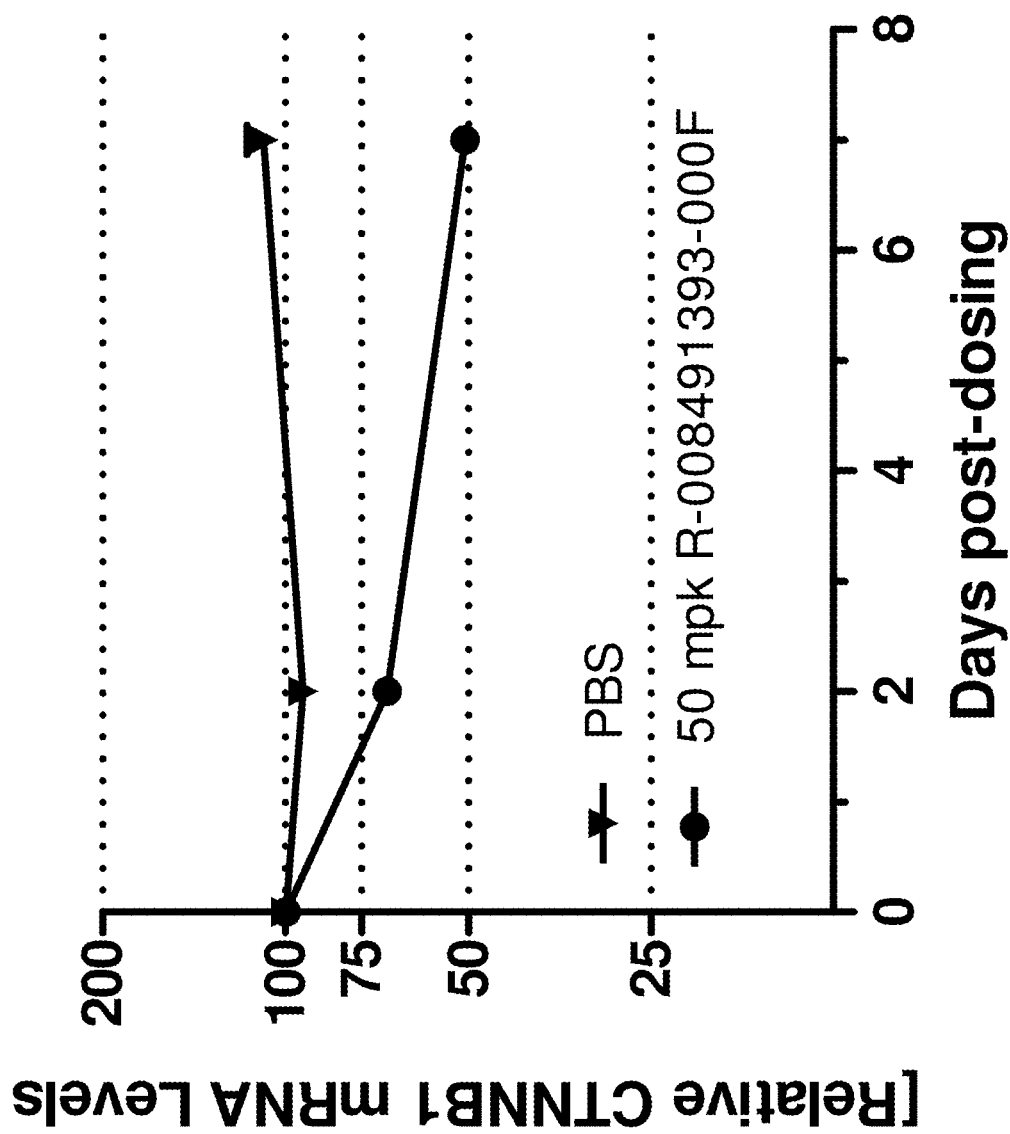

FIG. 13 shows representative data indicating the in vivo activity of subcutaneously delivered tetraGalNAc CTNNB1 siNA conjugates in rhesus liver at indicated times. Details on modification motifs and siNA sequences are provided in Table 1.

Figure 14:
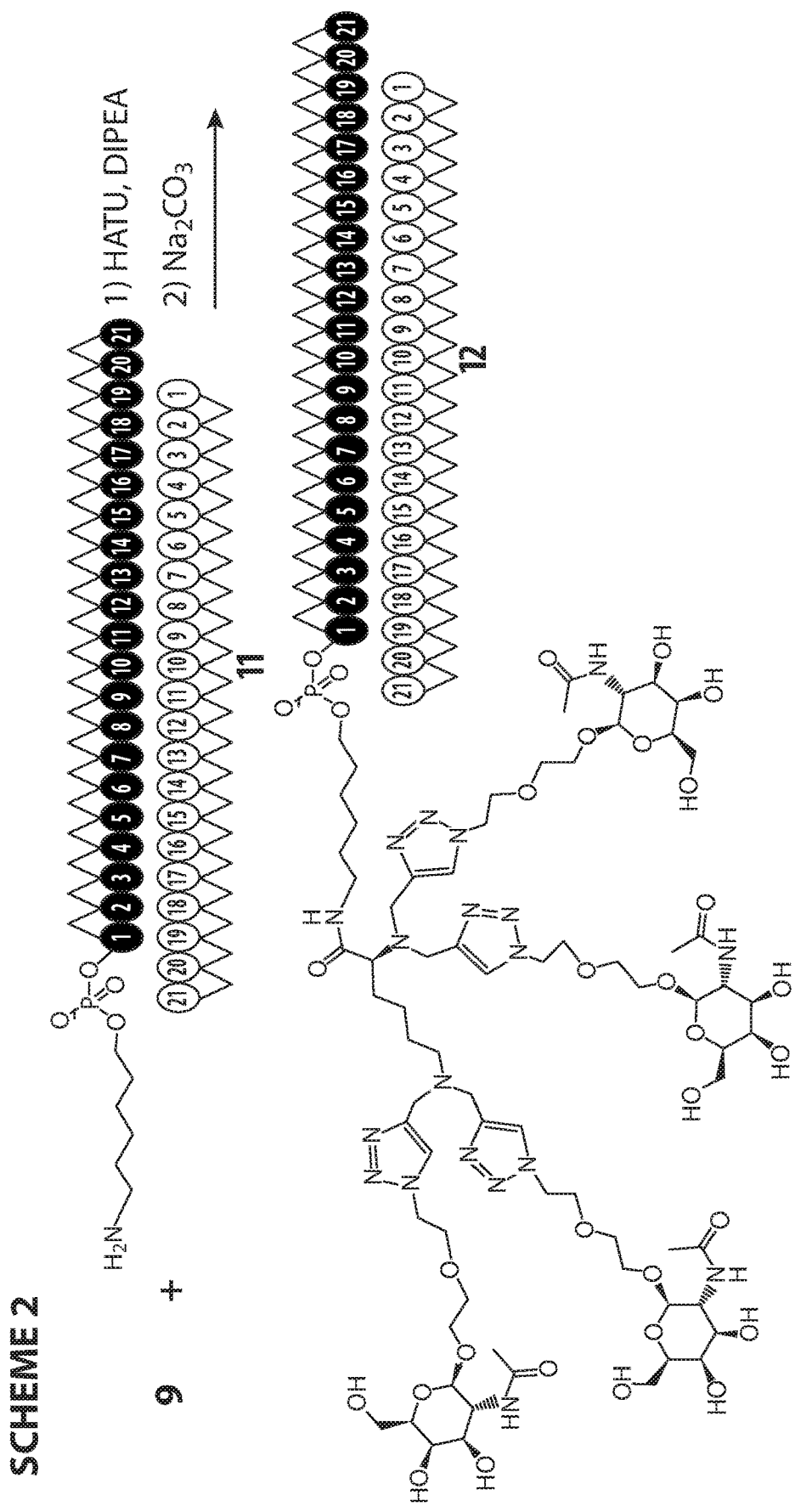

FIG. 14 shows the synthesis of tetraGalNAc-siNA conjugate (12) via tetraGalNAc acetate 9.

Figure 15:
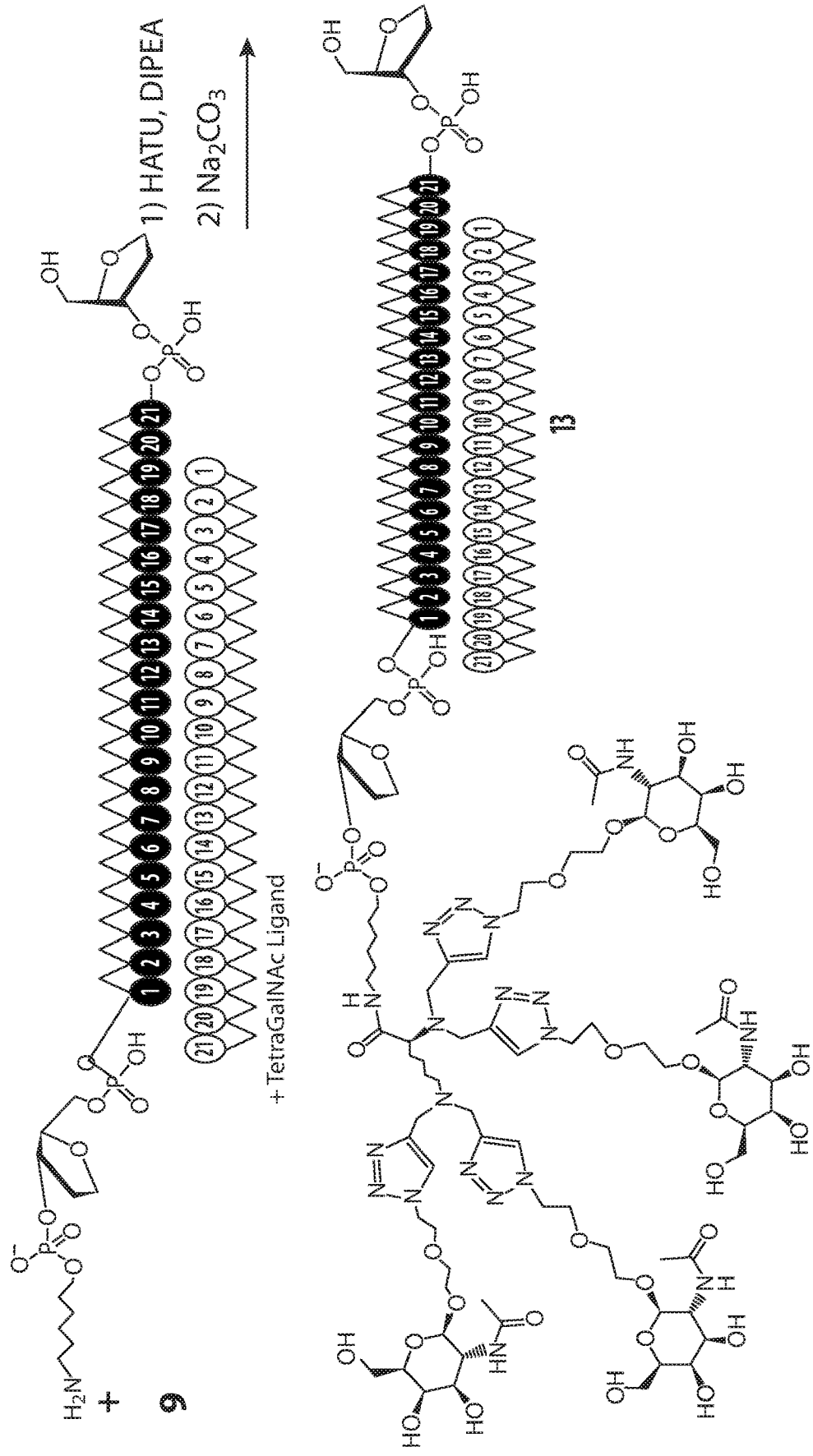

FIG. 15 shows synthesis of compound 13.

DETAILED DESCRIPTION OF THE INVENTION

Terms and Definitions

The following terminology and definitions apply as used in the present application.

As used in this specification and the appended claims, the singular forms "a," "an," and "the" include plural referents unless the content clearly dictates otherwise. Thus, for example, reference to "a cell" includes a combination of two or more cells, and the like.

Any concentration range, percentage range, ratio range or integer range is to be understood to include the value of any integer within the recited range, and when appropriate, fractions thereof (such as on tenth and one hundredth of an integer), unless otherwise indicated.

"About" or "approximately," as used herein, in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

The term "abasic" as used herein refers to its meaning as is generally accepted in the art. The term generally refers to sugar moieties lacking a nucleobase or having a hydrogen atom (H) or other non-nucleobase chemical groups in place of a nucleobase at the 1 position of the sugar moiety, see for example Adamic et al., U.S. Pat. No. 5,998,203. In one embodiment, an abasic moiety of the invention is a ribose, deoxyribose, or dideoxyribose sugar.

The term "acyclic nucleotide" as used herein refers to its meaning as is generally accepted in the art. The term generally refers to any nucleotide having an acyclic ribose sugar, for example where any of the ribose carbon/carbon or carbon/oxygen bonds are independently or in combination absent from the nucleotide.

The term "alkyl" as used herein refers to its meaning as is generally accepted in the art. The term generally refers to a saturated or unsaturated hydrocarbon, including straight-chain, branched-chain, alkenyl, alkynyl groups and cyclic groups, but excludes aromatic groups. Notwithstanding the foregoing, alkyl also refers to non-aromatic heterocyclic groups. Preferably, the alkyl group has 1 to 12 carbons. More preferably, it is a lower alkyl of from 1 to 7 carbons, more preferably 1 to 4 carbons. The alkyl group can be substituted or unsubstituted. When substituted, the substituted group(s) is preferably, hydroxyl, halogen, cyano, C1-C4 alkoxy, =O, =S, $NO_2$, SH, $NH_2$, or $NR_1R_2$, where $R_1$ and $R_2$ independently are H or C1-C4 alkyl.

The phrase "agents that interfere with cell cycle checkpoints" refers to compounds that inhibit protein kinases that transduce cell cycle checkpoint signals, thereby sensitizing the cancer cell to DNA damaging agents.

The phrase "agents that interfere with receptor tyrosine kinases (RTKs)" refers to compounds that inhibit RTKs and therefore inhibit mechanisms involved in oncogenesis and tumor progression.

The phrase "androgen receptor modulators" refers to compounds that interfere or inhibit the binding of androgens to the receptor, regardless of mechanism.

The phrase "angiogenesis inhibitors" refers to compounds that inhibit the formation of new blood vessels, regardless of mechanism.

The term "aryl" as used herein refers to its meaning as is generally accepted in the art. The term generally refers to an aromatic group that has at least one ring having a conjugated pi electron system and includes carbocyclic aryl, heterocyclic aryl and biaryl groups, all of which can be optionally substituted. The preferred substituent(s) of aryl groups are halogen, trihalomethyl, hydroxyl, SH, OH, cyano, C1-C4 alkoxy, C1-C4 alkyl, C2-C4 alkenyl, C2-C4 alkynyl, $NH_2$, and $NR_1R_2$ groups, where $R_1$ and $R_2$ independently are H or C1-C4 alkyl.

The term "alkylaryl" as used herein refers to its meaning as is generally accepted in the art. The term generally refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and examples of heterocyclic aryl groups having such heteroatoms include furanyl, thienyl, pyridyl, pyrrolyl, N-lower alkyl pyrrolo, pyrimidyl, pyrazinyl, imidazolyl and the like, all optionally substituted. Preferably, the alkyl group is a C1-C4 alkyl group.

The term "amide" as used herein refers to its meaning as is generally accepted in the art. The term generally refers to an —C(O)—NH—R, where R is either alkyl, aryl, alkylaryl or hydrogen.

The phrase "antisense region" as used herein refers to its meaning as is generally accepted in the art. With reference to exemplary nucleic acid molecules of the invention, the term refers to a nucleotide sequence of an siNA molecule having complementarity to a target nucleic acid sequence. In addition, the antisense region of an siNA molecule can optionally comprise a nucleic acid sequence having complementarity to a sense region of the siNA molecule. In one embodiment, the antisense region of the siNA molecule is referred to as the antisense strand or guide strand.

The phrase "asymmetric hairpin" refers to a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

The term "biodegradable" as used herein refers to its meaning as is generally accepted in the art. The term generally refers to degradation in a biological system, for example, enzymatic degradation or chemical degradation.

The term "biodegradable linker" as used herein refers to its meaning as is generally accepted in the art. With reference to exemplary nucleic acid molecules of the invention, the term refers to a linker molecule that is designed to connect one molecule to another molecule, and which is susceptible to degradation in a biological system. The linker can be a nucleic acid or non-nucleic acid based linker. For example, a biodegradable linker can be used to attach a ligand or biologically active molecule to an siNA molecule of the invention. Alternately, a biodegradable linker can be used to connect the sense and antisense strands of an siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically modified nucleotides, such as 2-O-methyl, 2-fluoro, 2-amino, 2-O-amino, 2-O-allyl, 2-O-allyl, and other 2-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The phrase "biologically active molecule" as used herein refers to its meaning as is generally accepted in the art. With reference to exemplary nucleic acid molecules of the invention, the term refers to compounds or molecules that are capable of eliciting or modifying a biological response in a system and/or are capable of modulating the pharmacokinetics and/or pharmacodynamics of other biologically active molecules. Examples of biologically active molecules, include siNA molecules alone or in combination with other molecules including, but not limited to therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, polyamines, polyamides, polyethylene glycol, other polyethers, 2-5 A chimeras, siNA, dsRNA, allozymes, aptamers, decoys and analogs thereof.

The phrase "biological system" as used herein refers to its meaning as is generally accepted in the art. The term generally refers to material, in a purified or unpurified form, from biological sources including, but not limited to, human or animal, wherein the system comprises the components required for RNAi activity. Thus, the phrase includes, for example, a cell, tissue, subject, or organism, or extract thereof. The term also includes reconstituted material from a biological source.

The phrase "blunt end" as used herein refers to its meaning as is generally accepted in the art. With reference to exemplary nucleic acid molecules of the invention, the term refers to termini of a double-stranded siNA molecule having no overhanging nucleotides. For example, the two strands of a double-stranded siNA molecule having blunt ends align with each other with matched base-pairs without overhanging nucleotides at the termini. A siNA duplex molecule of the invention can comprise blunt ends at one or both termini of the duplex, such as termini located at the 5-end of the antisense strand, the 5=end of the sense strand, or both termini of the duplex.

The term "cap" also referred to herein as "terminal cap," as used herein refers to its meaning as is generally accepted in the art. With reference to exemplary nucleic acid molecules of the invention, the term refers to a moiety, which can be a chemically modified nucleotide or non-nucleotide that can be incorporated at one or more termini of one or more nucleic acid molecules of the invention. These terminal modifications protect the nucleic acid molecule from exonuclease degradation, and can help in delivery and/or localization within a cell. The cap can be present at the 5-terminus (5-cap) or at the 3-terminal (3-cap) or can be present on both termini of any nucleic acid molecule of the invention. A cap can be present at the 5-end, 3-end and/or 5' and 3-ends of the sense strand of a nucleic acid molecule of the invention. Additionally, a cap can optionally be present at the 3-end of the antisense strand of a nucleic acid molecule of the invention. In non-limiting examples, the 5-cap includes, but is not limited to a polymer; a ligand; locked nucleic acid (LNA); glyceryl; an abasic ribose residue (moiety); inverted deoxy abasic residue (moiety); an inverted nucleotide; 4,5-methylene nucleotide; 1-(beta-D-erythrofuranosyl) nucleotide, 4-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3-seco nucleotide; acyclic 3,4-dihydroxybutyl nucleotide; acyclic 3,5-dihydroxypentyl nucleotide; 3-3-inverted nucleotide moiety; 3-3-inverted abasic moiety; 3-2-inverted nucleotide moiety; 3-2-inverted abasic moiety; 1,4-butanediol phosphate; 3-phosphoramidate; hexylphosphate; aminohexyl phosphate; 3-phosphate; 3-phosphorothioate; phosphorodithioate; or bridging or non-bridging methylphosphonate moiety. Non-limiting examples of the 3-cap include, but are not limited to, a polymer; a ligand; locked nucleic acid (LNA); glyceryl; an abasic ribose residue (moiety); inverted deoxy abasic residue (moiety); an inverted nucleotide; 4-5 i-ethylene nucleotide; 1-(beta-D-erythrofuranosyl) nucleotide; 4-thio nucleotide; carbocyclic nucleotide; 5-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3-4-seco nucleotide; 3,4-dihydroxybutyl nucleotide; 3,5-dihydroxypentyl nucleotide, 5-5-inverted nucleotide moiety; 5-5-inverted abasic moiety; 5 phosphoramidate; 5-phosphorothioate; 1,4-butanediol phosphate; 5-amino; bridging and/or non-bridging 5-phosphoramidate; phosphorothioate and/or phosphorodithioate; bridging or non bridging methylphosphonate; and 5-mercapto moieties (for more details see Beaucage and Iyer, 1993, Tetrahedron 49, 1925; incorporated by reference herein). In certain embodiments, a siNA molecule of the invention having Formula (A) can comprise one or more terminal cap molecules as described above (designated as B) that comprises or includes a covalent attachment to a polymer or ligand via a linker molecule as described herein or as is otherwise known in the art. Non-limiting examples of such linkers are provided in the examples and descriptions herein.

The term "cell" as used herein refers to its meaning as is generally accepted in the art. With reference to exemplary nucleic acid molecules of the invention, the term is used in its usual biological sense, and does not refer to an entire multicellular organism, e.g., specifically does not refer to a human being. The cell can be present in an organism, e.g., birds, plants and mammals, such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The phrase "chemical modification" as used herein refers to its meaning as is generally accepted in the art. With reference to exemplary nucleic acid molecules of the invention, the term refers to any modification of the chemical structure of the nucleotides that differs from nucleotides of native siRNA or RNA in general. The term "chemical modification" encompasses the addition, substitution, or modification of native siRNA or RNA at the sugar, base, or internucleotide linkage, as described herein or as is otherwise known in the art. In certain embodiments, the term "chemical modification" can refer to certain forms of RNA that are naturally occurring in certain biological systems, for example 2-O-methyl modifications or inosine modifications.

The term "complementarity" or "complementary" as used herein refers to its meaning as is generally accepted in the art. With reference to exemplary nucleic acid molecules of the invention, the terms generally refer to the formation or existence of hydrogen bond(s) between one nucleic acid sequence and another nucleic acid sequence by either traditional Watson-Crick or other non-traditional types of bonding as described herein. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, *CSH Symp. Quant. Biol.* LII pp. 123-133; Frier et al., 1986, *Proc. Nat. Acad. Sci. USA* 83:9373-9377; Turner et al., 1987, *J. Am. Chem. Soc.* 109:3783-3785). Perfect complementary means that all the contiguous residues of a nucleic acid sequence will hydrogen bond with the same number of contiguous residues in a second nucleic acid sequence. Partial complementarity can include various mismatches or non-based paired nucleotides (e.g., 1, 2, 3, 4, 5, 6, 7, 8, 9, 10 or more mismatches, non-nucleotide linkers, or non-based paired nucleotides) within the nucleic acid molecule, which can result in bulges, loops, or overhangs that result between the sense strand or sense region and the antisense strand or antisense region of the nucleic acid molecule or between the antisense strand or antisense region of the nucleic acid molecule and a corresponding target nucleic acid molecule. Such partial complementarity can be represented by a % complementarity that is determined by the number of non-base paired nucleotides, i.e., about 50%, 60%, 70%, 80%, 90% etc. depending on the total number of nucleotides involved. Such partial complementarity is permitted to the extent that the nucleic acid molecule (e.g., siNA) maintains its function, for example the ability to mediate sequence specific RNAi.

The terms "composition" or "formulation" as used herein refer to their generally accepted meaning in the art. These terms generally refer to a composition or formulation, such as in a pharmaceutically acceptable carrier or diluent, in a form suitable for administration, e.g., systemic or local administration, into a cell or subject, including, for example, a human. Suitable forms, in part, depend upon the use or the route of entry, for example oral, transdermal, inhalation, or by injection. Such forms should not prevent the composition or formulation from reaching a target cell (i.e., a cell to which the negatively charged nucleic acid is desirable for delivery). For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use. Non-limiting examples of agents suitable for formulation with the nucleic acid molecules of the instant invention include: Lipid Nanoparticles (see for example Semple et al., 2010, *Nat Biotechnol.*, February; 28(2): 172-6.); P-glycoprotein inhibitors (such as Pluronic P85); biodegradable polymers, such as poly (DL-lactide-coglycolide) microspheres for sustained release delivery (Emerich, D F et al, 1999, *Cell Transplant*, 8, 47-58); and loaded nanoparticles, such as those made of polybutylcyanoacrylate. Other non-limiting examples of delivery strategies for the nucleic acid molecules of the instant invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058. A "pharmaceutically acceptable composition" or "pharmaceutically acceptable formulation" can refer to a composition or formulation that allows for the effective distribution of the nucleic acid molecules of the instant invention to the physical location most suitable for their desired activity.

The phrase "cytotoxic/cytostatic agents" refer to compounds that cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, hematopoietic growth factors, monoclonal antibody targeted therapeutic agents, topoisomerase inhibitors, proteasome inhibitors and ubiquitin ligase inhibitors.

The phrase "estrogen receptor modulators" refers to compounds that interfere with or inhibit the binding of estrogen to the receptor, regardless of mechanism.

The term "gene" or "target gene" as used herein refers to their meaning as is generally accepted in the art. The terms generally refer a nucleic acid (e.g., DNA or RNA) sequence that comprises partial length or entire length coding sequences necessary for the production of a polypeptide. The target gene can also include the UTR or non-coding region of the nucleic acid sequence. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of fRNA or ncRNA involved in functional or regulatory cellular processes. Aberrant fRNA or ncRNA activity leading to disease can therefore be modulated by siNA molecules of the invention. siNA molecules targeting fRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts. For a review, see for example Snyder and Gerstein, 2003, *Science,* 300, 258-260. In certain embodiments, gene targets contemplated herein are also referred to herein generally as "target" sequences (including the target sequences listed by GenBank Accession numbers in U.S. Ser. No. 60/363,124, incorporated by reference herein).

The phrase "HMG-CoA reductase inhibitors" refers to inhibitors of 3-hydroxy-3-methylglutaryl-CoA reductase. The term HMG-CoA reductase inhibitor as used herein includes all pharmaceutically acceptable lactone and open-acid forms (i.e., where the lactone ring is opened to form the free acid) as well as salt and ester forms of compounds that have HMG-CoA reductase inhibitory activity, and therefore the use of such salts, esters, open-acid and lactone forms is included within the scope of this invention.

The phrase "highly conserved sequence region" refers to a nucleotide sequence of one or more regions in a target gene that does not vary significantly from one generation to the other or from one biological system to the other.

The phrase "homologous sequence" as used herein refers to its meaning as is generally accepted in the art. The term generally refers a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes. A homologous sequence can be a nucleotide sequence that is shared by two or more non-coding polynucleotides, such as noncoding DNA or RNA, regulatory sequences, introns, and sites of transcriptional control or regulation. Homologous sequences can also include sequence regions shared by more than one polynucleotide sequence. The term "perfect homology" (or "perfectly homologous") as used herein refers to complete (100%) homology or "identity" between a reference sequence and a subject nucleic acid sequence. Homology does not need to be perfect identity (100%), however, as partially homologous sequences are also contemplated by and within the scope of the instant invention (e.g., at least 95%, 94%, 93%, 92%, 91%, 90%, 89%, 88%, 87%, 86%, 85%, 84%, 83%, 82%, 81%, 80% etc.). Percent homology is the number of matching nucleotides between two sequences divided by the total length being compared, multiplied by 100.

The phrase "improved RNAi activity" refers to an increase in RNAi activity measured in vitro and/or in vivo, where the RNAi activity is a reflection of both the ability of the siNA to mediate RNAi and the stability of the siNAs of the invention. In this invention, the product of these activities can be increased in vitro and/or in vivo compared to an all RNA siNA or an siNA containing a plurality of ribonucleotides. In some cases, the activity or stability of the siNA molecule can be decreased (i.e., less than ten-fold), but the overall activity of the siNA molecule is enhanced in vitro and/or in vivo.

The term "including" (and any form thereof, such as "includes" and "include"), "comprising" (and any form thereof, such as "has" or "have") or "containing" (and any form thereof such as "contains" or "contain") are inclusive and open-ended and do not exclude additional, unrecited elements or method steps.

The terms "inhibit." "down-regulate." or "reduce" as used herein refers to its meaning as is generally accepted in the art. With reference to exemplary nucleic acid molecules of the invention, he term generally refers the reduction in the expression of the gene, or level of RNA molecules or equivalent RNA molecules encoding one or more proteins or protein subunits, or activity of one or more proteins or protein subunits, below that observed in the absence of the nucleic acid molecules (e.g., siNA) of the invention. Down-regulation can also be associated with post-transcriptional silencing, such as, RNAi mediated cleavage or by alteration in DNA methylation patterns or DNA chromatin structure. Inhibition, down-regulation or reduction with an siNA molecule can be in reference to an inactive molecule, an attenuated molecule, an siNA molecule with a scrambled sequence, or an siNA molecule with mismatches or alternatively, it can be in reference to the system in the absence of the nucleic acid.

The phrase "inhibitors of cell proliferation and survival signaling pathway" refers to pharmaceutical agents that inhibit cell surface receptors and signal transduction cascades downstream of those surface receptors.

The term "integrin blockers" refers to compounds which selectively antagonize, inhibit or counteract binding of a physiological ligand to the $\alpha_\nu\beta_3$ integrin, to compounds which selectively antagonize, inhibit or counteract binding of a physiological ligand to the $\alpha_\nu\beta_5$ integrin, to compounds which antagonize, inhibit or counteract binding of a physiological ligand to both the $\alpha_\nu\beta_3$ integrin and the $\alpha_\nu\beta_5$ integrin, and to compounds which antagonize, inhibit or counteract the activity of the particular integrin(s) expressed on capillary endothelial cells. The term also refers to antagonists of the $\alpha_\nu\beta_6$ $\alpha_\nu\beta_8$ $\alpha_1\beta_1$ $\alpha_2\beta_1$ $\alpha_5\beta_1$ $\alpha_6\beta_1$ and $\alpha_6\beta_4$ integrins. The term also refers to antagonists of any combination of $\alpha_\nu\beta_3$, $\alpha_\nu\beta_5$ $\alpha_\nu\beta_6$ $\alpha_\nu\beta_8$ $\alpha_1\beta_1$ $\alpha_2\beta_1$ $\alpha_5\beta_1$ $\alpha_6\beta_1$ and $\alpha_6\beta_4$ integrins.

The terms "intermittent" or "intermittently" as used herein refers to its meaning as is generally accepted in the art. The term generally refers to periodic stopping and starting at either regular or irregular intervals.

The terms "internucleoside linkage" or "internucleoside linker" or "internucleotide linkage" or "internucleotide linker" are used herein interchangeably and refer to any linker or linkage between two nucleoside units, as is known in the art, including, for example, but not limitation, phosphate, analogs of phosphate, phosphonate, guanidinium, hydroxylamine, hydroxylhydrazinyl, amide, carbamate, alkyl, and substituted alkyl linkages. The internucleoside linkages constitute the backbone of a nucleic acid molecule.

The term "ligand" refers to such compounds and compositions as are generally known in the art. Non-limiting examples of such ligands are described herein including in the documents specifically incorporated by reference herein. A siNA molecule of the invention can be formulated or administered with any covalently linked ligand as described herein or otherwise known in the art.

The term "linker" as used herein refers to its meaning as is generally known in the art. Non-limiting examples of linkers are described herein, for example in Table 8 and including in the documents specifically incorporated by reference herein.

The term "lipid nanoparticle" or "LNP" refers to lipid-based compositions and formulations as are generally known in the art. Non-limiting examples of such LNPs are described herein including in the documents specifically incorporated by reference herein. A siNA molecule of the invention can be formulated or administered with any LNP as described herein or otherwise known in the art.

The terms "mammalian" or "mammal" as used herein refers to its meaning as is generally accepted in the art. The term generally refers to any warm blooded vertebrate species, such as a human, mouse, rat, dog, cat, hamster, guinea pig, rabbit, livestock, and the like.

The phrase "metered dose inhaler" or MDI refers to a unit comprising a can, a secured cap covering the can and a formulation metering valve situated in the cap. MDI systems includes a suitable channeling device. Suitable channeling devices comprise for example, a valve actuator and a cylindrical or cone-like passage through which medicament can be delivered from the filled canister via the metering valve to the nose or mouth of a patient such as a mouthpiece actuator.

The term "microRNA" or "miRNA" as used herein refers to its meaning as is generally accepted in the art. The term generally refers to an endogenous short RNA molecule found in eukaryotes that is involved in RNA-based gene regulation. A representative set of known endogenous miRNA species is described in the publicly available miR-Base sequence database as described in Griffith-Jones et al., Nucleic Acids Research, 2004, 32:D109-DI 11 and Griffith-Jones et al., Nucleic Acids Research, 2006, 34:D 140-D 144, accessible on the World Wide Web at the Wellcome Trust Sanger Institute website. Each mature miRNA is partially complementary to one or more messenger RNA (mRNA) molecules, which are also called "miRNA targets," thereby regulating the expression of genes associated with the miRNA targets.

The term "modulate" as used herein refers to its meaning as is generally accepted in the art. With reference to exemplary nucleic acid molecules of the invention, the term refers to when the expression of a gene, or level of one or more RNA molecules (coding or non-coding), or activity of one or more RNA molecules or proteins or protein subunits, is up-regulated or down-regulated, such that expression, level, or activity is greater than or less than that observed in the absence of the molecule that effects modulation. For example, the term "modulate" in some embodiments can refer to inhibition and in other embodiments can refer to potentiation or up-regulation, e.g., of gene expression.

The phrase "modified nucleotide" as used herein refers to its meaning as is generally accepted in the art. The term generally refers a nucleotide, which contains a modification in the chemical structure of the base, sugar and/or phosphate of the unmodified (or natural) nucleotide as is generally known in the art. Non-limiting examples of modified nucleotides are described herein and in U.S. application Ser. No. 12/064,014.

The phrase "NSAIDs that are selective COX-2 inhibitors" for purposes herein, refers to NSAIDs, which possess a specificity for inhibiting COX-2 over COX-1 of at least 100 fold as measured by the ratio of $IC_{50}$ for COX-2 over $IC_{50}$ for COX-1 evaluated by cell or microsomal assays.

The phrase "non-base paired" refers to nucleotides that are not base paired between the sense strand or sense region and the antisense strand or antisense region of an double-stranded siNA molecule; and can include for example, but not limitation, mismatches, overhangs, single stranded loops, etc.

The term "non-nucleotide" refers to any group or compound which can be incorporated into a nucleic acid chain in the place of one or more nucleotide units, such as for example but not limitation abasic moieties or alkyl chains. The group or compound is "abasic" in that it does not contain a commonly recognized nucleotide base, such as adenosine, guanine, cytosine, uracil or thymine and therefore lacks a nucleobase at the 1-position.

The term "nucleotide" is used as is generally recognized in the art. Nucleotides generally comprise a nucleobase, a sugar, and an internucleoside linkage, e.g., a phosphate. The base can be a natural bases (standard), modified bases, or a base analog, as are well known in the art. Such bases are generally located at the 1 position of a nucleotide sugar moiety. Additionally, the nucleotides can be unmodified or modified at the sugar, internucleoside linkage, and/or base moiety, (also referred to interchangeably as nucleotide analogs, modified nucleotides, non-natural nucleotides, non-standard nucleotides and others; see, for example, U.S. application Ser. No. 12/064,014.

The term "overhang" as used herein refers to its meaning as is generally accepted in the art. With reference to exemplary double stranded nucleic acid molecules, the term generally refers to the terminal portion of a nucleotide sequence that is not base paired between the two strands of a double-stranded nucleic acid molecule. Overhangs, when present, are typically at the 3-end of one or both strands in a siNA duplex.

The term "parenteral" as used herein refers to its meaning as is generally accepted in the art. The term generally refers methods or techniques of administering a molecule, drug, agent, or compound in a manner other than through the digestive tract, and includes epicutaneous, subcutaneous, intravascular (e.g., intravenous), intramuscular, or intrathecal injection or infusion techniques and the like.

The phrase "pathway target" refers to any target involved in pathways of gene expression or activity. For example, any given target can have related pathway targets that can include upstream, downstream, or modifier genes in a biologic pathway. These pathway target genes can provide additive or synergistic effects in the treatment of diseases, conditions, and traits herein.

The term "phosphorothioate" refers to an internucleotide phosphate linkage comprising one or more sulfur atoms in place of an oxygen atom. Hence, the term phosphorothioate refers to both phosphorothioate and phosphorodithioate internucleotide linkages.

The term "polymer" refers to polymeric compounds, compositions and formulations as are generally known in the art. Non-limiting examples of such polymers, including polymeric delivery systems are described herein including in the documents specifically incorporated by reference herein. A siNA molecule of the invention can be formulated or administered with any polymer as described herein or otherwise known in the art.

The term "position 1" refers to the position of the first nucleotide at the end of a strand, e.g., antisense strand. All positions referred to herein are the positions of a nucleotide counting from the end of a strand, for example, positions 1-3 from the 5 end of the antisense strand, refer to the three nucleotides at positions 1, 2, and 3 counting from the 5 end of the antisense strand.

The term "ribonucleotide" as used herein refers to its meaning as is generally accepted in the art. The term generally refers to a nucleotide with a hydroxyl group at the 2 position of a 3-D-ribofuranose moiety.

The term "RNA" as used herein refers to its generally accepted meaning in the art. Generally, the term RNA refers to a molecule comprising at least one ribofuranoside moiety. The term can include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

The phrase "RNA interference" or term "RNAi" refer to the biological process of inhibiting or down regulating gene expression in a cell, as is generally known in the art, and which is mediated by short interfering nucleic acid molecules, see for example Zamore and Haley, 2005, *Science*, 309, 1519-1524; Vaughn and Martienssen, 2005, *Science*, 309, 1525-1526; Zamore et al., 2000, *Cell*, 101, 25-33; Bass, 2001, *Nature*, 411, 428-429; Elbashir et al., 2001, *Nature*, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237; Hutvagner and Zamore, 2002, *Science,* 297, 2056-60; McManus et al., 2002, *RNA,* 8, 842-850; Reinhart et al., 2002, *Gene & Dev.,* 16, 1616-1626; and Reinhart & Bartel, 2002, Science, 297, 1831). Additionally, the term RNAi is meant to be equivalent to other terms used to describe sequence specific RNA interference, such as post transcriptional gene silencing, translational inhibition, transcriptional inhibition, or epigenetics. For example, siNA molecules of the invention can be used to epigenetically silence genes at either the post-transcriptional level or the pre-transcriptional level. In a non-limiting example, epigenetic modulation of gene expression by siNA molecules of the invention can result from siNA mediated modification of chromatin structure or methylation patterns to alter gene expression (see, for example, Verdel et al., 2004, *Science,* 303, 672-676; Pal-Bhadra et al., 2004, *Science,* 303, 669-672; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237). In another non-limiting example, modulation of gene expression by siNA molecules of the invention can result from siNA mediated cleavage of RNA (either coding or non-coding RNA) via RISC, or via translational inhibition, as is known in the art or modulation can result from transcriptional inhibition (see for example Janowski et al., 2005, *Nature Chemical Biology,* 1, 216-222).

The phrase "RNAi inhibitor" refers to any molecule that can down regulate, reduce or inhibit RNA interference function or activity in a cell or organism. An RNAi inhibitor can down regulate, reduce or inhibit RNAi (e.g., RNAi mediated cleavage of a target polynucleotide, translational inhibition, or transcriptional silencing) by interaction with or interfering with the function of any component of the RNAi pathway, including protein components such as RISC, or nucleic acid components such as miRNAs or siRNAs. A RNAi inhibitor can be an siNA molecule, an antisense molecule, an aptamer, or a small molecule that interacts with or interferes with the function of RISC, a miRNA, or an siRNA or any other component of the RNAi pathway in a cell or organism. By inhibiting RNAi (e.g., RNAi mediated cleavage of a target polynucleotide, translational inhibition, or transcriptional silencing), a RNAi inhibitor of the invention can be used to modulate (e.g., up-regulate or down regulate) the expression of a target gene.

The phrase "sense region" as used herein refers to its meaning as is generally accepted in the art. With reference to exemplary nucleic acid molecules of the invention, the term refers to a nucleotide sequence of an siNA molecule having complementarity to an antisense region of the siNA molecule. In addition, the sense region of an siNA molecule can comprise a nucleic acid sequence having homology or sequence identity with a target nucleic acid sequence. In one embodiment, the sense region of the siNA molecule is also referred to as the sense strand or passenger strand.

The phrases "short interfering nucleic acid", "siNA", "short interfering RNA", "siRNA", "short interfering nucleic acid molecule", "short interfering oligonucleotide molecule", or "chemically modified short interfering nucleic acid molecule" refer to any nucleic acid molecule capable of inhibiting or down regulating gene expression or viral replication by mediating RNA interference ("RNAi") or gene silencing in a sequence-specific manner. These terms can refer to both individual nucleic acid molecules, a plurality of such nucleic acid molecules, or pools of such nucleic acid molecules. The siNA can be a double-stranded nucleic acid molecule comprising self-complementary sense and antisense strands, wherein the antisense strand comprises a nucleotide sequence that is complementary to a nucleotide sequence in a target nucleic acid molecule or a portion thereof and the sense strand comprises a nucleotide sequence corresponding to the target nucleic acid sequence or a portion thereof. The siNA can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region comprises a nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to a nucleotide sequence in a target nucleic acid molecule or a portion thereof and the sense region comprises a nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single-stranded polynucleotide having a nucleotide sequence complementary to nucleotide sequence in a target nucleic acid molecule or a portion thereof (for example, where such siNA molecule does not require the presence within the siNA molecule of a nucleotide sequence corresponding to the target nucleic acid sequence or a portion thereof), wherein the single-stranded polynucleotide can further comprise a terminal phosphate group, such as a 5'-phosphate (see for example, Martinez et al., 2002, *Cell,* 110, 563-574 and Schwarz et al., 2002, *Molecular Cell,* 10, 537-568), or 5',3'-diphosphate.

The term "subject" as used herein refers to its meaning as is generally accepted in the art. The term generally refers an organism to which the nucleic acid molecules of the invention can be administered. A subject can be a mammal or mammalian cells, including a human or human cells. The term also refers to an organism, which is a donor or recipient of explanted cells or the cells themselves.

The phrase "systemic administration" as used herein refers to its meaning as is generally accepted in the art. The term generally refers in vivo systemic absorption or accumulation of drugs in the blood stream followed by distribution throughout the entire body.

The term "target" as used herein refers, to any protein, peptide, or polypeptide, such as encoded by any gene in the GenBank database, including those described herein and/or in U.S. Provisional Patent Application No. 60/363,124, U.S. application Ser. No. 10/923,536 and/or PCT/US03/05028, all of which are incorporated herein by reference for purposes of identifying such targets. The term "target" also refers to one or more genes, nucleic acid sequences, or target polynucleotide sequences encoding any target protein, peptide, or polypeptide, such as proteins, peptides, or polypeptides encoded by the genes in the Genebank database or sequences having GenBank Accession Nos. shown herein and/or in U.S. Provisional Patent Application No. 60/363,124, U.S. application Ser. No. 10/923,536 and/or PCT/US03/05028, all of which are incorporated herein by reference for purposes of identify such targets. The target of interest can include target polynucleotide sequences, such as target DNA or target RNA. The term "target" is also meant to include other sequences, such as differing isoforms, mutant target genes, splice variants of target polynucleotides, target polymorphisms, and non-coding (e.g., ncRNA, miRNA, stRNA) or other regulatory polynucleotide sequences as described herein. Therefore, in various embodiments of the invention, a double stranded nucleic acid molecule of the invention (e.g., siNA) having complementarity to a target RNA can be used to inhibit or down regulate miRNA or other ncRNA activity. In one embodiment, inhibition of miRNA or ncRNA activity can be used to down regulate or inhibit gene expression (e.g., gene targets described herein or otherwise known in the art) that is dependent on miRNA or ncRNA activity. In another embodiment, inhibition of miRNA or ncRNA activity by double stranded nucleic acid molecules of the invention (e.g. siNA) having complementarity to the miRNA or ncRNA can be used to up regulate or promote target gene expression (e.g., gene targets described herein or otherwise known in the art) where the expression of such genes is down regulated, suppressed, or silenced by the miRNA or ncRNA. Such up-regulation of gene expression can be used to treat diseases and conditions associated with a loss of function or haploinsufficiency as are generally known in the art.

The phrase "target site" as used herein refers to its meaning as is generally accepted in the art. The term generally refers to a sequence within a target nucleic acid molecule, (e.g., RNA) that is "targeted", e.g., for cleavage mediated by an siNA construct, which contains sequences within its antisense region that are complementary to the target sequence.

The phrase "therapeutically effective amount" as used herein refers to its meaning as is generally accepted in the art. The term generally refers to the amount of the compound or composition that will elicit the biological or medical response of a cell, tissue, system, animal or human that is be sought by the researcher, veterinarian, medical doctor or other clinician. For example, if a given clinical treatment is considered effective when there is at least a 25% reduction in a measurable parameter associated with a disease or disorder, a therapeutically effective amount of a drug for the treatment of that disease or disorder is that amount necessary to effect at least a 25% reduction in that parameter.

The phrase "universal base" as used herein refers to its meaning as is generally accepted in the art. The term universal base generally refers to nucleotide base analogs that form base pairs with each of the natural DNA/RNA bases with little or no discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example, Loakes, 2001, *Nucleic Acids Research*, 29, 2437-2447).

The term "up-regulate" as used herein refers to its meaning as is generally accepted in the art. With reference to exemplary nucleic acid molecules of the invention, the term refers to an increase in the expression of a gene, or level of RNA molecules or equivalent RNA molecules encoding one or more proteins or protein subunits, or activity of one or more RNAs, proteins or protein subunits, above that observed in the absence of the nucleic acid molecules (e.g., siNA) of the invention. In certain instances, up-regulation or promotion of gene expression with an siNA molecule is above that level observed in the presence of an inactive or attenuated molecule. In other instances, up-regulation or promotion of gene expression with siNA molecules is above that level observed in the presence of, for example, an siNA molecule with scrambled sequence or with mismatches. In still other instances, up-regulation or promotion of gene expression with a nucleic acid molecule of the instant invention is greater in the presence of the nucleic acid molecule than in its absence. In some instances, up-regulation or promotion of gene expression is associated with inhibition of RNA mediated gene silencing, such as RNAi mediated cleavage or silencing of a coding or non-coding RNA target that down regulates, inhibits, or silences the expression of the gene of interest to be up-regulated. The down regulation of gene expression can, for example, be induced by a coding RNA or its encoded protein, such as through negative feedback or antagonistic effects. The down regulation of gene expression can, for example, be induced by a non-coding RNA having regulatory control over a gene of interest, for example by silencing expression of the gene via translational inhibition, chromatin structure, methylation, RISC mediated RNA cleavage, or translational inhibition. As such, inhibition or down regulation of targets that down regulate, suppress, or silence a gene of interest can be used to up-regulate expression of the gene of interest toward therapeutic use.

The term "vector" as used herein refers to its meaning as is generally accepted in the art. The term vector generally refers to any nucleic acid- and/or viral-based expression system or technique used to deliver one or more nucleic acid molecules.

siNA Molecules of the Invention

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (A):

$$5'-\quad B_1-N\ N\ N\ N\ N\ N\ N\ N\ N\ N\ N\ N\ N\ N\ N\ N\ N\ (_sN)_x-B_2$$

$$3'-\quad B_3-(N_s)_y\ N\ N\ N\ N\ N\ N\ N\ N\ N\ N\ N\ N\ N\ \overset{N_sN_sN_sN}{_3\ _2\ _1}$$

(A)

wherein, (a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;

(b) each N is independently a nucleotide wherein one or more Ns may be substituted with a non-nucleotide moiety so long as RNAi activity is maintained;

(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;

(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;

(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;

(f) N nucleotides of the guide strand are 2-deoxy-2-fluoro nucleotides and N nucleotides of the guide strand are 2-methyl nucleotides, with an optional variance of 1 or 2 N or N nucleotides being tolerated provided that as RNAi activity is maintained;

(g) S=a phosphorothioate or phosphorodithioate internucleotide linkage wherein $S_1$ is required and $S_2$ and $S_3$ are optional; and (h) N nucleotides of the passenger strand are independently selected from ribonucleotide, 2-O-alkyl nucleotide, 2-deoxy-2-fluoro nucleotide, 2-deoxy nucleotide, and LNA.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (B):

wherein, (a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;

(b) each N is independently a nucleotide wherein one or more Ns may be substituted with a non-nucleotide moiety so long as RNAi activity is maintained;

(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;

(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;

(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;

(f) N nucleotides of the guide strand are 2-deoxy-2-fluoro nucleotides and N nucleotides of the guide strand are 2-O-methyl nucleotides, with an optional variance of 1 or 2 N or N nucleotides being tolerated provided that as RNAi activity is maintained;

(g) S=a phosphorothioate or phosphorodithioate internucleotide linkage wherein $S_1$ is required and $S_2$ and $S_3$ are optional; and (h) N nucleotides of the passenger strand are independently selected from ribonucleotide, 2-O-alkyl nucleotide, 2-deoxy-2-fluoro nucleotide, 2-deoxy nucleotide, and LNA.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (C):

```
5'-    B1-N N N N N N N N N N N N N N N N N N N  (sN)x-B2

3'- B3-(Ns)y N N N N N N N N N N N N N N N  Ns Ns Ns N
                                              3   2  1
(B)
```

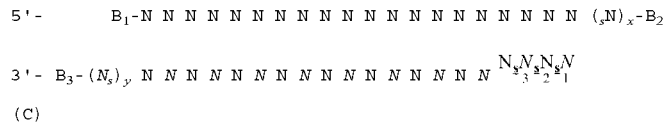

(C)

wherein, (a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;

(b) each N is independently a nucleotide wherein one or more Ns may be substituted with a non-nucleotide moiety so long as RNAi activity is maintained;

(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;

(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;

(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;

(f) N nucleotides of the guide strand are 2-deoxy-2-fluoro nucleotides and N nucleotides of the guide strand are 2-O-methyl nucleotides, with an optional variance of 1 or 2 N or N nucleotides being tolerated provided that as RNAi activity is maintained;

(g) S=a phosphorothioate or phosphorodithioate internucleotide linkage wherein $S_1$ is required and $S_2$ and $S_3$ are optional; and (h) N nucleotides of the passenger strand are independently selected from ribonucleotide, 2-O-alkyl nucleotide, 2-deoxy-2-fluoro nucleotide, 2-deoxy nucleotide, and LNA.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (D):

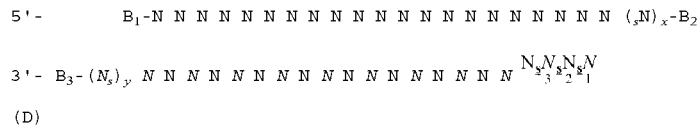

(D)

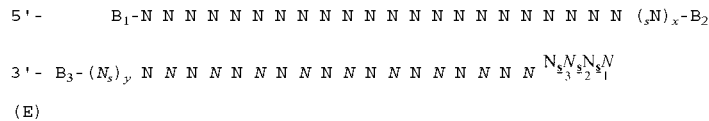

(E)

wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;
(b) each N is independently a nucleotide wherein one or more Ns may be substituted with a non-nucleotide moiety so long as RNAi activity is maintained;
(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;
(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;
(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;
(f) N nucleotides of the guide strand are 2-deoxy-2-fluoro nucleotides and N nucleotides of the guide strand are 2-O-methyl nucleotides, with an optional variance of 1 or 2 N or N nucleotides being tolerated provided that as RNAi activity is maintained;
(g) S=a phosphorothioate or phosphorodithioate internucleotide linkage wherein $S_1$ is required and $S_2$ and $S_3$ are optional; and
(h) N nucleotides of the passenger strand are independently selected from ribonucleotide, 2-O-alkyl nucleotide, 2-deoxy-2-fluoro nucleotide, 2-deoxy nucleotide, and LNA.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (F):

wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;
(b) each N is independently a nucleotide wherein one or more Ns may be substituted with a non-nucleotide moiety so long as RNAi activity is maintained;
(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;
(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;
(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;
(f) N nucleotides of the guide strand are 2-deoxy-2-fluoro nucleotides and N nucleotides of the guide strand are 2-O-methyl nucleotides, with an optional variance of 1 or 2 N or N nucleotides being tolerated provided that as RNAi activity is maintained;
(g) S=a phosphorothioate or phosphorodithioate internucleotide linkage wherein $S_1$ is required and $S_2$ and $S_3$ are optional; and
(h) N nucleotides of the passenger strand are independently selected from ribonucleotide, 2-O-alkyl nucleotide, 2-deoxy-2-fluoro nucleotide, 2-deoxy nucleotide, and LNA.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (G):

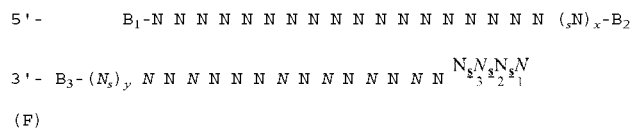

(F)

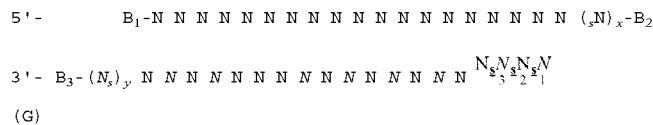

(G)

wherein, (a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;

(b) each N is independently a nucleotide wherein one or more Ns may be substituted with a non-nucleotide moiety so long as RNAi activity is maintained;

(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;

(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;

(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;

(f) N nucleotides of the guide strand are 2-deoxy-2-fluoro nucleotides and N nucleotides of the guide strand are 2-O-methyl nucleotides, with an optional variance of 1 or 2 N or N nucleotides being tolerated provided that as RNAi activity is maintained;

(g) S=a phosphorothioate or phosphorodithioate internucleotide linkage wherein $S_1$ is required and $S_2$ and $S_3$ are optional; and (h) N nucleotides of the passenger strand are independently selected from ribonucleotide, 2-O-alkyl nucleotide, 2-deoxy-2-fluoro nucleotide, 2-deoxy nucleotide, and LNA.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (H):

wherein, (a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;

(b) each N is independently a nucleotide wherein one or more Ns may be substituted with a non-nucleotide moiety so long as RNAi activity is maintained;

(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;

(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;

(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;

(f) N nucleotides of the guide strand are 2-deoxy-2=fluoro nucleotides and N nucleotides of the guide strand are 2-D-methyl nucleotides, with an optional variance of 1 or 2 N or N nucleotides being tolerated provided that as RNAi activity is maintained;

(g) S=a phosphorothioate or phosphorodithioate internucleotide linkage wherein $S_1$ is required and $S_2$ and $S_3$ are optional; and (h) N nucleotides of the passenger strand are independently selected from ribonucleotide, 2-O-alkyl nucleotide, 2-deoxy-2-fluoro nucleotide, 2-deoxy nucleotide, and LNA.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (I):

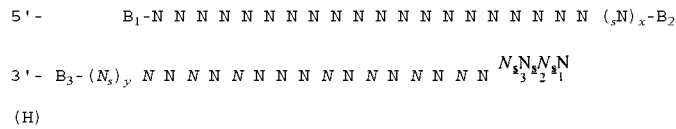

(H)

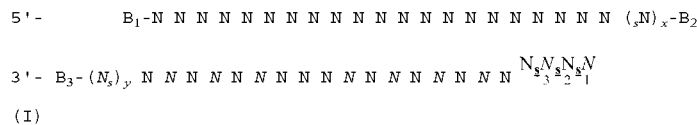

(I)

wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;
(b) each N is independently a nucleotide wherein one or more Ns may be substituted with a non-nucleotide moiety so long as RNAi activity is maintained;
(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;
(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;
(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;
(f) N nucleotides of the guide strand are 2-deoxy-2-fluoro nucleotides and N nucleotides of the guide strand are 2-O-methyl nucleotides, with an optional variance of 1 or 2 N or N nucleotides being tolerated provided that as RNAi activity is maintained;
(g) S=a phosphorothioate or phosphorodithioate internucleotide linkage wherein $S_1$ is required and $S_2$ and $S_3$ are optional; and
(h) N nucleotides of the passenger strand are independently selected from ribonucleotide, 2-O-alkyl nucleotide, 2-deoxy-2-fluoro nucleotide, 2-deoxy nucleotide, and LNA.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (J):

wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;
(b) each N is independently a nucleotide wherein one or more Ns may be substituted with a non-nucleotide moiety so long as RNAi activity is maintained;
(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;
(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;
(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;
(f) N nucleotides of the guide strand are 2-deoxy-2-fluoro nucleotides and N nucleotides of the guide strand are 2 D-methyl nucleotides, with an optional variance of 1 or 2 N or N nucleotides being tolerated provided that as RNAi activity is maintained;
(g) S=a phosphorothioate or phosphorodithioate internucleotide linkage wherein $S_1$ is required and $S_2$ and $S_3$ are optional; and
(h) N nucleotides of the passenger strand are independently selected from ribonucleotide, 2-O-alkyl nucleotide, 2-deoxy-2-fluoro nucleotide, 2-deoxy nucleotide, and LNA.

In some embodiments, each (N) of the passenger strand of a composition according to any of Formula A, B, C, D, E, F, G, H, I or J is independently selected from 2-alkyl, 2-deoxy-2-fluoro, 2-deoxy, and/or LNA modified nucleotide.

In some embodiments, each (N) of the passenger strand of a composition according to any of Formula A, B, C, D, E, F, G, H, I or J is a 2-alkyl modified nucleotide.

In some embodiments, each (N) of the passenger strand of a composition according to any of Formula A, B, C, D, E, F, G, H, I or J is a 2-O-methyl modified nucleotide.

(J)

In some embodiments, x and y of a composition according to any of Formula A, B, C, D, E, F, G, H, I or J are both equal to 2.

In some embodiments, all N nucleotides of the passenger strand of a composition according to any of Formula A, B, C, D, E, F, G, H, I or J are 2-deoxy-2-fluoro nucleotides.

In some embodiments, 5, 6, 7, 8, 9, or 10 or more pyrimidine N nucleotides of the passenger strand are 2-methyl nucleotides and 5, 6, 7, 8, 9, or 10 or more purine N nucleotides of the passenger strand of a composition according to any of Formula A, B, C, D, E, F, G, H, I or J are 2-deoxy-2-fluoro nucleotides.

In some embodiments, the 5-terminal N position of a composition according to any of Formula A, B, C, D, E, F, G, H, I or J comprises a terminal phosphate group.

In some embodiments, with respect to a composition according to any of Formula A, B, C, D, E, F, G, H, I or J, all N nucleotides of the guide strand are 2-deoxy-2=fluoro nucleotides and all N nucleotides of the guide strand are 2-O-methyl nucleotides, with no variance being permitted.

In some embodiments, B1 and B2 of a composition according to any of Formula A, B, C, D, E, F, G, H, I or J each comprise an inverted abasic 2-deoxyribose moiety and B3 is optionally absent.

In some embodiments, with respect to a composition according to any of Formula A, B, C, D, E, F, G, H, I or J, B1 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, B2 comprises an inverted abasic 2-deoxyribose moiety, and B3 is optionally absent.

In some embodiments, with respect to a composition according to any of Formula A, B, C, D, E, F, G, H, I or J, B1 comprises one or more galactosamine moieties optionally attached via a linker to an inverted abasic 2-deoxyribose moiety, B2 comprises an inverted abasic 2-deoxyribose moiety, and B3 is optionally absent.

In some embodiments, with respect to a composition according to any of Formula A, B, C, D, E, F, G, H, I or J, B1 comprises one or more N-acetylgalactosamine moieties optionally attached via a linker to an inverted abasic 2-deoxyribose moiety, B2 comprises an inverted abasic 2-deoxyribose moiety, and B3 is optionally absent.

In some embodiments, with respect to a composition according to any of Formula A, B, C, D, E, F, G, H, I or J, B1 comprises one or more folate moieties optionally attached via a linker to an inverted abasic 2-deoxyribose moiety, B2 comprises an inverted abasic 2-deoxyribose moiety, and B3 is optionally absent.

In some embodiments, with respect to a composition according to any of Formula A, B, C, D, E, F, G, H, I or J, B1 comprises one or more cholesterol moieties optionally attached via a linker to an inverted abasic 2-deoxyribose moiety, B2 comprises an inverted abasic 2 deoxyribose moiety, and B3 is optionally absent.

In some embodiments, with respect to a composition according to any of Formula A, B, C, D, E, F, G, H, I or J, B1 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, and B3 is optionally absent.

In some embodiments, with respect to a composition according to any of Formula A, B, C, D, E, F, G, H, I or J, B1 comprises one or more galactosamine moieties optionally attached via a linker to an inverted abasic 2-deoxyribose moiety, B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, and B3 is optionally absent.

In some embodiments, with respect to a composition according to any of Formula A, B, C, D, E, F, G, H, I or J, B1 comprises one or more N-acetylgalactosamine moieties optionally attached via a linker to an inverted abasic 2-deoxyribose moiety, B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, and B3 is optionally absent.

In some embodiments, with respect to a composition according to any of Formula A, B, C, D, E, F, G, H, I or J, B1 comprises one or more folate moieties optionally attached via a linker to an inverted abasic 2-deoxyribose moiety, B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, and B3 is optionally absent.

In some embodiments, with respect to a composition according to any of Formula A, B, C, D, E, F, G, H, I or J, B1 comprises one or more cholesterol moieties optionally attached via a linker to an inverted abasic 2-deoxyribose moiety, B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, and B3 is optionally absent.

In some embodiments, with respect to a composition according to any of Formula A, B, C, D, E, F, G, H, I or J, B1 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, B2 comprises any of SEQ ID NOS: 54-528 optionally attached via a linker to an inverted abasic 2-deoxyribose moiety, and B3 is optionally absent.

In some embodiments, with respect to a composition according to any of Formula A, B, C, D, E, F, G, H, I or J, B1 comprises one or more galactosamine moieties optionally attached via a linker to an inverted abasic 2-deoxyribose moiety, B2 comprises any of SEQ ID NOS: 54-528 optionally attached via a linker to an inverted abasic 2-deoxyribose moiety optionally attached via a linker to an inverted abasic 2-deoxyribose moiety, and B3 is optionally absent.

In some embodiments, with respect to a composition according to any of Formula A, B, C, D, E, F, G, H, I or J, B1 comprises one or more N-acetylgalactosamine moieties optionally attached via a linker to an inverted abasic 2-deoxyribose moiety, B2 comprises any of SEQ ID NOS: 54-528 optionally attached via a linker to an inverted abasic 2-deoxyribose moiety optionally attached via a linker to an inverted abasic 2-deoxyribose moiety, and B3 is optionally absent.

In some embodiments, with respect to a composition according to any of Formula A, B, C, D, E, F, G, H, I or J, B1 comprises one or more folate moieties optionally attached via a linker to an inverted abasic 2-deoxyribose moiety, B2 comprises any of SEQ ID NOS: 54-528 optionally attached via a linker to an inverted abasic 2-deoxyribose moiety optionally attached via a linker to an inverted abasic 2-deoxyribose moiety, and B3 is optionally absent.

In some embodiments, with respect to a composition according to any of Formula A, B, C, D, E, F, G, H, I or J, B1 comprises one or more cholesterol moieties optionally attached via a linker to an inverted abasic 2-deoxyribose moiety, B2 comprises any of SEQ ID NOS: 54-528 optionally attached via a linker to an inverted abasic 2-deoxyribose moiety optionally attached via a linker to an inverted abasic 2-deoxyribose moiety, and B3 is optionally absent.

In some embodiments, with respect to a composition according to any of Formula A, B, C, D, E, F, G, H, I or J, B1 comprises a folate, galactosamine, or cholesterol moiety as described in U.S. Pat. No. 7,491,805.

In some embodiments, with respect to a composition according to any of Formula A, B, C, D, E, F, G, H, I or J, $S_1$ and $S_2$ are required and $S_3$ is optional.

In some embodiments, with respect to a composition according to any of Formula A, B, C, D or E, $S_1$ and $S_3$ are required and $S_2$ is optional.

In some embodiments, with respect to a composition according to any of Formula A, B, C, D, E, F, G, H, I or J, $S_1$, $S_2$, and $S_3$ are required.

In some embodiments, with respect to a composition according to any of Formula A, B, C, D, E, F, G, H, I or J, B comprises:

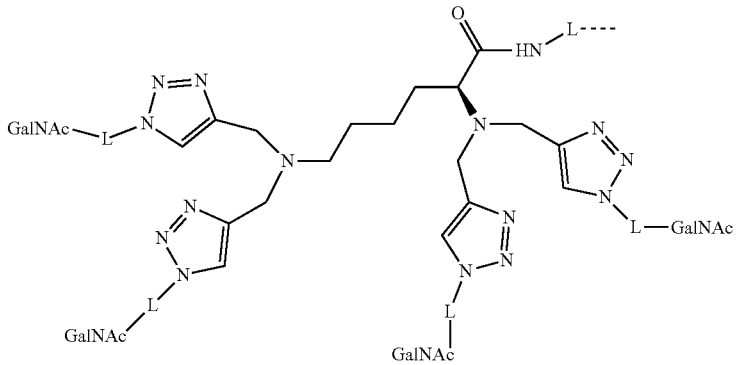

wherein each L is independently a linker and GalNAc is an N-acetyl galactosamine moiety.

In some embodiments, with respect to a composition according to any of Formula A, B, C, D, E, F, G, H, I or J, B1 comprises:

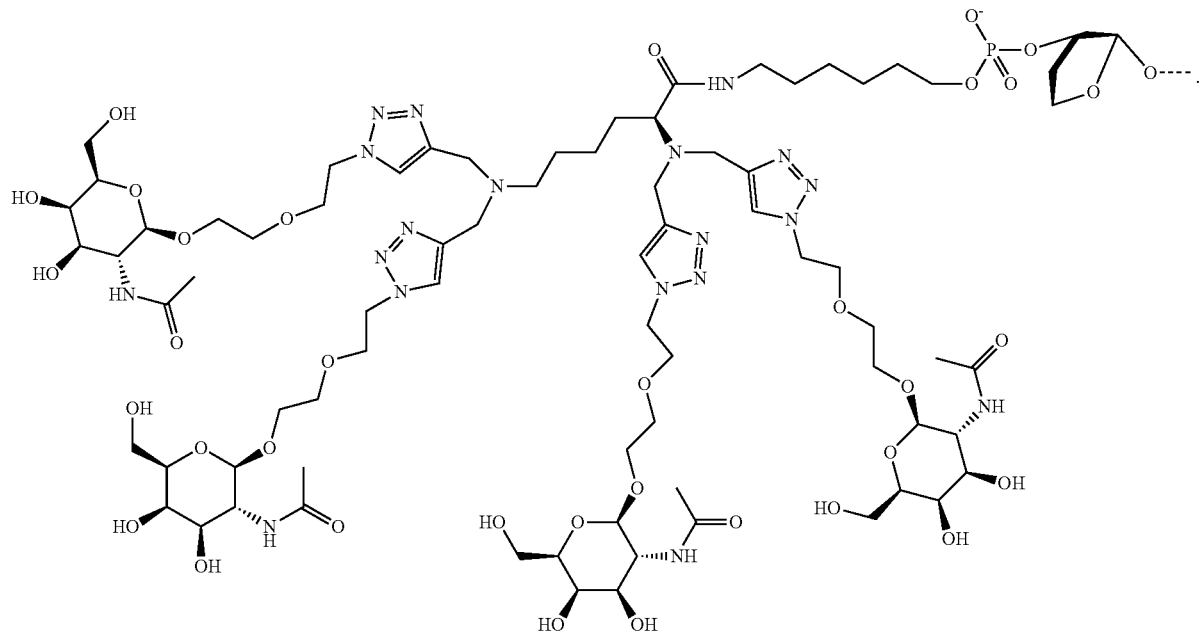

In some embodiments, with respect to a composition according to any of Formula A, B, C, D, E, F, G, H, I or J, B1 comprises:

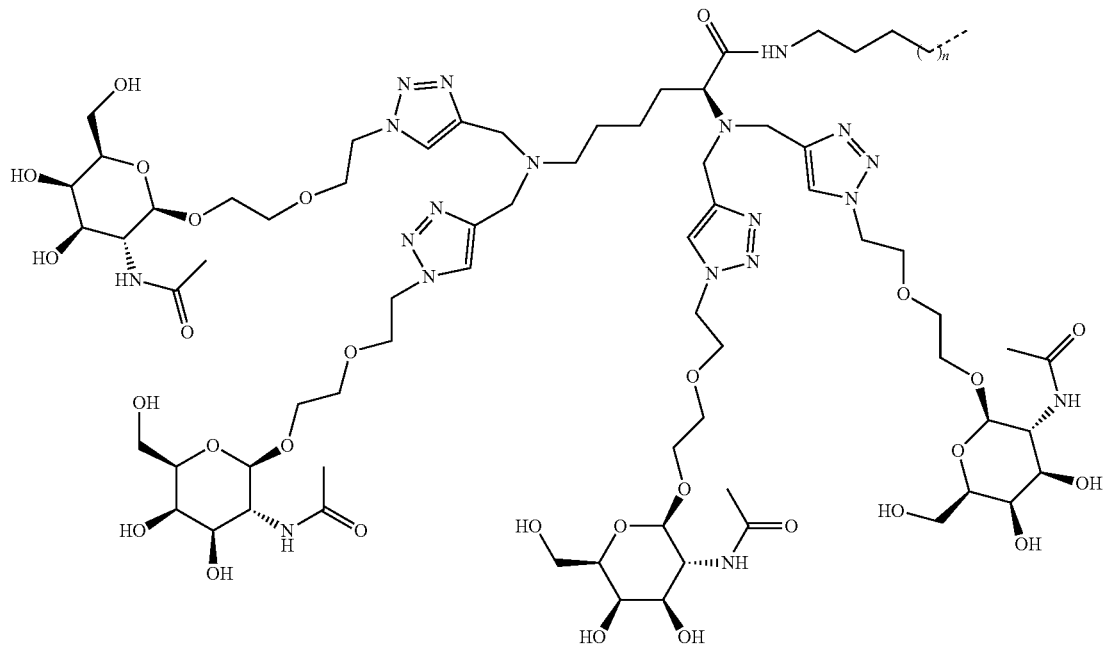

wherein n is an integer from 1 to 20.

In some embodiments, with respect to a composition according to any of Formula A, B, C, D, E, F, G, H, I or J, $B_1$ and/or $B_2$ comprises:

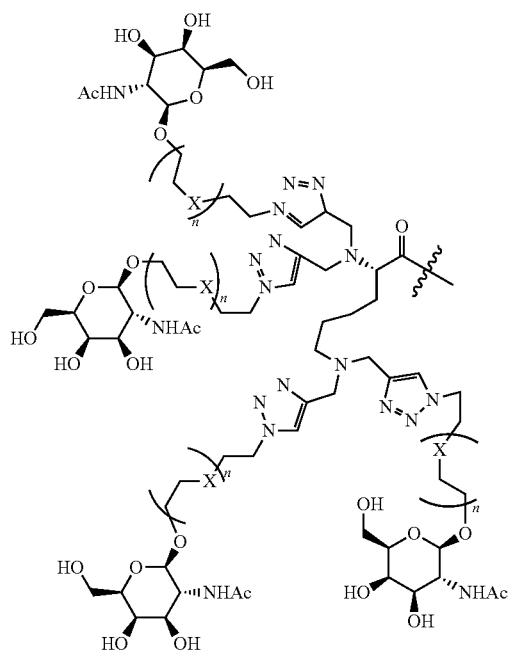

wherein X is —O—, —S—, —CH$_2$— or —NH—; n is 1, 2, 3, or 4; and the bond with "～～" indicates the point of attachment optionally including one or more linkers, which may be the same or different; and further optionally including one or more targeting ligands, solubilizing agents, pharmacokinetics enhancing agents, lipids, and/or masking agents. In certain embodiments, the linker is a linker shown in Table 8.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (K):

5'- B$_1$-N N N N N N N N N N N N N N N N N N N$_s$N-B$_2$

3'- N$_s$N N N N N N N N N N N N N N N N N$_s$N$_s$N$_s$N (K)

wherein, (a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;

(b) B$_1$ and B$_2$, are each independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker;

(c) every N nucleotide is a 2-deoxy-2-fluoro nucleotide and every N nucleotide is a 2-O-methyl nucleotide;

(d) each S is a phosphorothioate or phosphorodithioate internucleotide linkage.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (L):

5'- B₁-N *N* *N* N *N* N *N* N *N* N *N* N *N* N *N* N *N* N N$_s$N-B₂

3'- N$_s$N *N* N *N* N *N* N *N* N *N* N *N* N *N* N *N* N N$_s$N$_s$N (L)

wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;
(b) B₁ and B₂, are each independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker;
(c) every N nucleotide is a 2-deoxy-2=fluoro nucleotide and every N nucleotide is a 2-O-methyl nucleotide;
(d) each S is a phosphorothioate or phosphorodithioate internucleotide linkage.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (M):

5'- B₁-N *N* *N* N *N* N *N* N *N* N *N* N *N* N *N* N *N* N N$_s$N-B₂

3'- N$_s$N *N* N *N* N *N* N *N* N *N* N *N* N *N* N *N* N N$_s$N (M)

wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;
(b) B₁ and B₂, are each independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker;
(c) every N nucleotide is a 2-deoxy-2-fluoro nucleotide and every N nucleotide is a 2-O-methyl nucleotide;
(d) each S is a phosphorothioate or phosphorodithioate internucleotide linkage.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (N):

5'- B₁-*N* N *N* N *N* N *N* N *N* N *N* N *N* N *N* N *N* N N$_s$N-B₂

3'- N$_s$N *N* N *N* N *N* N *N* N *N* N *N* N *N* N *N* N N$_s$N$_s$N$_s$N (N)

wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;
(b) B₁ and B₂, are each independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker;
(c) every N nucleotide is a 2-deoxy-2-fluoro nucleotide and every N nucleotide is a 2-O-methyl nucleotide;
(d) each S is a phosphorothioate or phosphorodithioate internucleotide linkage.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (O):

5'- B₁-*N* N *N* N *N* N *N* N *N* N *N* N *N* N *N* N *N* N N$_s$N-B₂

3'- N$_s$N *N* N *N* N *N* N *N* N *N* N *N* N *N* N *N* N N$_s$N$_s$N (O)

wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;
(b) B₁ and B₂, are each independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker;
(c) every N nucleotide is a 2-deoxy-2-fluoro nucleotide and every N nucleotide is a 2-O-methyl nucleotide;
(d) each S is a phosphorothioate or phosphorodithioate internucleotide linkage.

In one embodiment, the invention features a composition comprising a double-stranded short interfering nucleic acid (siNA) molecule that modulates the expression and/or activity of a target RNA sequence via RNA interference, wherein the molecule has a passenger strand and a guide strand and comprises structure represented by formula (P):

5'- B₁-*N* N *N* N *N* N *N* N *N* N *N* N *N* N *N* N *N* N N$_s$N-B₂

3'- N$_s$N *N* N *N* N *N* N *N* N *N* N *N* N *N* N *N* N N$_s$N (P)

wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;

(b) $B_1$ and $B_2$, are each independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker;

(c) every N nucleotide is a 2-deoxy-2-fluoro nucleotide and every N nucleotide is a 2-O-methyl nucleotide;

(d) each S is a phosphorothioate or phosphorodithioate internucleotide linkage.

In some embodiments, the 5-terminal N position of a composition according to any of Formula K, L, M, N, O, or P comprises a terminal phosphate group.

In some embodiments, B1 and B2 of a composition according to any of Formula K, L, M, N, O, or P each comprise an inverted abasic 2-deoxyribose moiety.

In some embodiments, with respect to a composition according to any of Formula K, L, M, N, O, or P, B1 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, and B2 comprises an inverted abasic 2-deoxyribose moiety.

In some embodiments, with respect to a composition according to any of Formula K, L, M, N, O, or P, B1 comprises one or more galactosamine moieties optionally attached via a linker to an inverted abasic 2-deoxyribose moiety, and B2 comprises an inverted abasic 2-deoxyribose moiety.

In some embodiments, with respect to a composition according to any of Formula K, L, M, N, O, or P, B1 comprises one or more N-acetylgalactosamine moieties optionally attached via a linker to an inverted abasic 2-deoxyribose moiety, and B2 comprises an inverted abasic 2-deoxyribose moiety.

In some embodiments, with respect to a composition according to any of Formula K, L, M, N, O, or P, B1 comprises one or more folate moieties optionally attached via a linker to an inverted abasic 2-deoxyribose moiety, and B2 comprises an inverted abasic 2-deoxyribose moiety.

In some embodiments, with respect to a composition according to any of Formula K, L, M, N, O, or P, B1 comprises one or more cholesterol moieties optionally attached via a linker to an inverted abasic 2-deoxyribose moiety, and B2 comprises an inverted abasic 2-deoxyribose moiety.

In some embodiments, with respect to a composition according to any of Formula K, L, M, N, O, or P, B1 comprises a ligand, polymer, protein or peptide transduction domain, nuclear localization sequence, cell penetrating peptide, receptor, steroid, vitamin, antibody, protamine, and/or hormone, optionally attached via an inverted abasic 2-deoxyribose moiety, and B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety.

In some embodiments, with respect to a composition according to any of Formula K, L, M, N, O, or P, B1 comprises one or more galactosamine moieties optionally attached via a linker to an inverted abasic 2-deoxyribose moiety, and B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety.

In some embodiments, with respect to a composition according to any of Formula K, L, M, N, O, or P, B1 comprises one or more N-acetylgalactosamine moieties optionally attached via a linker to an inverted abasic 2-deoxyribose moiety, and B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety.

In some embodiments, with respect to a composition according to any of Formula K, L, M, N, O, or P, B1 comprises one or more folate moieties optionally attached via a linker to an inverted abasic 2-deoxyribose moiety, and B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety.

In some embodiments, with respect to a composition according to any of Formula K, L, M, N, O, or P, B1 comprises one or more cholesterol moieties optionally attached via a linker to an inverted abasic 2-deoxyribose moiety, and B2 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety.

In some embodiments, with respect to a composition according to any of Formula K, L, M, N, O, or P, B1 comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2-deoxyribose moiety, and B2 comprises any of SEQ ID NOS: 54-528 optionally attached via a linker to an inverted abasic 2-deoxyribose moiety.

In some embodiments, with respect to a composition according to any of Formula K, L, M, N, O, or P, B1 comprises one or more galactosamine moieties optionally attached via a linker to an inverted abasic 2-deoxyribose moiety, and B2 comprises any of SEQ ID NOS: 54-528 optionally attached via a linker to an inverted abasic 2-deoxyribose moiety optionally attached via a linker to an inverted abasic 2-deoxyribose moiety.

In some embodiments, with respect to a composition according to any of Formula K, L, M, N, O, or P, B1 comprises one or more N-acetylgalactosamine moieties optionally attached via a linker to an inverted abasic 2-deoxyribose moiety, and B2 comprises any of SEQ ID NOS: 54-528 optionally attached via a linker to an inverted abasic 2-deoxyribose moiety optionally attached via a linker to an inverted abasic 2-deoxyribose moiety.

In some embodiments, with respect to a composition according to any of Formula K, L, M, N, O, or P, B1 comprises one or more folate moieties optionally attached via a linker to an inverted abasic 2-deoxyribose moiety, and B2 comprises any of SEQ ID NOS: 54-528 optionally attached via a linker to an inverted abasic 2-deoxyribose moiety optionally attached via a linker to an inverted abasic 2-deoxyribose moiety.

In some embodiments, with respect to a composition according to any of Formula F, G, or H, B1 comprises one or more cholesterol moieties optionally attached via a linker to an inverted abasic 2-deoxyribose moiety, and B2 comprises any of SEQ ID NOS: 54-528 optionally attached via a linker to an inverted abasic 2-deoxyribose moiety optionally attached via a linker to an inverted abasic 2-deoxyribose moiety.

In some embodiments, with respect to a composition according to any of Formula K, L, M, N, O, or P, B1 comprises a folate, galactosamine, or cholesterol moiety as described in U.S. Pat. No. 7,491,805.

In some embodiments, with respect to a composition according to any of Formula K, L, M, N, O, or P, B1 comprises:

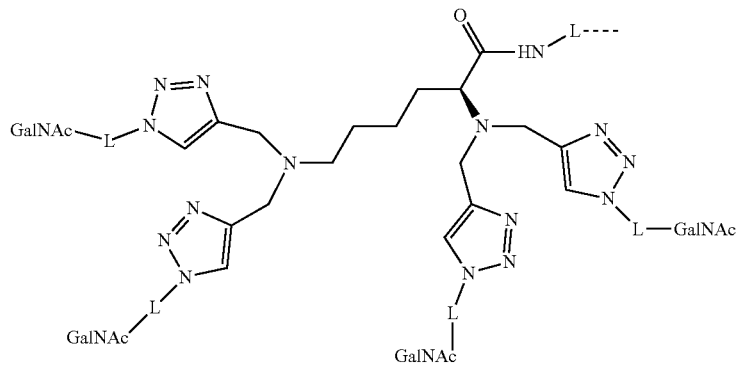

wherein each L is independently a linker and GalNAc is an N-acetyl galactosamine moiety.

In some embodiments, with respect to a composition according to any of Formula K, L, M, N, O, or P, B1 comprises:

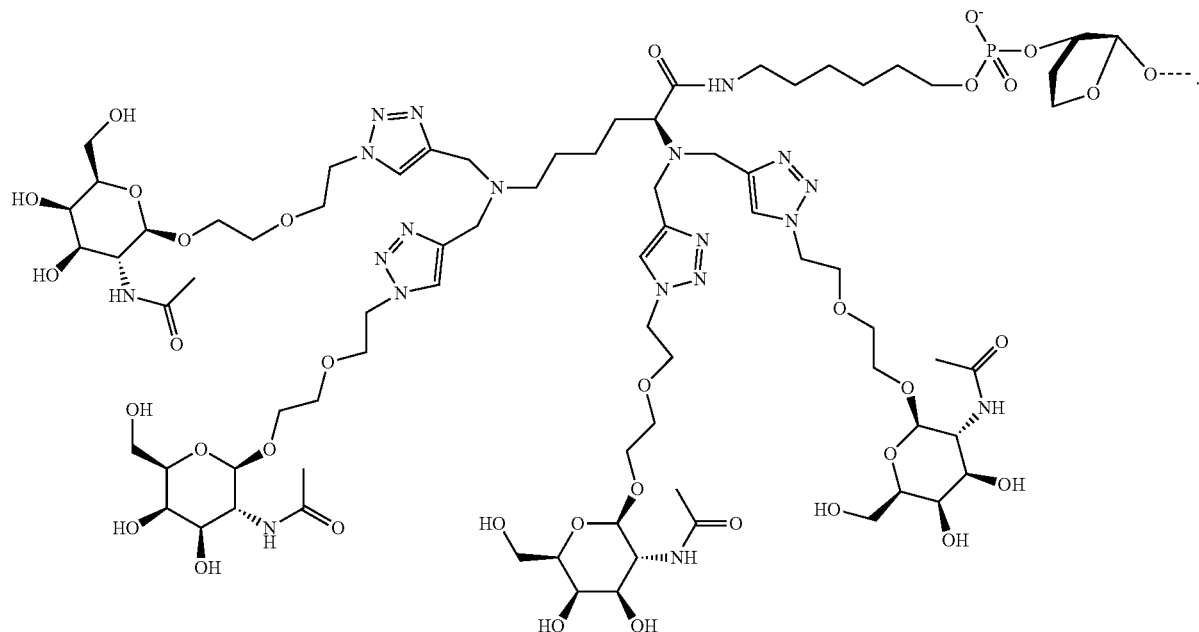

In some embodiments, with respect to a composition according to any of Formula K, L, M, N, O, or P, B1 comprises:

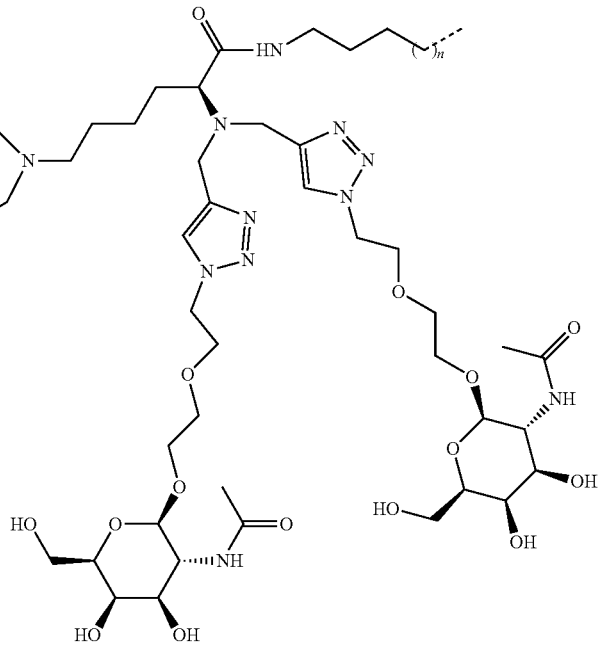

wherein n is an integer from 1 to 20.

In some embodiments, with respect to a composition according to any of Formula K, L, M, N, O, or P, B and/or B2 comprises:

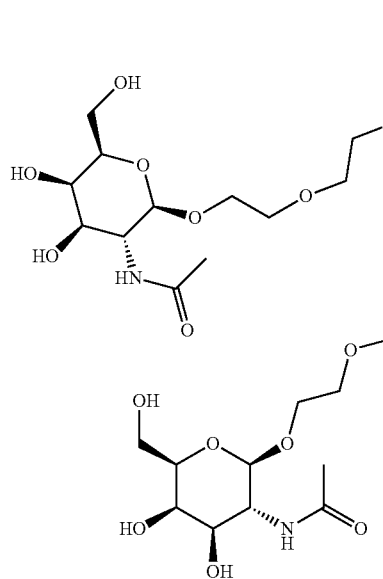

wherein X is —O—, —S—, —CH$_2$— or —NH—; n is 1, 2, 3, or 4; and the bond with "∿∿" indicates the point of attachment optionally including one or more linkers, which may be the same or different; and further optionally including one or more targeting ligands, solubilizing agents, pharmacokinetics enhancing agents, lipids, and/or masking agents. In certain embodiments, the linker is a linker shown in Table 8.

With respect to any siNA having Formula A, B, C, D, E, F, G, H, I, J, K, L, M, N, O, or P described herein, in certain embodiments, the siNA molecule is covalently attached to a polymer or ligand via a linker. In certain embodiments, the siNA molecule is covalently attached to the polymer or ligand via a linker moiety at the 5-nd of the passenger (sense) strand of the siNA molecule. In other embodiments, the siNA molecule is covalently attached to the polymer or ligand via a linker moiety at the 3-end of the passenger (sense) strand of the siNA molecule. In other embodiments, the siNA molecule is covalently attached to the polymer or ligand via a linker moiety at the 3-end of the guide (antisense) strand of the siNA molecule. In any of the above embodiments, the linker can be attached to the terminal 3- and/or 5-nucleotide position of the passenger or guide strand, or can alternately be attached to a terminal cap moiety such as an abasic moiety or other cap as described herein or otherwise known in the art. Therefore, in totality, a siNA molecule of the invention having Formula (A) can comprise a terminal cap (B) that includes a covalent attachment to a polymer or ligand via a linker molecule as described herein or as is otherwise known in the art. Non-limiting examples of such linkers are provided in the examples herein.

In certain embodiments, one or more terminal cap moieties of a siNA molecule of the invention (i.e. any B of any compound having Formula A, B, C, D, E, F, G, H, I, J, K, L, M, N, O, or P herein) can comprise a delivery modality. The delivery modality can comprise a ligand or polymer that further includes one or more linker molecules. Non-limiting examples of such linker molecules include phosphate ester based linkages, amino based linkers, disulfide based linkers, succinyl based linkers, alkyl or substituted alkyl based linkers, and/or amide based linkers as are generally known in the art.

In some embodiments, the siNA molecules of the invention are phosphorylated at the 5-end of the guide or antisense strand. The phosphate group can be a phosphate, a diphosphate or a triphosphate.

The present invention further provides compositions comprising the double-stranded nucleic acid molecules described herein with optionally a pharmaceutically acceptable carrier or diluent.

In some embodiments, a composition of the invention further comprises a cryo-protectant. In some embodiments, the cryo-protectant is Sucrose, Trehalose, Raffinose, Stachyose, Verbascose, Mannitol, Glucose, Lactose, Maltose, Maltotriose-heptaose, Dextran, Hydroxyethyl Starch, Insulin, Sorbitol, Glycerol, Arginine, Histidine, Lysine, Proline, Dimethylsulfoxide or any combination thereof. In some embodiments, the cryo-protectant is Sucrose. In some embodiments, the cryo-protectant is Trehalose. In some embodiments, the cryo-protectant is a combination of Sucrose and Trehalose.

The present invention further provides a compound comprising a double-stranded short interfering nucleic acid (siNA) molecule of the invention covalently attached to a ligand. Non limiting examples of ligands include steroidal compounds (e.g., cholesterol), galactosamines (e.g., N-acetylgalactosamine), vitamins (e.g., folate), proteins (e.g., monoclonal antibodies), and peptides (e.g., TAT) as are generally known in the art and further provided herein.

The administration of the compositions of the invention can be carried out by known methods, wherein the nucleic acid is introduced into a desired target cell in vitro or in vivo.

Commonly used techniques for introduction of the nucleic acid molecules of the invention into cells, tissues, and organisms include the use of various carrier systems, reagents and vectors. Non-limiting examples of such carrier systems suitable for use in the present invention include single chemical entity conjugates, nucleic-acid-lipid particles, lipid nanoparticles (LNP), liposomes, lipoplexes, micelles, virosomes, virus like particles (VLP), nucleic acid polymers, and mixtures thereof.

The compositions of the invention can be in the form of an aerosol, dispersion, solution (e.g., an injectable solution), a cream, ointment, tablet, powder, suspension or the like. These compositions may be administered in any suitable way, e.g. orally, sublingually, buccally, parenterally, nasally, or topically. In some embodiments, the compositions are aerosolized and delivered via inhalation.

The molecules and compositions of the present invention have utility over a broad range of therapeutic applications. Accordingly another aspect of this invention relates to the use of the compounds and compositions of the invention in treating a subject. The invention thus provides a method for treating a subject, such as a human, suffering from a condition which is associated with the expression of one or more genes, wherein the method comprises administering to the subject an effective amount of a double-stranded short interfering nucleic acid (siNA) molecule of the invention. Thus, the siNA molecules of the invention treat the disease or condition. In some embodiments, the condition is one as described herein or is otherwise generally known to one of skill in the art.

The present invention provides compositions and methods comprising siNAs having target specificity that may be used to treat diseases and conditions herein or otherwise known in the art that are associated with gene expression. In particular aspects and embodiments of the invention, the nucleic acid molecules of the invention comprise at least a 15 nucleotide sequence of the a target sequence, and/or comprises a nucleotide sequence of at least 15 nucleotides complimentary to the target sequence. The siNAs may be provided in several forms. For example, the siNA may be isolated as one or more siNA compounds, or it may be in the form of a transcriptional cassette in a DNA plasmid. The siNA may also be chemically synthesized and may include modifications as described herein or as is otherwise generally known in the art. The siNAs may be administered alone or co-administered with other siNA molecules or with conventional agents that treat a gene related disease or condition as described herein or otherwise known in the art.

The siNA molecules of the invention may be used to mediate gene silencing via interaction with RNA transcripts or alternately by interaction with particular gene sequences, wherein such interaction results in modulation of gene silencing either at the transcriptional level or post-transcriptional level such as, for example, but not limited to, RNAi or through cellular processes that modulate the chromatin structure or methylation patterns of the target and prevent transcription of the target gene, with the nucleotide sequence of the target thereby mediating silencing. More specifically, the target is any GenBank reference sequence as is presently known in the art.

In one aspect, the invention provides short interfering nucleic acid (siNA) molecules that may inhibit the expression of the target gene in a cell or mammal. The siNA may be single-stranded or double-stranded. When double-stranded, the siNA comprising a sense and an antisense stand. The antisense strand may be complementary to at least a part of an mRNA formed in the expression of the target gene. The sense strand comprises a region that may be complementary to the antisense strand.

The double stranded RNA molecules of the invention may comprise two distinct and separate strands that can be symmetric or asymmetric and are complementary, i.e., two single-stranded RNA molecules, or may comprise one single-stranded molecule in which two complementary portions, e.g., a sense region and an antisense region, are base-paired, and are covalently linked by one or more single-stranded "hairpin" areas (i.e. loops) resulting in, for example, a single-stranded short-hairpin polynucleotide or a circular single-stranded polynucleotide.

The linker may be polynucleotide linker or a non-nucleotide linker. In some embodiments, the linker is a non-nucleotide linker. In some embodiments, a hairpin or circular siNA molecule of the invention contains one or more loop motifs, wherein at least one of the loop portions of the siNA molecule is biodegradable. For example, a single-stranded hairpin siNA molecule of the invention is designed such that degradation of the loop portion of the siNA molecule in vivo can generate a double-stranded siNA molecule with 3-terminal overhangs, such as 3-terminal nucleotide overhangs comprising 1, 2, 3 or 4 nucleotides. Or alternatively, a circular siNA molecule of the invention is designed such that degradation of the loop portions of the siNA molecule in vivo can generate a double-stranded siNA molecule with 3 terminal overhangs, such as 3-terminal nucleotide overhangs comprising about 2 nucleotides.

In some embodiments, siNA molecules of the invention may have perfect complementarity between the sense strand or sense region and the antisense strand or antisense region of the siNA molecule. In other or the same embodiments, the antisense strand of the siNA molecules of the invention are perfectly complementary to a corresponding target nucleic acid molecule.

In yet other embodiments, siNA molecules of the invention have partial complementarity (i.e., less than 100% complementarity) between the sense strand or sense region and the antisense strand or antisense region of the siNA molecule or between the antisense strand or antisense region of the siNA molecule and a corresponding target nucleic acid molecule. Thus, in some embodiments, the double-stranded nucleic acid molecules of the invention, have between about 15 to about 30 (e.g., about 15, 16, 17, 18, 19, 20, 21, 22, 23, 24, 25, 26, 27, 28, 29, or 30) nucleotides in one strand that are complementary to the nucleotides of the other strand.

In other embodiments, the molecules have between about 15 to about 30 (e.g., about 15, 16, 17, 18, 19, 20, 21, 22, 23, 24, 25, 26, 27, 28, 29, or 30) nucleotides in the sense region that are complementary to the nucleotides of the antisense region. of the double-stranded nucleic acid molecule. In certain embodiments, the double-stranded nucleic acid molecules of the invention have between about 15 to about 30 (e.g., about 15, 16, 17, 18, 19, 20, 21, 22, 23, 24, 25, 26, 27, 28, 29, or 30) nucleotides in the antisense strand that are complementary to a nucleotide sequence of its corresponding target nucleic acid molecule.

In other embodiments, the siNA molecule may contain one or more nucleotide deletions, substitutions, mismatches and/or additions; provided, however, that the siNA molecule maintains its activity, for example, to mediate RNAi. In a non-limiting example, the deletion, substitution, mismatch and/or addition may result in a loop or bulge, or alternately a wobble or other alternative (non Watson-Crick) base pair. Thus, in some embodiments, for example, the double-stranded nucleic acid molecules of the invention, have 1 or more (e.g., 1, 2, 3, 4, 5, or 6) nucleotides, in one strand or region that are mismatches or non-base-paired with the other strand or region. In other embodiments, the double-stranded nucleic acid molecules of the invention, have 1 or more (e.g., 1, 2, 3, 4, 5, or 6) nucleotides in each strand or region that are mismatches or non-base-paired with the other strand or region. In a preferred embodiment, the siNA of the invention contains no more than 3 mismatches. If the antisense strand of the siNA contains mismatches to a target sequence, it is preferable that the area of mismatch not be located in the center of the region of complementarity.

In other embodiments, the siNA molecule may contain one or more nucleotide deletions, substitutions, mismatches and/or additions to a sequence provided herein, however, that the siNA molecule maintains its activity, for example, to mediate RNAi. In a non-limiting example, the deletion, substitution, mismatch and/or addition may result in a loop or bulge, or alternately a wobble or other alternative (non Watson-Crick) base pair.

The invention also comprises double-stranded nucleic acid (siNA) molecules as otherwise described hereinabove in which the first strand and second strand are complementary to each other and wherein at least one strand is hybridisable to the polynucleotide sequence of a target sequence under conditions of high stringency, and wherein any of the nucleotides is unmodified or chemically modified.

Hybridization techniques are well known to the skilled artisan (see for instance, Sambrook et al., Molecular Cloning: A Laboratory Manual, 2nd Ed., Cold Spring Harbor Laboratory Press, Cold Spring Harbor, N.Y. (1989)). Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5×Denhardt K solution, 10% dextran sulfate, and 20 microgram/ml denatured, sheared salmon sperm DNA; followed by washing the filters in 0.1×SSC at about 65° C.

In some embodiments, the first strand has about 18, 19, 20, 21 or 22 nucleotides that are complementary to the nucleotides of the other strand and at least one strand is hybridisable to target sequence such as a gene in the GenBank database. In a more preferred embodiment, the first strand has about 19, 20 or 21 nucleotides that are complementary to the nucleotides of the other strand and at least one strand is hybridisable at least one strand is hybridisable to the complement of a target sequence under conditions of high stringency.

In certain embodiments, the siNA molecules of the invention comprise overhangs of about 1 to about 4 (e.g., about 1, 2, 3 or 4) nucleotides. The nucleotides in the overhangs may be the same or different nucleotides. In some embodiments, the overhangs occur at the 3'-end at one or both strands of the double-stranded nucleic acid molecule. For example, a double-stranded nucleic acid molecule of the invention may comprise a nucleotide or non-nucleotide overhang at the 3'-end of the antisense strand/region, the 3'-end of the sense strand/region, or both the antisense strand/region and the sense strand/region of the double-stranded nucleic acid molecule.

In some embodiments, the nucleotides comprising the overhang portion of an siNA molecule of the invention comprise sequences based on the target polynucleotide sequence in which nucleotides comprising the overhang portion of the antisense strand/region of an siNA molecule of the invention can be complementary to nucleotides in the target polynucleotide sequence and/or nucleotides comprising the overhang portion of the sense strand/region of an siNA molecule of the invention can comprise the nucleotides in the target polynucleotide sequence. Thus, in some embodiments, the overhang comprises a two nucleotide overhang that is complementary to a portion of the target polynucleotide sequence. In other embodiments, however, the overhang comprises a two nucleotide overhang that is not complementary to a portion of the target polynucleotide sequence. In certain embodiments, the overhang comprises a 3'-UU overhang that is not complementary to a portion of the target polynucleotide sequence. In other embodiments, the overhang comprises a UU overhang at the 3 end of the antisense strand and a TT overhang at the 3-end of the sense strand. In other embodiments, the overhang comprises nucleotides as described in the examples, Tables, and Figures herein.

In any of the embodiments of the siNA molecules described herein having 3-terminal nucleotide overhangs, the overhangs are optionally chemically modified at one or more nucleic acid sugar, base, or backbone positions. Representative, but not limiting examples of modified nucleotides in the overhang portion of a double-stranded nucleic acid (siNA) molecule of the invention include: 2'-O-alkyl (e.g., 2-methyl), 2'-deoxy, 2'-deoxy-2'-fluoro. 2'-deoxy-2'-fluoroarabino (FANA), 4'-thio, 2'-O-trifluoromethyl, 2'-O-ethyl-trifluoromethoxy. 2'-O-difluoromethoxy-ethoxy, universal base, acyclic, or 5-C-methyl nucleotides. In more preferred embodiments, the overhang nucleotides are each independently, a 2-O-alkyl nucleotide, a 2-methyl nucleotide, a 2-dexoy-2-fluoro nucleotide, or a 2-deoxy ribonucleotide. In some instances the overhang nucleotides are linked by a one or more phosphorothioate linkages.

In yet other embodiments, siNA molecules of the invention comprise duplex nucleic acid molecules with blunt ends (i.e., without nucleotide overhangs), where both ends are blunt, or alternatively, where one of the ends is blunt. In some embodiments, the siNA molecules of the invention can comprises one blunt end, for example wherein the 5'-end of the antisense strand and the 3'-end of the sense strand do not have any overhanging nucleotides. In another example, the siNA molecule comprises one blunt end, for example wherein the 3'-end of the antisense strand and the 5'-end of the sense strand do not have any overhanging nucleotides. In other embodiments, siNA molecules of the invention comprise two blunt ends, for example wherein the 3'-end of the antisense strand and the 5'-end of the sense strand as well as the 5'-end of the antisense strand and 3'-end of the sense strand do not have any overhanging nucleotides.

In any of the embodiments or aspects of the siNA molecules of the invention, the sense strand and/or the antisense strand may further have a cap, such as described herein or as known in the art, at the 3-end, the 5-end, or both of the 3 land 5-ends of the sense strand and/or antisense strand. Or as in the case of a hairpin siNA molecule, the cap may be at either one or both of the terminal nucleotides of the polynucleotide. In some embodiments, the cap is at one of both of the ends of the sense strand of a double-stranded siNA molecule. In other embodiments, the cap is at the 3'-end of antisense (guide) strand. In preferred embodiments, the caps are at the 3-end of the sense strand and the 5-end of the sense strand.

Representative, but non-limiting examples of such terminal caps include an inverted abasic nucleotide, an inverted deoxy abasic nucleotide, an inverted nucleotide moiety, a group shown in the examples and Figures herein, a glyceryl modification, an alkyl or cycloalkyl group, a heterocycle, or any other cap as is generally known in the art.

Any of the embodiments of the siNA molecules of the invention may have a 5 phosphate termini. In some embodiments, the siNA molecules lack terminal phosphates.

Applicants describe herein chemically modified siNA molecules that may have improved RNAi activity and/or stability compared to corresponding unmodified siNA molecules. Various chemically modified siNA motifs disclosed herein may provide the capacity to maintain RNAi activity that is substantially similar to unmodified or minimally modified active siRNA (see for example Elbashir et al., 2001, EMBO J., 20:6877-6888) while at the same time providing nuclease resistance and pharmacokinetic properties suitable for use in therapeutic applications.

Any of the above described modifications, or combinations thereof, including those in the references cited, can be applied to any of these embodiments.

In certain embodiments, siNA molecules having Formula A, B, C, D, E, F, G, H, I, J, K, L, M, N, O, or P have at position 14 from the 5'-end of the antisense strand a ribonucleotide when the nucleotide at that position 14 is a purine.

In certain embodiments, siNA molecules having Formula A, B, C, D, E, F, G, H, I, J, K, L, M, N, O, or P have at position 14 from the 5'-end of the antisense strand a ribonucleotide or a 2'-deoxy-2'-fluoro nucleotide when the nucleotide at that position 14 is a purine.

In certain embodiments, siNA molecules having Formula A, B, C, D, E, F, G, H, I, J, K, L, M, N, O, or P have at position 14 from the 5'-end of the antisense strand is a 2'-deoxy-2'-fluoro nucleotide when the nucleotide at that position 14 is a pyrimidine nucleotide. In particularly preferred embodiments, position 14 from the 5'-end of the antisense strand is a 2'-deoxy-2'-fluoro nucleotide regardless of whether it is a purine or a pyrimidine.

In some embodiments, siNA molecules having Formula A, B, C, D, E, F, G, H, I, J, K, L, M, N, O, or P comprises (N) nucleotides in the antisense strand (lower strand) that are complementary to nucleotides in a target polynucleotide sequence, which also has complementarity to the N and [N] nucleotides of the antisense (lower) strand.

Any of the above described modifications, or combinations thereof, discussed above as applicable to siNAs of the invention, including those in the references cited, may be applied to any of the embodiments to siNA molecules having Formula A, B, C, D, E, F, G, H, I, J, K, L, M, N, O, or P.

In some embodiments, the compounds disclosed herein (e.g., having Formula A, B, C, D, E, F, G, H, I, J, K, L, M, N, O, or P) include a transduction moiety. Transduction moieties can include, but are not limited to, cell-penetrating peptide (CPP), peptide transduction domain (PTD), nucleic acid binding proteins, such as RNA binding proteins, or any combination thereof. In certain embodiments, any B1, B2, and/or B3 of a compound having any of Formula A, B, C, D, E, F, G, H, I, J, K, L, M, N, O, or P comprises a transduction moiety.

Nucleic acid binding proteins, including double-stranded RNA binding domains, can been used to enhance delivery of oligonucleotides into cells. (See, e.g., Eguchi et al. Nat. Biotech. 27:567-571 (2009)). Exemplary nucleic acid binding domains useful in the embodiments disclosed herein include, but are not limited to, those listed in U.S. Patent Application Publication No. US 2009/0093026.

Cell-penetrating peptides (CPPs) or peptide transfer domains (PTDs) can be been used successfully to induce intracellular uptake of DNA, antisense oligonucleotides (Astriab-Fisher et al., Pharm. Res. 19:744-54, 2002), small molecules (Polyakov et al. Biocong. Chem. 11:762-71, 2000), and iron particles (Dodd et al. J. Immunol. Methods 256:89-105, 2001; Wunderbaldinger et al., Bioconjug. Chem. 13:264-8, 2002; Lewin et al., Nat. Biotechnol. 18:410-4, 2000; Josephson et al., Bioconjug. Chem. 10:186-91, 1999), suggesting that the size of the cargo is not a limiting factor.

The peptides may be conjugated at either end or both ends by addition of a cysteine or other thiol containing moiety to the C- or N-terminus. When not functionalized on the N-terminus, peptides may be capped by an acetyl group, or may be capped with a lipid, a PEG, or a targeting moiety. When the C-terminus of the peptides is unconjugated or unfunctionalized, it may be capped as an amide, or may be capped with a lipid, a PEG, or a targeting moiety. Suitable peptides that can be used in the conjugates disclosed herein are listed in Table 2.

In some embodiments, a PTD of the invention can be defined as one or more cationic peptides that are able to interact with the cell membrane in a manner that enhances macromolecular uptake. In some embodiments, these peptides can be configured in a linear sequence or attached via a branched linker as is generally known in the art. Alternatively the branching mechanism can be built into the peptide by having multiple cysteines or lysines that are specifically used to form linkages. The methods for synthesizing branched amino acid constructs are well established in the art. In some embodiments, a transduction moiety can be a cell penetrating peptide (CPP), a cationic polymer, an antibody, a cholesterol or cholesterol derivative, a vitamin compound (e.g., vitamin E, B12, B6, etc.), a tocol, a tocotrienol, a tocopherol, glucose, receptor ligand, antibody or the like capable of cell type specific targeting, to further facilitate the uptake of the anionic biomolecule, such as oligonucleotides and polynucleotides.

In some embodiments, the PTD domain comprises a peptide represented by the following general formula: B1-X1-X2-X3-B2-X4-X5-B3, wherein B1, B2, and B3 are each independently a basic amino acid, the same or different; and X1, X2, X3, X4 and X5 are each independently an alpha-helix enhancing amino acid, the same or different.

In some embodiments, the PTD domain comprises a polypeptide represented by the following general formula:

X—X—R—X—(P/X)—(B/X)—B—(P/X)—X—B—(B/X), wherein X is any alpha helical promoting residue such as alanine; P/X is either proline or X as previously defined; B is a basic amino acid residue, e.g., Arginine (Arg) or lysine (Lys); R is Arginine (Arg) and B/X is either B or X as defined herein.

In some embodiments, the PTD can be cationic. For example, in some embodiments, the PTD can include between 7 and 10 amino acids and have the general formula K—X1-R—X2-X1 wherein X1 is R or K and X2 is any amino acid. An example of such a cationic polypeptide can include the sequence RKKRRQRRR (SEQ ID NO: 528), or functional fragments and variants thereof.

A number of protein transduction domains/peptides are known in the art and may facilitate uptake of heterologous molecules linked to the transduction domains (e.g., cargo molecules). Such peptide transduction domains (PTDs) may facilitate uptake through a process referred to as macropinocytosis. Macropinocytosis is a nonselective form of endocytosis.

PTDs and CPPs useful in the embodiments disclosed herein include the PTDs and CPPs described in, for example, Langel, Ulo, "Cell Penetrating Peptides, Processes and Applications," In Langel, Ulo; (Ed.); Handbook of Cell-Penetrating Peptides, 2.sup.nd Ed (2007); Langel, Ulo, (Ed.). "Cell-Penetrating Peptides, Mechanisms and Applications;" In Curr. Pharm. Des.; 2005, 11(28)(2005); Langel, Ulo, "Cell-Penetrating Peptides: Processes and Applications" (2002); Wadia, Jehangir S.; Becker-Hapak, Michelle; Dowdy, Steven F. Protein transport. Cell-Penetrating Peptides (2002), pp. 365-375.

Exemplary peptide transduction domains (PTDs) may be derived from the Drosophila homeoprotein Antennapedia transcription protein (AntHD) (Joliot et al., New Biol. 3:1121-34, 1991; Joliot et al., Proc. Natl. Acad. Sci. USA, 88:1864-8, 1991; Le Roux et al., Proc. Natl. Acad. Sci. USA, 90:9120-4, 1993), the herpes simplex virus structural protein VP22 (Elliott and O Hare, Cell 88:223-33, 1997), the HIV-1 transcriptional activator TAT protein (Green and Loewenstein, Cell 55:1179-1188, 1988; Frankel and Pabo, Cell 55:1189-1193, 1988), and more recently the cationic N-terminal domain of prion proteins. Other exemplary peptide transduction domains are described in International Patent Application Publication No. WO 08/008,476. The peptide transduction domain may increase uptake of the biomolecule to which it is fused in a receptor independent fashion, may be capable of transducing a wide range of cell types, and may exhibit minimal or no toxicity (Nagahara et al., Nat. Med. 4:1449-52, 1998).

In some embodiments, the siNA molecules disclosed herein include PTDs that are cationic in nature. Cationic protein transduction domains track into lipid raft endosomes carrying with them their linked cargo and release their cargo into the cytoplasm by disruption of the endosomal vesicle. The invention provides, in one aspect, methods and compositions that combine the use of PTDs such as TAT and poly-Arg, with a siNA molecule of the invention.

In general, protein transduction domains of the embodiments disclosed herein may be any synthetic or naturally-occurring amino acid sequence that can transduce or assist in the transduction of the fusion molecule. For example, transduction may be achieved in accord with the disclosure by use of a nucleic acid construct including phosphodiester and/or phosphorothioate protecting groups and a protein sequence such as an HIV TAT protein or fragment thereof that is linked at the N-terminal or C-terminal end to an oligonucleotide or polynucleotide comprising a phosphodiester and/or phosphorothioate protecting group. In some aspects, the nucleic acid may comprise a phosphodiester and/or phosphorothioate protecting group and may also comprise a nucleic acid binding domain (e.g., a DRBD). The transducing protein domain, for example, may be the Antennapedia homeodomain or the HSV VP22 sequence, the N-terminal fragment of a prion protein or suitable transducing fragments thereof such as those generally known in the art.

In some embodiments, the siNA compositions disclosed herein may include a PTD that has substantial alpha-helicity, for example, to optimize transduction of the biomolecule. In another embodiment, the PTD comprises a sequence containing basic amino acid residues that are substantially aligned along at least one face of the peptide. Alpha-helicity can be estimated as is generally known in the art.

In some embodiments, with respect to certain siNA compositions described herein, the PTD is as described in PCT Pub. Nos. WO 08/008,476 and WO 07/095,152, the PTD disclosure of which is hereby expressly incorporated by this reference. Additional transducing domains useful in the embodiments disclosed herein include but are not limited to a TAT fragment that comprises at least amino acids 49 to 56 of TAT up to about the full-length TAT sequence as described in PCT Pub. No. WO 08/008,476. In some embodiments, a TAT fragment may include one or more amino acid changes sufficient to increase the alpha-helicity of the fragment. In some embodiments, amino acid changes are introduced in the PTDs that add a recognized alpha-helix enhancing amino acid. In some embodiments, amino acids are introduced in the PTD s that remove one or more amino acids from the TAT fragment that impede alpha helix formation or stability. In some embodiments, for example, the PTD may be a TAT fragment that includes at least one amino acid substitution with an alpha-helix enhancing amino acid.

Additional transduction proteins (PTDs) useful in the embodiments disclosed herein include a TAT fragment in which the TAT 49-56 sequence has been modified so that at least two basic amino acids in the sequence are substantially aligned along at least one face of the TAT fragment. Exemplary TAT fragments useful as PTDs in the embodiments disclosed herein may include at least one specified amino acid substitution in at least amino acids 49-56 of TAT which substitution aligns the basic amino acid residues of the 49-56 sequence along at least one face of the segment.

In some embodiments, the PTD used in the embodiments disclosed herein may be a naturally occurring PTD, such as include the homeodomain of the *Drosophila melanogaster* protein Antennapedia (Lindsay (2002) Curr. Op. Pharmacol. 2:587-94; Derossi et al. (1994) J. Biol. Chem. 269:10444-50), HSV-1 VP22 (Bennett et al. (2002) Nat. Biotechnol. 20:20), and Buforin II (Park et al. (2000) Proc. Natl. Acad. Sci. U.S.A. 97:8245-50), or the like, or fragments thereof.

In some embodiments, the PTD used in the embodiments disclosed herein may be a recombinant or synthetic PTD designed to mimic and/or enhance the translocating properties of known PTDs, based on consideration of parameters such as electrostatic and hydrophobic properties or secondary structure (Wender et al. (2000) Proc. Natl. Acad. Sci. U.S.A. 97:13003-8; Futaki et al. (2001) J. Biol. Chem. 276:5836-40). An exemplary artificial PTD is transportan (Pooga et al. (1998) FASEB J. 12:67-77; Soomets et al. (2000) Biochim. Biophys. Acta 1467:165-76). Synthetic PTDs such as polylysine, polyarginine, and polyhistidine (which can be positively charged based on the pH of the formulation) e.g., polyarginine (6-15 amino acids) (SEQ ID NO: 537) may be useful in the embodiments disclosed herein.

Other PTDs useful in the embodiments disclosed herein include, but are not limited to those provided in Table 2 herein.

Yet other PTDs useful in the embodiments described herein include PTDs derived from protamine (AAA39985), penetratin (1OMQ_A), TAT (NP_057853), pVEC, Cationic prion protein domains, P101 (ACT78456), MATa2 (Q6B184), HIV-1 rev (CAA41586), Polyomavirus Vpl (AAP14004), NF-kappaB (NP_003989), M9 (BAA76626), Vpr (BAH97661), FP_NLS (MPG), Sp-NPS (ACU27162), SN50, Importins and Karyopherins, e.g., Karyopherin alpha (NP_002255), and Karyopherin beta (NP_002256), and the like. Other PTDs useful in the embodiments disclosed herein include those found in International Patent Application Publication Not WO 09/041,902, WO 05/084158; WO 00/062067, WO 00/034308, and WO 99/55899, each of which is herein incorporated by reference.

In some embodiments, the transduction moiety may be a chimeric PTD domain comprising sequences derived from at least two different transducing proteins. For example, chimeric transducing proteins useful in the embodiments disclosed herein include a chimera between two different TAT fragments, e.g., one from HIV-1 and the other from HIV-2 or one from a prion protein and one from HIV. S. Deshayes, M. C. Morris, G. Divita and F. Heitz Cell-penetrating peptides: tools for intracellular delivery of therapeutics 2005, V62, N 16, p 1839.

In some embodiments, the transduction moiety may be a nucleic acid binding polypeptide, such as an RNA binding protein, or the like optionally linked to a PTD selected from the examples listed above. Exemplary RNA binding proteins (e.g., DRBD) include histone, RDE-4 protein, or protamine. Exemplary dsRNA binding proteins (with Accession numbers listed in parenthesis) include but are not limited to: PKR (AAA36409, AAA61926, Q03963), TRBP (P97473, AAA36765), PACT (AAC25672, AAA49947, NP609646), Staufen (AAD17531, AAF98119, AAD17529, P25159), NFAR1 (AF167569), NFAR2 (AF167570, AAF31446, AAC71052, AAA19960, AAA19961, AAG22859), SPNR (AAK20832, AAF59924, A57284), RHA (CAA71668, AAC05725, AAF57297), NREBP (AAK07692, AAF23120, AAF54409, T33856), kanadaptin (AAK29177, AAB88191, AAF55582, NP499172, NP198700, BAB19354), HYL1 (NP563850), hyponastic leaves (CAC05659, BAB00641), human rhinovirus polyprotein (ACT09659), ADAR1 (AAB97118, P55266, AAK16102, AAB51687, AF051275), ADAR2P78563, P51400, AAK17102, AAF63702), ADAR3 (AAF78094, AAB41862, AAF76894), TENR (XP059592, CAA59168), RNaseIII (AAF80558, AAF59169, Z81070Q02555/S55784, P05797), and Dicer (BAA78691, AF408401, AAF56056, 544849, AAF03534, Q9884), RDE-4 (AY071926), F1120399 (NP060273, BAB26260), CG1434 (AAF48360, EAA12065, CAA21662), CG13139 (XP059208, XP143416, XP110450, AAF52926, EEA14824), DGCRK6 (BAB83032, XP110167) CG1800 (AAF57175, EAA08039), F1120036 (AAH22270, XP134159), MRP-L45 (BAB14234, XP129893), CG2109 (AAF52025), CG12493 (NP647927), CG10630 (AAF50777), CG17686 (AAD50502), T22A3.5 (CAB03384) and Accession number EAA 14308. Nucleic acid binding polypeptides can comprise any of the full length polypeptides of the foregoing accession numbers, as well as fragments or variants thereof, including as modified polypeptides comprising from 1-14 amino acid substitutions.

The skilled artisan will readily appreciate that the CPP and PTD domains described herein include modified peptides such as glycoproteins, the L-optical isomer or the D-optical isomer of amino acids or a combination of both, as well as retro-inverso polypeptides. As used herein, the term "retro-inverso" refers a peptide that comprises an amino-carboxy inversion as well as enantiomeric change in one or more amino acids (i.e., levorotatory (L) to dextrorotary (D)). The CPP and PTD domains described herein encompass D-amino acid modified polypeptides, amino-carboxy inversions of the amino acid sequence, amino-carboxy inversions containing one or more D-amino acids, naturally occurring proteins, recombinantly or synthetically synthesized peptides, non-inverted sequence containing one or more D-amino acids, peptidomimetics, Beta-amino acid analogs, gamma amino acid analogs, and the like.

The CPP or PTD peptides disclosed herein may also encompass peptide fragments as are generally known in the art.

In some embodiments, in addition to including one or more protecting groups disclosed herein, anionic biomolecules disclosed herein may be operably linked to an additional transduction moiety. In some embodiments, the transduction moiety can be a synthetic or non-synthetic, linear or branched peptide transduction domain (PTD) as described herein or as is otherwise known in the art. The PTD can be a cationic peptide optionally connected via a branching linker installed during automated nucleotide synthesis. These linkers have been established and are described by Horn et al., 1989: Chang et al., 1991; Foldesi et al, 1991, M. S. Shchepinov, I. A. Udalova, A. J. Bridgman, and E. M. Southern, Nucleic Acids Res, 1997, 25, 4447-4454, T. Horn, C. A. Chang, and M. S. Urdea, Nucleic Acids Res, 1997, 25, 4842-4849, M. S. Shchepinov, K. U. Mir, J. K. Elder, M. D. Frank-Kamenetskii, and E. M. Southern, Nucleic Acids Res, 1999, 27, 3035-41 The branching linker can be trebler, symmetrical or combinations thereof. The transduction moieties disclosed herein can be linked or fused with another transduction moiety as described herein or as is otherwise known in the art, a linker, such as a peptide linker or a nucleotide linker, or can be directly linked to an siNA molecule disclosed herein. Non-limiting examples of linkers useful in the embodiments disclosed herein include, but are not limited to GG (SEQ ID NO: 529), GGGGS (SEQ ID NO: 530), GGGGSN (SEQ ID NO: 531), GKSSGSGSESKS (SEQ ID NO: 532), GSTSGS-GKSSEGKG (SEQ ID NO: 533), GSTSGS-GKSSEGSGSTKG (SEQ ID NO: 534), GSTSGSGKPGS-GEGSTKG (SEQ ID NO: 535), or EGKSSGSGSESKEF (SEQ ID NO: 536) Linking moieties are described, for example, in Huston et al., Proc. Natl Acad. Sci. 85:5879, 1988; Whitlow et al., Protein Engineering 6:989, 1993; and Newton et al., Biochemistry 35:545, 1996. Other suitable peptide linkers are those described in U.S. Pat. Nos. 4,751, 180 and 4,935,233, which are hereby incorporated by reference.

In some embodiments, the compositions disclosed herein comprise targeting moieties and the like.

For example, in some embodiments, two or more transduction moieties, such as PTDs (e.g., 1-5, 2-4, typically 3) may be linked in series or separated by one or more other domains (e.g., a nucleic acid domain or peptide linkers). Transduction moieties, siNA molecules of the invention, and peptide linkers, may be organized in nearly any fashion provided that the construct has the function for which it was intended. Each of several domains (e.g., transduction moieties and siNA molecules) may be directly linked or can be separated by a linker peptide. The domains may be presented in any order. Additionally, the fusion polypeptides may include tags, e.g., to facilitate identification and/or purification of the fusion polypeptide, such as a 6×HIS tag (SEQ ID NO: 538), a maltose binding protein domain, a GST tag, or the like.

In some embodiments, the siNA compositions described herein include a peptide linker. For example, in some embodiments, a peptide linker comprises up to about 20 or 30 amino acids, commonly up to about 10 or 15 amino acids, and still more often from about 1 to 5 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more amino acids. In some embodiments, the amino acid sequence of the linker is engineered to be flexible so as not to hold the fusion molecule in a single rigid conformation. Peptide linker sequences can be used, e.g., to space the transduction moieties from the siNA molecules of the invention. For example, the peptide linker sequence can be positioned between a transduction moiety, and one or more strands of a siNA molecule, e.g., to provide molecular flexibility. The length of the linker moiety is chosen to optimize the biological activity of the polypeptide comprising a PTD domain fusion construct and can be determined empirically without undue experimentation. The linker moiety should be long enough and flexible enough to allow a nucleic acid binding domain to freely interact with a nucleic acid or vice versa. Exemplary peptide linkers and linker moieties are described in Int. Pub. No. WO/2008/008476, in Huston et al., Proc. Natl. Acad. Sci. 85:5879, 1988; Whitlow et al., Protein Engineering 6:989, 1993; and Newton et al., Biochemistry 35:545, 1996. Other suitable peptide linkers are those described in U.S. Pat. Nos. 4,751,180 and 4,935,233, which are incorporated herein by reference.

Generation/Synthesis of siNA Molecules

The siNAs of the invention may be obtained using a number of techniques known to those of skill in the art. For example the siNA may be chemically synthesized or may be encoded by plasmid (e.g., transcribed as sequences that automatically fold into duplexes with hairpin loops.). siNA may also be generated by cleavage of longer dsRNA (e.g., dsRNA greater than about 25 nucleotides in length) by the *E coli* RNase II or Dicer. These enzymes process the dsRNA into biologically active siNA (see, e.g., Yang et al., *PNAS USA* 99:9942-9947 (2002); Calegari et al. *PNAS USA* 99:14236 (2002) Byron et al. *Ambion Tech Notes;* 10 (1):4-6 (2009); Kawaski et al., *Nucleic Acids Res.,* 31:981-987 (2003), *Knight and Bass, Science,* 293:2269-2271 (2001) and Roberston et al., *J. Biol. Chem* 243:82(1969).

Preferably, siNA of the invention are chemically synthesized. Oligonucleotides (e.g., certain modified oligonucleotides or portions of oligonucleotides lacking ribonucleotides) are synthesized using protocols known in the art, for example as described in Caruthers et al., 1992, *Methods in Enzymology* 211, 3-19, Thompson et al., International PCT Publication No. WO 99/54459, Wincott et al., 1995, *Nucleic Acids Res.* 23, 2677-2684, Wincott et al., 1997, Methods Mol. Bio., 74, 59, Brennan et al., 1998, *Biotechnol Bioeng.,* 61, 33-45, and Brennan, U.S. Pat. No. 6,001,311. The synthesis of oligonucleotides makes use of common nucleic acid protecting and coupling groups, such as dimethoxytrityl at the 5-end, and phosphoramidites at the 3_end.

siNA molecules without modifications may be synthesized using procedures as described in Usman et al., 1987, *J. Am. Chem. Soc.,* 109, 7845; Scaringe et al., 1990, *Nucleic Acids Res.,* 18, 5433. These syntheses makes use of common nucleic acid protecting and coupling groups, such as dimethoxytrityl at the 5-end, and phosphoramidites at the 3-end that can be used for certain siNA molecules of the invention.

In certain embodiments, the siNA molecules of the invention may be synthesized, deprotected, and analyzed according to methods described in U.S. Pat. Nos. 6,995,259, 6,686,463, 6,673,918, 6,649,751, 6,989,442, and U.S. patent application Ser. No. 10/190,359.

Alternatively, the siNA molecules of the present invention may be synthesized separately and joined together post-synthetically, for example, by ligation (Moore et al., 1992, Science 256, 9923; Draper et al., International PCT Publication No. WO 93/23569; Shabarova et al., 1991, *Nucleic Acids Research* 19, 4247; Bellon et al., 1997, Nucleosides & Nucleotides, 16, 951; Bellon et al., 1997, *Bioconjugate Chem.* 8, 204), or by hybridization following synthesis and/or deprotection.

Various siNA molecules of the invention may also be synthesized using the teachings of Scaringe et al., U.S. Pat. Nos. 5,889,136; 6,008,400; and 6,111,086.

Carrier/Delivery Systems

The siNA molecules of the invention may be added directly or may be conjugated with a delivery vehicle, or otherwise delivered to target cells or tissues. In certain embodiments, the invention features conjugates and/or complexes of siNA molecules of the invention. Such conjugates and/or complexes include ligand based and polymer based delivery modalities that may be used to facilitate delivery of siNA molecules into a biological system, such as a cell. The conjugates and complexes provided by the instant invention may impart therapeutic activity by transferring therapeutic compounds across cellular membranes, altering the pharmacokinetics, and/or modulating the localization of nucleic acid molecules of the invention. Non-limiting, examples of such conjugates are described in U.S. Publication Nos. US2008/0152661 A1 and US 2004/0162260 A1 (e.g., CDM-LBA, CDM-Pip-LBA, CDM-PEG, CDM-NAG, etc.) and U.S. patent application Ser. Nos. 10/427,160 10/201,394, 61/322,422, 61/378,609, and 61/315,223; and U.S. Pat. Nos. 6,528,631; 6,335,434; 6,235,886; 6,153,737; 5,214,136; and 5,138,045.

In various embodiments, polyethylene glycol (PEG) may be covalently attached to siNA compounds of the present invention. The attached PEG may be any molecular weight, preferably from about 100 to about 50,000 daltons (Da).

Kits

The present invention also provides nucleic acids in kit form. The kit may comprise a container. The kit typically contains a nucleic acid of the invention with instructions for its administration. In certain instances, the nucleic acids may have a targeting moiety or delivery agent attached. Methods of attaching targeting moieties (e.g. antibodies, proteins) or delivery agents (conjugates) are known to those of skill in the art. In certain instances, the kit contains more than one siNA molecule of the invention. The kits may comprise an siNA molecule of the invention with a pharmaceutically acceptable carrier or diluent. The kits may further comprise excipients.

Therapeutic Uses/Pharmaceutical Compositions

The nucleic acid molecules and pharmaceutical compositions of the invention may be used to treat diseases, conditions, or phenotypes related to gene expression. Non-limiting examples of such diseases, conditions, and phenotypes are described herein and are otherwise known in the art Indications Particular conditions and disease states that may be associated with gene expression modulation include, but are not limited to cancer, proliferative, inflammatory, autoimmune, neurologic, ocular, respiratory, metabolic, dermatological, auditory, liver, kidney, infectious etc. diseases, conditions, or disorders as described herein or otherwise known in the art, and any other diseases, conditions or disorders that may be related to or may respond to the levels of a target (e.g., target DNA, RNA, protein or polynucleotide) in a cell or tissue, alone or in combination with other therapies.

Proliferative diseases (cancer) may include any disease or condition characterized by unregulated cell growth or replication as is known in the art; including leukemias, for example, acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewings sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas. Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and any other cancer or proliferative disease, condition, trait, genotype or phenotype that can respond to the modulation of disease related gene expression in a cell or tissue, alone or in combination with other therapies.

Inflammatory diseases may include any disease or condition characterized by an inflammatory or allergic process as is known in the art, such as inflammation, acute inflammation, chronic inflammation, respiratory disease, atherosclerosis, psoriasis, dermatitis, restenosis, asthma, allergic rhinitis, atopic dermatitis, septic shock, rheumatoid arthritis, inflammatory bowl disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses, and any other inflammatory disease, condition, trait, genotype or phenotype that can respond to the modulation of disease related gene expression in a cell or tissue, alone or in combination with other therapies.

Autoimmune diseases may include any disease or condition characterized by autoimmunity as is known in the art, such as multiple sclerosis, diabetes mellitus, lupus, celiac disease. Crohn's disease, ulcerative colitis. Guillain-Barre syndrome, scleroderms, Goodpasture's syndrome. Wegener's granulomatosis. autoimmune epilepsy. Rasmussen's encephalitis, Primary biliary sclerosis, Sclerosing cholangitis. Autoimmune hepatitis. Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren s syndrome, lupus erythematosus, multiple sclerosis, myasthenia gravis, Reiters syndrome, Grave s disease, and any other autoimmune disease, condition, trait, genotype or phenotype that can respond to the modulation of disease related gene expression in a cell or tissue, alone or in combination with other therapies.

Infectious diseases may include any disease or condition associated with an infectious agent, such as a virus, bacteria, fungus, prion, or parasite. Non-limiting examples of various viral genes that can be targeted using siNA molecules of the invention include Hepatitis C Virus (HCV, for example GenBank Accession Nos: D11168, D50483.1, L38318 and $S_{82227}$), Hepatitis B Virus (HBV, for example GenBank Accession No. AF100308.1), Human Immunodeficiency Virus type 1 (HIV-1, for example GenBank Accession No. U51188), Human Immunodeficiency Virus type 2 (HIV-2, for example GenBank Accession No. X60667), West Nile Virus (WNV for example GenBank accession No. NC_001563), cytomegalovirus (CMV for example GenBank Accession No. NC_001347), respiratory syncytial virus (RSV for example GenBank Accession No. NC_001781), influenza virus (for example GenBank Accession No. AF037412, rhinovirus (for example, GenBank accession numbers: D00239, X02316, X01087, L24917, M16248, K02121, X01087), papillomavirus (for example GenBank Accession No. NC_001353), Herpes Simplex Virus (HSV for example GenBank Accession No. NC_001345), and other viruses such as HTLV (for example GenBank Accession No. AJ430458). Due to the high sequence variability of many viral genomes, selection of siNA molecules for broad therapeutic applications would likely involve the conserved regions of the viral genome. Nonlimiting examples of conserved regions of the viral genomes include but are not limited to 5'-Non Coding Regions (NCR), 3'-Non Coding Regions (NCR) and/or internal ribosome entry sites (IRES). siNA molecules designed against conserved regions of various viral genomes will enable efficient inhibition of viral replication in diverse patient populations and may ensure the effectiveness of the siNA molecules against viral quasi species which evolve due to mutations in the non-conserved regions of the viral genome. Non-limiting examples of bacterial infections include Actinomycosis, Anthrax, Aspergillosis, Bacteremia, Bacterial Infections and Mycoses, Bartonella Infections, Botulism, Brucellosis, Burkholderia Infections, Campylobacter Infections, Candidiasis, Cat-Scratch Disease, Chlamydia Infections, Cholera, Clostridium Infections, Coccidioidomycosis, Cross Infection, Cryptococcosis, Dermatomycoses, Dermatomycoses, Diphtheria, Ehrlichiosis, Escherichia coli Infections, Fasciitis, Necrotizing, Fusobacterium Infections, Gas Gangrene, Gram-Negative Bacterial Infections, Gram-Positive Bacterial Infections, Histoplasmosis, Impetigo, Klebsiella Infections, Legionellosis, Leprosy, Leptospirosis, Listeria Infections, Lyme Disease, Maduromycosis, Melioidosis, Mycobacterium Infections, Mycoplasma Infections, Mycoses, Nocardia Infections, Onychomycosis, Ornithosis, Plague, Pneumococcal Infections, Pseudomonas Infections, Q Fever, Rat-Bite Fever, Relapsing Fever, Rheumatic Fever, Rickettsia Infections, Rocky Mountain Spotted Fever, Salmonella Infections, Scarlet Fever, Scrub Typhus, Sepsis, Sexually Transmitted Diseases—Bacterial, Bacterial Skin Diseases, Staphylococcal Infections, Streptococcal Infections, Tetanus, Tick-Borne Diseases, Tuberculosis, Tularemia, Typhoid Fever, Typhus, Epidemic Louse-Borne, Vibrio Infections, Yaws, Yersinia Infections, Zoonoses, and Zygomycosis. Non-limiting examples of fungal infections include Aspergillosis, Blastomycosis, Coccidioidomycosis, Cryptococcosis, Fungal Infections of Fingernails and Toenails, Fungal Sinusitis, Histoplasmosis, Histoplasmosis, Mucormycosis, Nail Fungal Infection, Paracoccidioidomycosis, Sporotrichosis, Valley Fever (Coccidioidomycosis), and Mold Allergy.

Neurologic diseases may include any disease or condition affecting the central or peripheral nervous system, including ADHD, AIDS—Neurological Complications, Absence of the Septum Pellucidum, Acquired Epileptiform Aphasia, Acute Disseminated Encephalomyelitis, Adrenoleukodystrophy, Agenesis of the Corpus Callosum, Agnosia, Aicardi Syndrome, Alexander Disease, AlpersDisease, Alternating Hemiplegia, Alzheimeri Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Aspartame, Asperger Syndrome, Ataxia Telangiectasia, Ataxia, Attention Deficit-Hyperactivity Disorder, Autism, Autonomic Dysfunction, Back Pain, Barth Syndrome, Batten Disease, Behcets Disease, Bells Palsy, Benign Essential Blepharospasm, Benign Focal Amyotrophy, Benign Intracranial Hypertension, Bernhardt-Roth Syndrome, Binswangerk Disease, Blepharospasm, Bloch-Sulzberger Syndrome, Brachial Plexus Birth Injuries, Brachial Plexus Injuries, Bradbury-Eggleston Syndrome, Brain Aneurysm, Brain Injury, Brain and Spinal Tumors, Brown-Sequard Syndrome, Bulbospinal Muscular Atrophy, Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Palsy, Cerebro-Oculo-Facio-Skeletal Syndrome, Charcot-Marie-Tooth Disorder, Chiari Malformation, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Coma, including Persistent Vegetative State, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Creutzfeldt-Jakob Disease, Cumulative Trauma Disorders, Cushing s Syndrome, Cytomegalic Inclusion Body Disease (CIBD), Cytomegalovirus Infection, Dancing Eyes-Dancing Feet Syndrome, Dandy-Walker Syndrome, Dawson Disease, De Morsiers Syndrome, Dejerine-Klumpke Palsy, Dementia—Multi-Infarct, Dementia—Subcortical, Dementia With Lewy Bodies, Dermatomyositis, Developmental Dyspraxia, Devic s Syndrome, Diabetic Neuropathy, Diffuse Sclerosis, Dravet's Syndrome, Dysautonomia, Dysgraphia, Dyslexia, Dysphagia, Dyspraxia, Dystonias, Early Infantile Epileptic Encephalopathy, Empty Sella Syndrome, Encephalitis Lethargica, Encephalitis and Meningitis, Encephaloceles, Encephalopathy, Encephalotrigeminal Angiomatosis, Epilepsy, Erb s Palsy, Erb-Duchenne and Dejerine-Klumpke Palsies, Fabry Disease, Fahrs Syndrome, Fainting, Familial Dysautonomia, Familial Hemangioma, Familial Idiopathic Basal Ganglia Calcification, Familial Spastic Paralysis, Febrile Seizures (e.g., GEFS and GEFS plus), Fisher Syndrome, Floppy Infant Syndrome, Friedreich s Ataxia, Gaucher s Disease, Gerstmanns Syndrome, Gerstmann-Straussler-Scheinker Disease, Giant Cell Arteritis, Giant Cell Inclusion Disease, Globoid Cell Leukodystrophy, Glossopharyngeal Neuralgia, Guillain-Barre Syndrome, HTLV-1 Associated Myelopathy, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster Oticus, Herpes Zoster, Hirayama Syndrome, Holoprosencephaly, Huntingtoni Disease, Hydranencephaly, Hydrocephalus—Normal Pressure, Hydrocephalus, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Phytanic Acid Storage Disease, Infantile Refsum Disease, Infantile Spasms, Inflammatory Myopathy, Intestinal Lipodystrophy, Intracranial Cysts, Intracranial Hypertension, Isaac K Syndrome, Joubert Syndrome, Kearns-Sayre Syndrome. Kennedy's Disease, Kinsbourne syndrome, Kleine-Levin syndrome, Klippel Feil Syndrome, Klippel-Trenaunay Syndrome (KTS), Kliver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh Disease, Lennox-Gastaut Syndrome, Lesch-Nyhan Syndrome, Leukodystrophy, Levine-Critchley Syndrome, Lewy Body Dementia, Lissencephaly, Locked-In Syndrome, Lou Gehrig Disease, Lupus—Neurological Sequelae, Lyme Disease—Neurological Complications, Machado-Joseph Disease, Macrencephaly, Megalencephaly, Melkersson-Rosenthal Syndrome, Meningitis, Menkes Disease, Meralgia Paresthetica, Metachromatic Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy with Orthostatic Hypotension, Multiple System Atrophy, Muscular Dystrophy, Myasthenia—Congenital, Myasthenia Gravis, Myelinoclastic Diffuse Sclerosis, Myoclonic Encephalopathy of Infants, Myoclonus, Myopathy—Congenital, Myopathy—Thyrotoxic, Myopathy, Myotonia Congenita, Myotonia, Narcolepsy, Neuroacanthocytosis, Neurodegeneration with Brain Iron Accumulation, Neurofibromatosis, Neuroleptic Malignant Syndrome, Neurological Complications of AIDS, Neurological Manifestations of Pompe Disease, Neuromyelitis Optica, Neuromyotonia, Neuronal Ceroid Lipofuscinosis, Neuronal Migration Disorders, Neuropathy—Hereditary, Neurosarcoidosis, Neurotoxicity, Nevus Cavernosus, Niemann-Pick Disease, O Sullivan-McLeod Syndrome, Occipital Neuralgia, Occult Spinal Dysraphism Sequence, Ohtahara Syndrome, Olivopontocerebellar Atrophy, Opsoclonus Myoclonus, Orthostatic Hypotension, Overuse Syndrome, Pain—Chronic, Paraneoplastic Syndromes, Paresthesia, Parkinson Disease, Parmyotonia Congenita, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Picks Disease, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Lateral Sclerosis, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Pseudotumor Cerebri, Pyridoxine Dependent and Pyridoxine Responsive Siezure Disorders, Ramsay Hunt Syndrome Type I, Ramsay Hunt Syndrome Type II, Rasmussens Encephalitis and other autoimmune epilepsies, Reflex Sympathetic Dystrophy Syndrome, Refsum Disease—Infantile, Refsum Disease, Repetitive Motion Disorders, Repetitive Stress Injuries, Restless Legs Syndrome, Retrovirus-Associated Myelopathy, Rett Syndrome, Reye K Syndrome, Riley-Day Syndrome, SUNCT Headache, Sacral Nerve Root Cysts, Saint Vitus Dance, Salivary Gland Disease, Sandhoff Disease, Schilders Disease, Schizencephaly, Seizure Disorders, Septo-Optic Dysplasia, Severe Myoclonic Epilepsy of Infancy (SMEI), Shaken Baby Syndrome, Shingles, Shy-Drager Syndrome, Sjogren Syndrome, Sleep Apnea, Sleeping Sickness, Soto Syndrome, Spasticity, Spina Bifida, Spinal Cord Infarction, Spinal Cord Injury, Spinal Cord Tumors, Spinal Muscular Atrophy, Spinocerebellar Atrophy, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen Disease, Thoracic Outlet Syndrome, Thyrotoxic Myopathy, Tic Douloureux, Todds Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau disease (VHL), Von Recklinghausens Disease, Wallenbergi Syndrome, Werdnig-Hoffman Disease, Wernicke-Korsakoff Syndrome, West Syndrome, Whipples Disease, Williams Syndrome, Wilsons Disease, X-Linked Spinal and Bulbar Muscular Atrophy, and Zellweger Syndrome.

Respiratory diseases may include any disease or condition affecting the respiratory tract, such as asthma, chronic obstructive pulmonary disease or "COPD". allergic rhinitis, sinusitis, pulmonary vasoconstriction, inflammation, allergies, impeded respiration, respiratory distress syndrome, cystic fibrosis, pulmonary hypertension, pulmonary vasoconstriction, emphysema, and any other respiratory disease, condition, trait, genotype or phenotype that can respond to the modulation of disease related gene expression in a cell or tissue, alone or in combination with other therapies.

Ocular diseases may include any disease or condition affecting eye and related structures as is known in the art, such as Cystoid Macular Edema, Asteroid Hyalosis, Pathological Myopia and Posterior Staphyloma, Toxocariasis (Ocular Larva Migrans), Retinal Vein Occlusion, Posterior Vitreous Detachment, Tractional Retinal Tears, Epiretinal Membrane, Diabetic Retinopathy, Lattice Degeneration, Retinal Vein Occlusion, Retinal Artery Occlusion, Macular Degeneration (e.g., age related macular degeneration such as wet AMD or dry AMD), Toxoplasmosis, Choroidal Melanoma, Acquired Retinoschisis, Hollenhorst Plaque, Idiopathic Central Serous Chorioretinopathy, Macular Hole, Presumed Ocular Histoplasmosis Syndrome, Retinal Macroaneurysm, Retinitis Pigmentosa, Retinal Detachment, Hypertensive Retinopathy, Retinal Pigment Epithelium (RPE) Detachment, Papillophlebitis, Ocular Ischemic Syndrome, Coats' Disease, Leber's Miliary Aneurysm, Conjunctival Neoplasms, Allergic Conjunctivitis, Vernal Conjunctivitis, Acute Bacterial Conjunctivitis, Allergic Conjunctivitis &Vernal Keratoconjunctivitis, Viral Conjunctivitis, Bacterial Conjunctivitis, Chlamydial & Gonococcal Conjunctivitis, Conjunctival Laceration, Episcleritis, Scleritis, Pingueculitis, Pterygium, Superior Limbic Keratoconjunctivitis (SLK of Theodore), Toxic Conjunctivitis, Conjunctivitis with Pseudomembrane, Giant Papillary Conjunctivitis, Terriens Marginal Degeneration, Acanthamoeba Keratitis, Fungal Keratitis, Filamentary Keratitis, Bacterial Keratitis, Keratitis Sicca/Dry Eye Syndrome, Bacterial Keratitis, Herpes Simplex Keratitis, Sterile Corneal Infiltrates, Phlyctenulosis, Corneal Abrasion & Recurrent Corneal Erosion, Corneal Foreign Body, Chemical Burs, Epithelial Basement Membrane Dystrophy (EBMD), Thygeson Superficial Punctate Keratopathy, Corneal Laceration, Salzmann's Nodular Degeneration, Fuchs' Endothelial Dystrophy. Crystalline Lens Subluxation, Ciliary-Block Glaucoma, Primary Open-Angle Glaucoma, Pigment Dispersion Syndrome and Pigmentary Glaucoma, Pseudoexfoliation Syndrom and Pseudoexfoliative Glaucoma, Anterior Uveitis, Primary Open Angle Glaucoma, Uveitic Glaucoma & Glaucomatocyclitic Crisis, Pigment Dispersion Syndrome & Pigmentary Glaucoma, Acute Angle Closure Glaucoma, Anterior Uveitis, Hyphema, Angle Recession Glaucoma, Lens Induced Glaucoma, Pseudoexfoliation Syndrome and Pseudoexfoliative Glaucoma, Axenfeld-Rieger Syndrome, Neovascular Glaucoma, Pars Planitis, Choroidal Rupture, Duane K Retraction Syndrome, Toxic/Nutritional Optic Neuropathy, Aberrant Regeneration of Cranial Nerve III, Intracranial Mass Lesions, Carotid-Cavernous Sinus Fistula, Anterior Ischemic Optic Neuropathy, Optic Disc Edema & Papilledema, Cranial Nerve III Palsy, Cranial Nerve IV Palsy, Cranial Nerve VI Palsy, Cranial Nerve VII (Facial Nerve) Palsy, Horners Syndrome, Internuclear Ophthalmoplegia, Optic Nerve Head Hypoplasia, Optic Pit, Tonic Pupil, Optic Nerve Head Drusen, Demyelinating Optic Neuropathy (Optic Neuritis, Retrobulbar Optic Neuritis), Amaurosis Fugax and Transient Ischemic Attack, Pseudotumor Cerebri, Pituitary Adenoma, Molluscum Contagiosum, Canaliculitis, Verruca and Papilloma, Pediculosis and Pthiriasis, Blepharitis, Hordeolum, Preseptal Cellulitis, Chalazion, Basal Cell Carcinoma, Herpes Zoster Ophthalmicus, Pediculosis & Phthiriasis, Blow-out Fracture, Chronic Epiphora, Dacryocystitis, Herpes Simplex Blepharitis, Orbital Cellulitis, Senile Entropion, and Squamous Cell Carcinoma.

Dermatologic diseases may include any disease or condition affecting the skin, dermis, or any substructure therein such as hair, follicle, etc. Dermatological diseases, disorders, conditions, and traits can include psoriasis, ectopic dermatitis, skin cancers such as melanoma and basal cell carcinoma, hair loss, hair removal, alterations in pigmentation, and any other disease, condition, or trait associated with the skin, dermis, or structures therein.

Auditory diseases may include any disease or condition affecting the auditory system, including the ear, such as the inner ear, middle ear, outer ear, auditory nerve, and any substructures therein. Auditory diseases, disorders, conditions, and traits can include hearing loss, deafness, tinnitus, Menieres Disease, vertigo, balance and motion disorders, and any other disease, condition, or trait associated with the ear, or structures therein.

Metabolic diseases may include any disease or condition affecting metabolic pathways as in known in the art. Metabolic disease can result in an abnormal metabolic process, either congenital due to inherited enzyme abnormality (inborn errors of metabolism) or acquired due to disease of an endocrine organ or failure of a metabolically important organ such as the liver. In one embodiment, metabolic disease includes hyperlipidemia, hypercholesterolemia, cardiovascular disease, atherosclerosis, hypertension, diabetes (e.g., type I and/or type II diabetes), insulin resistance, and/or obesity.

Cardiovascular diseases may include any disease or condition affecting the heart and vasculature, including but not limited to, coronary heart disease (CHD), cerebrovascular disease (CVD), aortic stenosis, peripheral vascular disease, atherosclerosis, arteriosclerosis, myocardial infarction (heart attack), cerebrovascular diseases (stroke), transient ischemic attacks (TIA), angina (stable and unstable), atrial fibrillation, arrhythmia, vavular disease, congestive heart failure, hypercholoesterolemia, type I hyperlipoproteinemia, type II hyperlipoproteinemia, type III hyperlipoproteinemia, type IV hyperlipoproteinemia, type V hyperlipoproteinemia, secondary hypertrigliceridemia, and familial lecithin cholesterol acyltransferase deficiency.

It is understood that the siNA molecules of the invention may silence the expression of target genes and thus amenable to the treatment of various diseases and conditions herein or otherwise known in the art. Treatment of a disease may be evaluated by directly measuring the progress of the disease in a subject. It may also be inferred through observing a change or reversal in a condition associated with the disease. Additionally, the siNA molecules of the invention may be used as a prophylaxis. Thus, the use of the nucleic acid molecules and pharmaceutical compositions of the invention may be used to ameliorate, treat, prevent, and/or cure these diseases and others associated with gene expression and/or activity.

Subjects (e.g., mammalian, human) that may be amendable for treatment using the siNA molecules of the invention (optionally further substituted or modified or conjugated), compositions thereof, and methods of the present disclosure may include those suffering from one or more disease or condition mediated, at least in part, by an aberrant expression level of the target gene or sequence, those at risk of developing a disease caused by or associated with the aberrant levels of a target gene/sequence, or those which may be amenable to treatment by replenishing or increasing the level of RNAi mediated by the corresponding siNA molecule, including a hyperproliferative (e.g., cancer), angiogenic, metabolic, or inflammatory (e.g., arthritis) disease or disorder or condition.

Compositions and methods disclosed herein may be useful in the treatment of a wide variety of target viruses, including retrovirus, such as human immunodeficiency virus (HIV), Hepatitis C Virus, Hepatitis B Virus, Coronavirus, as well as respiratory viruses, including human Respiratory Syncytial Virus, human Metapneumovirus, human Parainfluenza virus, Rhinovirus and Influenza virus.

In other examples, the compositions and methods of this disclosure may be useful as therapeutic tools to treat or prevent symptoms of, for example, hyperproliferative disorders. Exemplary hyperproliferative disorders may include neoplasms, carcinomas, sarcomas, tumors, or cancer. More exemplary hyperproliferative disorders may include oral cancer, throat cancer, laryngeal cancer, esophageal cancer, pharyngeal cancer, nasopharyngeal cancer, oropharyngeal cancer, gastrointestinal tract cancer, gastrointestinal stromal tumors (GIST), small intestine cancer, colon cancer, rectal cancer, colorectal cancer, anal cancer, pancreatic cancer, breast cancer, cervical cancer, uterine cancer, vulvar cancer, vaginal cancer, urinary tract cancer, bladder cancer, kidney cancer, adrenocortical cancer, islet cell carcinoma, gallbladder cancer, stomach cancer, prostate cancer, ovarian cancer, endometrial cancer, trophoblastic tumor, testicular cancer, penial cancer, bone cancer, osteosarcoma, liver cancer, extrahepatic bile duct cancer, skin cancer, basal cell carcinoma (BCC), lung cancer, small cell lung cancer, non-small cell lung cancer (NSCLC), brain cancer, melanoma, Kaposi s sarcoma, eye cancer, head and neck cancer, squamous cell carcinoma of head and neck, tymoma, thymic carcinoma, thyroid cancer, parathyroid cancer, Hippel-Lindau syndrome, leukemia, acute myeloid leukemia, chronic myelogenous leukemia, acute lymphoblastic leukemia, hairy cell leukemia, lymphoma, non-Hodgkins lymphoma, Burkitti lymphoma, T-cell lymphoma, multiple myeloma, malignant pleural mesothelioma, Barretts adenocarcinoma, Wilms tumor, or the like. In other examples, the compositions and methods of this disclosure are useful as therapeutic tools to regulate expression of one or more target gene to treat or prevent symptoms of, for example, inflammatory disorders. Exemplary inflammatory disorders may include diabetes mellitus, rheumatoid arthritis, pannus growth in inflamed synovial lining, collagen-induced arthritis, spondylarthritis, ankylosing spondylitis, multiple sclerosis, encephalomyelitis, inflammatory bowel disease, Crohns disease, psoriasis or psoriatic arthritis, myasthenia gravis, systemic lupus erythematosis, graft-versus-host disease, atherosclerosis, and allergies.

Other exemplary disorders that may be treated with the siNA molecules, compositions and methods of the instant disclosure include metabolic disorders, cardiac disease, pulmonary disease, neovascularization, ischemic disorders, age-related macular degeneration, diabetic retinopathy, glomerulonephritis, diabetes, asthma, chronic obstructive pulmonary disease, chronic bronchitis, lymphangiogenesis, and atherosclerosis.

Pharmaceutical Compositions

The siNA molecules of the instant invention may provide useful reagents and methods for a variety of therapeutic, prophylactic, cosmetic, veterinary, diagnostic, target validation, genomic discovery, genetic engineering, and pharmacogenomic applications.

Formulations

Thus, the present invention, in one aspect, also provides for pharmaceutical compositions of the siNA molecules of the invention, i.e., compositions in a pharmaceutically acceptable carrier or diluent. These pharmaceutical compositions include salts, esters, or salts of such esters, of the above compounds, e.g., acid addition salts, for example, salts of hydrochloric, hydrobromic, hydroiodic, acetic acid, and benzene sulfonic acid. Other salts include for example, sodium, potassium, manganese, ammonium, and calcium salts. These formulations or compositions can comprise a pharmaceutically acceptable carrier or diluent as is generally known in the art. The pharmaceutical compositions of the present disclosure are formulated to all the siNA molecule(s) described herein to be bioavailable upon administration to a subject.

In one embodiment, the invention features a pharmaceutical composition comprising any siNA comprising any formula A, B, C, D, E, F, G, H, I, J, K, L, M, N, O, or P as described herein.

The siNA molecules of the invention may preferably be formulated as pharmaceutical compositions prior to administering to a subject, according to techniques known in the art. Pharmaceutical compositions of the present invention may be characterized as being at least sterile and pyrogen-free. Methods for preparing pharmaceutical compositions of the invention are within the skill in the art for example as described in Remington s Pharmaceutical Science, 21$^{st}$ ed., Mack Publishing Company, Easton, Pa., A. R. Gennaro edit., 2005.

Non-limiting examples of various types of formulations for local administration include ointments, lotions, creams, gels, foams, preparations for delivery by transdermal patches, powders, sprays, aerosols, capsules or cartridges for use in an inhaler or insufflator or drops (for example eye or nose drops), solutions/suspensions for nebulization, suppositories, pessaries, retention enemas and chewable or suckable tablets or pellets (for example for the treatment of aphthous ulcers) or liposome or microencapsulation preparations.

Ointments, creams and gels, may, for example, be formulated with an aqueous or oily base with the addition of suitable thickening and/or gelling agent and/or solvents. Non limiting examples of such bases can thus, for example, include water and/or an oil such as liquid paraffin or a vegetable oil such as arachis oil or castor oil, or a solvent such as polyethylene glycol. Various thickening agents and gelling agents can be used depending on the nature of the base. Non-limiting examples of such agents include soft paraffin, aluminum stearate, cetostearyl alcohol, polyethylene glycols, woolfat, beeswax, carboxypolymethylene and cellulose derivatives, and/or glyceryl monostearate and/or non-ionic emulsifying agents.

In one embodiment lotions may be formulated with an aqueous or oily base and will in general also contain one or more emulsifying agents, stabilizing agents, dispersing agents, suspending agents or thickening agents.

In one embodiment powders for external application may be formed with the aid of any suitable powder base, for example, talc, lactose or starch. Drops may be formulated with an aqueous or non-aqueous base also comprising one or more dispersing agents, solubilizing agents, suspending agents or preservatives.

Compositions intended for oral use may be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients may be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they can be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate; or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringers solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The nucleic acid molecules of the invention may also be administered in the form of suppositories, e.g., for rectal administration of the drug. These compositions may be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention may be administered parenterally in a sterile medium. The drug, depending on the vehicle and concentration used, may either be suspended or dissolved in the vehicle. Advantageously, adjuvants such as local anesthetics, preservatives and buffering agents may be dissolved in the vehicle.

In other embodiments, the siNA compositions, or conjugates, and/or delivery formulations provided herein for use in pulmonary delivery further comprise one or more surfactants. Suitable surfactants or surfactant components for enhancing the uptake of the compositions of the invention include synthetic and natural as well as full and truncated forms of surfactant protein A, surfactant protein B, surfactant protein C, surfactant protein D and surfactant Protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly (vinyl amine) with dextran and/or alkanoyl side chains, Brij 35, Triton X-100 and synthetic surfactants ALEC, Exosurf, Survan and Atovaquone, among others. These surfactants may be used either as single or part of a multiple component surfactant in a formulation, or as covalently bound additions to the 5 and/or 3 ends of the nucleic acid component of a pharmaceutical composition herein.

b. Combinations

The siNAs and pharmaceutical formulations according to the invention may be administered to a subject alone or used in combination with or include one or more other therapeutic agents, for example, antiviral or anticancer agents. Thus, combinations of the presently disclosed compounds with other antiviral or anti-cancer or chemotherapeutic agents are within the scope of the invention Examples of anti-cancer or chemotherapeutic agents may be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints.

In a further embodiment, therefore, the invention provides a combination comprising an siNA molecule of the invention or a pharmaceutically acceptable salt, solvate or physiologically functional derivative thereof together with one or more therapeutic agents as described herein or as is otherwise known in the art.

Examples of estrogen receptor modulators that may be used in combination with the compounds of the invention include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

Examples of androgen receptor modulators that may be used in combination with the compounds of the invention include, but are not limited to, finasteride and other 5α-reductase inhibitors, nilutamide, flutamide, bicalutamide, liarozole, and abiraterone acetate.

Examples of such retinoid receptor modulators that may be used in combination with the compounds of the invention include, but are not limited to, bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

Examples of cytotoxic agents that may be used in combination with the compounds of the invention include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound that may be used in combination with the compounds of the invention is tirapazamine.

Examples of proteasome inhibitors that may be used in combination with the compounds of the invention include, but are not limited to, lactacystin and bortezomib.

Examples of microtubule inhibitors/microtubule-stabilising agents that may be used in combination with the compounds of the invention include, but are not limited to, paclitaxel, vindesine sulfate. 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide (SEQ ID NO: 539), TDX258, the epothilones (see for example U.S. Pat. Nos. 6,284,781 and 6,288,237) and BMS188797.

Some examples of topoisomerase inhibitors that may be used in combination with the compounds of the invention include, but are not limited to, are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13 (9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane. 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofiro(3,4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, that may be used in combination with the compounds of the invention include, but are not limited to, inhibitors described in PCT Publications WO 01/30768, WO 01/98278, WO 03/050,064, WO 03/050,122, WO 03/049,527, WO 03/049,679, WO 03/049,678, WO04/039774, WO003/079973, WO03/099211, WO003/105855, WO003/106417, WO004/037171, WO04/058148, WO004/058700, WO004/126699, WO05/018638, WO005/019206, WO05/019205, WO05/018547, WO05/017190, US2005/0176776. In an embodiment inhibitors of mitotic kinesins include, but are not limited to inhibitors of KSP, inhibitors of MKLP 1, inhibitors of CENP-E, inhibitors of MCAK, inhibitors of Kif14, inhibitors of Mphosphl and inhibitors of Rab6-KIFL.

Examples of "histone deacetylase inhibitors" that may be used in combination with the compounds of the invention include, but are not limited to, TSA, oxamflatin, PXD101, MG98, valproic acid and scriptaid. Further reference to other histone deacetylase inhibitors may be found in the following manuscript; Miller, T. A. et al. *J. Med. Chem.* 46(24):5097-5116 (2003).

Inhibitors of kinases involved in mitotic progression that may be used in combination with the compounds of the invention include, but are not limited to, inhibitors of aurora kinase, inhibitors of Polo-like kinases (PLK) (in particular inhibitors of PLK-1), inhibitors of bub-1 and inhibitors of bub-R1.

Antiproliferative agents that may be used in combination with the compounds of the invention include, but are not limited to, antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl] adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo (7.4.1.0.0)-tetradeca-2,4,6-trien-9-yl acetic acid ester, swainsonine, lometrexol, dexrazoxane, methioninasc, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents that may be used in combination with the compounds of the invention include those therapeutic agents which have cytotoxic agents or radioisotopes attached to a cancer cell specific or target cell specific monoclonal antibody, such as, for example, Bexxar.

Examples of HMG-CoA reductase inhibitors that may be used that may be used in combination with the compounds of the invention include, but are not limited to, lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314.

Examples of prenyl-protein transferase inhibitors that may be used in combination with the compounds of the invention include, but are not limited to, may be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

Examples of angiogenesis inhibitors that may be used in combination with the compounds of the invention include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); JNCI, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); Cell, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, Nature Biotechnology, Vol. 17, pp. 963-968 (October 1999); Kim et al., *Nature*, 362, 841-844 (1993); WO 00/44777; and WO 00/61186).

Other therapeutic agents that modulate or inhibit angiogenesis may also be used in combination with the compounds of the instant invention and include agents that modulate or inhibit the coagulation and fibrinolysis systems (see review in *Clin. Chem.* La. Med. 38:679-692 (2000)). Examples of such agents that modulate or inhibit the coagulation and fibrinolysis pathways that may be used in combination with the compounds of the invention include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

Agents that interfere with cell cycle checkpoints that may be used in combination with the compounds of the invention include, but are not limited to, inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

Agents that interfere with receptor tyrosine kinases (RTKs) that may be used in combination with the compounds of the invention include, but are not limited to, inhibitors of c-Kit, Eph, PDGF, Flt3 and HBV. Further agents include inhibitors of RTKs as described by Bume-Jensen and Hunter, *Nature*, 411:355-365, 2001.

Inhibitors of cell proliferation and survival signaling pathway that may be used in combination with the compounds of the invention include, but are not limited to, inhibitors of EGFR (for example gefitinib and erlotinib), inhibitors of ERB-2 (for example trastuzumab), inhibitors of IGFR, inhibitors of cytokine receptors, inhibitors of HBV, inhibitors of PI3K (for example LY294002), serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

Apoptosis inducing agents that may be used in combination with the compounds of the invention include, but are not limited to, activators of TNF receptor family members (including the TRAIL receptors).

NSAIDs that are selective COX-2 inhibitors that may be used in combination with the compounds of the invention include, but are not limited to, those NSAIDs disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344, 991, 5,134,142, 5,380,738, U.S. Pat. Nos. 5,393,790, 5,466, 823, 5,633,272, and 5,932,598, all of which are hereby incorporated by reference.

Inhibitors of COX-2 that are particularly useful in combination with the compounds of the invention include: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Angiogenesis inhibitors that may be used in combination with the compounds of the invention include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)-phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Tyrosine kinase inhibitors that may be used in combination with the compounds of the invention include, but are not limited to, N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD 121974.

Combinations with compounds other than anti-cancer compounds are also encompassed in the instant compositions and methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 31:909-913

(1998); *J. Biol. Chem.* 274:9116-9121 (1999); Invest. *Ophthalmol Vis. Sci.* 41:2309-2317 (2000)). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 119:709-717 (2001)). Examples of PPAR-γ agonists and PPAR-γ/α agonists that may be used in combination with the compounds of the invention include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782, 856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al. (*Am J Hum Genet* 61:785-789 (1997)) and Kufe et al. (*Cancer Medicine,* 5th Ed, pp 876-889, BC Decker, Hamilton, 2000). Gene therapy may be used to deliver any tumor suppressing gene. Examples of such genes include, but are not limited to, p53, which may be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy,* August 5(8): 1105-13 (1998)), and interferon gamma (*J Immunol* 164:217-222 (2000)).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim and PEG-filgrastim.

A compound of the instant invention may also be administered with an immunologic-enhancing drug, such as levamisole, isoprinosine and Zadaxin.

A compound of the instant invention may also be useful for treating or preventing liver disease or cancer in combination with other siNA therapeutics.

The compounds of the instant invention may also be administered in combination with γ-secretase inhibitors and/ or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bendamustine hydrochloride (Treanda®; bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott iB Solution (ElliottK B Solution®); eltrombopag (Promacta®); epirubicin (Ellence®; Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®); Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

The invention also provides a combination comprising an siNA molecule of the invention targeting one gene together with another inhibitor targeting a second target gene.

The combinations referred to above may conveniently be presented for use in the form of a pharmaceutical formulation and thus pharmaceutical compositions comprising a combination as defined above together with a pharmaceutically acceptable diluent or carrier represent a further aspect of the invention.

To practice the coordinate administration methods of this disclosure, an siNA molecule is administered simultaneously or sequentially in a coordinated treatment protocol with one or more secondary or adjunctive therapeutic agents described herein or known in the art. The coordinate administration may be done in either order, and there may be a time period while only one or both (or all) active therapeutic agents, individually or collectively, exert their biological activities. A distinguishing aspect of all such coordinate treatment methods is that the siNA molecule(s) present in a composition elicits some favorable clinical response, which may or may not be in conjunction with a secondary clinical response provided by the secondary therapeutic agent. For example, the coordinate administration of an siNA molecule with a secondary therapeutic agent as contemplated herein may yield an enhanced (e.g., synergistic) therapeutic response beyond the therapeutic response elicited by either or both the purified siNA molecule and the secondary therapeutic agent alone.

The individual compounds of such combinations may be administered either sequentially or simultaneously in separate or combined pharmaceutical formulations. In one embodiment, the individual compounds will be administered simultaneously in a combined pharmaceutical formulation.

Thus, the described molecules could be used in combination with one or more known compounds, treatments, or procedures to prevent or treat diseases, disorders, conditions, and traits described herein in a subject or organism as are known in the art, such as other gene inhibitors.

Therapeutic Applications

The present body of knowledge in RNAi research indicates the need for methods that can modulate gene expression for therapeutic use.

Thus, one aspect of the invention comprises a method of treating a subject including, but not limited to, a human suffering from a disease or a condition which is mediated by the action of target gene expression, which method comprises administering to said subject an effective amount of a double-stranded siNA molecule of the invention. In one embodiment of this aspect, the siNA molecules comprises sequence having at least a 15 nucleotides complementary to a target nucleic acid. In other embodiments, the siNA molecule comprises any molecule herein having formula A, B, C, D, E, F, G, H, I, J, K, L, M, N, O or P.

In some embodiments of this aspect, the disease or condition may be cancer, a proliferative, inflammatory, autoimmune, neurologic, ocular, respiratory, metabolic, dermatological, auditory, liver, kidney, or infectious disease as described herein or otherwise known in the art. Thus, in certain embodiments the molecules and compositions of the instant invention may be useful in a method for treating cancer, proliferative, inflammatory, autoimmune, neurologic, ocular, respiratory, metabolic, dermatological, auditory, liver, kidney, or infectious diseases.

In certain embodiments, the administration of the siNA molecule may be via local administration or systemic administration. In other embodiments, the invention features contacting the subject or organism with an siNA molecule of the invention via local administration to relevant tissues or cells, such as lung cells and tissues, such as via pulmonary delivery. In yet other embodiments, the invention features contacting the subject or organism with an siNA molecule of the invention via systemic administration (such as via intravenous or subcutaneous administration of siNA) to relevant tissues or cells in a subject or organism.

siNA molecules of the invention may also used as reagents in ex vivo applications. For example, siNA reagents may be introduced into tissue or cells that are transplanted into a subject for therapeutic effect. The cells and/or tissue may be derived from an organism or subject that later receives the explant, or may be derived from another organism or subject prior to transplantation. The siNA molecules may be used to modulate the expression of one or more genes in the cells or tissue, such that the cells or tissue obtain a desired phenotype or are able to perform a function when transplanted in vivo. In one embodiment, certain target cells from a patient are extracted. These extracted cells are contacted with siNAs targeting a specific nucleotide sequence within the cells under conditions suitable for uptake of the siNAs by these cells (e.g., using delivery reagents such as cationic lipids, liposomes and the like or using techniques such as electroporation to facilitate the delivery of siNAs into cells). The cells are then reintroduced back into the same patient or other patients.

For therapeutic applications, a pharmaceutically effective dose of the siNA molecules or pharmaceutical compositions of the invention is administered to the subject. A pharmaceutically effective dose is that dose required to prevent, inhibit the occurrence, or treat (alleviate a symptom to some extent, preferably all of the symptoms) a disease state. One skilled in the art may readily determine a therapeutically effective dose of the siNA of the invention to be administered to a given subject, by taking into account factors, such as the size and weight of the subject, the extent of the disease progression or penetration, the age, health, and sex of the subject, the route of administration, and whether the administration is regional or systemic. Generally, an amount between 0.1 µg/kg and 140 mg/kg body weight/day of active ingredients is administered dependent upon potency of the siNA of the disclosure. The amount of active ingredient that may be combined with the carrier materials to produce a single dosage form varies depending upon the host treated and the particular mode of administration. Optimal dosing schedules may be calculated from measurements of drug accumulation in the body of the patient. The siNA molecules of the invention may be administered in a single dose or in multiple doses.

siNA molecules of the instant invention may be administered once monthly, once weekly, once daily (QD), or divided into multiple monthly, weekly, or daily doses, such as, for example, but not limitation, twice daily (BID), three times daily (TID), once every two weeks. Persons of ordinary skill in the art may easily estimate repetition rates for dosing based on measured residence times and concentrations of the drug in bodily fluids or tissues.

In addition, the administration may be continuous, i.e., every day, or intermittently. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

Administration

Compositions or formulations may be administered in a variety of ways. Non-limiting examples of administration methods of the invention include oral, buccal, sublingual, parenteral (i.e., intraarticularly, intravenously, intraperitoneally, subcutaneously, or intramuscularly), local rectal administration or other local administration. In one embodiment, the composition of the invention may be administered by insufflation and inhalation. Administration may be accomplished via single or divided doses. In some embodiments, the pharmaceutical compositions are administered intravenously or intraperitoneally by a bolus injection (see, e.g., U.S. Pat. No. 5,286,634).

An siNA molecule with or without a vehicle may be locally delivered by direct injection or by use of an infusion pump. Direct injection of the siNA molecules of this disclosure, whether subcutaneous, intramuscular, or intradermal, may take place using standard needle and syringe methodologies, or by needle free technologies, such as those described in Conroy et al, (1999, *Clin. Cancer Res.* 5:2330) and PCT Publication No. WO 99/31262. For example, but not limitation, lipid nucleic acid particles may be administered by direct injection at the site of disease or by injection at a site distal from the site of disease (see, e.g., Culver, HUMAN GENE THERAPY, MaryAnn Liebert, Inc., Publishers, New York. pp. 70-71(1994)). In one embodiment, the siNA molecules of the invention and formulations or compositions thereof are administered to a cell, subject, or organism as is described herein and as is generally known in the art.

In Vivo Administration

In any of the methods of treatment of the invention, the siNA may be administered to the subject systemically as described herein or otherwise known in the art, either alone as a monotherapy or in combination with additional therapies described herein or as are known in the art. Systemic administration may include, for example, pulmonary (inhalation, nebulization etc.) intravenous, subcutaneous, intramuscular, catheterization, nasopharyngeal, transdermal, or oral/gastrointestinal administration as is generally known in the art.

In any of the methods of treatment or prevention of the invention, the siNA may be administered to the subject locally or to local tissues as described herein or otherwise known in the art, either alone as a monotherapy or in combination with additional therapies as are known in the art. Local administration may include, for example, inhalation, nebulization, catheterization, implantation, direct injection, dermal/transdermal application, patches, stenting, ear/eye drops, or portal vein administration to relevant tissues, or any other local administration technique, method or procedure, as is generally known in the art.

In one embodiment, the siNA molecules of the invention and formulations or compositions thereof are administered to the liver as is generally known in the art (see for example Wen et al., 2004, *World J Gastroenterol.*, 10, 244-9; Murao et al., 2002, *Pharm Res.*, 19, 1808-14; Liu et al., 2003, *gene Ther.*, 10, 180-7; Hong et al., 2003, *J Pharm Pharmacol.*, 54, 51-8; Herrmann et al., 2004, *Arch Virol.*, 149, 1611-7; and Matsuno et al., 2003, *gene Ther.*, 10, 1559-66).

In one embodiment, the invention features the use of methods to deliver the siNA molecules of the instant invention to hematopoietic cells, including monocytes and lymphocytes. These methods are described in detail by Hartmann et al., 1998, *J. Phamacol. Exp. Ther.*, 285(2), 920-928; Kronenwett et al., 1998, *Blood*, 91(3), 852-862; Filion and Phillips, 1997, *Biochim. Biophys. Acta.*, 1329(2), 345-356; Ma and Wei, 1996, *Leuk. Res.*, 20(11/12), 925-930; and Bongartz et al., 1994, *Nucleic Acids Research*, 22(22), 4681-8.

In one embodiment, the siNA molecules of the invention and formulations or compositions thereof are administered directly or topically (e.g., locally) to the dermis or follicles as is generally known in the art (see for example Brand, 2001, *Curr. Opin. Mol. Ther.*, 3, 244-8; Regnier et al., 1998, *J. Drug Target*, 5, 275-89; Kanikkannan, 2002, *BioDrugs*, 16, 339-47; Wraight et al., 2001, *Pharmacol. Ther.*, 90, 89-104; and Preat and Dujardin, 2001, *STP PharmaSciences*, 11, 57-68). In one embodiment, the siNA molecules of the invention and formulations or compositions thereof are administered directly or topically using a hydroalcoholic gel formulation comprising an alcohol (e.g., ethanol or isopropanol), water, and optionally including additional agents such isopropyl myristate and carbomer 980. In other embodiments, the siNA are formulated to be administered topically to the nasal cavity. Topical preparations may be administered by one or more applications per day to the affected area; over skin areas occlusive dressings may advantageously be used. Continuous or prolonged delivery may be achieved by an adhesive reservoir system.

In one embodiment, an siNA molecule of the invention is administered iontophoretically, for example to a particular organ or compartment (e.g., the eye, back of the eye, heart, liver, kidney, bladder, prostate, tumor, CNS etc.). Non-limiting examples of iontophoretic delivery are described in, for example, WO 03/043689 and WO 03/030989, which are incorporated by reference in their entireties herein.

In one embodiment, the siNA molecules of the invention and formulations or compositions thereof are administered to the lung as is described herein and as is generally known in the art. In another embodiment, the siNA molecules of the invention and formulations or compositions thereof are administered to lung tissues and cells as is described in U.S. Patent Publication Nos. 2006/0062758; 2006/0014289; and 2004/0077540.

Aerosols and Delivery Devices a. Aerosol Formulations

The compositions of the present invention, either alone or in combination with other suitable components, may be made into aerosol formulations (i.e., they may be "nebulized") to be administered via inhalation (e.g., intranasally or intratracheally) (see, Brigham et al., *Am. J. Sci.*, 298:278 (1989)). Aerosol formulations may be placed into pressurized acceptable propellants, such as dichlorodifluoromethane, propane, nitrogen, and the like.

In one embodiment, the siNA molecules of the invention and formulations thereof are administered via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions may be prepared by grinding dried or lyophilized nucleic acid compositions, and then passing the micronized composition through, for example, a 400 mesh screen to break up or separate out large agglomerates. A solid particulate composition comprising the siNA compositions of the invention may optionally contain a dispersant which serves to facilitate the formation of an aerosol as well as other therapeutic compounds. A suitable dispersant is lactose, which may be blended with the nucleic acid compound in any suitable ratio, such as a 1 to 1 ratio by weight.

Spray compositions comprising siNA molecules or compositions of the invention may, for example, be formulated as aqueous solutions or suspensions or as aerosols delivered from pressurized packs, such as a metered dose inhaler, with the use of a suitable liquefied propellant. In one embodiment, aerosol compositions of the invention suitable for inhalation may be either a suspension or a solution and generally contain an siNA molecule comprising formula (A), and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants. Non-limiting examples include oleic acid, lecithin or an oligolactic acid or derivative such as those described in WO94/21229 and WO98/34596 and co-solvents for example ethanol. In one embodiment a pharmaceutical aerosol formulation of the invention comprising a compound of the invention and a fluorocarbon or hydrogen-containing chlorofluorocarbon or mixtures thereof as propellant, optionally in combination with a surfactant and/or a co-solvent. The aerosol formulations of the invention may be buffered by the addition of suitable buffering agents.

Aerosol formulations may include optional additives including preservatives if the formulation is not prepared sterile. Non-limiting examples include, methyl hydroxybenzoate, anti-oxidants, flavorings, volatile oils, buffering agents and emulsifiers and other formulation surfactants. In one embodiment, fluorocarbon or perfluorocarbon carriers are used to reduce degradation and provide safer biocompatible non-liquid particulate suspension compositions of the invention (e.g., siNA and/or LNP formulations thereof).

In another embodiment, a device comprising a nebulizer delivers a composition of the invention (e.g., siNA and/or LNP formulations thereof) comprising fluorochemicals that are bacteriostatic thereby decreasing the potential for microbial growth in compatible devices.

Capsules and cartridges comprising the composition of the invention for use in an inhaler or insufflator, of for example gelatin, may be formulated containing a powder mix for inhalation of a compound of the invention and a suitable powder base such as lactose or starch. In one embodiment, each capsule or cartridge contains an siNA molecule comprising formula (A), and one or more excipients. In another embodiment, the compound of the invention may be presented without excipients such as lactose The aerosol compositions of the present invention may be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. In one embodiment, the particulate range may be from 1 to 5 microns. In another embodiment, the particulate range may be from 2 to 3 microns. Particles of non-respirable size which are included in the aerosol tend to deposit in the throat and be swallowed, and the quantity of non-respirable particles in the aerosol is thus minimized. For nasal administration, a particle size in the range of 10-500 um is preferred to ensure retention in the nasal cavity.

In some embodiments, an siNA composition of the invention is administered topically to the nose for example, for the treatment of rhinitis, via pressurized aerosol formulations, aqueous formulations administered to the nose by pressurized pump or by nebulization. Suitable formulations contain water as the diluent or carrier for this purpose. In certain embodiments, the aqueous formulations for administration of the composition of the invention to the lung or nose may be provided with conventional excipients such as buffering agents, tonicity modifying agents and the like.

b. Devices

The siNA molecules of the invention may be formulated and delivered as particles and/or aerosols as discussed above and dispensed from various aerosolization devices known by those of skill in the art.

Aerosols of liquid or non-liquid particles comprising an siNA molecule or formulation of the invention may be produced by any suitable means, such as with a device comprising a nebulizer (see for example U.S. Pat. No. 4,501,729) such as ultrasonic or air jet nebulizers.

Solid particle aerosols comprising an siNA molecule or formulation of the invention and surfactant may be produced with any solid particulate aerosol generator. One type of solid particle aerosol generator used with the siNA molecules of the invention is an insufflator. A second type of illustrative aerosol generator comprises a metered dose inhaler ("MDI"). MDIs containing siNA molecules or formulations taught herein may be prepared by methods of the art (for example, see Byron, above and WO96/32099).

The siNA molecules may also be formulated as a fluid formulation for delivery from a fluid dispenser, such as those described and illustrated in WO05/044354.

In certain embodiments of the invention, nebulizer devices are used in applications for conscious, spontaneously breathing subjects, and for controlled ventilated subjects of all ages. The nebulizer devices may be used for targeted topical and systemic drug delivery to the lung. In one embodiment, a device comprising a nebulizer is used to deliver an siNA molecule or formulation of the invention locally to lung or pulmonary tissues. In another embodiment, a device comprising a nebulizer is used to deliver a an siNA molecule or formulation of the invention systemically.

Other Applications/Uses of siNA Molecules of the Invention

The siNA molecules of the invention may also be used for diagnostic applications, research applications, and/or manufacture of medicants.

In one aspect, the invention features a method for diagnosing a disease, trait, or condition in a subject comprising administering to the subject a composition of the invention under conditions suitable for the diagnosis of the disease, trait, or condition in the subject.

In one embodiment, siNA molecules of the invention may be used to down regulate or inhibit the expression of proteins arising from haplotype polymorphisms that are associated with a trait, disease or condition in a subject or organism. Analysis of genes, or protein or RNA levels may be used to identify subjects with such polymorphisms or those subjects who are at risk of developing traits, conditions, or diseases described herein. These subjects may be amenable to treatment, for example, treatment with siNA molecules of the invention and any other composition useful in treating diseases related to target gene expression. As such, analysis of protein or RNA levels may be used to determine treatment type and the course of therapy in treating a subject. Monitoring of protein or RNA levels may be used to predict treatment outcome and to determine the efficacy of compounds and compositions that modulate the level and/or activity of certain peptides and/or proteins associated with a trait, disorder, condition, or disease.

In another embodiment, the invention comprises use of a double-stranded nucleic acid according to the invention for use in the manufacture of a medicament. In an embodiment, the medicament is for use in treating a disease or a condition that is mediated by the action of one or more target genes. In one embodiment, the medicant is for use in treating any disease or condition herein or otherwise known in the art. In some embodiments, the medicament is for use in the treatment of cancer.

In certain embodiments, the siNA molecules of the invention may be for use in a method for treating any disease or condition contemplated herein.

In certain embodiments, the siNA molecules of the invention may be used in a method for treating cancer.

EXAMPLES

The invention will now be illustrated with the following non-limiting examples. Those of skill in the art will readily recognize a variety of non-critical parameters which can be changed or modified to yield essentially the same results.

Example 1: Identification of Highly Potent Stabilized siNA Molecules with Prolonged Duration The development of therapeutic siRNAs with drug-like properties is dependent on the incorporation of chemical modifications to improve duration of RNA knockdown and potency while minimizing non-specific (off-target) effects and stimulation of innate immunity. The growing diversity of siRNA delivery vehicles has expanded beyond traditional lipid encapsulated nano-particles to include dynamic polymer conjugates and conjugation with various targeting ligands including antibodies, sugars, and cholesterol. Many of these delivery strategies expose the siRNA cargo to serum and/or cellular nucleases which can compromise the structural integrity and in vivo efficacy of both unmodified siRNAs and modified siRNAs which have not been optimized for nuclease stability. Additionally, these alternative delivery strategies employ different targeting ligands and mechanisms of endosomal escape, thereby exposing the siRNA cargo to different cellular micro-environments with varied pH and nuclease content. Therefore optimization of siRNA stability is needed for development of therapeutic siRNAs with cross-delivery platform compatibility and potentially enhanced duration due to improvement of stability attributes along with pharmacokinetic and pharmacodynamic profiles of the siRNA molecule.

The modified siNA molecules disclosed herein may improve serum stability while maintaining robust potency. The modification criteria of the present invention may be applied to any siRNA sequence.

Traditional lipid nanoparticle (LNP) delivery vehicles encapsulate the siRNA and thus limit exposure to serum nucleases upon intravenous dosing of siRNA-LNP complexes in animals. The adoption of alternative delivery platforms such as polymer conjugates (PC) or direct attachment of delivery targeting ligands (e.g., galactosamine, folate, cholesterol, etc.) exposes the siRNA molecule to serum nucleases and potentially hostile intracellular environments. Therefore the development of a stabilized siRNAs with strategies that may be applied to siRNA irrespective of sequence to improve nuclease/chemical stability while retaining requisite RNA knockdown and potency may be useful in conjunction with heterogeneous delivery vehicle platforms.

Short Interfering Nucleic Acid Molecules of Formula a, B, C, D, E, F, G, H, I, J, K, L, M, N, O and P The discovery and development of siNA molecules having Formula A-P originated with experiments aimed that exploring the role of placing 2-O-methyl chemical modifications at specific positions within the siNA guide strand. The rationale was to identify specific positions of the guide strand that were tolerant or sensitive to chemical modifications and to use this information to map interactions between the guide strand and the RNA binding pocket within the Ago2 protein. This position-based approach was also a distinct and complementary to the approach of assigning modifications based on the sequence content of the siNA (e.g. purine or pyrimidine).

As a starting point, a siNA motif having alternating 2-O-methyl modifications at odd positions on the guide strand (e.g. positions 1, 3, 5, etc) and ribonucleotides at even positions (e.g. positions 2, 4, 6, etc.) was altered in such a manner that the unmodified ribose residues at the even positions were replaced with 2-deoxy-2-fluoro modifications. siNA molecules with such alternating motifs were then designed to target ApoB and were complexed with a PVE-based polymer conjugate delivery vehicle for characterization in vivo. The siNA complexes were administered to mice by intravenous injection at a concentration of 3 mg per kg (mpk). A significant improvement in ApoB mRNA reduction was conferred by the inclusion of 2-deoxy-2-fluoro modifications within the guide strand as shown in FIG. 5.

Despite the promising results seen with the R-008357859-000V guide strand having alternating 2-O-methyl and 2-deoxy-2-fluoro modifications in the context of polymer conjugate delivery (FIG. 5), the same guide strand motif was not effective when delivered to mice using a tetra-GalNAc conjugate (4GalNAc) single chemical entity (SCE) delivery platform. FIG. 6 shows that for both ApoB and SSB targets, the SCE delivered guide strands having alternating 2-O-methyl and 2-deoxy-2-fluoro modifications did not significantly reduce mRNA expression levels in mice. Nevertheless, an ApoB targeted tetra-GalNAc conjugate (4GalNAc) single chemical entity (SCE) siNA having 2-O-methyl pyrimidines and 2-deoxy-2-fluoro purines with phosphorothioate modified ribonucleotides at positions 1-3 of the guide strand, when administered to mice via SC delivery, did demonstrate dose dependent activity in mice (FIG. 7). However, when a SSB targeted sequence having 2-O-methyl pyrimidines and 2-deoxy-2-fluoro purines with 2-deoxy, 2-deoxy-2-fluoro, and 2-O-methyl respectively at positions 1, 2, and 3 of the guide strand was tested as a tetra-GalNAc conjugate, no knockdown was observed (FIG. 7). This result is surprising since both of these siNAs were shown to be very stable in serum and in $S_9$ fractions (Table 6) and were functional when delivered as a polymer conjugate.

The key difference between the sequences tested is the presence of three phosphorothioate linkages at the 5 end of guide strand in the active motif. To determine if the presence of the three 5-terminal phosphorothioates could rescue activity of SSB-GalNAc conjugate, the SSB siNA construct was modified accordingly. As shown in FIG. 8, the SSB siNA construct having phosphorothioates at the 5-end of the guide strand showed activity as a tetra-GalNAc conjugate. This was a surprising and unexpected result based on the serum/S9 stability and robust activity of the SSB sequence having 2-O-methyl pyrimidines and 2-deoxy-2-fluoro purines with 2-deoxy, 2-deoxy-2-fluoro, and 2-O-methyl at positions 1, 2, and 3 of the guide strand when administered as a polymer conjugate (data not shown).

Next, increasing the phosphorothioate content was explored to determine if the siNA SCE activity could be increased further since the phosphorothioate linkages could be playing role in improving pharmacokinetics, for example by binding to serum proteins. As shown as in FIG. 9, increasing the phosphorothioate linkages on either the guide or passenger strand did not improve activity. Note that all these constructs retained the three 5-terminal guide strand phosphorothioate linkages. To elucidate this further, the specific placement of phosphorothioate linkages was investigated in both the guide and passenger strands. The data clearly showed that the placement of phosphorothioate linkages at the 5-end of the guide strand, specifically between first and second nucleotide, is important for activity (FIG. 10). Because the phosphorothioate linkages at other positions did not impact the RNAi activity, it is the placement of phosphorothioate linkages at the 5-end of the guide strand, and not their general presence within the siNA sequence, that was found to be important for in vivo activity with single chemical entity delivery modalities.

To investigate the role of phosphorothioate linkages, the stability of various siNA modification motifs were tested in different biological media including serum, S9, and lysosomal lysate fractions. This data was compared to in vivo metabolism data observed in mouse and rhesus. The lysosomal lysate fractions are enriched for late endosome/lysosome vesicles and serve as a source of lysosomal enzymes. The benefit of improved stability in lysosomal lysates at pH 5.5 and in mouse or rhesus liver was observed with the inclusion of 5-terminal guide strand phosphorothioate linkages (Table 6). These results demonstrate that the siNA single chemical entity conjugates require more stability in during exposure to the endocytosis pathway compared to polymer conjugate delivery systems.

The presence of phosphorothioates or 2 modifications alone may not be sufficient to provide adequate stability for siNA conjugate. For example, siNA molecules having phosphorothioates at the 5-end of the guide strand are still susceptible to degradation in lysosomal lysates as well in mouse or rhesus liver (Table 6). The poor in vivo activity of the siNA molecules having 2-modifications at the 5 end of the guide strand can be rescued by the inclusion of phosphorothioate modifications at the 5-end of the guide strands at position 1 and optionally through position 3. In one example, siNAs targeting CTNNB1 were synthesized and conjugated to the same SCE delivery vehicle used in FIG. 6. In vivo knockdown of CTNNB1 mRNA demonstrates that the inclusion of phosphorothioates in conjunction with 2 sugar modifications at the 5-end of the guide strand may result in significantly improved efficacy (FIG. 11). Therefore, the presence of 2-sugar modifications in combination with phosphorothioate modification of the 5-end of the guide strand appear to provide optimized stability and activity (Table 6 and 7). Application of this principle has resulted in alternate 2-O-methyl and 2-deoxy-2-fluoro modified siNA molecules that show robust activity as GalNAc conjugates. As shown in FIG. 12, these molecules demonstrate >90% knockdown of ApoC3 mRNA in vivo. As shown in Table 6, application of this principle demonstrates robust stability in lysosomal lysates as well as in vivo in mice. These results hold true in vivo in non-human primes (rhesus) as well (FIG. 13).

Materials and Methods
siNA Synthesis

For each oligonucleotide of a target sequence, the two individual, complementary strands of the siNA were synthesized separately using solid phase synthesis, then purified separately by reversed phase solid phase extraction (SPE). The complementary strands were annealed to form the double strand (duplex) and delivered in the desired concentration and buffer of choice.

Briefly, the single strand oligonucleotides were synthesized using phosphoramidite chemistry on an automated solid-phase synthesizer, using procedures as are generally known in the art (see for example U.S. application Ser. No. 12/064,014). A synthesis column was packed with solid support derivatized with the first nucleoside residue (natural or chemically modified). Synthesis was initiated by detritylation of the acid labile 5'-O-dimethoxytrityl group to release the 5'-hydroxyl. A suitably protected phosphoramidite and a suitable activator in acetonitrile were delivered simultaneously to the synthesis column resulting in coupling of the amidite to the 5'-hydroxyl. The column was then washed with a solvent, such as acetonitrile. An oxidizing solution, such as an iodine solution was pumped through the column to oxidize the phosphite triester linkage P(III) to its phosphotriester P(V) analog. Unreacted 5 hydroxyl groups were capped using reagents such as acetic anhydride in the presence of 2,6-lutidine and N-methylimidazole. The elongation cycle was resumed with the detritylation step for the next phosphoramidite incorporation. This process was repeated until the desired sequence was synthesized. The synthesis concluded with the final 5'-terminus protecting group (trityl or 5'-O-dimethoxytrityl).

Upon completion of the synthesis, the solid-support and associated oligonucleotide were dried under argon pressure or vacuum. Aqueous base was added and the mixture was heated to effect cleavage of the succinyl linkage, removal of the cyanoethyl phosphate protecting group, and deprotection of the exocyclic amine protection.

The following process was performed on single strands that do not contain ribonucleotides. After treating the solid support with the aqueous base, the mixture was filtered to separate the solid support from the deprotected crude synthesis material. The solid support was then rinsed with water, which is combined with the filtrate. The resultant basic solution allows for retention of the 5'-O-dimethoxytrityl group to remain on the 5' terminal position (trityl-on).

For single strands that contain ribonucleotides, the following process was performed. After treating the solid support with the aqueous base, the mixture was filtered to separate the solid support from the deprotected crude synthesis material. The solid support was then rinsed with dimethylsulfoxide (DMSO), which was combined with the filtrate. Fluoride reagent, such as triethylamine trihydrofluoride, was added to the mixture, and the solution was heated. The reaction was quenched with suitable buffer to provide a solution of crude single strand with the 5'-O-dimethoxytrityl group on the final 5' terminal position.

The trityl-on solution of each crude single strand was purified using chromatographic purification, such as SPE RPC purification. The hydrophobic nature of the trityl group permits stronger retention of the desired full-length oligo than the non-tritylated truncated failure sequences. The failure sequences were selectively washed from the resin with a suitable solvent, such as low percent acetonitrile. Retained oligonucleotides were then detritylated on-column with trifluoroacetic acid to remove the acid-labile trityl group. Residual acid was washed from the column, a salt exchange was performed, and a final desalting of the material commenced. The full-length oligo was recovered in a purified form with an aqueous-organic solvent. The final product was then analyzed for purity (HPLC), identity (Maldi-TOF MS), and yield (UV A260). The oligos were dried via lyophilization or vacuum condensation.

Annealing:

Based on the analysis of the product, the dried oligos were dissolved in appropriate buffers followed by mixing equal molar amounts (calculated using the theoretical extinction coefficient) of the sense and antisense oligonucleotide strands. The solution was then analyzed for purity of duplex by chromatographic methods and desired final concentration. If the analysis indicated an excess of either strand, then the additional non-excess strand was titrated until duplexing was complete. When analysis indicated that the target product purity has been achieved the material was delivered and ready for use.

Further Synthesis Steps for Commercial Preparations

Once analysis indicates that the target product purity has been achieved after the annealing step, the material is transferred to the tangential flow filtration (TFF) system for concentration and desalting, as opposed to doing this prior to the annealing step.

Ultrafiltration: The annealed product solution is concentrated using a TFF system containing an appropriate molecular weight cut-off membrane. Following concentration, the product solution is desalted via diafiltration using Milli-Q water until the conductivity of the filtrate is that of water.

Lyophilization: The concentrated solution is transferred to a bottle, flash frozen and attached to a lyophilizer. The product is then freeze-dried to a powder. The bottle is removed from the lyophilizer and is now ready for use.

Synthesis of siNA Single Chemical Entities (SCE)

TetraGalNAc Synthesis and Preparation of TetraGalNAc-siNA Conjugates

Synthesis of (2S)-2, 6-bis[bis (prop-2-yn-1-yl) amino]hexanoic acid (1)

Into a 2000-mL 3-necked round-bottom flask purged and maintained with an inert atmosphere of nitrogen was placed a solution of (2S)-2,6-diaminohexanoic acid (50 g, 342.03 mmol, 1.00 equiv) in acetonitrile (1000 mL) and heated to 50° C. To this was added potassium hydroxide (22.6 g, 0.4025 mol, 1.00 equiv, 85%). The resulting solution was stirred for 30 min. Then 3-bromoprop-1-yne (29.5 mL, 1.00 equiv) was added. The resulting solution was stirred for 1 hour at 50° C. additional potassium hydroxide (22.6 g, 0.4025 mol, 1.00 equiv) was added to the solution and stirred for 30 min at 50° C. To this was added 3-bromoprop-1-yne (29.5 mL, 1.00 equiv). The resulting solution was stirred for 1 hour. To this was added potassium hydroxide (22.6 g, 0.4025 mol, 1.00 equiv) again. The resulting solution was stirred for 30 min at 50° C., followed by addition of more 3-bromoprop-1-yne (29.5 mL, 1.00 equiv). The resulting solution was stirred for 1 hour. To this was added potassium hydroxide (22.6 g, 0.4025 mol, 1.00 equiv). The resulting solution was stirred for 30 min. To this was added 3-bromoprop-1-yne (29.5 mL, 1.00 equiv). The resulting solution was stirred for 3 hours. The reaction mixture was cooled to 25° C. with a water/ice bath. The solid was filtered out. The filtrate was adjusted to pH 4 with HCl (6M). The solid was filtered out. The filtrate was concentrated under vacuum. The residue was applied onto a silica gel column and eluted with dichloromethane/methanol (100:1-25:1). This resulted in (2S)-2, 6-bis[bis (prop-2-yn-1-yl)amino] hexanoic acid (1) as a light yellow oil.

MS(ES, m/z): 297.2, [M−H]$^-$ $^1$HNMR (CDCl$_3$, 500 MHz, ppm): 3.62 (d, J=2.0 Hz, 4H), 3.52-3.49 (m, 1H), 3.50 (d, J=2.4 Hz, 4H), 2.62 (t, J=7.1 Hz, 2H), 2.30 (t, J=2.4 Hz, 2H), 2.27 (t, J=2.4 Hz, 2H), 1.88-1.79 (m, 2H), 1.60-1.53 (m, 2H), 1.52-1.43 (m, 2H).

Synthesis of 2-(2-hydroxyethoxy)ethyl 4-methylbenzenesulfonate (3)

Into a 2000-mL 3-necked round-bottom flask purged and maintained with an inert atmosphere of nitrogen was placed a solution of 2-(2-hydroxyethoxy)ethan-1-ol (2, 42.4 g, 399.55 mmol, 1.00 equiv) in dichloromethane (1000 mL) and triethylamine (27.9 g, 275.72 mmol, 0.25 equiv). To the above was added p-toluenesulfonyl chloride (19.1 g, 100.18 mmol, 0.50 equiv). After stirred for 1 h at 25° C., the resulting mixture was washed with 1×500 mL of aq. potassium hydrosulfate (IM) and 1×500 mL of aq. sodium bicarbonate (5%) respectively. The organic layer was dried over anhydrous sodium sulfate and concentrated under vacuum. The residue was applied onto a silica gel column and eluted with dichloromethane/methanol (100:1). This resulted in 2-(2-hydroxyethoxy)ethyl 4-methylbenzenesulfonate (3) as a colorless oil.

Synthesis of 2-(2-azidoethoxy)ethan-1-ol (4)

Into a 500-mL round-bottom flask purged and maintained with an inert atmosphere of nitrogen was placed a solution of 2-(2-[[(4-2-(2-hydroxyethoxy)ethyl 4-methylbenzenesulfonate (3, 50 g, 192.08 mmol, 1.00 equiv) in N,N-dimethylformamide (250 mL). This was followed by the addition of sodium azide (18.79 g, 289.03 mmol, 1.50 equiv) at 25° C. The resulting solution was stirred for 5 h at 100° C. in an oil bath. The reaction mixture was cooled and filtered. The filtrate was concentrated under vacuum. The residual solution was diluted with 1000 mL of dichloromethane and washed with 1×500 mL of water. The organic layer was dried over anhydrous sodium sulfate and concentrated under vacuum. The residue was applied onto a silica gel column and eluted with dichloromethane/methanol (80:1). This resulted in 2-(2-azidoethoxy)ethan-1-ol (4) as a colorless oil.

$^1$HNMR (CDCl$_3$, 400 MHz, ppm): 3.42-3.45 (t, J=4.8 Hz, 2H), 3.63-3.65 (t, J=4.8 Hz, 2H), 3.71-3.74 (t, J=4.8 Hz, 2H), 3.71-3.79 (m, 2H).

Synthesis of (3R,4R,5R,6R)-3-acetamido-6-(acetoxymethyl)tetrahydro-2H-pyran-2,4,5-triyl triacetate (6)

Into a 2000-mL 3-necked round-bottom flask purged and maintained with an inert atmosphere of nitrogen was placed a solution of (3R,4R,5R,6R)-3-amino-6-(hydroxymethyl) tetrahydro-2H-pyran-2,4,5-triol hydrochloride (5, 120 g, 556.50 mmol, 1.00 equiv) in pyridine (1200 mL). This was followed by the addition of acetic anhydride (341.6 g, 3.35 mol, 6.00 equiv) dropwise with stirring at 0° C. The resulting solution was stirred overnight at 25° C. The reaction was then quenched by the addition of 8000 mL of water/ice. The solid was collected by filtration. This resulted in (3R,4R, 5R,6R)-3-acetamido-6-(acetoxymethyl)tetrahydro-2H-pyran-2,4,5-triyl triacetate (6) as a white solid.

Synthesis of (3aR,5R,6R,7R,7aR)-5-(acetoxymethyl)-2-methyl-5,6,7,7a-tetrahydro-3aH-pyrano[3,2-d]oxazole-6,7-diyl diacetate (7)

Into a 2000-mL round-bottom flask purged and maintained with an inert atmosphere of nitrogen was placed a solution of (3R,4R,5R,6R)-3-acetamido-6-(acetoxymethyl) tetrahydro-2H-pyran-2,4,5-triyl triacetate (6, 30 g, 77.05 mmol, 1.00 equiv) in dichloromethane (1500 mL), then added iron (III) chloride (30 g, 184.95 mmol, 2.40 equiv). The resulting mixture was stirred for 2 h at 25° C. The reaction was then quenched by the addition of 1000 mL of water/ice. The organic layer was washed with 1×1000 mL of sodium aq. bicarbonate and 1×1000 mL of water, dried over anhydrous sodium sulfate and concentrated under vacuum. This resulted in (3aR,5R,6R,7R,7aR)-5-(acetoxymethyl)-2-methyl-5,6,7,7a-tetrahydro-3aH-pyrano[3,2-d]oxazole-6,7-diyl diacetate (7, 20 g, 79%) as yellow oil.

$^1$HNMR (CDCl$_3$, 300 MHz, ppm): 2.03 (s, 9H), 2.12 (s, 3H), 3.97-4.27 (m, 4H), 4.90-4.93 (m, J=3.3 Hz, 1H), 5.45-5.47 (t, J=3.0 Hz, 1H), 5.98-6.00 (d, J=6.6 Hz, 1H).

Synthesis of (2R,3R,4R,5R,6R)-5-acetamido-2-(acetoxymethyl)-6-[2-(2-azidoethoxy)ethoxy]tetrahydro-2H-pyran-3,4-diyl diacetate (8)

Into a 500-mL round-bottom flask purged and maintained with an inert atmosphere of nitrogen was placed a solution of (3aR,5R,6R,7R,7aR)-5-(acetoxymethyl)-2-methyl-5,6,7, 7a-tetrahydro-3aH-pyrano[3,2-d]oxazole-6,7-diyl diacetate (7, 40 g, 121.47 mmol, 1.00 equiv) in 1,2-dichloroethane (200 mL), 2-(2-azidoethoxy)ethan-1-ol (4, 23.89 g, 182.18 mmol, 1.50 equiv). To the above several 4A zeolite was added. The resulting mixture was stirred for 1 h at 25° C. Then trimethylsilyl trifluoromethanesulfonate (10.8 mL, 0.50 equiv) was added. After stirred overnight at 25° C., the reaction mixture was diluted with 500 mL of dichloromethane and washed with 1×500 mL of water, 1×500 mL of aq. sodium bicarbonate and 1×500 mL of water. The organic layer was dried over anhydrous sodium sulfate and concentrated under vacuum. The residue was applied onto a silica gel column and eluted with dichloromethane/methanol (100: 1). This resulted in (2R,3R,4R,5R,6R)-5-acetamido-2-(acetoxymethyl)-6-[2-(2-azidoethoxy)ethoxy]tetrahydro-2H-pyran-3,4-diyl diacetate (8) as a colorless oil.

MS(m/z): 461.1, [M+H]+

$^1$HNMR (CDCl$_3$, 500 MHz, ppm) 5.78 (d, J=8.90 Hz, 1H), 5.36 (d, J=2.9 Hz, 1H), 5.22 (dd, J=11.2, 3.6 Hz, 1H), 4.77 (d, J=8.3 Hz, 1H), 4.19-4.12 (m, 2H), 4.11-4.05 (m, 1H), 3.98-3.92 (m, 2H), 3.82-3.78 (m, 1H), 3.71-3.63 (m, 4H), 3.49-3.38 (m, 2H), 2.16 (s, 3H), 2.05 (s, 3H), 2.01 (s, 3H), 1.97 (s, 3H).

Synthesis of (S)-2,6-bis(bis((I-(2-(2-(((2R,3R,4R,5R,6R)-3-acetamido-4,5-diacetoxy-6-(acetoxymethyl)tetrahydro-2H-pyran-2-yloxy)ethoxy)ethyl)-1H-1,2,3-triazol-4-yl)methyl)amino)hexanoic acid (9, tetraGalNAc acetate)

Into a 250-mL round bottom flask purged and maintained with an inert atmosphere of nitrogen was charged (2S)-2,6-bis [bis (prop-2-yn-1-yl) amino]hexanoic acid (1, 1.0 g, 1.0 equiv), (2R,3R,4R,5R,6R)-5-acetamido-2-(acetoxymethyl)-6-[2-(2-azidoethoxy)ethoxy]tetrahydro-2H-pyran-3,4-diyl diacetate (8, 9.26 g, 6.0 equiv), anhydrous THF 50 mL, CuBrSMe$_2$ (0.138 g, 0.20 equiv), and anhydrous DBU (1.5 ml, 3.0 equiv) in respective order. The resulting solution was stirred for 16 h at room temperature, quenched with acetic acid (0.75 mL, 4.0 equiv), treated with MP-TMT resin (Part No: 801472, from Biotage) (9 g), aged at room temperature for 16 h, filtered, and concentrated the filtrate to a foam solid. The solid was then dissolved in CH$_2$Cl$_2$ (140 mL), and washed with AcOH/NaCl solution (140 mL). The AcOH/NaCl solution was prepared with 1 mL AcOH and 100 mL 20% NaCl solution. The bottom organic layer was concentrated, and purified on a SiO$_2$ column (220 g), eluting with CH$_2$Cl$_2$/MeOH. This resulted in (S)-2,6-bis(bis((1-(2-(2-(((2R,3R,4R,5R,6R)-3-acetamido-4,5-diacetoxy-6-(acetoxymethyl)tetrahydro-2H-pyran-2-yl)oxy)ethoxy)ethyl)-1H-1,2,3-triazol-4-yl)methyl)amino)hexanoic acid (9) as a white solid. MS(m/z): 2139.5, [M+H]+

Synthesis of (S)-2,6-bis(bis((1-(2-(2-(((2R,3R,4R,5R,6R)-3-acetamido-4,5-dihydroxy-6-(hydroxymethyl)tetrahydro-2H-pyran-2-yl)oxy)ethoxy)ethyl)-1H-1,2,3-triazol-4-yl)methyl)amino)hexanoic acid (10, tetraGalNAc)

Into a 250-mL round-bottom flask purged and maintained with an inert atmosphere of nitrogen was charged (S)-2,6-bis(bis((1-(2-(2-(((2R,3R,4R,5R,6R)-3-acetamido-4,5-diacetoxy-6-(acetoxymethyl)tetrahydro-2H-pyran-2-yl)oxy)ethoxy)ethyl)-1H-1,2,3-triazol-4-yl)methyl)amino)hexanoic acid (9, 6.9 g, 1.0 equiv), Na$_2$CO$_3$ (6.83 g, 20 eq), water (56 mL), and MeOH (32 mL) in respective order. The reaction was aged at room temperature for 16 h, concentrated to residue, redissoved in water (50 mL), and purified on Combiflash C18 gold reverse column (415 g), eluting with water/MeCN. After concentration under vacuum, the product was dissolved in minimum amount of water, and lyophilized to obtain (S)-2,6-bis(bis((1-(2-(2-(((2R,3R,4R,5R,6R)-3-acetamido-4,5-dihydroxy-6-(hydroxymethyl)tetrahydro-2H-pyran-2-yl)oxy)ethoxy)ethyl)-1H-1,2,3-triazol-4-yl)methyl)amino)hexanoic acid (10) as a white solid.

MS(m/z): 1657 [M+Na]+

$^1$HNMR (D20, 500 MHz, ppm): 8.05 (s, 2H), 7.91 (s, 2H), 4.62 (t, J=5.0 Hz, 4H), 4.57 (t, J=5.0 Hz, 4H), 4.45-4.41 (d, J=8.6 Hz, 4H), 3.99-3.82 (m, 28H), 3.80-3.61 (m, 28H), 3.14 (t, J=7.1 Hz, 1H), 2.52 (broad s, 2H), 1.99 (s, 6H), 1.98 (s, 6H), 1.73 (m, 2H), 1.60 (m, 2H), 1.29 (m, 2H).

Synthesis of tetraGalNAc-siNA conjugate (12) via tetraGalNAc acetate 9

To a solution of tetraGalNAc acetate (9, 58.7 mg, 0.027 mmol) in acetonitrile (1.5 ml) was added DIPEA (2.2 mg, 0.055 mmol) and HATU (10.44 mg, 0.027 mmol). The mixture was stirred at room temperature for 30 min, transferred into a solution siNA (11, 0.014 mmol) in water (1.5 ml) and acetonitrile (1.5 ml) via a syringe pump over 20 min, and stirred for 30 min before it was concentrated under vacuum down to 1.5 mL. Sodium carbonate (218 mg, 2.059 mmol) was then added, followed by MeOH (0.50 ml). The resulting solution was stirred at room temperature for 16 h, concentrated, purified via dialysis, and lyophilized to yield compound 12. The same approach can be used to generate compound 13.

RNA Silencing Activity of Compounds Transfected with Lipofectamine in Luciferase Constructs:

HEK293 cells stably transfected with luciferase vector that contains target sites for siNA in 3 UJTR of renilla luciferase were generated. These cells were seeded on 96-well tissue culture plates (Corning: #3903) at a density of 7.5e3 cells per well in DMEM 10% serum media. Cellular plates were then incubated at 37° C./5% CO2 for 24 hr. After incubation, plates were treated with test compounds co-transfected with transfection reagent Lipofectamine 2000 (invitrogen: #11668-019) in Opti-MEM (Gibco: #31985) in accordance to manufacturers protocol. The treatment concentrations ranged from 10 nM to 0.03 pM. Treated plates were then incubated for 24 hr at 37° C./5% CO2. Following treatment incubation, cells were lysed and processed in accordance to Dual-Glo™ Luciferase Assay (Promega: E2920) and read on a TECAN safire2 plate reader.

RNA Silencing Activity of Compounds Transfected with Lipofectamine in HepG2 Cells:

HepG2 cells (ATCC: HB-8065) were seeded on collagen coated plates (BioCoat: 356649) at a density of 7.5e3 cells per well in DMEM 10% serum media. Cellular plates were then incubated at 37° C./5% CO2 for 24 hr. After incubation, plates were treated with test compounds co-transfected with transfection reagent Lipofectamine 2000 (invitrogen: 11668-019) in Opti-MEM (Gibco: 31985) in accordance to invitrogen protocol. The treatment concentrations ranged from 10 nM to 0.03 pM. Treated plates were then incubated for 24 hr at 37° C./5% CO$_2$. Following treatment incubation, cells were lysed with PLA Buffer (AB: 4448542) in accordance to supplied protocol. Resulting cell lysate was reverse transcribed to cDNA using High Capacity cDNA Kit (AB: 4368813) and run through qPCR using Life Technology 7900.

RNA Silencing Activity of Compounds in Cryopreserved Primary Rhesus Hepatocytes:

Cryogenically preserved male rhesus primary hepatocyte cells were obtained from Celsis. Frozen cells were defrosted for 2 minutes in a 37° C. water bath and resuspended using thawing/plating media (Gibco: CM3000) at a ratio of 1-3 mL frozen cells per 50 mL of T/P media, in order to dilute out DMSO. Cells were spun down at 80×g for 5 minutes to pellet cells. Pelleted cell were then diluted in T/P media for seeding of cells to center 60 wells of a 96 well collagen coated plate (Biocoat: 354649) at 4.0e4 cells per well. Seeded cells were incubated for 18 hr at 37° C./5% CO$_2$. After incubation, cells were washed once with Maintenance media (Gibco: CM4000) and aspirated dry. Immediately following wash, cells were treated with SCE diluted in maintenance media at a concentration range of 2 uM to 5 pM and allowed to incubate for 48 hr at 37° C./5% $CO_2$. Following treatment incubation, cells were lysed with PLA Buffer (AB: 4448542) in accordance to provided protocol. Resulting cell lysate was reverse transcribed to cDNA using High Capacity cDNA Kit (AB: 4368813) and run through qPCR using Life Technology 7900.

In Vivo Evaluation of RNAi Activity.

CD1 female mice were dosed by subcutaneous injection in 200 ul volume. Animals were observed for behavioral or physiological changes. Animals were sacrificed 72 hrs post dose by CO2 asphyxiation followed by ex-sanguination via cardiac puncture. The liver samples were as 3 mm punches from the medial lobe and put into RNAlater tubes for isolation of total RNA. The mRNA knockdown analysis was conducted by Taqman analysis using standard procedures.

In Vitro siNA Metabolic Stability Assay

Test siNAs were incubated in either 100% mouse serum or 0.4 mg/mL rat lysosomal lysate at 20 ug/mL. To extract oligonucleotides from biomatrices the 96-well Clarity OTX cartridge plates (Phenomenex, Torrance, Calif.) were used with a 96-well plate vacuum manifold following the manufacturer's instructions. The eluants were next lyophilized over night then reconstituted in 1 mM EDTA for LC/MS analysis. Data acquisition and processing for the LC/MS system wereperformed using Excalibur software. A Hypersil Gold C18 reversed phase column (2.1×50 mm) was used. The column temperature was maintained at 70 C. The mobile phases used were as follows: A, 1.7 mM triethylamine (TEA) and 100 mM 1,1,1,3,3,3-hexafluoro-2-propanol (HFIP) in HPLC water; and B, methanol. The sample injection volume was 10 uL, and the flow rate was maintained at 0.4 mL/min. The mass spectrometer was a linear ion trap coupled to an Orbitrap allowing high-resolution mass measurements (LTQ-Orbitrap, Thermo Fisher Scientific, San Jose, Calif.), fitted with an ESI source, and operated in negative ion mode. Zero charge state siNA and metabolite masses were obtained by deconvolution of charge states using Thermo Extract software. Metabolites were identified by comparison of experimental masses to theoretical nuclease metabolite masses.

In Vivo siNA Liver Metabolite Identification

Approximately 150 mg to 300 mg liver tissue was homogenized in 1 mL of Tris-EDTA buffer, pH 7.2 using a tissue homogenizer with a stainless steel ball at 4 C, for 2 min. siNA and their metabolites were extracted from liver lysates using a combination liquid-liquid and solid phase extraction. A 500 mL volume of 5% ammonium hydroxide solution was added to each sample mixture, vortexed for and centrifuged for 10 min at 14 000 rpm. The aqueous phase was transferred to a fresh tube and an equal volume of a buffer (17.2 mM TEA and 200 mM HFIP, pH8.5) was added to the aqueous phase and the sample tubes were vortexed. The sample solutions were then extracted on an Oasis HLB SPE cartridge (10 mg, Waters, MA, USA). The SPE cartridges were first conditioned with 1 mL of acetonitrile followed by two aliquots of 1 mL of buffer (8.6 mM TEA and 100 mM HFIP, pH 8.5). The sample solutions were then loaded onto the SPE cartridges. The cartridges were washed with two aliquots of 0.5 mL buffer (8.6 mM TEA and 100 mM HFIP, pH8.5) followed by 0.5 mL of 100 mM triethylammonium bicarbonate (TEAB). Samples were eluted with two aliquots of 0.5 mL 100 mM TEA in 60:40 (v/v) acetonitrile/water solution. The eluants were next lyophilized over night then reconstituted in 1 mM EDTA for LC/MS analysis. All LC/MS analyses were performed using a Thermo LTQ-Orbitrap mass spectrometer (Thermo Scientific, Inc.) Chromatographic separation of siNAs and their metabolites was conducted using a Thermo Hypersil Gold C18 column (2.1×50 mm) at a flow rate of 0.2 mL/min. The column was heated to 70 C to denature the siNA duplex. Mobile phase 'A' consisted of 1.7 mM TEA and 100 mM HFIP (pH 7.5) in water, and mobile phase 'B' consisted of methanol. The effluent from the HPLC column was introduced into the ion source of the LTQ-Orbitrap mass spectrometer operated in negative mode. Zero charge state siNA and metabolite masses were obtained by deconvolution of charge states using Thermo Extract software. Metabolites were identified by comparison of experimental masses to theoretical nuclease metabolite masses.

SCHEME 1

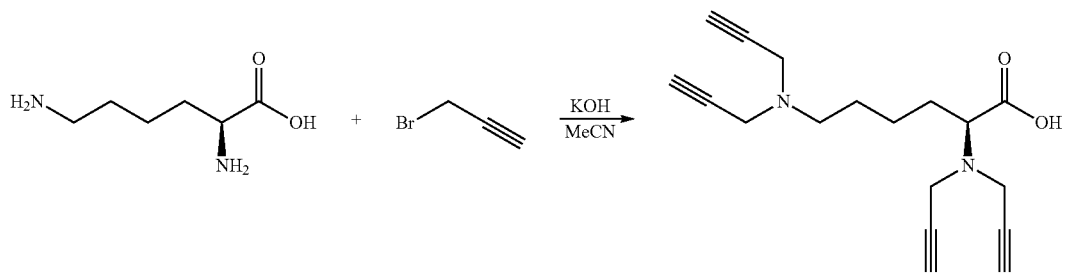

91 92
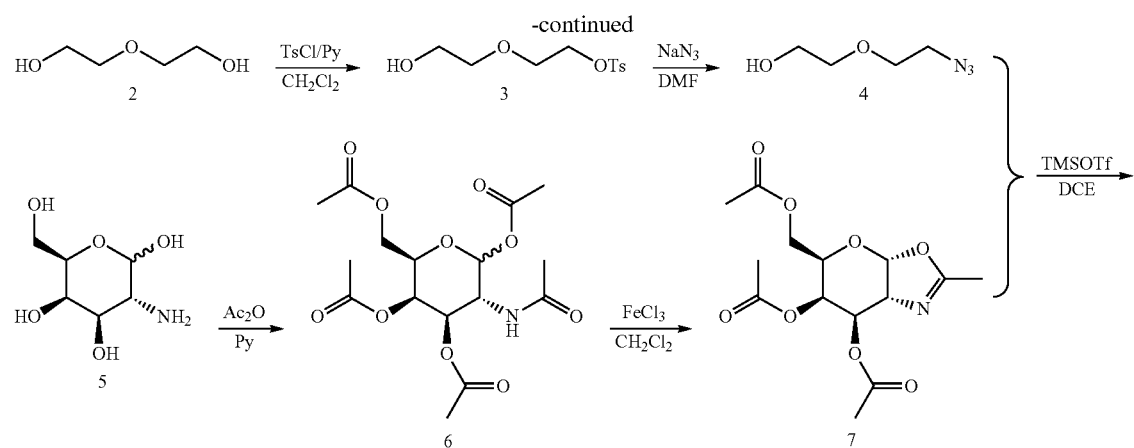
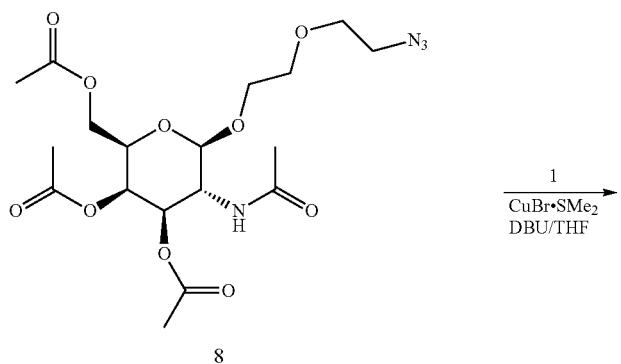
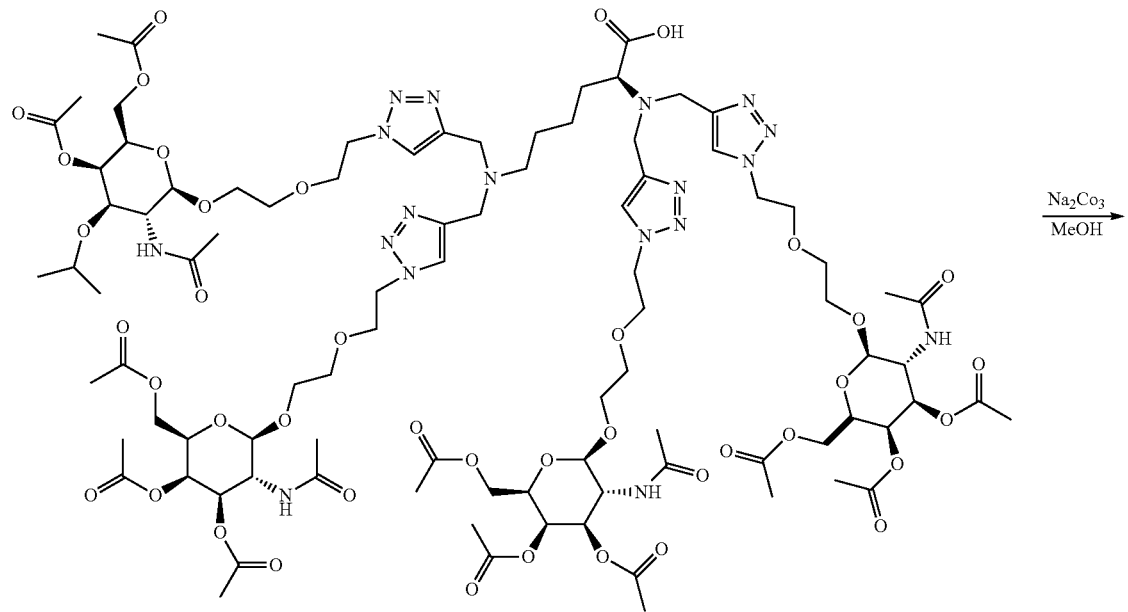

-continued

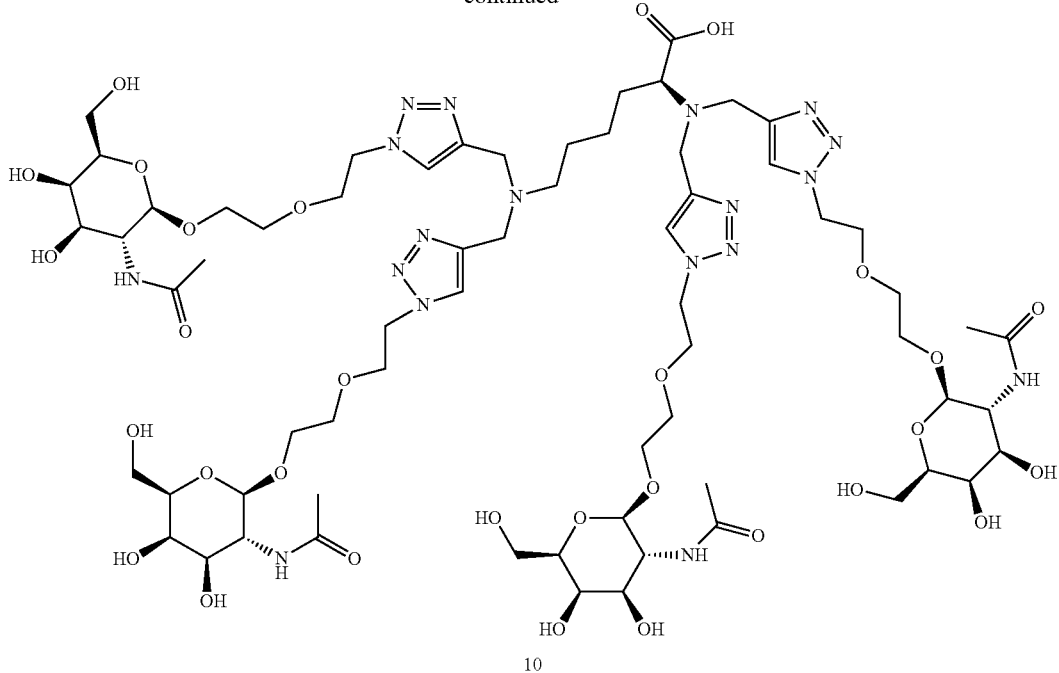

10

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

TABLE 1

| Duplex ID | R Number | Target Site (human) | SEQ ID NO: 1 | Target Sequence | Modified Sequence | SEQ ID NO: 2 |
|---|---|---|---|---|---|---|
| 129302-DC | R-008491391-000N | 1797 | 1 | CUGUUGGAUUGAUUCGAAA | UuUcGaAuCaAuCcAaCaGUsU | 7 |
| 129302-DC | R-008491391-000N | 1797 | 1 | CUGUUGGAUUGAUUCGAAA | GalNAcB CUgUUggaUUgaUUCgaaaUsU B | 8 |
| 129303-DC | R-008491393-000F | 1797 | 1 | CUGUUGGAUUGAUUCGAAA | GalNAcB CUgUUggaUUgaUUCgaaaUsU B | 8 |
| 129303-DC | R-008491393-000F | 1797 | 1 | CUGUUGGAUUGAUUCGAAA | UsUsUscGaAuCaAuCcAaCaGUsU | 9 |
| 129304-DC | R-008491389-000R | 1797 | 1 | CUGUUGGAUUGAUUCGAAA | GalNAcB CUgUUggaUUgaUUCgaaaUsU B | 8 |
| 129304-DC | R-008491389-000R | 1797 | 1 | CUGUUGGAUUGAUUCGAAA | uuuCgaaUCaaUCcaaCagUsU | 10 |
| 129305-DC | R-008491392-000X | 1797 | 1 | CUGUUGGAUUGAUUCGAAA | GalNAcB CUgUUggaUUgaUUCgaaaUsU B | 8 |
| 129305 DC | R-008491392-000X | 1797 | 1 | CUGUUGGAUUGAUUCGAAA | usususCgaaUCaaUCcaaCagUsU | 11 |
| 132037-DC | R-008499711-000V | 1797 | 1 | CUGUUGGAUUGAUUCGAAA | GalNAcB CUgUUggaUUgaUUCgaaaUsU B | 8 |
| 132037-DC | R-008499711-000V | 1797 | 1 | CUGUUGGAUUGAUUCGAAA | pUsusUscGaAuCaAuCcAaCaGUsU | 12 |
| 132038-DC | R-008499712-000D | 1797 | 1 | CUGUUGGAUUGAUUCGAAA | GalNAcB CUgUUggaUUgaUUCgaaaUsU B | 6 |

TABLE 1-continued

| Duplex ID | R Number | Target Site (human) | SEQ ID NO: 1 | Target Sequence | Modified Sequence | SEQ ID NO: 2 |
|---|---|---|---|---|---|---|
| 132038-DC | R-008499712-000D | 1797 | 1 | CUGUUGGAUUGAUUCGAAA | pususUscGaAuCaAuCcAaCaGUsU | 13 |
| 131992-DC | R-00849416-000P | 1797 | 1 | CUGUUGGAUUGAUUCGAAA | GalNAcB CUgUUggaUUgaUUCgaaaUsU B | 8 |
| 131992-DC | R-008498416-000P | 1797 | 1 | CUGUUGGAUUGAUUCGAAA | pUsusUscGaAuCaAuCcAaCaGUsU | 14 |
| 131996-DC | R-00849418-000G | 1797 | 1 | CUGUUGGAUUGAUUCGAAA | GalNAcB CUgUUggaUUgaUUCgaaaUsU B | 8 |
| 131996-DC | R-00849418-000G | 1797 | 1 | CUGUUGGAUUGAUUCGAAA | pususUscGaAuCaAuCcAaCaGUsU | 15 |
| 132039-DC | R-008499709-000X | 1797 | 1 | CUGUUGGAUUGAUUCGAAA | GalNAcB CUgUUggaUUgaUUCgaaaUsU B | 8 |
| 132039-DC | R-008499709-000X | 1797 | 1 | CUGUUGGAUUGAUUCGAAA | UsusUscGaAuCaAuCcAaCaGUsU | 16 |
| 132040-DC | R-008499710-000L | 1797 | 1 | CUGUUGGAUUGAUUCGAAA | GalNAcB CUgUUggaUUgaUUCgaaaUsU B | 8 |
| 132040-DC | R-008499710-000L | 1797 | 1 | CUGUUGGAUUGAUUCGAAA | ususUscGaAuCaAuCcAaCaGUsU | 17 |
| 132041-DC | R-008499713-000M | 1797 | 1 | CUGUUGGAUUGAUUCGAAA | GalNAcB CUgUUggaUUgaUUCgaaaUsU B | 8 |
| 132041-DC | R-008499713-000M | 1797 | 1 | CUGUUGGAUUGAUUCGAAA | ususUscGaAuCaAuCcAaCaGUsU | 18 |
| 142795-DC | R-008543009-000U | 273 | 2 | GGAGCAAGUUUACUGACAA | pUsusGsuCaGuAaAcUuGcUcCUsU | 19 |
| 142795-DC | R-008543009-000U | 273 | 2 | GGAGCAAGUUUACUGACAA | GalNAcB gGaGcAaGuUuAcUgAcAaUsU B | 20 |
| 142804-DC | R-008543018-000C | 442 | 3 | AAGUAUGUUCUCAUGUCUU | pasAsgsAcAuGaGaAcauAcUuUsU | 21 |
| 142804-DC | R-008543018-000C | 442 | 3 | AAGUAUGUUCUCAUGUCUU | GalNAcB AaGuAuGuUcUcAuGuCuUUsU B | 22 |
| 126735-DC | R-008417879-000B | 9514 | 4 | CUUUAACAAUUCCUGAAAU | AsUsUsUCaggaaUUguUaaagUsU | 23 |
| 126735-DC | R-008417879-000B | 9514 | 4 | CUUUAACAAUUCCUGAAAU | GalNAcB CUUUaaCaaUUCCUgaaaUTsT B | 24 |
| 129230-DC | R-008480267-000V | 291 | 5 | ACAACAGACUUUAAUGUAA | TuACaUUaaagUCugUUgUUsU | 25 |
| 129230-DC | R-008480267-000V | 291 | 5 | ACAACAGACUUUAAUGUAA | GalNAcB aCaaCagaCUUUaaUgUaaTsT B | 26 |
| 129282-DC | R-008484697-000P | 291 | 5 | ACAACAGACUUUAAUGUAA | GalNAcB aCaaCagaCUUUaaUgUaaTsT B | 26 |
| 129282-DC | R-008484607-000P | 291 | 5 | ACAACAGACUUUAAUGUAA | UsUsAsCaUUaaagUCugUUgUUsU | 27 |
| 129283-DC | R-008491315-000J | 291 | 5 | ACAACAGACUUUAAUGUAA | TsusAsCaUUaaagUCugUUgUUsU | 28 |
| 129283-DC | R-008491315-000J | 291 | 5 | ACAACAGACUUUAAUGUAA | GalNAcaCaaCagaCUUUaaUgUaaTsT B | 29 |
| 133061-DC | R-008502422-000F | 1797 | 6 | UUUCGAAUCAAUCCAACAG | GalNAcB CUgUUggaUUgaUUCgaaaUsU B | 8 |
| 133061-DC | R-008502422-000F | 1797 | 6 | UUUCGAAUCAAUCCAACAG | UsUsUcGaAuCaAuCcAaCaGUsU | 30 |

TABLE 1-continued

| Duplex ID | R Number | Target Site (human) | SEQ ID NO: 1 | Target Sequence | Modified Sequence | SEQ ID NO: 2 |
|---|---|---|---|---|---|---|
| 133064-DC | R-008502424-000Y | 1797 | 6 | UUUCGAAUCAAUCCAACAG | GalNAcB CUgUUggaUUgaUUCgaaaUsU B | 8 |
| 133064-DC | R-008502424-000Y | 1797 | 6 | UUUCGAAUCAAUCCAACAG | UusUcGaAuCaAuCcAaCaGUsU | 31 |
| 133064-DC | R-008502424-000Y | 1797 | 6 | UUUCGAAUCAAUCCAACAG | GalNAcB CUgUUggaUUgaUUCgaaaUsU B | 8 |
| 133064-DC | R-008502424-000Y | 1797 | 6 | UUUCGAAUCAAUCCAACAG | UusUcGaAuCaAuCcAaCaGUsU | 31 |
| 61657-DC | R-008291260-000L | 9514 | 4 | CUUUAACAAUUCCUGAAAU | LB CUUUAACAAUUCCUGAAAUTsT B | 32 |
| 61657-DC | R-008291260-000L | 9514 | 4 | CUUUAACAAUUCCUGAAAU | AUUUCAGGAAUUGUUAAAGUsU | 33 |
| 81858-DC | R-008357859-000V | 9514 | 4 | CUUUAACAAUUCCUGAAAU | LB CUUUAACAAUUCCUGAAAUTsT B | 32 |
| 81858-DC | R-008357859-000V | 9514 | 4 | CUUUAACAAUUCCUGAAAU | AuUuCaGgAaUuGuUaAaGUsU | 34 |
| 115748-DC | R-008461704-000E | 9514 | 4 | CUUUAACAAUUCCUGAAAU | AuUuCaGgAaUuGuUaAaGUsU | 34 |
| 115748-DC | R-008461704-000E | 9514 | 4 | CUUUAACAAUUCCUGAAAU | LB CUUUaaCaaUUCCUgaaaUTsT B | 35 |
| 115750-DC | R-008462079-000W | 291 | 5 | ACAACAGACUUUAAUGUAA | LB aCaaCagaCUUUaaUgUaaTsT B | 36 |
| 115750-DC | R-008462079-000W | 291 | 5 | ACAACAGACUUUAAUGUAA | UuAcAuUaAaGuCuGuUgUUsU | 37 |
| 110573-DC | R-008428355-000S | 1797 | 1 | CUGUUGGAUUGAUUCGAAA | UuUcGaAuCaAuCcAaCaGUsU | 7 |
| 110573-DC | R-008428355-000S | 1797 | 1 | CUGUUGGAUUGAUUCGAAA | LB CUgUUggaUUgaUUCgaaaUsU B | 38 |
| 128797-DC | R-008490480-000C | 1797 | 1 | CUGUUGGAUUGAUUCGAAA | UsusUscGaAuCaAuCcAaCaGUsU | 9 |
| 128797-DC | R-008490480-000C | 1797 | 1 | CUGUUGGAUUGAUUCGAAA | LB CUgUUggaUUgaUUCgaaaUsU B | 38 |
| 57407-DC | R-008277564-000P | 9514 | 4 | CUUUAACAAUUCCUGAAAU | AsUsUsUCaggaaUUguUaaagUsU | 23 |
| 57407-DC | R-008277564-000P | 9514 | 4 | CUUUAACAAUUCCUGAAAU | LB CUUUaaCaaUUCCUgaaaUTsT B | 35 |
| 129288-DC | R-008491383-000N | 9514 | 4 | CUUUAACAAUUCCUGAAAU | AsUsUsUsCaggaaUUguUaasasgsUsU | 39 |
| 129288-DC | R-008491383-000N | 9514 | 4 | CUUUAACAAUUCCUGAAAU | GalNAcB CsUsUsUsaaCaaUUCCUgaasasUsTsT B | 40 |
| 129289-DC | R-008491382-000E | 9514 | 4 | CUUUAACAAUUCCUGAAAU | AsUsUsUsCaggaaUUguUaaagUsU | 23 |
| 129289-DC | R-008491382-000E | 9514 | 4 | CUUUAACAAUUCCUGAAAU | GalNAcB CsUsUsUsaaCaaUUCCUgaasasUsTsT B | 40 |
| 129290-DC | R-008491377-000F | 9514 | 4 | CUUUAACAAUUCCUGAAAU | AsUsUsUsCaggaaUUguUaaagUsU | 41 |
| 129290-DC | R-008491377-000F | 9514 | 4 | CUUUAACAAUUCCUGAAAU | GalNAcB CUUUaaCaaUUCCUgaasasUsTsT B | 42 |
| 129291-DC | R-008491378-000P | 9514 | 4 | CUUUAACAAUUCCUGAAAU | GalNAcB CUUUaaCaaUUCCUgaaaUTsT B | 24 |

TABLE 1-continued

| Duplex ID | R Number | Target Site (human) | SEQ ID NO: 1 | Target Sequence | Modified Sequence | SEQ ID NO: 2 |
|---|---|---|---|---|---|---|
| 129291-DC | R-008491378-000P | 9514 | 4 | CUUUAACAAUUCCUGAAAU | AsUsUsUsCaggaaUUguUaasasgsUsU | 39 |
| 129292-DC | R-008491380-000M | 9514 | 4 | CUUUAACAAUUCCUGAAAU | AsUsUsUCaggaaUUguUaaagUsU | 23 |
| 129292-DC | R-008491380-000M | 9514 | 4 | CUUUAACAAUUCCUGAAAU | GalNAcB CsUsUsUsaaCaaUUCCUgaaaUTsT B | 43 |
| 133063-DC | R-008502423-000P | 1797 | 6 | UUUCGAAUCAAUCCAACAG | GalNAcB CUgUUggaUUgaUUCgaaaUsU B | 8 |
| 133063-DC | R-008502423-000P | 1797 | 6 | UUUCGAAUCAAUCCAACAG | UuUscGaAuCaAuCcAaCaGUsU | 44 |
| 133057-DC | R-008502426-000R | 1797 | 6 | UUUCGAAUCAAUCCAACAG | GalNAcB CUgUUggaUUgaUUCgaaaUsU B | 8 |
| 133057-DC | R-008502426-000R | 1797 | 6 | UUUCGAAUCAAUCCAACAG | UsuUscGaAuCaAuCcAaCaGUsU | 45 |
| 133058-DC | R-008502427-000Z | 1797 | 6 | UUUCGAAUCAAUCCAACAG | GalNAcB CUgUUggaUUgaUUCgaaaUsU B | 8 |
| 133058-DC | R-008502427-000Z | 1797 | 6 | UUUCGAAUCAAUCCAACAG | UusUscGaAuCaAuCcAaCaGUsU | 46 |
| 133066-DC | R-008502428-000H | 1797 | 6 | UUUCGAAUCAAUCCAACAG | GalNAcB CUuUUggaUUgaUUCgaaaUsU B | 8 |
| 133066-DC | R-008502428-000H | 1797 | 6 | UUUCGAAUCAAUCCAACAG | UsusUcGaAuCaAuCcAaCaGUsU | 47 |
| 133055-DC | R-008502429-000S | 1797 | 6 | UUUCGAAUCAAUCCAACAG | GalNAcB CUuUUggaUUgaUUCgaaaUsU B | 8 |
| 133055-DC | R-008502429-000S | 1797 | 6 | UUUCGAAUCAAUCCAACAG | UsuUcGaAuCasAuCcAaCaGsUsU | 48 |
| 133056-DC | R-008502430-000F | 1797 | 6 | UUUCGAAUCAAUCCAACAG | GalNAcB CUgUUggaUUgaUUCgaaaUsU B | 8 |
| 133056-DC | R-008502430-000F | 1797 | 6 | UUUCGAAUCAAUCCAACAG | UuUcGaAuCaAuCcAaCsasGsUsU | 49 |
| 133062-DC | R-008502431-000P | 1797 | 6 | UUUCGAAUCAAUCCAACAG | GalNAcB CUgUUggaUUgaUUCgaaaUsU B | 8 |
| 133062-DC | R-008502431-000P | 1797 | 6 | UUUCGAAUCAAUCCAACAG | UuUcGaAuCsasAsuCcAaCaGUsU | 50 |
| 133065-DC | R-008502432-000Y | 1797 | 6 | UUUCGAAUCAAUCCAACAG | GalNAcB CUgUUggaUUgaUUCgaaaUsU B | 8 |
| 133065-DC | R-008502432-000Y | 1797 | 6 | UUUCGAAUCAAUCCAACAG | UsusUscsGaAuCaAuCcAaCaGUsU | 51 |
| 129278-DC | R-008489620-000E | 9514 | 4 | CUUUAACAAUUCCUGAAAU | GalNAcB CUUUaaCaaUUCCUgaaaUTsT B | 24 |
| 129278-DC | R-008489620-000E | 9514 | 4 | CUUUAACAAUUCCUGAAAU | AuUuCaGgAaUuGuUaAaGUsU | 34 |
| 129287-DC | R-008489628-000Z | 291 | 5 | ACAACAGACUUUAAUGUAA | GalNAcB aCaaCagaCUUUaaUgUaaTsT B | 26 |
| 129287-DC | R-008489628-000Z | 291 | 5 | ACAACAGACUUUAAUGUAA | UuAcAuUaAaGuCuGuUgUUsU | 37 |

TABLE 1-continued

| Duplex ID | R Number | Target Site (human) | SEQ ID NO: 1 | Target Sequence | Modified Sequence | SEQ ID NO: 2 |
|---|---|---|---|---|---|---|
| 104995-DC | R-008415011-000K | 9514 | 4 | CUUUAACAAUUCCUGAAAU | LB CUUUaaCaaUUCCUgaaaUUsU B | 52 |
| 104995-DC | R-008415011-000K | 9514 | 4 | CUUUAACAAUUCCUGAAAU | au TUCaggaaUUguUaaagUsU | 53 | wherein:
A, U, C, and G = Adenosine, Uridine, Cytidine and Guanosine ribonucleotides respectively
a, u, c and g = 2'-deoxy-2'-fluoro(2'-F) modified Adenosine, Uridine, Cytidine and Guanosine respectively
A, U, C, and G = 2'-O-methyl (2'-OMe) modified Adenosine, Uridine, Cytidine and Guanosine respectively
A, U, C, and G = 2'-deoxy-2' (2'-H) modified Adenosine, Uridine, Cytidine and Guanosine respectively
B = inverted abasic
T = thymidine
s = phosphorothioate linkage
u = 2'-benzyl Uridine
p = terminal phosphate
LB = animohexyl phosphate linker - inverted abasic cap-------
GalNAcB = tetraGalNAc-animohexyl phosphate linker - inverted abasic cap-------

TABLE 2

| Sequence | SEQ ID |
|---|---|
| CGLFEAIEEFIENLWELLIDGWYGYGRKKRRQRR | 54 |
| CGLFEAIEGFIENGWEGMIDGWYGYGHKKHHQHH | 55 |
| C-bAla-LFEAIEGFIENGWEGMIDGWYGYGRKKRRQRR | 56 |
| CGLFEAIEGFIENGLKGLIDWWYGYGRKKRRQRR | 57 |
| CGLFEAIEGFIEWGWEGMIDGWYGYGRKKRRQRR | 58 |
| CRRQRRKKRGYGYWGDIMGEWGNEIFGEIAEFLG | 59 |
| CGLFEAIEGFIENGWEGMIDGWYGYGRKKRRQR | 60 |
| CYGRKKRRQRRGLFEAIEGFIENGWEGMIDGWYG | 61 |
| CIFGAIAGFIKNILKGLIDG | 62 |
| CIFGAIAGFIRNIW | 63 |
| CGLFHALLHLLHSLWHGLLHAWYGYGHKKHHQHR | 64 |
| CGLFEAIEGLIENGWEGMIDGWYGYGRKKRRQRR | 65 |
| CGLFELIEGFIENGWEGMIDGWYGYGRKKRRQRR | 66 |
| CGLFEAIEGFIENGWEGLIDGWYGYGOOOOOQRR (O = ornithine) | 67 |
| CGLFGAIEGFIENGWEGLIDGWYGYGRKKRRQRR | 68 |
| CGLFEAIEGFLENGWEGMIDGWYGYGRKKRRQRR | 69 |
| CGLFEAIEGFIENGLEGMIDGWYGYGRKKRRQRR | 70 |
| CGLFGAIEGFIENGWEGMIDGWYGYGRKKRRQRR | 71 |
| CGLFEAIEGFIENGWEG-Nle-IDGWYGYGRKKRRQRR | 72 |
| CGIFGAIAGFIKNIWKGLIDW | 73 |
| CYGRKKRRQRRGLFEAIEGFIENGWKGLIDAWYG | 74 |
| CGLLEALEGLLESLWEGLLEAWYGYGRKKRRQRR | 75 |
| CGLFEAIEGFIENGWEGMIDNWYGYGRKKRRQRR | 76 |
| CIFGAIAGFIKNIWEGLIEAWYGLHLLHHLLHHLHHLLHHLHL | 77 |
| CIFGAIAGFIKNIWEGLIDAF | 78 |
| CIFGAIAGFIKNIWEGLI | 79 |

TABLE 2-continued

| Sequence | SEQ ID |
|---|---|
| CGLFEAIEGFIENGWEGMIDGWYGYGRKKRRQRRK(stearyl) | 80 |
| CGLFEAIAGFIEGGWPGLINGWYGYGRKKRRQRRLHLLHHLLHHLHHLLHHLLHLLHHLLHHL | 81 |
| CGLFEAIEGFIENGWEGMIDGWYGGGGLHLLHHLLHHLHHLLHHLLHLLHHLLHHL | 82 |
| CGLFEAIEGFIENGWEGMIDGWYGLHLLHHLLHHLHHLLHHLLHL | 83 |
| CGLFEALLELLESLWELLLEAYGRKKRRQRR | 84 |
| CGLFEAIEGFIENGWEGMIDGWYGYGRKKRRQRR | 85 |
| CGLFEAIEGFIENGWEGMADGWYGYGRKKRRQRR | 86 |
| CGIFGAIAGFIKNIWEGLIDWWYGYGRKKRRQRR | 87 |
| CGFLPAIAGILSQLFEGLIDGWYGYGRKKRRQRR | 88 |
| CFFGAIWGFIKSIL | 89 |
| CIFGAIAGFIKNIWKGLIDWWYG | 90 |
| CGLFEAIEGFIWNGWEGMIDGWYGYGRKKRRQRR | 91 |
| CGLFEAIAEFIENGWEGMIDGWYGYGRKKRRQRR | 92 |
| CYGRKKRRQRRGLFEAIEGFIENGWKGLIDWWYG | 93 |
| CGLFEAIEGFIEEGWEGMIDGWYGYGRKKRRQRR | 94 |
| CGLFEAIEGFIENAWEGMIDGWYGYGRKKRRQRR | 95 |
| CGLFEAIEGFIENGWEGMIDLWYGYGRKKRRQRR | 96 |
| CRLLRLLLRLWRRLLRLLR | 97 |
| CGGFEAIEGFIENGWEGMIDGWYGYGRKKRRQRR | 98 |
| CGLFEKIEGFIENGWEGMIDGWYGYGRKKRRQRR | 99 |
| CGLFEAIEGFIENGWENMIDGWYGYGRKKRRQRR | 100 |
| CIFGAIAGFIKNILKGL | 101 |
| CIFGAIAGFIKNILKGLIDGWYG | 102 |
| CGLFEAIEGFIENGWEGMIDGWYG-(PEG)3-YGRKKRRQRR | 103 |
| CGLFEALLELLESLWELLLEAYGRKKRRQRRLHLLHHLLHHLHHLLHHLLHLLHHLLHHL | 104 |
| CYGRKKRRQRRWEAALAEALAEALAEHLAEALAEALEALAA | 105 |
| CIFGAIAGFIKNIWEGLIDGWYGKLALKLALKALKAALKLA | 106 |
| CFFGAIWEFIRSILEGLIDGWYGYGRKKRRQRR | 107 |
| CGLFHALLHLLHSLWHLLLHAWYGYGRKKRRQRR | 108 |
| CGLFHALLHLLHSLWHLLLHAWYGYGHKKHHQHR | 109 |
| CGLFGALLELLESLWKGLLEWYGRKKRRQRR | 110 |
| CRRQRRKKRGYGYWGDILGEWGNEIFGEIAEFLG | 111 |
| CGLFEALEGFLENGWEGLLDGWYGYGROORRQRR (O = ornithine) | 112 |
| CGLFGEIEELIENGLKNLIDWWYGYGRKKRRQRR | 113 |
| CRRQRRKKRGYGYWWDILGKWGNEIFGEIAEFLG all (D) aminos | 114 |
| CGIFGAIAGFIKNIL | 115 |
| CGIFGAIAGLLKNIFK | 116 |
| CIFGAIAGFIKNIWKGLIDW | 117 |
| CIFGAIAGFIKNIWK | 118 |

TABLE 2-continued

| Sequence | SEQ ID |
|---|---|
| CGLFEEIEGFIENGWEGLIDWWYGYGHKKHHQHR | 119 |
| CGLFGEIEELIENGLKNLIDWWYGYGHKKHHQHR | 120 |
| CGLFEEIEEFIENGWEGLIDWWYGYGHKKHHQHR | 121 |
| stearyl-WEAALAEALAEALAEHLAEALAEALEALAAYGRKKRRQRRC | 122 |
| CGLFEAIEGFIENGWKGLIDGWYGGLFEAIEGFIENGWKGLIDWWYG | 123 |
| CGFFHAFFHFFHSFWHGFFEA | 124 |
| CGNFGEIEELIEEGLENLIDWWNG | 125 |
| CFFGAIWEFIRNILEGF | 126 |
| CFPGAIWEFIHSIL | 127 |
| CGLFHALLHLLHSLWHGLLEA | 128 |
| CIFGAIAGFIKNIWEGL | 129 |
| CIFGAIAGLLKNIFEGLIDGWYGYGRKKRRQRR | 130 |
| CGFIGAIANLLSKIFEGLIDGWYGYGRKKRRQRR | 131 |
| CGLFEAIEELIENLWKGLIDAWYGYGRKKRRQRR | 132 |
| CGIFGAIAGLLKNIFKGLIDA | 133 |
| CGIFGAIAGLLKNIFKGLIDW | 134 |
| CGIFFAIAGLLKNIFK | 135 |
| CGIFEEIAGLLKNIFK | 136 |
| CGLFEAIAGFIEGGWPGLINGWYGYGRKKRRQRRLHLLHHLLHHLHHLLHHLLHL | 137 |
| CGLFEAIEGFIENGWKGMIDWWYGYGRKKRRQRRK(stearyl) | 138 |
| CGLFGEIEEFIENGWKGLIDWWYG | 139 |
| CIFGAIAGFIKNIWLHLLHHLLHHLHHLLHHLLHL | 140 |
| CGIFGAIEGFIENGWKGLIDAWYGYRKKRRQRR | 141 |
| CELFGAIEGFIENGWKGLIDWWYGYGRKKRRQRR | 142 |
| CIFGIDDLIIGLLFVAIVEAGIGGYLLGSYGRKKRRQRR | 143 |
| GLFGALAEALAEALAEHLAEALAEALEALAAGGSC | 144 |
| CGFIGAIANLLSKIFEGLIDGWYGYGRKKRRQRR all (D) | 145 |
| CFFGAIWEFIRSILKGLI | 146 |
| CFFGAIWERFIRSILK | 147 |
| CFFGAIWEFIRSILE | 148 |
| CIFGAIAGFIKNIWE | 149 |
| CIFGAIAGFIKNIWKGLIDA | 150 |
| CFFEAIEEFIKNILK | 151 |
| CIFGAIAGLLRNIF | 152 |
| CGIFGAIAGLLKNIW | 153 |
| CLFGAIWEFIKSIL | 154 |
| CFWGAIWEFIKSIL | 155 |
| CFGGAIWEFIKSIL | 156 |
| CFAGAIWEFIKSIL | 157 |

TABLE 2-continued

| Sequence | SEQ ID |
|---|---|
| CGLFEAIEGFIENGWEGM(SO2)IDGWYGYGRKKRRQRR | 158 |
| CGLFEAIEGFIENGWEGMIDWWYGYGRKKRRQRR | 159 |
| CFFGAIWEFIKSIG | 160 |
| CFFGAIWEFIKSIA | 161 |
| CFFGAIWEFIKSIN | 162 |
| CFFGAIWEFIKSIW | 163 |
| CFFGAIWEFIKSILEGLIDWWYGYGHKKHHQHR | 164 |
| Ac-CLHLLHHLLHHLHHLLHHLLHLLHHLLHHL-NH2 | 165 |
| Ac-LHLLHHLLHHLHHLLHHLLHLLHHLLHHLGGGRKKRRQRRRPPQC-NH2 | 166 |
| CRKKRRQRRRPPQGGGLHLLHHLLHHLHHLLHHLLHLLHHLLHHL | 167 |
| CLHLLHHLLHHLHHLLHHLLHLLHHLLHHLGGGRKKRRQRRRPPQ | 168 |
| CGLFHAIAHFIHGGWHGLIHGWYGYGRKKRRQRR | 169 |
| CGLFKAIAKFIKGGWKGLIKGWYGYGRKKRRQRR | 170 |
| CGLFEAIAGFIENGWEGMIDGWYGYGRKKRRQRR | 171 |
| CWEAALAEALAEALAEHLAEALAEALEALAAYGRKKRRQRR | 172 |
| CGLFEAIEGFIENGWEGMIDGWYGRKKRRQRRRPPQ | 173 |
| GLFEAIEGFIENGWEGMIDGWYGYGRKKRRQRRC | 174 |
| Ac-LHLLHHLLHHLHHLLHHLLHLLHHLLHHLRKKRRQRRRPPQ-NH2 | 175 |
| Ac-LHLLHHLLHHLHHLLHHLLHLLHHLLHHLGPGRKKRRQRRRPPQ-NH2 | 176 |
| Ac-LIRLWSHLIHIWFQNRRLKWKKK-NH2 | 177 |
| Ac-RKKRRQRRRPPQQQQQQ-NH2 | 178 |
| Ac-GLFEAIEGFIENGWEGMIDGWYGYGRKKRRQRR-NH2 | 179 |
| Ac-LHLLHHLLHHLHHLLHHLLHLLHHLLHHLGGGRRRRRRRRR-NH2 | 180 |
| Ac-LHLLHHLLHHLHHLLHHLLHLLHHLLHHL-(Peg)12-RKKRRQRRRPPQ-NH2 | 181 |
| Ac-GLFGAIAGFIENGWEGMIDGWYGLIRLWSHLIWFQNRRLKWLLL-NH2 | 182 |
| Ac-HHHHHRKKRRQRRRPPQGGGLHLLHHLLHHLHHLLHHLLHLLHHLLHHL-NH2 | 183 |
| Ac-LHLLHHLLHHLHHLLHHLLHLLHHLLHHL-(Peg)2-RKKRRQRRRPPQ-NH2 | 184 |
| Ac-LHLLHHLLHHLHHLLHHLLLLHHLLHHLGGGRQIKIWFQNRRMKWKKGG-NH2 | 185 |
| Ac-KLLKLLLKLWLKLLKLLLKLLGGGRKKRRQRRRPPQ-NH2 | 186 |
| Ac-LHHLLHHLLHLLHHLLHHLHHLLHHLLHLC-NH2 all (D) | 187 |
| Ac-LHLLHHLLHHLHHLLHHLLHLLHHLLHHL-PEG6-RKKRRQRRRPPQC-NH2 | 188 |
| Ac-GLFEAIEGFIENGWEGMIDGWYGYGRKKRRQRRC-NH2 | 189 |
| CGLFEAIEGFIENGWEGMIDGWYGYGRKKRRQRR all (D) | 190 |
| CGLFEAIEGFIENGWEGMIDGWYGYGRRRRRRRRR-NH2 | 191 |
| YGRKKRRQRRGLFEAIEGFIENGWEGMIDGWYGC-NH2 | 192 |
| CGVFVLGFLGFLATAGSYGRKKRRQRR-NH2 | 193 |
| CGLFKAIAKFIKGGWKGLIKGWYG-NH2 | 194 |
| CGLFEAIEGFIENGWEGMIDGWYGYGRKKR | 195 |
| CGLFEAIEGFIENGWEGMIDGWYGYGRKKRRQRRYGRKKRRQRR | 196 |

TABLE 2-continued

| Sequence | SEQ ID |
|---|---|
| CGLFEAIEGFIENGWEGMIDGWYGYGRKKRRQRRYGRKKRRQRR | 197 |
| CGLFEAIKGFIENGWEGMIDGWYGYGRKKRRQRR | 198 |
| CGLFEAIHGFIENGWEGMIDGWYGYGRKKRRQRR | 199 |
| CGLFEAIRGFIENGWEGMIDGWYGYGRKKRRQRR | 200 |
| CGLFEAIDGFIENGWEGMIDGWYGYGRKKRRQRR | 201 |
| CRLFEAIEGFIENGWEGMIDGWYGYGRKKRRQRR | 202 |
| CGGGLFEAIEGFIENGWEGMIDGWYGYGRKKRRQRR | 203 |
| CGLFEAIEGFIENGWEGMIDGWYGGGGYGRKKRRQRR | 204 |
| CGLFEAIEGFIENGWEGMIDGWYG-(PEG)11-YGRKKRRQRR | 205 |
| CFLGFLLGVGSAIASGIAVSKVLHL | 206 |
| CGVFVLGFLGFLATAGSAMGARSLTLSAYGRKKRRQRR | 207 |
| Ac-GLWRALWRLLRSLWRLLWRA-mercaptoethylamide | 208 |
| C-Nle-LFEAIEGFIENGWEGMIDGWYGYGRKKRRQRR | 209 |
| CELFEAIEGFIENGWEGMIDGWYGYGRKKRRQRR | 210 |
| CGFFGAIAGFLEGGWEGMIAGWHGYGRKKRRQRR | 211 |
| CFLGFLLGVGSAIASGIAVSKVLHLYGRKKRRQRR | 212 |
| GLFEAIEGFIENGWEGLAEALAEALEALAAGGSC | 213 |
| CGLFEAIEGFIENGWEGMIDGWYGLHLLHHLLHHLHHLLHHLLHLLHHLLHHL | 214 |
| CGLFEAIEGFIENGWEGMIDGWYGYGRKKRRQRRLHLLHHLLHHLHHLLHHLLHLLHHLLHHL | 215 |
| CGLFGAIAGFIEGGWTGMIDGWYGYGRKKRRQRR | 216 |
| CGLFGAIAGFIEGGWQGMVDGWYGYGRKKRRQRR | 217 |
| CGLFGAIAGFIENGWQGLIDGWYGYGRKKRRQRR | 218 |
| CGLFGAIAGFIENGWEGLVDGWYGYGRKKRRQRR | 219 |
| CGLFGAIAGFIEGGWSGMIDGWYGYGRKKRRQRR | 220 |
| CGLFGAIAGFIEGGWPGLVAGWYGYGRKKRRQRR | 221 |
| CGLFGAIAGFIENGWEGMVDGWYGYGRKKRRQRR | 222 |
| CGLFGAIAGFIEGGWPGLINGWYGYGRKKRRQRR | 223 |
| CGLFGAIAGFIENGWEGLIDGWYGYGRKKRRQRR | 224 |
| CGLFGAIAGFIENGWEGMIDGWYGYGRKKRRQRR | 225 |
| CGLFGAIAGFIENGWEGMIDGWYGSSKKKK | 226 |
| CGLFGAIAGFIENGWEGLIDGWYGYGRKKRRQRR | 227 |
| CGLFEAIEGFIENGWEGLIDGWYGYGRKKRRQRR | 228 |
| CGLFGAIAGFIENGWEGLIEGWYGGGRKKRRQRR | 229 |
| CGLFEAIEGFIENGWEGMIDGWYGGGRKKRRQRR | 230 |
| CGLFEAIAGFIENGWEGLIDGWYGYGRKKRRQRR | 231 |
| CGLFEAIAEFIENGWEGLIEGWYGGRKKRRQRR | 232 |
| CGLFEAIEGFIENGWEGMIDGWYGRKKRRQRRR | 233 |
| CKLLKLLLKLWLKLLKLLLKLL | 234 |
| CKLLKLLLKLWLKLLKLLLKLLYGRKKRRQRR | 235 |

TABLE 2-continued

| Sequence | SEQ ID |
|---|---|
| GLFEAIEGFIENGWEGMIDGWYGC | 236 |
| CVLFEAIEGFIENGWEGMIDGWYGYGRKKRRQRR | 237 |
| CSLFEAIEGFIENGWEGMIDGWYGYGRKKRRQRR | 238 |
| CGLFEAIEGFIENGWEGMIDGWYGYGRKKRRQ | 239 |
| CGLFEAIEGFIENGWEGMIDGWYGYGRKKRR | 240 |
| CGLFEAIEGFIENGWEGMIDGWYGYGKKKKQKK | 241 |
| CGLFEAIEGFIENGWEGMIDGWYGGLFEAIEGFIENGWEGMIDGWYG | 242 |
| CGLFEAIEGFIENGWEGMIDGWYGYGRKKRRQRRGLFEAIEGFIENGWEGMIDGWYGYGRKKRRQRR | 243 |
| RRQRRKKRGYGYWGDIMGEWGNEIFGEIAEFLGC | 244 |
| CRRQRRKKRGYGYWGDIMGEWGNEIFGEIAEFLG | 245 |
| GLFEAIEGFIENGWEGMIDGWYGYGRK-K(D)-RRQRR | 246 |
| GLFEAIEGFIENGWEGMIDGWYGYGRKK-R(D)-RQRR | 247 |
| GL-F(D)-EAIEGFIENGWEGMIDGWYGYGRKKRRQRR | 248 |
| GLF-E(D)-AIEGFIENGWEGMIDGWYGYGRKKRRQRR | 249 |
| CGLFEAIEGFIENGWEGMIDGWYG | 250 |
| CYGRKKRRQRR | 251 |
| YGRKKRRQRRC | 252 |
| RRQRRKKRGYGYWGDIMGEWGNEIFGEIAEFLGC all(D) | 253 |
| CRRQRRKKRGYGYWGDIMGEWGNEIFGEIAEFLG all(D) | 254 |
| CGLFEAIEGFIENGWEGMIDGAYGYGRKKRRQRR | 255 |
| CGLFEALLELLESLWELLLEAWYGYGRKKRRQRR | 256 |
| CGLFEAIEGFNENGWEGMIDGWYGYGRKKRRQRR | 257 |
| CGLFEAIEGFIENEWEGMIDGWYGYGRKKRRQRR | 258 |
| K(stearoyl)GLFEAIEGFIENGWEGMIDGWYGYGRKKRRQRRC | 259 |
| CGLFEAIK(stearoyl)GFIENGWEGMIDGWYGYGRKKRRQRR | 260 |
| CGLFEAIKGFIENGWEGMIDGWYGYGRK(stearoyl)KRRQRR | 261 |
| CGLFEAIEGFIENPWEGMIDGWYGYGRKKRRQRR | 262 |
| (stearyl)GLFEAIEGFIENPWEGMIDGWYGYGRKKRRQRRC | 263 |
| CGLFGAIAGFIEGGWPGLINGWYGYGRKKRRQRRLHLLHHLLHHLHHLLHHLLHLLHHLLHHL | 264 |
| CGLFGAIAGFIEGGWPGLINGWYGYGRKKRRQRRLHLLHHLLHHLHHLLHHLLHL | 265 |
| CGLFEAIAGFIEGGWPGLINGWYGYGRKKRRQRR | 266 |
| CGLEEAIEGFIENGWEGMIDGWYGYGRKKRRQRR | 267 |
| CGLFNAIEGFIENGWEGMIDGWYGYGRKKRRQRR | 268 |
| CGLFAAIEGFIENGWEGMIDGWYGYGRKKRRQRR | 269 |
| CGLFEAIENFIENGWEGMIDGWYGYGRKKRRQRR | 270 |
| CGLFEAIEKFIENGWEGMIDGWYGYGRKKRRQRR | 271 |
| CGLFEAIEGFAENGWEGMIDGWYGYGRKKRRQRR | 272 |
| CGLFEAIEGFIENWWEGMIDGWYGYGRKKRRQRR | 273 |
| CGLFEAIEGFIENNWEGMIDGWYGYGRKKRRQRR | 274 |

TABLE 2-continued

| Sequence | SEQ ID |
|---|---|
| CGLFEAIEGFIENGEEGMIDGWYGYGRKKRRQRR | 275 |
| CGLFEAIEGFIENGWAGMIDGWYGYGRKKRRQRR | 276 |
| CGLFEAIEGFIENGWNGMIDGWYGYGRKKRRQRR | 277 |
| CGLFEAIEGFIENGWGGMIDGWYGYGRKKRRQRR | 278 |
| CGLFEAIEGFIENGWEGMIDAWYGYGRKKRRQRR | 279 |
| CGLFEAIEGFIENGWLGMIDGWYGYGRKKRRQRR | 280 |
| CGLFEAIEGFIENGWKGMIDGWYGYGRKKRRQRR | 281 |
| CGLFEAIEGFIENGWEGMIDKWYGYGRKKRRQRR | 282 |
| CGLFEAIEGFIENGWEGMIDEWYGYGRKKRRQRR | 283 |
| CGLFEAIEGFIENGWEGMIDGLYGYGRKKRRQRR | 284 |
| CGLFEAIEGFIENGWEGMIDGNYGYGRKKRRQRR | 285 |
| CGLFEAIEGFIENGWEGMIDGKYGYGRKKRRQRR | 286 |
| CGLFEAIEGFIENGWEGMIDGEYGYGRKKRRQRR | 287 |
| CGLFEALEELLEGGWEGLIEAWYGYGRKKRRQRR | 288 |
| CELFGAIWEFIEGGWEGLIEAWYGYGRKKRRQRR | 289 |
| CGLFEALEEFIEGGWEGLLEAWYGYGRKKRRQRR | 290 |
| CGLFEALEEFIENGWEGLLEAWYGYGRKKRRQRR | 291 |
| CGLFEAIEGFIESGWEGLIDGWYGYGRKKRRQRR | 292 |
| CGLFEAIEEFIEGGWEGLIEAWYGYGRKKRRQRR | 293 |
| CGLFEAIEGFIENGWEGLIDAWYGYGRKKRRQRR | 294 |
| CGLFEAIEGFILNGWEGMIDGWYGYGRKKRRQRR | 295 |
| CGLFEAIEGFIKNGWEGMIDGWYGYGRKKRRQRR | 296 |
| CGLFEAIEGFIGNGWEGMIDGWYGYGRKKRRQRR | 297 |
| CGLFEATEGFIELGWEGMIDGWYGYGRKKRRQRR | 298 |
| CGLFEAIEGFIEKGWEGMIDGWYGYGRKKRRQRR | 299 |
| CGLFEAIAEFIEGGWEGLIEGWYGYGRKKRRQRR | 300 |
| CRGWEVLKYWWNLLQY | 301 |
| CRGWEVLKYWWNLLQYYGRKKRRQRR | 302 |
| CGLFGAIAGFIENGWEGMIDGWYGFRYGRKKRRQRR | 303 |
| Ac-CGLFEAIEGFIENGWEGMIDGWYGYGRKKRRQRR-CO2H | 304 |
| CGLLEALEGLLENGWEGLLEAWYGYGRKKRRQRR | 305 |
| CLRHLLRHLLRHLRHLLRHLRHLLRHLLRH | 306 |
| CGIFEAIEGFIENGWEGIIDGWYGYGROORRQRR (O = ornithine) | 307 |
| CGIGAVLKVLTTGLPALISWIKRKRQQ | 308 |
| CGIGAVLKVLTTGLPALISWIHHHHQQ | 309 |
| CGAFEAIEGFIENGWEGMIDGWYGYGRKKRRQRR | 310 |
| Ac-LHLLHHLLHHLHHLHHLLHLLHHLLHHLRRRRR | 311 |
| CGLFGAIWGFIENWWKGLIDWWYGYGRKKRRQRR | 312 |
| CGLFGAIEGFIENGWKGLIDAWYGYGRKKRRQRR | 313 |

TABLE 2-continued

| Sequence | SEQ ID |
|---|---|
| CGLFEAIAGFIENGWKGLIDWWYGYGRKKRRQRR | 314 |
| GLFEAIEGFIENGWKGLIDWWYGYGRKKRRQRRC | 315 |
| YGRKKRRQRRGLFEAIEGFIENGWKGLIDAWYGC | 316 |
| YGRKKRRQRRGLFEAIEGFIENGWKGLIDWWYGC | 317 |
| CGLFHAIHGFIENGWHGLIDWWYGYGRKKRRQRR | 318 |
| CGLFEAIEGFIENGWKGLIDWWYGYGRKKRRQRRK(stearyl) | 319 |
| CGLFKALLKLLKSLWKLLLKAWYGYGHKKHHQHR | 320 |
| CGLFKALLKLLKSLWKGLLKAWYGYGHKKHHQHR | 321 |
| CGLAKALLKLLKSLWKGLIEAWYGYGRKKRRQRR | 322 |
| CGIFGAIAGFIKNIW | 323 |
| CIFGAIAGFIKNIWEGLIDGWYGYGRKKRRQRR | 324 |
| CGIFGAIAGFIKNIWEGLIDGYGRKKRRQRR | 325 |
| CGIFGAIAGFIKNIWKGLIDAWYGYGRKKRRQRR | 326 |
| CIFGAIAGFIKNIWKGLIDWWYGYGRKKRRQRR | 327 |
| CLFGAIAGFIKNIW | 328 |
| CGL(R5)EAIEGF(S8)ENGWEGMIDGWYGYGRKKRRQRR | 329 |
| CGLFEA(S5)EGF(S5)ENGWEGMIDGWYGYGRKKRRQRR | 330 |
| CGLFEAIEGFIENGWEGAIDGWYGYGRKKRRQRR | 331 |
| CGLFEAIEGFIENGWEGEIDGWYGYGRKKRRQRR | 332 |
| CGIFGAIAGFIKNGWEGMVDWYGYGRKKRRQRR | 333 |
| CGLFEAIAGFIENGWEGMIDGWYGFYGRKKRRQRR | 334 |
| CGIFGAIAGFIKNGWEGMIDGWYGYGRKKRRQRR | 335 |
| CIFGAIAGFIKNIW | 336 |
| CIFGAIAGFIKNIWYGRKKRRQRR | 337 |
| CGIFGAIAGFIKNIWEGMIDGWYGYGRKKRRQRR | 338 |
| CGLFEAIEGFIENGWEGLIEAYGRKKRRQRR | 339 |
| CGLFEALLGFIENGWEGLIDGYGRKKRRQRR | 340 |
| CGLFGAIEGFIENGWEGLIDGWYGYGRKKRRQRRR | 341 |
| CELFGAIEGFIENGWEGMIDGWYGYGRKKRRQRRR | 342 |
| CGLFEAIEGFIENGWEGMIDGWYGYGHKKHHQHR | 343 |
| CGLFGAIEGFIEGGWPGLINGWYGYGRKKRRQRRR | 344 |
| CGLFKALLKLLKSLWKLLLKAYGRKKRRQRR | 345 |
| CGLFKALLKLLKSLWKLLLKAWYGYGRKKRRQRR | 346 |
| CGLFRALLRLLRSLWRLLLRAYGRKKRRQRR | 347 |
| CGLFEAILGFIENGWEGLIDGWYGYGRKKRRQRR | 348 |
| CGLFEAIWEFIENGWEGLIDGWYGYGRKKRRQRR | 349 |
| CGLFEAIEGFIENGWEGMIDGWYGGGGLHLLHHLLHHLHHLLHHLLHL | 350 |
| CGPVEDAITAAIGRVADTVGTYGRKKRRQRR | 351 |
| CMDGTLFPGDDDLAIPATEFFSTKA | 352 |

TABLE 2-continued

| Sequence | SEQ ID |
|---|---|
| CGLFEALEEFIEGGWEGLLEAWYGYGRKKRRQRR | 353 |
| CGLFEALEEFIENGWEGLLEAWYGYGRKKRRQRR | 354 |
| CELFGAIWEFIEGGWEGLIEAYGRKKRRQRR | 355 |
| CGLFEAIEGFIEEGWEGMIDGWYGYGRKKRRQRR | 356 |
| CGLFEAIAEFIENGWEGMIDGWYGYGRKKRRQRR | 357 |
| CGLFEAIAEFIEGLWEGLIEGWYGYGRKKRRQRR | 358 |
| CGLLEALEGLLESLWEGLLEAWYGYGRKKRRQRR | 359 |
| CGLFEAIEGFIENGWEGMIDIWYGYGRKKRRQRR | 360 |
| CGLFEAIEGFIENGWRGMIDGWYGYGRKKRRQRR | 361 |
| CGLFEAIEGFIENGWDGMIDGWYGYGRKKRRQRR | 362 |
| CGLFEAIEGFIENHWEGMIDGWYGYGRKKRRQRR | 363 |
| CGLFEAIEGFIENWWKGLIDWWYGYGRKKRRQRR | 364 |
| GLFEAIEGFIENGWKGLIDAWYGYGRKKRRQRRC | 365 |
| CGLFEAIEGFIENGWKGMIDAWYGYGRKKRRQRR | 366 |
| CGLFEAIEGFIENGWKGMIDWWYGYGRKKRRQRR | 367 |
| CGLAEAIEGFIENGLKGLIDWWYGYGRKKRRQRR | 368 |
| RRQRRKKRGYGYWGDILGEWGNEIFGEIAEFLGC all(D) | 369 |
| CRRQRRKKRGYGYWGDILGEWGNEIFGEIAEFLG all(D) | 370 |
| CGLFEAIEGFIENGWKGLIDWWYGYGRKKRRQRR | 371 |
| CGFFEAIEGFIENGLKGLIDAWYGYGRKKRRQRR | 372 |
| CGLFEAIEGFIENGLKGLIDAWYGYGRKKRRQRR | 373 |
| CELFGAIEGFIENGWKGLIDAWYGYGRKKRRQRR | 374 |
| CGLFKAIKGFIKNGWKGLIKAWYGYGRKKRRQRR | 375 |
| CGLAEALLELLESLWKGLIEAYGRKKRRQRR | 376 |
| CGIFGAIEGFIENGWKGLIDAWYGYGRKKRRQRR | 377 |
| CGIAGAIAGFIKNIWEGLIDWWYGYGRKKRRQRR | 378 |
| CGIAGAIAGFIKNIWKGLIDAWYGYGRKKRRQRR | 379 |
| CGIFGAIAGFIKNIWEGLIDGWYGKKKKKKKKK | 380 |
| CG(R5)FEAIEG(S8)IENGWEGMIDGWYGYGRKKRRQRR | 381 |
| CGLFEAIEGF(R5)ENGWEG(S8)IDGWYGYGRKKRRQRR | 382 |
| GLFEAIEGFIENGWEGMIDGWYGCYGRKKRRQRR | 383 |
| GLFEAIEGFIENGWEGMIDGWYGGCYGRKKRRQRR | 384 |
| GLLEALEGLLENGWEGLLDGWYGYGRKKRRQRR | 385 |
| CFFGAIWEFIRNIL | 386 |
| CIFGAIAGFIRSIL | 387 |
| CGLFEEIEEFIENGWEGLIDWWYGYGRKKRRQRR | 388 |
| CGFFGAIWEFIKSIL | 389 |
| GFFGAIWEFIKSILC | 390 |
| CGLFEALEGFIENGWEGLLDGWYGYGROORRQRR (O = ornithine) | 391 |

TABLE 2-continued

| Sequence | SEQ ID |
|---|---|
| CGLFEALLELLENGWELLLEAWYGYGRKKRRQRR | 392 |
| CGLFEALLELLENGWELLLDGWYGYGRKKRRQRR | 393 |
| CALFEAIEAFIENGWEAMIDAWYGYGRKKRRQRR | 394 |
| CGLFGAIWGFIENGWEGLIDGWYGYGRKKRRQRR | 395 |
| CGLFEAIEELIENLWKGLIDWWYGYGRKKRRQRR | 396 |
| CGLFEEIEGFIENGWKGLIDWWYGYGRKKRRQRR | 397 |
| CGLFEEIEGFIENGWKGLIDWWYGYGHKKHHQHR | 398 |
| CFFGAIWEFIKNILKGLIDGWYG | 399 |
| CGIFGAIAGFIRSIL | 400 |
| CGLFEEIEGFIENGWEGMIDGWYGYGRKKRRQRR | 401 |
| CGLFEAIEGFIENGWEGMIDGWNGYGRKKRRQRR | 402 |
| AGYLLGKINLKALAALAKKILHHHHHKKKKKKC | 403 |
| Bis CGLFEAIEGFIENGWEGMIDWWYGYGRKKRRQRR | 404 |
| CGLFEAIEGFIENGWEGMIDGWYG-(PEG)6-YGRKKRRQRR | 405 |
| CGIFGAIWNGIKSLFEGLIDGWYGYGRKKRRQRR | 406 |
| CGIFGAIEGFIENGWEGLIDWWYGYGRKKRRQRR | 407 |
| CIFGAIAGFIKNIWEGLIDWWYGYGRKKRRQRR | 408 |
| CGLFEAIEGFIENGWKGLIDGWYGGLFEAIEGFIENGWKGLIDWWYG | 409 |
| CWEAALAEALAEHLAEALAEALEALAAYGRKKRRQRRK(stearyl) | 410 |
| CGLFEAIEGFIENGWKGLIDWWYGYGRKKRRQRR | 411 |
| CGLFEELEELLEEGWEGLLEAYGRKKRRQRR | 412 |
| CGNFEEIEEFIEEGLRNFIDWWYGYGHKKHHQHR | 413 |
| CFFGAIWEFIRNILEGLIDWWYGYGRKKRRQRR | 414 |
| CFFGAIWEFIKNILLHLLHHLLHHLHHLLHHLLHL | 415 |
| CGLFEAIEGFIENGWEGMIDGWYGYGRKKRRQRR all(D) | 416 |
| CGFFHAFFHFFHSFWHGFFEA | 417 |
| CGLFHALLHLLHSLWHGLLHWWYGYGHKKHHQHR | 418 |
| CGLFGALLELLESLWEGLLEWYGRKKRRQRR | 419 |
| CGLFGALLELLESLWEGLLEWYGHKKHHQHR | 420 |
| CGLFHALLHLLHSLWKGLLEWWYGF | 421 |
| CIFGAIAGFIRSILEGF | 422 |
| CGIFGAIAGFIKNIWKGLIDA | 423 |
| CFFEAIEEFIKNIWK | 424 |
| CGLFEAIEGFIENGWKGLIDWLAEALAEALEALAA | 425 |
| GCGIFGAIAEFIKNIW | 426 |
| CIFGAIAEFIKNIWKGLIDW | 427 |
| CFFGAIWEFIKSILELLLEAYGHKKHHQHRR | 428 |
| CWFGAIWEFIKSIL | 429 |
| CAFGAIWEFIKSIL | 430 |

TABLE 2-continued

| Sequence | SEQ ID |
|---|---|
| CFLGAIWEFIKSIL | 431 |
| CFFGAIWEFIKSIK | 432 |
| CGFIGAIANLLSKIFEGLIDGWYGYGRKKRRQRR all(D) | 433 |
| CFFGAIWEFIKSIL | 434 |
| CIFGAIAGFIKNIWLHLLHHLLHHLHHLLHHLLHL all(D) | 435 |
| CFFGAIAEFIKNIW | 436 |
| CIFEAIWGFIKNIW | 437 |
| stearyl-AGYLLGKINLKALAALAKKILHHHHHHKKKKKC | 438 |
| CIFEAIAGFIKNIWKGLIDWWYGYGRKKRRQRR | 439 |
| CGLFEAIEGFIENGWKGLIDWWYGGRPRESGKKRKRKRLKP | 440 |
| C(b-Ala)GFGEIEEFIENGLKNLIDWWYGYGHKKHHQHR | 441 |
| C(b-Ala)GFEFIEEFIENGLKNLIDWWYGYGRKKRRQRR | 442 |
| C(b-Ala)GFEFIEEFIENGLKNLIDWWYGYGHKKHHQHR | 443 |
| CGGIEEIAGLLSKILKGLIDWWYGYGHKKHHQHR | 444 |
| CGFIGAIANLLSKIFEGLIDWWYGYGRKKRRQRR | 445 |
| CGFIGAIAELLEKIFEGLIDWWYGYGRKKRRQRR | 446 |
| CGFIGAIAELLEKIFEGLIDWWYGYGHKKHHQHR | 447 |
| CFFGAIWEFIRNILEGLIDWWYGYGHKKHHQHR | 448 |
| CFFGAIWEFIKSILLHLLHHLLHHLHHLLHHLLHL | 449 |
| CFFGAIWEFIRSILLHLLHHLLHHLHHLLHHLLHL | 450 |
| CGFFGAIWEFIRSILEGFIDWWYGYGYGHKKHHQHR | 451 |
| CGLFEAIWEFIKSILEGLLEAYGHKKHHQHR | 452 |
| CGLFEAIWEFIKSILEGLLEAWYGYGHKKHHQHR | 453 |
| CGIFGAIAGFIKNIWKYGRKKRRQRR | 454 |
| CGLFEALLELLESLWELLLEAWYGYGHKKHHQHR | 455 |
| CIFGAIAGFIRNIWKGLIDGWYG | 456 |
| CGIFGAIAGFIRNIWKGLIDGWYG | 457 |
| CFFGAIWEFIKNILKLHLLHHLLHHLHHLLHHLLHL | 458 |
| CFFGAIWEFIRNILLHLLHHLLHHLHHLLHHLLHL | 459 |
| CFPGKIWEFIKSIL | 460 |
| CYGRKKRRQRRGLFEALLELLESLWELLLEA | 461 |
|  | 462 |
| CWWGAIEGFIKSIL | 463 |
| CFFGAIWEWIKSIL | 464 |
| CFFGAIWEFWKSIL | 465 |
| CFFGAIWEFIKFIL | 466 |
| CFFGAIWEFIKKIL | 467 |
| CFFGAIWEFIKGIL | 468 |
| CFFGAIWEFIKLIL | 469 |

TABLE 2-continued

| Sequence | SEQ ID |
|---|---|
| CFFGAIWEFIKWIL | 470 |
| CFFGAIWEFIKSFL | 471 |
| CFFGAIWEFIKSKL | 472 |
| CFFGFIWEFIKSIL | 473 |
| CIFGAIAGFIKNILKGLIDAF | 474 |
| CFFGKIWELWEWIL | 475 |
| CFFGAIWEFAKSIL | 476 |
| CFFGAIWEFIKSAL | 477 |
| CFFGAIWEFIKSWL | 478 |
| CFFGAIWEFIKSILK | 479 |
| CFFGAIWEFIKSILE | 480 |
| CFFKAIWEFIKSIL | 481 |
| CFFNAIWEFIKSIL | 482 |
| CFFGGIWEFIKSIL | 483 |
| CFFGNIWEFIKSIL | 484 |
| CFFGALWEFIKSIL | 485 |
| CFFGAAWEFIKSIL | 486 |
| CGLFHALLHLLHSLWHGLLDG | 487 |
| CGLFHALLHLLHSLWHGLLEW | 488 |
| CGLFHALLHLLHSLWHLLLEA | 489 |
| CGLFHALLHLLHSLWKLLLEW | 490 |
| CKFGAIWEFIKSIL | 491 |
| CFKGAIWEFIKSIL | 492 |
| CFFGAIWKFIKSIL | 493 |
| CFFGAIWAFIKSIL | 494 |
| CFFGAIWLFIKSIL | 495 |
| CFFGAIWFFIKSIL | 496 |
| CFFGAIWNFIKSIL | 497 |
| CFFGAIWELIKSIL | 498 |
| CFFGAIWEAIKSIL | 499 |
| CGLFEAIEGFIENGWEGLAEALAEALEALAAYGRKKRRQRR | 500 |
| CIFGAIAGFIKNIWEGMIDGWYGYGRKKRRQRR | 501 |
| CIFGAIAGFIKNIWEGLIDAWYGYGRKKRRQRR | 502 |
| CIFGAIAGFIKNIWKGLIDAWYGYGRKKRRQRR | 503 |
| CIFGAIAGFIKNIWIFGAIAGFIKNIWWYGYGRKKRRQRR | 504 |
| CGLFGAIAGFIENGWEGLIEGWYG | 505 |
| CGLFEAIEGFIENGWEGLIDGWYGYGOOOOOQRR (O = ornithine) | 506 |
| CGLFEAIEGFIENGWKGLIDWWYGYGRKKRRQRR | 507 |
| CGLFEAIEGFIENGWEGLIDGWYGYGRKKRRQRRK(stearyl) | 508 |

TABLE 2-continued

| Sequence | SEQ ID |
|---|---|
| CYGHKKHHQHRGLFEAIEGFIENGWKGLIDWWYG | 509 |
| CYGHKKHHQHRGLFEAIEEFIENGWEGLIDGWYG | 510 |
| CGLFEAIEGFIENGWKGLIDGWYGYGRKKRRQRRK(stearyl) | 511 |
| CGLFEAIEGFIENGWHGMIDGWYGYGRKKRRQRR | 512 |
| IFGIDDLIIGLLFVAIVEAGIGGYLLGSYGRKKRRQRRC | 513 |
| CGFFGEIAELIEEGLKGLIDWWNG | 514 |
| CGLFGEIEELIEEGLENLIDWWNG | 515 |
| CFPGAIWEFIHSIL all (D) | 516 |
| CFFGAIWEFIHNIL | 517 |
| CFPGAIWEFIHSIFK | 518 |
| CGIFEAIAGLLKWIFK | 519 |
| CGIFELIAGLLKNIFK | 520 |
| CGIFEAIAGLLKSILKK(stearyl) | 521 |
| CGIFGAIAGLLKSILKK(stearyl) | 522 |
| CIFGAIAGFIKNILKGL all (D) | 523 |
| CIFGAIAGFIKNILKGLIDGWWYG | 524 |
| CIFGAIAGFIKNIWHGLI | 525 |
| CIFGAIAGFIKNILKGLK(stearyl) | 526 |
| GLGKLINKIFGAIAGFIC all (D) | 527 |

TABLE 3

| motif | pyrimidine | purine | 5' end | 3' end |
|---|---|---|---|---|
| PS02 | 2'OMe | 2'F | iB | dTs; dT; iB |
| PS03 | 2'OMe | 2'OH | iB | dTs; dT; iB |
| PS05 | 2'OMe | 2'F | iB | omeUs; omeU; iB |

TABLE 4

| motif | pyrimidine | purine | 5' end | 3' end | position 14 |
|---|---|---|---|---|---|
| GS10 | 2'OMe | 2'F | rXs; rXs; rXs & YA = 2'OMe | mUs; mU | 2'F |
| GS10ffd | 2'OMe | 2'F | fX; fX; dX | mUs; mU | 2'F |
| GS13 | | | 1, 3 ... 17, 19 = 2'OMe | mUs; mU | |
| GS13b | | | 1, 3 ... 17, 19 = 2'OMe & 2, 4 ... 16, 18 = 2'F | mUs; mU | 2'F |
| GS13b-s | | | 1, 3 ... 17, 19 = 2'OMe & 2, 4 ... 16, 18 = 2'F (position 1-3 thioates) | mUs; mU | 2'F |

TABLE 5

| Target Name | Start Seq Loc | Motif Name | Duplex R-number | ORS # | Passenger strand | Guide strand |
|---|---|---|---|---|---|---|
| ApoB | 9514 | Sci13 (PS03GS13) | R-008291260-000L | 9122 | 6amiL; iB; omeC; omeU; omeU; omeU; rA; rA; omeC; rA; rA; omeU; omeU; omeC; omeC; omeU; rG; rA; rA; rA; omeU; dTs; dT; iBSup (SEQ ID NO: 540) | omeA; rU; omeU; rU; omeC; rA; omeG; rG; omeA; rA; omeU; rU; omeG; rU; omeU; rA; omeA; rA; omeG; omeUs; omeUSup (SEQ ID NO: 545) |
| ApoB | 9514 | PS03GS13b | R-008357859-000V | 15792 | 6amiL; iB; omeC; omeU; omeU; omeU; rA; rA; omeC; rA; rA; omeU; omeU; omeC; omeC; omeU; rG; rA; rA; rA; omeU; dTs; dT; iBSup (SEQ ID NO: 540) | omeA; fluU; omeU; fluU; omeC; fluA; omeG; fluG; omeA; fluA; omeU; fluU; omeG; fluU; omeU; fluA; omeA; fluA; omeG; omeUs; omeUSup (SEQ ID NO: 546) |

TABLE 5-continued

| Target Name | Start Seq Loc | Motif Name | Duplex R-number | ORS # | Passenger strand | Guide strand |
|---|---|---|---|---|---|---|
| ApoB | 9514 | PS02GS13b | R-008461704-000E | 24314 | 6amiL; iB; omeC; omeU; omeU; omeU; fluA; fluA; omeC; fluA; fluA; omeU; omeU; omeC; omeC; omeU; fluG; fluA; fluA; fluA; omeU; dTs; dT; iBSup (SEQ ID NO: 541) | omeA; fluU; omeU; fluU; omeC; fluA; omeG; fluG; omeA; fluA; omeU; fluU; omeG; fluU; omeU; fluA; omeA; fluA; omeG; omeUs; omeUSup (SEQ ID NO: 546) |
| SSB | 291 | PS02GS13b | R-008462079-000W | 24314 | 6amiL; iB; fluA; omeC; fluA; fluA; omeC; fluA; fluG; fluA; omeC; omeU; omeU; omeU; fluA; fluA; omeU; fluG; omeU; fluA; fluA; omeU; dTs; dT; iBSup (SEQ ID NO: 542) | omeU; fluU; omeA; fluC; omeA; fluU; omeU; fluA; omeA; fluA; omeG; fluU; omeC; fluU; omeG; fluU; fluU; omeG; omeU; omeUs; omeUSup (SEQ ID NO: 547) |
| CTNNB1 | 1797 | PS05GS13b | R-008428355-000S | 23491 | 6amiL; iB; omeC; omeU; fluG; omeU; omeU; fluG; fluG; fluA; omeU; omeU; fluG; fluA; omeU; omeU; omeC; fluG; fluA; fluA; fluA; omeUs; omeU; iBSup (SEQ ID NO: 543) | omeU; fluU; omeU; fluC; omeG; fluA; omeA; fluU; omeC; fluA; omeA; fluU; omeC; fluC; omeA; fluA; omeC; fluA; omeG; omeUs; omeUSup (SEQ ID NO: 548) |
| CTNNB1 | 1797 | PS05GS13b-s | R-008490480-000C | 28071 | 6amiL; iB; omeC; omeU; fluG; omeU; omeU; fluG; fluG; fluA; omeU; omeU; fluG; fluA; omeU; omeU; omeC; fluG; fluA; fluA; fluA; omeUs; omeU; iBSup (SEQ ID NO: 543) | omeUs; fluUs; omeUs; fluC; omeG; fluA; omeA; fluU; omeC; fluA; omeA; fluU; omeC; fluC; omeA; fluA; omeC; fluA; omeG; omeUs; omeUSup (SEQ ID NO: 549) |
| ApoB | 9514 | Sci10 (PS02GS10) | R-008277564-000P | 6922 | 6amiL; iB; omeC; omeU; omeU; omeU; fluA; fluA; omeC; fluA; fluA; omeU; omeU; omeC; omeC; omeU; fluG; fluA; fluA; fluA; omeU; dTs; dT; iBSup (SEQ ID NO: 541) | rAs; rUs; rUs; omeC; omeC; fluA; fluG; fluG; fluA; fluA; omeU; omeU; fluG; fluU; omeU; fluA; fluA; fluA; fluG; omeUs; omeUSup (SEQ ID NO: 550) |
| ApoB | 9514 | Sci10ffd (PS05GS10ffd) | R-008415011-000K | 21732 | 6amiL; iB; omeC; omeU; omeU; omeU; fluA; fluA; omeC; fluA; fluA; omeU; omeU; omeC; omeC; omeU; fluG; fluA; fluA; fluA; omeU; omeU; omeU; iBSup (SEQ ID NO: 544) | fluA; fluU; dT; omeU; omeC; fluA; fluG; fluG; fluA; fluA; omeU; omeU; fluG; fluU; omeU; fluA; fluA; fluA; fluG; omeUs; omeUSup (SEQ ID NO: 551) |

TABLE 6

| R# | | % of Parent Mouse Serum 2 hr incubation | % of Parent Monkey S9@pH 5.5 4 hr incubation | % of Parent Rat Lysosomal Lysate 4 hr incubation | % of Parent in vivo mouse liver 4 hr post dose | % of Parent in vivo mouse liver 24 hr post dose | % of Parent in vivo rhesus liver 6 hr post dose | % of Parent in vivo rhesus liver 24 hr post dose | % of Parent in vivo rhesus liver 48 hr post dose |
|---|---|---|---|---|---|---|---|---|---|
| R-008417879-000B | PS | 97 | 93 | 121 | | 0 | nd | 0 | nd |
| | GS | 97 | 102 | 35 | | 51 | nd | 3 | nd |
| R-008480267-000V | PS | 99 | 48 | nd | 0 | nd | nd | nd | nd |
| | GS | 94 | 7 | nd | 0 | nd | nd | nd | nd |
| R-008491315-000J | PS | nd | nd | nd | 0 | nd | nd | nd | nd |
| | GS | nd | nd | nd | 13 | nd | nd | nd | nd |
| R-008484697-000P | PS | 100 | nd | nd | nd | nd | nd | nd | nd |
| | GS | 0 | nd | nd | nd | nd | nd | nd | nd |
| R-008491391-000N | PS | 98 | 95 | 120 | 50 | nd | 31 | nd | 0 |
| | GS | 99 | 109 | 0 | 0 | nd | 0 | nd | 0 |
| R-008491393-000F | PS | 100 | 99 | 143 | 39 | nd | 25 | nd | 0 |
| | GS | 100 | 106 | 123 | 95 | nd | 84 | nd | 87 |
| R-008502422-000F | PS | nd | nd | 100 | 0 | nd | nd | nd | nd |
| | GS | nd | nd | 100 | 100 | nd | nd | nd | nd |
| R-008502424-000Y | PS | nd | nd | 100 | 0 | nd | nd | nd | nd |
| | GS | nd | nd | 2 | 10 | nd | nd | nd | nd |

PS—Paasenger
GS—Guide
nd—not determined

TABLE 7

| Entry | Gene Target | R # | SC Dose mpk | % KD in mouse liver | IC50 w/ LF2K in HEK-Luc [pM] | IP in rhesus pri. hepatocytes [nM] |
|---|---|---|---|---|---|---|
| 1 | CTNNB1 | R-008491391-000N | 30 | 33 | 8.7 | 0.81 |
| 2 | CTNNB1 | R-008491393-000F | 30 | 76 | 52 | 1.01 |
| 3 | CTNNB1 | R-008491389-000R | 30 | 17 | 16.1 | 0.37 |
| 4 | CTNNB1 | R-008491392-000X | 30 | 76 | 7.5 | 0.97 |
| 5 | CTNNB1 | R-008499711-000V | 5 | 27 | 3.6 | 1.12 |
| 6 | CTNNB1 | R-008499712-000D | 5 | 39 | 4 | 1.64 |

TABLE 7-continued
| Entry | Gene Target | R # | SC Dose mpk | % KD in mouse liver | IC50 w/ LF2K in HEK-Luc [pM] | IP in rhesus pri. hepatocytes [nM] |
|---|---|---|---|---|---|---|
| 7 | CTNNB1 | R-008498416-000P | 5 | 45 | 6.7 | 2.36 |
| 8 | CTNNB1 | R-008498418-000G | 5 | 39 | 5.6 | 3.78 |
| 9 | CTNNB1 | R-008499709-000X | 5 | 38 | 4.3 | 39.48 |
| 10 | CTNNB1 | R-008499710-000L | 5 | 37 | 6.8 | 5.18 |
| 11 | CTNNB1 | R-008499713-000M | 5 | 40 | 28.9 | 3.20 |
| 12 | ApoC3 | R-008543009-000U | 15 | 97 | nd | nd |
| 13 | ApoC3 | R-008543018-000C | 15 | 92 | nd | nd |
| 15 | ApoB | R-008417879-000B | 5 | 43 | 85.3 | 1.5 |
| 16 | SSB | R-008480267-000V | 50 | 12 | 29.1 | 4.23 |
| 17 | SSB | R-008484697-000P | 15 | 59 | 23.4 | nd |
TABLE 8
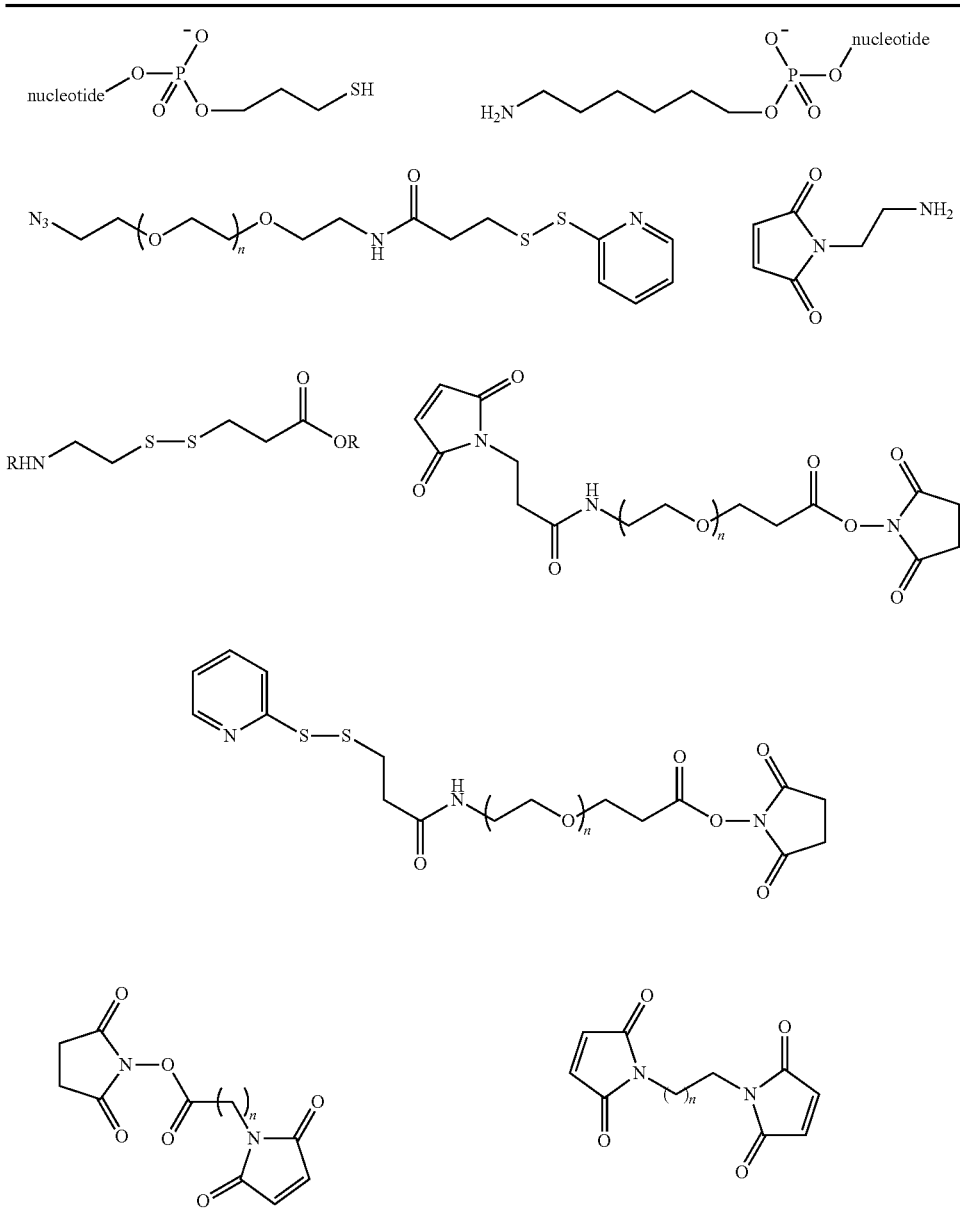

TABLE 8-continued

R = H, Boc, Cbz, Ac, PEG, lipid, targeting ligand, linker(s) and/or peptide(s).
"nucleotide" can be substituted with non-nucleotide moiety such as abasic or linkers as are generally known in the art.
n = 0 to 750.

What is claimed is:

1. A composition comprising:
a double-stranded short interfering nucleic acid (siNA) molecule that modulates expression of a target RNA sequence via RNA interference, wherein the molecule has a passenger strand and a guide strand and comprises structure selected from the structures represented by

```
formula (D):
5'-      B_1-N N N N N N N N N N N N N N N
   N N N N N (_sN)_x-B_2
3'- B_3-(N_s)_y N N N N N N N N N N N N N N
    N  N_sN_sN_sN  (D);
``` wherein,
(a) the upper strand is the passenger strand and the lower strand is the guide strand of the double-stranded nucleic acid molecule; the guide strand is complementary to the target sequence and the passenger strand is complementary to the guide strand, wherein one or more mismatches between the guide strand and passenger strand and/or between the guide strand and the target sequence are tolerated so long as RNAi activity is maintained;
(b) each N is independently a nucleotide wherein one or more Ns may be substituted with a non-nucleotide moiety so long as RNAi activity is maintained;
(c) each $B_1$, $B_2$, and $B_3$ is independently a terminal cap optionally including a ligand, polymer, protein or peptide transduction domain, nuclear localization sequence, cell penetrating peptide, receptor, steroid, vitamin, antibody, protamine, and/or hormone, optionally attached via a linker, wherein any of $B_1$, $B_2$, and/or $B_3$ is optionally absent;
(d) x is an integer from 0 to 4, provided that when x is 1, 2, 3, or 4, one or more of the $(N)_x$ nucleotides can be complementary to nucleotides in target sequence, and one or more phosphorothioate internucleotide linkage(s) "s" can be present in the $(N)_x$ region when x is 1, 2, 3, or 4;
(e) y is an integer from 0 to 4, provided that when y is 1, 2, 3, or 4, one or more of the $(N)_y$ nucleotides can be complementary to nucleotides in target sequence, and one or more phosphorothioate internucleotide linkage(s) "s" can be present in the $(N)_y$ region when y is 1, 2, 3, or 4;
(f) N nucleotides of the guide strand are 2'-deoxy-2'-fluoro nucleotides and N nucleotides of the guide strand are 2'-O-methyl nucleotides, with an optional variance of 1 or 2 N or N nucleotides being tolerated provided that as RNAi activity is maintained;
(g) S=a phosphorothioate or phosphorodithioate internucleotide linkage wherein $S_1$ is required and $S_2$ and $S_3$ are optional; and
(h) N nucleotides of the passenger strand are independently selected from ribonucleotide, 2'-O-alkyl nucleotide, 2'-deoxy-2'-fluoro nucleotide, 2'-deoxy nucleotide, and LNA.

2. The composition according to claim 1, wherein each (N) of the passenger strand is independently selected from 2'-O-alkyl, 2'-deoxy-2'-fluoro, 2'-deoxy, and/or LNA modified nucleotide.

3. The composition according to claim 1, wherein each (N) of the passenger strand is a 2'-O-alkyl modified nucleotide.

4. The composition according to claim 1, wherein each (N) of the passenger strand is a 2'-O-methyl modified nucleotide.

5. The composition according to claim 1, wherein x=2 and y=2.

6. The composition according to claim 1, wherein each N nucleotide of the guide strand is a 2'-deoxy-2'-fluoro nucleotide and each N nucleotide of the guide strand is a 2'-O-methyl nucleotide.

7. The composition according to claim 1, wherein 5 or more pyrimidine N nucleotides of the passenger strand are 2'-O-methyl nucleotides and 5 or more purine N nucleotides of the passenger strand are 2'-deoxy-2'-fluoro nucleotides.

8. The composition according to claim 1, wherein the 5'-terminal N position comprises a terminal phosphate group.

9. The composition according to claim 1, wherein $B_1$ and $B_2$ each comprise an inverted abasic 2'-deoxyribose moiety and $B_3$ is optionally absent.

10. The composition according to claim 1, wherein $B_1$ comprises one or more galactosamine moieties optionally attached via a linker to an inverted abasic 2'-deoxyribose moiety, $B_2$ comprises an inverted abasic 2'-deoxyribose moiety, and $B_3$ is optionally absent.

11. The composition according to claim 1, wherein $B_1$ comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2'-deoxyribose moiety, $B_2$ comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2'-deoxyribose moiety, and $B_3$ is optionally absent.

12. The composition according to claim 1, wherein $B_1$ comprises a ligand, polymer, protein or peptide transduction domain, nuclear localization sequence, cell penetrating peptide, receptor, steroid, vitamin, antibody, protamine, and/or hormone, optionally attached via a linker to an inverted abasic 2'-deoxyribose moiety, $B_2$ comprises any of SEQ ID NOS: 54-528 optionally attached via a linker to an inverted abasic 2'-deoxyribose moiety, and $B_3$ is optionally absent.

13. The composition according to claim 1, wherein $S_1$ and $S_2$ are required and $S_3$ is optional.

14. The composition according to claim 1, wherein $S_1$ and $S_3$ are required and $S_2$ is optional.

15. The composition according to claim 1, wherein $S_1$, $S_2$, and $S_3$ are required.

16. The composition according to claim 1, further comprising a terminal phosphate group at the 5'-end of the guide strand.

17. A composition comprising the double-stranded short interfering nucleic acid (siNA) molecule according to claim 1, and a pharmaceutically acceptable carrier or diluent.

18. The composition according to claim 1, wherein y is 1, 2, 3, or 4.

19. The composition according to claim 1, wherein $S_1$ is a first phosphorothioate internucleotide linkage and $S_3$ is a second phosphorothioate internucleotide linkage.

* * * * *

```
                            SEQUENCE LISTING

<160> NUMBER OF SEQ ID NOS: 551

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cuguuggauu gauucgaaa                                                  19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ggagcaaguu uacugacaa                                                  19

<210> SEQ ID NO 3
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 3
aaguauguuc ucaugucuu                                                    19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cuuuaacaau uccugaaau                                                    19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
acaacagacu uuaauguaa                                                    19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uuucgaauca auccaacag                                                    19

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uuucgaauca auccaacagu u                                                 21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
cuguuggauu gauucgaaau u                                                 21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 9
uuucgaauca auccaacagu u                                              21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uuucgaauca auccaacagu u                                              21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uuucgaauca auccaacagu u                                              21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uuucgaauca auccaacagu u                                              21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uuucgaauca auccaacagu u                                              21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uuucgaauca auccaacagu u                                              21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 15
uuucgaauca auccaacagu u                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uuucgaauca auccaacagu u                                              21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uuucgaauca auccaacagu u                                              21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uuucgaauca auccaacagu u                                              21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uugucaguaa acuugcuccu u                                              21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ggagcaaguu uacugacaau u                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 21
aagacaugag aacauacuuu u                                          21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
aaguauguuc ucaugucuuu u                                          21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
auuucaggaa uuguuaaagu u                                          21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
cuuuaacaau uccugaaaut t                                          21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
tuacauuaaa gucuguuguu u                                          21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
acaacagacu uuaauguaat t                                          21

```
<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uuacauuaaa gucuguuguu u                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
tuacauuaaa gucuguuguu u                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
acaacagacu uuaauguaat t                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uuucgaauca auccaacagu u                                              21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
uuucgaauca auccaacagu u                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 32
cuuuaacaau uccugaaaut t                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
auuucaggaa uuguuaaagu u                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
auuucaggaa uuguuaaagu u                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
cuuuaacaau uccugaaaut t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
acaacagacu uuaauguaat t                                              21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uuacauuaaa gucuguuguu u                                              21
```

-continued

```
<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cuguuggauu gauucgaaau u                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
auuucaggaa uuguuaaagu u                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
cuuuaacaau uccugaaaut t                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
auuucaggaa uuguuaaagu u                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
cuuuaacaau uccugaaaut t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 43
cuuuaacaau uccugaaaut t                                              21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uuucgaauca auccaacagu u                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uuucgaauca auccaacagu u                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uuucgaauca auccaacagu u                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uuucgaauca auccaacagu u                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uuucgaauca auccaacagu u                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
                                        oligonucleotide

<400> SEQUENCE: 49
uuucgaauca auccaacagu u                                               21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
uuucgaauca auccaacagu u                                               21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uuucgaauca auccaacagu u                                               21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cuuuaacaau uccugaaauu u                                               21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
autucaggaa uuguuaaagu u                                               21

<210> SEQ ID NO 54
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Cys Gly Leu Phe Glu Ala Ile Glu Glu Phe Ile Glu Asn Leu Trp Glu
 1               5                   10                  15

Leu Leu Ile Asp Gly Trp Tyr Gly Tyr Gly Arg Lys Lys Arg Arg Gln
            20                  25                  30

Arg Arg
```

```
<210> SEQ ID NO 55
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly His Lys Lys His His Gln
            20                  25                  30

His His

<210> SEQ ID NO 56
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: b-Ala

<400> SEQUENCE: 56

Cys Ala Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Cys Gly Leu Phe Glu Ala Ile Glu Gly Phe Ile Glu Asn Gly Leu Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 58
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Cys Gly Leu Phe Glu Ala Ile Glu Gly Phe Ile Glu Trp Gly Trp Glu
1               5                   10                  15

Gly Met Ile Asp Gly Trp Tyr Gly Tyr Gly Arg Lys Lys Arg Arg Gln
            20                  25                  30
```

Arg Arg

<210> SEQ ID NO 59
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Cys Arg Arg Gln Arg Arg Lys Lys Arg Gly Tyr Gly Tyr Trp Gly Asp
1               5                   10                  15

Ile Met Gly Glu Trp Gly Asn Glu Ile Phe Gly Glu Ile Ala Glu Phe
            20                  25                  30

Leu Gly

<210> SEQ ID NO 60
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg

<210> SEQ ID NO 61
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Cys Tyr Gly Arg Lys Lys Arg Arg Gln Arg Arg Gly Leu Phe Glu Ala
1               5                   10                  15

Ile Glu Gly Phe Ile Glu Asn Gly Trp Glu Gly Met Ile Asp Gly Trp
            20                  25                  30

Tyr Gly

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Ile Phe Gly Ala Ile Ala Gly Phe Ile Lys Asn Ile Leu Lys Gly
1               5                   10                  15

Leu Ile Asp Gly
            20

<210> SEQ ID NO 63
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Ile Phe Gly Ala Ile Ala Gly Phe Ile Arg Asn Ile Trp
1               5                   10

<210> SEQ ID NO 64
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Cys Gly Leu Phe His Ala Leu Leu His Leu Leu His Ser Leu Trp His
1               5                   10                  15

Gly Leu Leu His Ala Trp Tyr Gly Tyr Gly His Lys Lys His His Gln
            20                  25                  30

His Arg

<210> SEQ ID NO 65
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Cys Gly Leu Phe Glu Ala Ile Glu Gly Leu Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 66
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Cys Gly Leu Phe Glu Leu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 67
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(31)
```

<223> OTHER INFORMATION: Ornithine

<400> SEQUENCE: 67

Cys Gly Leu Phe Glu Ala Ile Glu Gly Phe Ile Glu Asn Gly Trp Glu
1               5                   10                  15

Gly Leu Ile Asp Gly Trp Tyr Gly Tyr Gly Xaa Xaa Xaa Xaa Gln
            20                  25                  30

Arg Arg

<210> SEQ ID NO 68
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Cys Gly Leu Phe Gly Ala Ile Glu Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 69
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Cys Gly Leu Phe Glu Ala Ile Glu Gly Phe Leu Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 70
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Cys Gly Leu Phe Glu Ala Ile Glu Gly Phe Ile Glu Asn Gly Leu Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 71
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Cys Gly Leu Phe Gly Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
                20                  25                  30

Arg Arg
```

<210> SEQ ID NO 72
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Nle

<400> SEQUENCE: 72

```
Cys Gly Leu Phe Glu Ala Ile Glu Gly Phe Ile Glu Asn Gly Trp Glu
1               5                   10                  15

Gly Leu Ile Asp Gly Trp Tyr Gly Tyr Gly Arg Lys Lys Arg Arg Gln
                20                  25                  30

Arg Arg
```

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Cys Gly Ile Phe Gly Ala Ile Ala Gly Phe Ile Lys Asn Ile Trp Lys
1               5                   10                  15

Gly Leu Ile Asp Trp
                20
```

<210> SEQ ID NO 74
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Cys Tyr Gly Arg Lys Lys Arg Arg Gln Arg Arg Gly Leu Phe Glu Ala
1               5                   10                  15

Ile Glu Gly Phe Ile Glu Asn Gly Trp Lys Gly Leu Ile Asp Ala Trp
                20                  25                  30

Tyr Gly
```

<210> SEQ ID NO 75
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Cys Gly Leu Leu Glu Ala Leu Glu Gly Leu Glu Ser Leu Trp Glu
1               5                   10                  15

Gly Leu Leu Glu Ala Trp Tyr Gly Tyr Gly Arg Lys Lys Arg Arg Gln
            20                  25                  30

Arg Arg

<210> SEQ ID NO 76
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Cys Gly Leu Phe Glu Ala Ile Glu Gly Phe Ile Glu Asn Gly Trp Glu
1               5                   10                  15

Gly Met Ile Asp Asn Trp Tyr Gly Tyr Gly Arg Lys Lys Arg Arg Gln
            20                  25                  30

Arg Arg

<210> SEQ ID NO 77
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Cys Ile Phe Gly Ala Ile Ala Gly Phe Ile Lys Asn Ile Trp Glu Gly
1               5                   10                  15

Leu Ile Glu Ala Trp Tyr Gly Leu His Leu Leu His His Leu Leu His
            20                  25                  30

His Leu His His Leu Leu His His Leu Leu His Leu
        35                  40

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Ile Phe Gly Ala Ile Ala Gly Phe Ile Lys Asn Ile Trp Glu Gly
1               5                   10                  15

Leu Ile Asp Ala Phe
            20

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Ile Phe Gly Ala Ile Ala Gly Phe Ile Lys Asn Ile Trp Glu Gly
1               5                   10                  15

Leu Ile

<210> SEQ ID NO 80
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Lys
        35

<210> SEQ ID NO 81
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Cys Gly Leu Phe Glu Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Leu His Leu Leu His His Leu Leu His His Leu His His Leu
        35                  40                  45

Leu His His Leu Leu His Leu Leu His His Leu Leu His His Leu
    50                  55                  60

<210> SEQ ID NO 82
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Cys Gly Leu Phe Glu Ala Ile Glu Gly Phe Ile Glu Asn Gly Trp Glu
1               5                   10                  15

Gly Met Ile Asp Gly Trp Tyr Gly Gly Gly Leu His Leu Leu His
            20                  25                  30

His Leu Leu His His Leu His His Leu Leu His His Leu Leu His Leu
        35                  40                  45

Leu His His Leu Leu His His Leu
    50                  55

<210> SEQ ID NO 83
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Cys Gly Leu Phe Glu Ala Ile Glu Gly Phe Ile Glu Asn Gly Trp Glu

```
                1               5                  10                 15
Gly Met Ile Asp Gly Trp Tyr Gly Leu His Leu Leu His Leu Leu
                20                 25                 30

His His Leu His His Leu Leu His His Leu Leu His Leu
                35                 40                 45

<210> SEQ ID NO 84
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Cys Gly Leu Phe Glu Ala Leu Leu Glu Leu Leu Glu Ser Leu Trp Glu
1               5                  10                 15

Leu Leu Leu Glu Ala Tyr Gly Arg Lys Lys Arg Arg Gln Arg Arg
                20                 25                 30

<210> SEQ ID NO 85
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Cys Gly Leu Phe Glu Ala Ile Glu Gly Phe Ile Glu Asn Gly Trp Glu
1               5                  10                 15

Gly Met Ile Asp Gly Trp Tyr Gly Tyr Gly Arg Lys Lys Arg Arg Gln
                20                 25                 30

Arg Arg

<210> SEQ ID NO 86
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Cys Gly Leu Phe Glu Ala Ile Glu Gly Phe Ile Glu Asn Gly Trp Glu
1               5                  10                 15

Gly Met Ala Asp Gly Trp Tyr Gly Tyr Gly Arg Lys Lys Arg Arg Gln
                20                 25                 30

Arg Arg

<210> SEQ ID NO 87
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Cys Gly Ile Phe Gly Ala Ile Ala Gly Phe Ile Lys Asn Ile Trp Glu
1               5                  10                 15

Gly Leu Ile Asp Trp Trp Tyr Gly Tyr Gly Arg Lys Lys Arg Arg Gln
                20                 25                 30
```

Arg Arg

<210> SEQ ID NO 88
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Cys Gly Phe Leu Pro Ala Ile Ala Gly Ile Leu Ser Gln Leu Phe Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Cys Phe Phe Gly Ala Ile Trp Gly Phe Ile Lys Ser Ile Leu
1               5                   10

<210> SEQ ID NO 90
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Cys Ile Phe Gly Ala Ile Ala Gly Phe Ile Lys Asn Ile Trp Lys Gly
1               5                   10                  15

Leu Ile Asp Trp Trp Tyr Gly
            20

<210> SEQ ID NO 91
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Cys Gly Leu Phe Glu Ala Ile Glu Gly Phe Ile Trp Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 92
<211> LENGTH: 34
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 92

Cys Gly Leu Phe Glu Ala Ile Ala Glu Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 93
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Cys Tyr Gly Arg Lys Lys Arg Arg Gln Arg Arg Gly Leu Phe Glu Ala
1               5                   10                  15

Ile Glu Gly Phe Ile Glu Asn Gly Trp Lys Gly Leu Ile Asp Trp Trp
            20                  25                  30

Tyr Gly

<210> SEQ ID NO 94
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Cys Gly Leu Phe Glu Ala Ile Glu Gly Phe Ile Glu Glu Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 95
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Cys Gly Leu Phe Glu Ala Ile Glu Gly Phe Ile Glu Asn Ala Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 96
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

-continued

```
Cys Gly Leu Phe Glu Ala Ile Glu Gly Phe Ile Glu Asn Gly Trp Glu
1               5                   10                  15

Gly Met Ile Asp Leu Trp Tyr Gly Tyr Gly Arg Lys Lys Arg Arg Gln
            20                  25                  30

Arg Arg

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Arg Leu Leu Arg Leu Leu Leu Arg Leu Trp Arg Arg Leu Leu Arg
1               5                   10                  15

Leu Leu Arg

<210> SEQ ID NO 98
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Cys Gly Gly Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 99
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Cys Gly Leu Phe Glu Lys Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 100
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Cys Gly Leu Phe Glu Ala Ile Glu Gly Phe Ile Glu Asn Gly Trp Glu
1               5                   10                  15

Asn Met Ile Asp Gly Trp Tyr Gly Tyr Gly Arg Lys Lys Arg Arg Gln
            20                  25                  30
```

Arg Arg

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Ile Phe Gly Ala Ile Ala Gly Phe Ile Lys Asn Ile Leu Lys Gly
1               5                   10                  15

Leu

<210> SEQ ID NO 102
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Cys Ile Phe Gly Ala Ile Ala Gly Phe Ile Lys Asn Ile Leu Lys Gly
1               5                   10                  15

Leu Ile Asp Gly Trp Tyr Gly
            20

<210> SEQ ID NO 103
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (24)..(25)
<223> OTHER INFORMATION: Residues at these positions separated by a
      (PEG)3 moiety

<400> SEQUENCE: 103

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 104
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Cys Gly Leu Phe Glu Ala Leu Leu Glu Leu Leu Glu Ser Leu Trp Glu
1               5                   10                  15

Leu Leu Leu Glu Ala Tyr Gly Arg Lys Lys Arg Arg Gln Arg Arg Leu
            20                  25                  30

His Leu Leu His His Leu Leu His Leu His Leu Leu His His
            35                  40                  45

Leu Leu His Leu
    50

<210> SEQ ID NO 105
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Cys Tyr Gly Arg Lys Lys Arg Arg Gln Arg Arg Trp Glu Ala Ala Leu
1               5                   10                  15

Ala Glu Ala Leu Ala Glu Ala Leu Ala Glu His Leu Ala Glu Ala Leu
            20                  25                  30

Ala Glu Ala Leu Glu Ala Leu Ala Ala
        35                  40

<210> SEQ ID NO 106
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Cys Ile Phe Gly Ala Ile Ala Gly Phe Ile Lys Asn Ile Trp Glu Gly
1               5                   10                  15

Leu Ile Asp Gly Trp Tyr Gly Lys Leu Ala Leu Lys Leu Ala Leu Lys
            20                  25                  30

Ala Leu Lys Ala Ala Leu Lys Leu Ala
        35                  40

<210> SEQ ID NO 107
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Cys Phe Phe Gly Ala Ile Trp Glu Phe Ile Arg Ser Ile Leu Glu Gly
1               5                   10                  15

Leu Ile Asp Gly Trp Tyr Gly Tyr Gly Arg Lys Lys Arg Arg Gln Arg
            20                  25                  30

Arg

<210> SEQ ID NO 108
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Cys Gly Leu Phe His Ala Leu Leu His Leu Leu His Ser Leu Trp His
1               5                   10                  15

Leu Leu Leu His Ala Trp Tyr Gly Tyr Gly Arg Lys Lys Arg Arg Gln
            20                  25                  30

Arg Arg

<210> SEQ ID NO 109
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Cys Gly Leu Phe His Ala Leu Leu His Leu Leu His Ser Leu Trp His
1               5                   10                  15

Leu Leu Leu His Ala Trp Tyr Gly Tyr Gly His Lys Lys His His Gln
            20                  25                  30

His Arg

<210> SEQ ID NO 110
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Cys Gly Leu Phe Gly Ala Leu Leu Glu Leu Leu Glu Ser Leu Trp Lys
1               5                   10                  15

Gly Leu Leu Glu Trp Tyr Gly Arg Lys Lys Arg Arg Gln Arg Arg
            20                  25                  30

<210> SEQ ID NO 111
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Cys Arg Arg Gln Arg Arg Lys Lys Arg Gly Tyr Gly Tyr Trp Gly Asp
1               5                   10                  15

Ile Leu Gly Glu Trp Gly Asn Glu Ile Phe Gly Glu Ile Ala Glu Phe
            20                  25                  30

Leu Gly

<210> SEQ ID NO 112
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(29)
<223> OTHER INFORMATION: Ornithine

<400> SEQUENCE: 112

Cys Gly Leu Phe Glu Ala Leu Glu Gly Phe Leu Glu Asn Gly Trp Glu
1               5                   10                  15

Gly Leu Leu Asp Gly Trp Tyr Gly Tyr Gly Arg Xaa Xaa Arg Arg Gln
            20                  25                  30

Arg Arg

<210> SEQ ID NO 113
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Cys Gly Leu Phe Gly Glu Ile Glu Glu Leu Ile Glu Asn Gly Leu Lys
1               5                   10                  15

Asn Leu Ile Asp Trp Trp Tyr Gly Tyr Gly Arg Lys Lys Arg Arg Gln
            20                  25                  30

Arg Arg

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: D-amino acid

<400> SEQUENCE: 114

Cys Arg Arg Gln Arg Arg Lys Lys Arg Gly Tyr Gly Tyr Trp Trp Asp
1               5                   10                  15

Ile Leu Gly Lys Trp Gly Asn Glu Ile Phe Gly Glu Ile Ala Glu Phe
            20                  25                  30

Leu Gly

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Gly Ile Phe Gly Ala Ile Ala Gly Phe Ile Lys Asn Ile Leu
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Gly Ile Phe Gly Ala Ile Ala Gly Leu Leu Lys Asn Ile Phe Lys
1               5                   10                  15

<210> SEQ ID NO 117
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Cys Ile Phe Gly Ala Ile Ala Gly Phe Ile Lys Asn Ile Trp Lys Gly
1               5                   10                  15

Leu Ile Asp Trp
            20

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Cys Ile Phe Gly Ala Ile Ala Gly Phe Ile Lys Asn Ile Trp Lys
1               5                   10                  15

<210> SEQ ID NO 119
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Cys Gly Leu Phe Glu Glu Ile Glu Gly Phe Ile Glu Asn Gly Trp Glu
1               5                   10                  15

Gly Leu Ile Asp Trp Trp Tyr Gly Tyr Gly His Lys Lys His His Gln
            20                  25                  30

His Arg

<210> SEQ ID NO 120
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Cys Gly Leu Phe Gly Glu Ile Glu Glu Leu Ile Glu Asn Gly Leu Lys
1               5                   10                  15

Asn Leu Ile Asp Trp Trp Tyr Gly Tyr Gly His Lys Lys His His Gln
            20                  25                  30

His Arg

<210> SEQ ID NO 121
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Cys Gly Leu Phe Glu Glu Ile Glu Glu Phe Ile Glu Asn Gly Trp Glu
1               5                   10                  15

Gly Leu Ile Asp Trp Trp Tyr Gly Tyr Gly His Lys Lys His His Gln
            20                  25                  30

His Arg

<210> SEQ ID NO 122
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala Tyr Gly
            20                  25                  30

Arg Lys Lys Arg Arg Gln Arg Arg Cys
        35                  40

<210> SEQ ID NO 123
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Cys Gly Leu Phe Glu Ala Ile Glu Gly Phe Ile Glu Asn Gly Trp Lys
1               5                   10                  15

Gly Leu Ile Asp Gly Trp Tyr Gly Gly Leu Phe Glu Ala Ile Glu Gly
            20                  25                  30

Phe Ile Glu Asn Gly Trp Lys Gly Leu Ile Asp Trp Trp Tyr Gly
        35                  40                  45

<210> SEQ ID NO 124
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys Gly Phe Phe His Ala Phe Phe His Phe His Ser Phe Trp His
1               5                   10                  15

Gly Phe Phe Glu Ala
            20

<210> SEQ ID NO 125
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Cys Gly Asn Phe Gly Glu Ile Glu Glu Leu Ile Glu Glu Gly Leu Glu
1               5                   10                  15

Asn Leu Ile Asp Trp Trp Asn Gly
            20

<210> SEQ ID NO 126
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Cys Phe Phe Gly Ala Ile Trp Glu Phe Ile Arg Asn Ile Leu Glu Gly
1               5                   10                  15
Phe

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Cys Phe Phe Gly Ala Ile Trp Glu Phe Ile His Ser Ile Leu
1               5                   10

<210> SEQ ID NO 128
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Cys Gly Leu Phe His Ala Leu Leu His Leu His Ser Leu Trp His
1               5                   10                  15
Gly Leu Leu Glu Ala
            20

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Cys Ile Phe Gly Ala Ile Ala Gly Phe Ile Lys Asn Ile Trp Glu Gly
1               5                   10                  15
Leu

<210> SEQ ID NO 130
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Cys Ile Phe Gly Ala Ile Ala Gly Leu Leu Lys Asn Ile Phe Glu Gly
1               5                   10                  15
Leu Ile Asp Gly Trp Tyr Gly Tyr Gly Arg Lys Lys Arg Arg Gln Arg
            20                  25                  30
Arg
```

<210> SEQ ID NO 131
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Cys Gly Phe Ile Gly Ala Ile Ala Asn Leu Leu Ser Lys Ile Phe Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 132
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Cys Gly Leu Phe Glu Ala Ile Glu Glu Leu Ile Glu Asn Leu Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 133
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Gly Ile Phe Gly Ala Ile Ala Gly Leu Leu Lys Asn Ile Phe Lys
1               5                   10                  15

Gly Leu Ile Asp Ala
            20

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Cys Gly Ile Phe Gly Ala Ile Ala Gly Leu Leu Lys Asn Ile Phe Lys
1               5                   10                  15

Gly Leu Ile Asp Trp
            20

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 135

Cys Gly Ile Phe Glu Ala Ile Ala Gly Leu Leu Lys Asn Ile Phe Lys
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Gly Ile Phe Glu Glu Ile Ala Gly Leu Leu Lys Asn Ile Phe Lys
1               5                   10                  15

<210> SEQ ID NO 137
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Cys Gly Leu Phe Glu Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Leu His Leu Leu His His Leu Leu His His Leu His His Leu
        35                  40                  45

Leu His His Leu Leu His Leu
        50                  55

<210> SEQ ID NO 138
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Cys Gly Leu Phe Glu Ala Ile Glu Gly Phe Ile Glu Asn Gly Trp Lys
1               5                   10                  15

Gly Met Ile Asp Trp Trp Tyr Gly Tyr Gly Arg Lys Lys Arg Arg Gln
            20                  25                  30

Arg Arg Lys
        35

<210> SEQ ID NO 139
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Cys Gly Leu Phe Gly Glu Ile Glu Glu Phe Ile Glu Asn Gly Trp Lys
1               5                   10                  15

Gly Leu Ile Asp Trp Trp Tyr Gly
            20
```

```
<210> SEQ ID NO 140
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Cys Ile Phe Gly Ala Ile Ala Gly Phe Ile Lys Asn Ile Trp Leu His
1               5                   10                  15

Leu Leu His His Leu Leu His His Leu His Leu Leu His His Leu
            20                  25                  30

Leu His Leu
        35

<210> SEQ ID NO 141
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Cys Gly Ile Phe Gly Ala Ile Glu Gly Phe Ile Glu Asn Gly Trp Lys
1               5                   10                  15

Gly Leu Ile Asp Ala Trp Tyr Gly Tyr Arg Lys Lys Arg Arg Gln Arg
            20                  25                  30

Arg

<210> SEQ ID NO 142
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Cys Glu Leu Phe Gly Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 143
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Cys Ile Phe Gly Ile Asp Asp Leu Ile Ile Gly Leu Leu Phe Val Ala
1               5                   10                  15

Ile Val Glu Ala Gly Ile Gly Gly Tyr Leu Leu Gly Ser Tyr Gly Arg
            20                  25                  30

Lys Lys Arg Arg Gln Arg Arg
        35
```

<210> SEQ ID NO 144
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 145
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: D-amino acid

<400> SEQUENCE: 145

Cys Gly Phe Ile Gly Ala Ile Ala Asn Leu Leu Ser Lys Ile Phe Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Phe Phe Gly Ala Ile Trp Glu Phe Ile Arg Ser Ile Leu Lys Gly
1               5                   10                  15

Leu Ile

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Cys Phe Phe Gly Ala Ile Trp Glu Phe Ile Arg Ser Ile Leu Lys
1               5                   10                  15

<210> SEQ ID NO 148
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 148

Cys Phe Phe Gly Ala Ile Trp Glu Phe Ile Arg Ser Ile Leu Glu
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Cys Ile Phe Gly Ala Ile Ala Gly Phe Ile Lys Asn Ile Trp Glu
1               5                   10                  15

<210> SEQ ID NO 150
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Cys Ile Phe Gly Ala Ile Ala Gly Phe Ile Lys Asn Ile Trp Lys Gly
1               5                   10                  15

Leu Ile Asp Ala
            20

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Cys Phe Phe Glu Ala Ile Glu Glu Phe Ile Lys Asn Ile Leu Lys
1               5                   10                  15

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Cys Ile Phe Gly Ala Ile Ala Gly Leu Leu Arg Asn Ile Phe
1               5                   10

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153
```

```
Cys Gly Ile Phe Gly Ala Ile Ala Gly Leu Leu Lys Asn Ile Trp
1               5                   10                  15
```

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

```
Cys Leu Phe Gly Ala Ile Trp Glu Phe Ile Lys Ser Ile Leu
1               5                   10
```

<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

```
Cys Phe Trp Gly Ala Ile Trp Glu Phe Ile Lys Ser Ile Leu
1               5                   10
```

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

```
Cys Phe Gly Gly Ala Ile Trp Glu Phe Ile Lys Ser Ile Leu
1               5                   10
```

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

```
Cys Phe Ala Gly Ala Ile Trp Glu Phe Ile Lys Ser Ile Leu
1               5                   10
```

<210> SEQ ID NO 158
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
                20                  25                  30

Arg Arg
```

```
<210> SEQ ID NO 159
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Cys Gly Leu Phe Glu Ala Ile Glu Gly Phe Ile Glu Asn Gly Trp Glu
1               5                   10                  15

Gly Met Ile Asp Trp Trp Tyr Gly Tyr Gly Arg Lys Lys Arg Arg Gln
            20                  25                  30

Arg Arg

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Phe Phe Gly Ala Ile Trp Glu Phe Ile Lys Ser Ile Gly
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Phe Phe Gly Ala Ile Trp Glu Phe Ile Lys Ser Ile Ala
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Cys Phe Phe Gly Ala Ile Trp Glu Phe Ile Lys Ser Ile Asn
1               5                   10

<210> SEQ ID NO 163
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Phe Phe Gly Ala Ile Trp Glu Phe Ile Lys Ser Ile Trp
1               5                   10

<210> SEQ ID NO 164
<211> LENGTH: 33
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 164

Cys Phe Phe Gly Ala Ile Trp Glu Phe Ile Lys Ser Ile Leu Glu Gly
1               5                   10                  15

Leu Ile Asp Trp Trp Tyr Gly Tyr Gly His Lys Lys His His Gln His
            20                  25                  30

Arg

<210> SEQ ID NO 165
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Cys Leu His Leu Leu His His Leu Leu His Leu His His Leu Leu
1               5                   10                  15

His His Leu Leu His Leu Leu His His Leu Leu His His Leu
            20                  25                  30

<210> SEQ ID NO 166
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Leu His Leu Leu His His Leu His His Leu His His Leu Leu His
1               5                   10                  15

His Leu Leu His Leu Leu His His Leu Leu His His Leu Gly Gly Gly
            20                  25                  30

Arg Lys Lys Arg Arg Gln Arg Arg Pro Pro Gln Cys
        35                  40                  45

<210> SEQ ID NO 167
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Cys Arg Lys Lys Arg Arg Gln Arg Arg Pro Pro Gln Gly Gly Gly
1               5                   10                  15

Leu His Leu Leu His His Leu Leu His His Leu His His Leu Leu His
            20                  25                  30

His Leu Leu His Leu Leu His His Leu Leu His His Leu
        35                  40                  45

<210> SEQ ID NO 168
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 168

Cys Leu His Leu Leu His His Leu Leu His Leu His Leu His Leu Leu
1               5                   10                  15

His His Leu Leu His Leu Leu His His Leu Leu His His Leu Gly Gly
                20                  25                  30

Gly Arg Lys Lys Arg Arg Gln Arg Arg Arg Pro Pro Gln
            35                  40                  45

<210> SEQ ID NO 169
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Cys Gly Leu Phe His Ala Ile Ala His Phe Ile His Gly Gly Trp His
1               5                   10                  15

Gly Leu Ile His Gly Trp Tyr Gly Tyr Gly Arg Lys Lys Arg Arg Gln
                20                  25                  30

Arg Arg

<210> SEQ ID NO 170
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Cys Gly Leu Phe Lys Ala Ile Ala Lys Phe Ile Lys Gly Gly Trp Lys
1               5                   10                  15

Gly Leu Ile Lys Gly Trp Tyr Gly Tyr Gly Arg Lys Lys Arg Arg Gln
                20                  25                  30

Arg Arg

<210> SEQ ID NO 171
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Cys Gly Leu Phe Glu Ala Ile Ala Gly Phe Ile Glu Asn Gly Trp Glu
1               5                   10                  15

Gly Met Ile Asp Gly Trp Tyr Gly Tyr Gly Arg Lys Lys Arg Arg Gln
                20                  25                  30

Arg Arg

<210> SEQ ID NO 172
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
Cys Trp Glu Ala Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Tyr
            20                  25                  30

Gly Arg Lys Lys Arg Arg Gln Arg Arg
        35                  40

<210> SEQ ID NO 173
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Cys Gly Leu Phe Glu Ala Ile Glu Gly Phe Ile Glu Asn Gly Trp Glu
1               5                   10                  15

Gly Met Ile Asp Gly Trp Tyr Gly Arg Lys Lys Arg Arg Gln Arg Arg
            20                  25                  30

Arg Pro Pro Gln
        35

<210> SEQ ID NO 174
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gly Leu Phe Glu Ala Ile Glu Gly Phe Ile Glu Asn Gly Trp Glu Gly
1               5                   10                  15

Met Ile Asp Gly Trp Tyr Gly Tyr Gly Arg Lys Lys Arg Arg Gln Arg
            20                  25                  30

Arg Cys

<210> SEQ ID NO 175
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Leu His Leu Leu His His Leu Leu His His Leu His His Leu Leu His
1               5                   10                  15

His Leu Leu His Leu Leu His His Leu Leu His His Leu Arg Lys Lys
            20                  25                  30

Arg Arg Gln Arg Arg Arg Pro Pro Gln
        35                  40

<210> SEQ ID NO 176
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176
```

```
Leu His Leu Leu His His Leu Leu His Leu His His Leu Leu His
1               5                   10                  15

His Leu Leu His Leu Leu His His Leu Leu His His Leu Gly Pro Gly
                20                  25                  30

Arg Lys Lys Arg Arg Gln Arg Arg Pro Pro Gln
            35                  40
```

<210> SEQ ID NO 177
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Leu Ile Arg Leu Trp Ser His Leu Ile His Ile Trp Phe Gln Asn Arg
1               5                   10                  15

Arg Leu Lys Trp Lys Lys Lys
            20
```

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Arg Lys Lys Arg Arg Gln Arg Arg Pro Pro Gln Gln Gln Gln Gln Gln
1               5                   10                  15

Gln
```

<210> SEQ ID NO 179
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

```
Gly Leu Phe Glu Ala Ile Glu Gly Phe Ile Glu Asn Gly Trp Glu Gly
1               5                   10                  15

Met Ile Asp Gly Trp Tyr Gly Tyr Gly Arg Lys Lys Arg Arg Gln Arg
                20                  25                  30

Arg
```

<210> SEQ ID NO 180
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

```
Leu His Leu Leu His His Leu Leu His Leu His His Leu Leu His
1               5                   10                  15

His Leu Leu His Leu Leu His His Leu Leu His His Leu Gly Gly Gly
                20                  25                  30
```

```
Arg Arg Arg Arg Arg Arg Arg Arg Arg
        35                  40

<210> SEQ ID NO 181
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (29)..(30)
<223> OTHER INFORMATION: Residues at these positions separated by a
      (PEG)12 moiety

<400> SEQUENCE: 181

Leu His Leu Leu His His Leu Leu His His Leu His His Leu His
1               5                   10                  15

His Leu Leu His Leu Leu His His Leu Leu His His Leu Arg Lys Lys
                20                  25                  30

Arg Arg Gln Arg Arg Arg Pro Pro Gln
        35                  40

<210> SEQ ID NO 182
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Leu Phe Gly Ala Ile Ala Gly Phe Ile Glu Asn Gly Trp Glu Gly
1               5                   10                  15

Met Ile Asp Gly Trp Tyr Gly Leu Ile Arg Leu Trp Ser His Leu Ile
                20                  25                  30

Trp Phe Gln Asn Arg Arg Leu Lys Trp Leu Leu Leu
        35                  40

<210> SEQ ID NO 183
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

His His His His His Arg Lys Lys Arg Arg Gln Arg Arg Pro Pro
1               5                   10                  15

Gln Gly Gly Gly Leu His Leu Leu His Leu Leu His Leu His
                20                  25                  30

His Leu Leu His His Leu Leu His Leu His His Leu Leu His His
        35                  40                      45

Leu

<210> SEQ ID NO 184
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: misc_feature
<222> LOCATION: (29)..(30)
<223> OTHER INFORMATION: Residues at these positions separated by a
      (PEG)2 moiety

<400> SEQUENCE: 184
```

Leu His Leu Leu His His Leu Leu His His Leu His His Leu Leu His
1               5                   10                  15

His Leu Leu His Leu Leu His His Leu Leu His His Leu Arg Lys Lys
            20                  25                  30

Arg Arg Gln Arg Arg Arg Pro Pro Gln
        35                  40

```
<210> SEQ ID NO 185
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185
```

Leu His Leu Leu His His Leu Leu His His Leu His His Leu Leu His
1               5                   10                  15

His Leu Leu Leu Leu His His Leu Leu His His Leu Gly Gly Gly Arg
            20                  25                  30

Gln Ile Lys Ile Trp Phe Gln Asn Arg Arg Met Lys Trp Lys Lys Gly
        35                  40                  45

Gly

```
<210> SEQ ID NO 186
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186
```

Lys Leu Leu Lys Leu Leu Leu Lys Leu Trp Leu Lys Leu Leu Lys Leu
1               5                   10                  15

Leu Leu Lys Leu Leu Gly Gly Gly Arg Lys Lys Arg Arg Gln Arg Arg
            20                  25                  30

Arg Pro Pro Gln
        35

```
<210> SEQ ID NO 187
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(30)
<223> OTHER INFORMATION: D-amino acid

<400> SEQUENCE: 187
```

Leu His His Leu Leu His His Leu Leu His Leu Leu His His Leu Leu
1               5                   10                  15

His His Leu His His Leu Leu His Leu Leu His Leu Cys
            20                  25                  30

```
<210> SEQ ID NO 188
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (29)..(30)
<223> OTHER INFORMATION: Residues at these positions separated by a
      (PEG)6 moiety

<400> SEQUENCE: 188

Leu His Leu Leu His His Leu Leu His His Leu His His Leu Leu His
1               5                   10                  15

His Leu Leu His Leu Leu His His Leu Leu His His Leu Arg Lys Lys
            20                  25                  30

Arg Arg Gln Arg Arg Arg Pro Pro Gln Cys
        35                  40

<210> SEQ ID NO 189
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gly Leu Phe Glu Ala Ile Glu Gly Phe Ile Glu Asn Gly Trp Glu Gly
1               5                   10                  15

Met Ile Asp Gly Trp Tyr Gly Tyr Gly Arg Lys Lys Arg Arg Gln Arg
            20                  25                  30

Arg Cys

<210> SEQ ID NO 190
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: D-amino acid

<400> SEQUENCE: 190

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 191
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Cys Gly Leu Phe Glu Ala Ile Glu Gly Phe Ile Glu Asn Gly Trp Glu
```

```
                1               5                  10                  15
Gly Met Ile Asp Gly Trp Tyr Gly Tyr Gly Arg Arg Arg Arg Arg
                20                  25                  30

Arg Arg Arg
        35

<210> SEQ ID NO 192
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Tyr Gly Arg Lys Lys Arg Arg Gln Arg Arg Gly Leu Phe Glu Ala Ile
1               5                   10                  15

Glu Gly Phe Ile Glu Asn Gly Trp Glu Gly Met Ile Asp Gly Trp Tyr
                20                  25                  30

Gly Cys

<210> SEQ ID NO 193
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Gly Val Phe Val Leu Gly Phe Leu Gly Phe Leu Ala Thr Ala Gly
1               5                   10                  15

Ser Tyr Gly Arg Lys Lys Arg Arg Gln Arg Arg
                20                  25

<210> SEQ ID NO 194
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Gly Leu Phe Lys Ala Ile Ala Lys Phe Ile Lys Gly Gly Trp Lys
1               5                   10                  15

Gly Leu Ile Lys Gly Trp Tyr Gly
                20

<210> SEQ ID NO 195
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg
                20                  25                  30
```

```
<210> SEQ ID NO 196
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Tyr Gly Arg Lys Lys Arg Arg Gln Arg Arg
        35                  40

<210> SEQ ID NO 197
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Tyr Gly Arg Lys Lys Arg Arg Gln Arg Arg
        35                  40

<210> SEQ ID NO 198
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Cys Gly Leu Phe Glu Ala Ile Lys Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 199
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Cys Gly Leu Phe Glu Ala Ile His Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 200
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Cys Gly Leu Phe Glu Ala Ile Arg Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 201
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Cys Gly Leu Phe Glu Ala Ile Asp Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 202
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Cys Arg Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 203
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Cys Gly Gly Gly Leu Phe Glu Ala Ile Glu Gly Phe Ile Glu Asn Gly
1               5                   10                  15

Trp Glu Gly Met Ile Asp Gly Trp Tyr Gly Tyr Gly Arg Lys Lys Arg
            20                  25                  30

Arg Gln Arg Arg
        35

<210> SEQ ID NO 204
<211> LENGTH: 37
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 204

Cys Gly Leu Phe Glu Ala Ile Glu Gly Phe Ile Glu Asn Gly Trp Glu
1               5                   10                  15

Gly Met Ile Asp Gly Trp Tyr Gly Gly Gly Tyr Gly Arg Lys Lys
            20                  25                  30

Arg Arg Gln Arg Arg
        35

<210> SEQ ID NO 205
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (24)..(25)
<223> OTHER INFORMATION: Residues at these positions separated by a
      (PEG)11 moiety

<400> SEQUENCE: 205

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 206
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Cys Phe Leu Gly Phe Leu Leu Gly Val Gly Ser Ala Ile Ala Ser Gly
1               5                   10                  15

Ile Ala Val Ser Lys Val Leu His Leu
            20                  25

<210> SEQ ID NO 207
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Cys Gly Val Phe Val Leu Gly Phe Leu Gly Phe Leu Ala Thr Ala Gly
1               5                   10                  15

Ser Ala Met Gly Ala Arg Ser Leu Thr Leu Ser Ala Tyr Gly Arg Lys
            20                  25                  30

Lys Arg Arg Gln Arg Arg
        35

<210> SEQ ID NO 208

<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Leu Trp Arg Ala Leu Trp Arg Leu Leu Arg Ser Leu Trp Arg Leu
1               5                   10                  15

Leu Trp Arg Ala
            20

<210> SEQ ID NO 209
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Nle

<400> SEQUENCE: 209

Cys Leu Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 210
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Cys Glu Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 211
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Cys Gly Phe Phe Gly Ala Ile Ala Gly Phe Leu Glu Gly Gly Trp Glu
1               5                   10                  15

Gly Met Ile Ala Gly Trp His Gly Tyr Gly Arg Lys Lys Arg Arg Gln
            20                  25                  30

Arg Arg

<210> SEQ ID NO 212
<211> LENGTH: 35

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Cys Phe Leu Gly Phe Leu Leu Gly Val Gly Ser Ala Ile Ala Ser Gly
1               5                   10                  15

Ile Ala Val Ser Lys Val Leu His Leu Tyr Gly Arg Lys Lys Arg Arg
                20                  25                  30

Gln Arg Arg
        35

<210> SEQ ID NO 213
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
                20                  25                  30

Ser Cys

<210> SEQ ID NO 214
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Cys Gly Leu Phe Glu Ala Ile Glu Gly Phe Ile Glu Asn Gly Trp Glu
1               5                   10                  15

Gly Met Ile Asp Gly Trp Tyr Gly Leu His Leu Leu His His Leu Leu
                20                  25                  30

His His Leu His His Leu Leu His His Leu Leu His Leu Leu His His
        35                  40                  45

Leu Leu His His Leu
    50

<210> SEQ ID NO 215
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
                20                  25                  30

Arg Arg Leu His Leu Leu His His Leu His Leu His Leu His His Leu
        35                  40                  45
```

```
Leu His Leu Leu His Leu Leu His His Leu His His Leu
        50                  55                  60
```

<210> SEQ ID NO 216
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

```
Cys Gly Leu Phe Gly Ala Ile Ala Gly Phe Ile Glu Gly Gly Trp Thr
1               5                   10                  15

Gly Met Ile Asp Gly Trp Tyr Gly Tyr Gly Arg Lys Lys Arg Arg Gln
            20                  25                  30

Arg Arg
```

<210> SEQ ID NO 217
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

```
Cys Gly Leu Phe Gly Ala Ile Ala Gly Phe Ile Glu Gly Gly Trp Gln
1               5                   10                  15

Gly Met Val Asp Gly Trp Tyr Gly Tyr Gly Arg Lys Lys Arg Arg Gln
            20                  25                  30

Arg Arg
```

<210> SEQ ID NO 218
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

```
Cys Gly Leu Phe Gly Ala Ile Ala Gly Phe Ile Glu Asn Gly Trp Gln
1               5                   10                  15

Gly Leu Ile Asp Gly Trp Tyr Gly Tyr Gly Arg Lys Lys Arg Arg Gln
            20                  25                  30

Arg Arg
```

<210> SEQ ID NO 219
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

```
Cys Gly Leu Phe Gly Ala Ile Ala Gly Phe Ile Glu Asn Gly Trp Glu
1               5                   10                  15

Gly Leu Val Asp Gly Trp Tyr Gly Tyr Gly Arg Lys Lys Arg Arg Gln
            20                  25                  30

Arg Arg
```

<210> SEQ ID NO 220
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Cys Gly Leu Phe Gly Ala Ile Ala Gly Phe Ile Glu Gly Gly Trp Ser
1               5                   10                  15

Gly Met Ile Asp Gly Trp Tyr Gly Tyr Gly Arg Lys Lys Arg Arg Gln
            20                  25                  30

Arg Arg

<210> SEQ ID NO 221
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Cys Gly Leu Phe Gly Ala Ile Ala Gly Phe Ile Glu Gly Gly Trp Pro
1               5                   10                  15

Gly Leu Val Ala Gly Trp Tyr Gly Tyr Gly Arg Lys Lys Arg Arg Gln
            20                  25                  30

Arg Arg

<210> SEQ ID NO 222
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Cys Gly Leu Phe Gly Ala Ile Ala Gly Phe Ile Glu Asn Gly Trp Glu
1               5                   10                  15

Gly Met Val Asp Gly Trp Tyr Gly Tyr Gly Arg Lys Lys Arg Arg Gln
            20                  25                  30

Arg Arg

<210> SEQ ID NO 223
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Cys Gly Leu Phe Gly Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg

<210> SEQ ID NO 224
<211> LENGTH: 34

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Cys Gly Leu Phe Gly Ala Ile Ala Gly Phe Ile Glu Asn Gly Trp Glu
1               5                   10                  15
Gly Leu Ile Asp Gly Trp Tyr Gly Tyr Gly Arg Lys Lys Arg Arg Gln
            20                  25                  30
Arg Arg

<210> SEQ ID NO 225
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Cys Gly Leu Phe Gly Ala Ile Ala Gly Phe Ile Glu Asn Gly Trp Glu
1               5                   10                  15
Gly Met Ile Asp Gly Trp Tyr Gly Tyr Gly Arg Lys Lys Arg Arg Gln
            20                  25                  30
Arg Arg

<210> SEQ ID NO 226
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Cys Gly Leu Phe Gly Ala Ile Ala Gly Phe Ile Glu Asn Gly Trp Glu
1               5                   10                  15
Gly Met Ile Asp Gly Trp Tyr Gly Ser Ser Lys Lys Lys Lys
            20                  25                  30

<210> SEQ ID NO 227
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Cys Gly Leu Phe Gly Ala Ile Ala Gly Phe Ile Glu Asn Gly Trp Glu
1               5                   10                  15
Gly Leu Ile Asp Gly Trp Tyr Gly Tyr Gly Arg Lys Lys Arg Arg Gln
            20                  25                  30
Arg Arg

<210> SEQ ID NO 228
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 228

Cys Gly Leu Phe Glu Ala Ile Glu Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 229
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Cys Gly Leu Phe Gly Ala Ile Ala Gly Phe Ile Glu Asn Gly Trp Glu
1               5                   10                  15

Gly Leu Ile Glu Gly Trp Tyr Gly Gly Gly Arg Lys Lys Arg Arg Gln
            20                  25                  30

Arg Arg

<210> SEQ ID NO 230
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Cys Gly Leu Phe Glu Ala Ile Glu Gly Phe Ile Glu Asn Gly Trp Glu
1               5                   10                  15

Gly Met Ile Asp Gly Trp Tyr Gly Gly Gly Arg Lys Lys Arg Arg Gln
            20                  25                  30

Arg Arg

<210> SEQ ID NO 231
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Cys Gly Leu Phe Glu Ala Ile Ala Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 232
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

```
Cys Gly Leu Phe Glu Ala Ile Ala Glu Phe Ile Glu Asn Gly Trp Glu
1               5                   10                  15

Gly Leu Ile Glu Gly Trp Tyr Gly Arg Lys Lys Arg Arg Gln Arg
            20                  25                  30

Arg

<210> SEQ ID NO 233
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Cys Gly Leu Phe Glu Ala Ile Glu Gly Phe Ile Glu Asn Gly Trp Glu
1               5                   10                  15

Gly Met Ile Asp Gly Trp Tyr Gly Arg Lys Lys Arg Arg Gln Arg Arg
            20                  25                  30

Arg

<210> SEQ ID NO 234
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Cys Lys Leu Leu Lys Leu Leu Leu Lys Leu Trp Leu Lys Leu Leu Lys
1               5                   10                  15

Leu Leu Leu Lys Leu Leu
            20

<210> SEQ ID NO 235
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Cys Lys Leu Leu Lys Leu Leu Leu Lys Leu Trp Leu Lys Leu Leu Lys
1               5                   10                  15

Leu Leu Leu Lys Leu Leu Tyr Gly Arg Lys Lys Arg Arg Gln Arg Arg
            20                  25                  30

<210> SEQ ID NO 236
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Leu Phe Glu Ala Ile Glu Gly Phe Ile Glu Asn Gly Trp Glu Gly
1               5                   10                  15

Met Ile Asp Gly Trp Tyr Gly Cys
            20
```

```
<210> SEQ ID NO 237
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Cys Val Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 238
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Cys Ser Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 239
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

<210> SEQ ID NO 240
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg
            20                  25                  30

<210> SEQ ID NO 241
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 241

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Lys Lys Lys Lys Gln
            20                  25                  30

Lys Lys

<210> SEQ ID NO 242
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Cys Gly Leu Phe Glu Ala Ile Glu Gly Phe Ile Glu Asn Gly Trp Glu
1               5                   10                  15

Gly Met Ile Asp Gly Trp Tyr Gly Gly Leu Phe Glu Ala Ile Glu Gly
            20                  25                  30

Phe Ile Glu Asn Gly Trp Glu Gly Met Ile Asp Gly Trp Tyr Gly
        35                  40                  45

<210> SEQ ID NO 243
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Gly Leu Phe Glu Ala Ile Glu Gly Phe Ile Glu Asn Gly Trp
        35                  40                  45

Glu Gly Met Ile Asp Gly Trp Tyr Gly Tyr Gly Arg Lys Lys Arg Arg
    50                  55                  60

Gln Arg Arg
65

<210> SEQ ID NO 244
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Arg Arg Gln Arg Arg Lys Lys Arg Gly Tyr Gly Tyr Trp Gly Asp Ile
1               5                   10                  15

Met Gly Glu Trp Gly Asn Glu Ile Phe Gly Glu Ile Ala Glu Phe Leu
            20                  25                  30

Gly Cys

<210> SEQ ID NO 245
<211> LENGTH: 34

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Cys Arg Arg Gln Arg Arg Lys Lys Arg Gly Tyr Gly Tyr Trp Gly Asp
1               5                   10                  15

Ile Met Gly Glu Trp Gly Asn Glu Ile Phe Gly Glu Ile Ala Glu Phe
            20                  25                  30

Leu Gly

<210> SEQ ID NO 246
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: D-amino acid

<400> SEQUENCE: 246

Gly Leu Phe Glu Ala Ile Glu Gly Phe Ile Glu Asn Gly Trp Glu Gly
1               5                   10                  15

Met Ile Asp Gly Trp Tyr Gly Tyr Gly Arg Lys Lys Arg Arg Gln Arg
            20                  25                  30

Arg

<210> SEQ ID NO 247
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: D-amino acid

<400> SEQUENCE: 247

Gly Leu Phe Glu Ala Ile Glu Gly Phe Ile Glu Asn Gly Trp Glu Gly
1               5                   10                  15

Met Ile Asp Gly Trp Tyr Gly Tyr Gly Arg Lys Lys Arg Arg Gln Arg
            20                  25                  30

Arg

<210> SEQ ID NO 248
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: D-amino acid

<400> SEQUENCE: 248

Gly Leu Phe Glu Ala Ile Glu Gly Phe Ile Glu Asn Gly Trp Glu Gly
1               5                   10                  15
```

```
Met Ile Asp Gly Trp Tyr Gly Tyr Gly Arg Lys Lys Arg Gln Arg
            20                  25                  30

Arg

<210> SEQ ID NO 249
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: D-amino acid

<400> SEQUENCE: 249

Gly Leu Phe Glu Ala Ile Glu Gly Phe Ile Glu Asn Gly Trp Glu Gly
1               5                   10                  15

Met Ile Asp Gly Trp Tyr Gly Tyr Gly Arg Lys Lys Arg Gln Arg
            20                  25                  30

Arg

<210> SEQ ID NO 250
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Cys Gly Leu Phe Glu Ala Ile Glu Gly Phe Ile Glu Asn Gly Trp Glu
1               5                   10                  15

Gly Met Ile Asp Gly Trp Tyr Gly
            20

<210> SEQ ID NO 251
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Cys Tyr Gly Arg Lys Lys Arg Arg Gln Arg Arg
1               5                   10

<210> SEQ ID NO 252
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Tyr Gly Arg Lys Lys Arg Arg Gln Arg Arg Cys
1               5                   10

<210> SEQ ID NO 253
<211> LENGTH: 34
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: D-amino acid

<400> SEQUENCE: 253

Arg Arg Gln Arg Arg Lys Lys Arg Gly Tyr Gly Tyr Trp Gly Asp Ile
1               5                   10                  15

Met Gly Glu Trp Gly Asn Glu Ile Phe Gly Glu Ile Ala Glu Phe Leu
            20                  25                  30

Gly Cys

<210> SEQ ID NO 254
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: D-amino acid

<400> SEQUENCE: 254

Cys Arg Arg Gln Arg Arg Lys Lys Arg Gly Tyr Gly Tyr Trp Gly Asp
1               5                   10                  15

Ile Met Gly Glu Trp Gly Asn Glu Ile Phe Gly Glu Ile Ala Glu Phe
            20                  25                  30

Leu Gly

<210> SEQ ID NO 255
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Cys Gly Leu Phe Glu Ala Ile Glu Gly Phe Ile Glu Asn Gly Trp Glu
1               5                   10                  15

Gly Met Ile Asp Gly Ala Tyr Gly Tyr Gly Arg Lys Lys Arg Arg Gln
            20                  25                  30

Arg Arg

<210> SEQ ID NO 256
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Cys Gly Leu Phe Glu Ala Leu Leu Glu Leu Leu Glu Ser Leu Trp Glu
1               5                   10                  15

Leu Leu Leu Glu Ala Trp Tyr Gly Tyr Gly Arg Lys Lys Arg Arg Gln
            20                  25                  30

Arg Arg
```

<210> SEQ ID NO 257
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Cys Gly Leu Phe Glu Ala Ile Glu Gly Phe Asn Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 258
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 259
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Lys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Cys
        35

<210> SEQ ID NO 260
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Cys Gly Leu Phe Glu Ala Ile Lys Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 261

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Cys Gly Leu Phe Glu Ala Ile Lys Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 262
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Cys Gly Leu Phe Glu Ala Ile Glu Gly Phe Ile Glu Asn Pro Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 263
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Gly Leu Phe Glu Ala Ile Glu Gly Phe Ile Glu Asn Pro Trp Glu Gly
1               5                   10                  15

Met Ile Asp Gly Trp Tyr Gly Tyr Gly Arg Lys Lys Arg Arg Gln Arg
            20                  25                  30

Arg Cys

<210> SEQ ID NO 264
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Cys Gly Leu Phe Gly Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Leu His Leu Leu His His Leu Leu His Leu His His Leu
            35                  40                  45

Leu His His Leu Leu His Leu Leu His His Leu Leu His His Leu
        50                  55                  60
```

```
<210> SEQ ID NO 265
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Cys Gly Leu Phe Gly Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Leu His Leu Leu His Leu Leu His Leu His His Leu
        35                  40                  45

Leu His His Leu Leu His Leu
    50                  55

<210> SEQ ID NO 266
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Cys Gly Leu Phe Glu Ala Ile Ala Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg

<210> SEQ ID NO 267
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Cys Gly Leu Glu Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 268
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Cys Gly Leu Phe Asn Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg
```

<210> SEQ ID NO 269
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Cys Gly Leu Phe Ala Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 270
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Cys Gly Leu Phe Glu Ala Ile Glu Asn Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 271
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Cys Gly Leu Phe Glu Ala Ile Glu Lys Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 272
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Cys Gly Leu Phe Glu Ala Ile Glu Gly Phe Ala Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 273
<211> LENGTH: 34

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Cys Gly Leu Phe Glu Ala Ile Glu Gly Phe Ile Glu Asn Trp Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 274
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Cys Gly Leu Phe Glu Ala Ile Glu Gly Phe Ile Glu Asn Asn Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 275
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Cys Gly Leu Phe Glu Ala Ile Glu Gly Phe Ile Glu Asn Gly Glu Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 276
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Cys Gly Leu Phe Glu Ala Ile Glu Gly Phe Ile Glu Asn Gly Trp Ala
1               5                   10                  15

Gly Met Ile Asp Gly Trp Tyr Gly Tyr Gly Arg Lys Lys Arg Arg Gln
            20                  25                  30

Arg Arg

<210> SEQ ID NO 277
<211> LENGTH: 34
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 277

Cys Gly Leu Phe Glu Ala Ile Glu Gly Phe Ile Glu Asn Gly Trp Asn
1               5                   10                  15

Gly Met Ile Asp Gly Trp Tyr Gly Tyr Gly Arg Lys Lys Arg Arg Gln
            20                  25                  30

Arg Arg

<210> SEQ ID NO 278
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Cys Gly Leu Phe Glu Ala Ile Glu Gly Phe Ile Glu Asn Gly Trp Gly
1               5                   10                  15

Gly Met Ile Asp Gly Trp Tyr Gly Tyr Gly Arg Lys Lys Arg Arg Gln
            20                  25                  30

Arg Arg

<210> SEQ ID NO 279
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Cys Gly Leu Phe Glu Ala Ile Glu Gly Phe Ile Glu Asn Gly Trp Glu
1               5                   10                  15

Gly Met Ile Asp Ala Trp Tyr Gly Tyr Gly Arg Lys Lys Arg Arg Gln
            20                  25                  30

Arg Arg

<210> SEQ ID NO 280
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Cys Gly Leu Phe Glu Ala Ile Glu Gly Phe Ile Glu Asn Gly Trp Leu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 281
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 281

Cys Gly Leu Phe Glu Ala Ile Glu Gly Phe Ile Glu Asn Gly Trp Lys
1               5                   10                  15

Gly Met Ile Asp Gly Trp Tyr Gly Tyr Gly Arg Lys Lys Arg Arg Gln
            20                  25                  30

Arg Arg

<210> SEQ ID NO 282
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Cys Gly Leu Phe Glu Ala Ile Glu Gly Phe Ile Glu Asn Gly Trp Glu
1               5                   10                  15

Gly Met Ile Asp Lys Trp Tyr Gly Tyr Gly Arg Lys Lys Arg Arg Gln
            20                  25                  30

Arg Arg

<210> SEQ ID NO 283
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Cys Gly Leu Phe Glu Ala Ile Glu Gly Phe Ile Glu Asn Gly Trp Glu
1               5                   10                  15

Gly Met Ile Asp Glu Trp Tyr Gly Tyr Gly Arg Lys Lys Arg Arg Gln
            20                  25                  30

Arg Arg

<210> SEQ ID NO 284
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Cys Gly Leu Phe Glu Ala Ile Glu Gly Phe Ile Glu Asn Gly Trp Glu
1               5                   10                  15

Gly Met Ile Asp Gly Leu Tyr Gly Tyr Gly Arg Lys Lys Arg Arg Gln
            20                  25                  30

Arg Arg

<210> SEQ ID NO 285
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Cys Gly Leu Phe Glu Ala Ile Glu Gly Phe Ile Glu Asn Gly Trp Glu

```
1               5                   10                  15
Gly Met Ile Asp Gly Asn Tyr Gly Tyr Gly Arg Lys Lys Arg Arg Gln
                20                  25                  30

Arg Arg

<210> SEQ ID NO 286
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Cys Gly Leu Phe Glu Ala Ile Glu Gly Phe Ile Glu Asn Gly Trp Glu
1               5                   10                  15

Gly Met Ile Asp Gly Lys Tyr Gly Tyr Gly Arg Lys Lys Arg Arg Gln
                20                  25                  30

Arg Arg

<210> SEQ ID NO 287
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Cys Gly Leu Phe Glu Ala Ile Glu Gly Phe Ile Glu Asn Gly Trp Glu
1               5                   10                  15

Gly Met Ile Asp Gly Glu Tyr Gly Tyr Gly Arg Lys Lys Arg Arg Gln
                20                  25                  30

Arg Arg

<210> SEQ ID NO 288
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Cys Gly Leu Phe Glu Ala Leu Glu Gly Leu Leu Glu Gly Gly Trp Glu
1               5                   10                  15

Gly Leu Ile Glu Ala Trp Tyr Gly Tyr Gly Arg Lys Lys Arg Arg Gln
                20                  25                  30

Arg Arg

<210> SEQ ID NO 289
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Cys Glu Leu Phe Gly Ala Ile Trp Glu Phe Ile Glu Gly Gly Trp Glu
1               5                   10                  15

Gly Leu Ile Glu Ala Trp Tyr Gly Tyr Gly Arg Lys Lys Arg Arg Gln
```

-continued

```
                     20                  25                  30

Arg Arg

<210> SEQ ID NO 290
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Cys Gly Leu Phe Glu Ala Leu Glu Glu Phe Ile Glu Gly Gly Trp Glu
1               5                   10                  15

Gly Leu Leu Glu Ala Trp Tyr Gly Tyr Gly Arg Lys Lys Arg Arg Gln
            20                  25                  30

Arg Arg

<210> SEQ ID NO 291
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Cys Gly Leu Phe Glu Ala Leu Glu Glu Phe Ile Glu Asn Gly Trp Glu
1               5                   10                  15

Gly Leu Leu Glu Ala Trp Tyr Gly Tyr Gly Arg Lys Lys Arg Arg Gln
            20                  25                  30

Arg Arg

<210> SEQ ID NO 292
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Cys Gly Leu Phe Glu Ala Ile Glu Gly Phe Ile Glu Ser Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 293
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Cys Gly Leu Phe Glu Ala Ile Glu Glu Phe Ile Glu Gly Gly Trp Glu
1               5                   10                  15

Gly Leu Ile Glu Ala Trp Tyr Gly Tyr Gly Arg Lys Lys Arg Arg Gln
            20                  25                  30

Arg Arg
```

<210> SEQ ID NO 294
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Cys Gly Leu Phe Glu Ala Ile Glu Gly Phe Ile Glu Asn Gly Trp Glu
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 295
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Cys Gly Leu Phe Glu Ala Ile Glu Gly Phe Ile Leu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 296
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Cys Gly Leu Phe Glu Ala Ile Glu Gly Phe Ile Lys Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 297
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Cys Gly Leu Phe Glu Ala Ile Glu Gly Phe Ile Gly Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 298

<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Cys Gly Leu Phe Glu Ala Ile Glu Gly Phe Ile Glu Leu Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 299
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Cys Gly Leu Phe Glu Ala Ile Glu Gly Phe Ile Glu Lys Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 300
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Cys Gly Leu Phe Glu Ala Ile Ala Glu Phe Ile Glu Gly Gly Trp Glu
1               5                   10                  15

Gly Leu Ile Glu Gly Trp Tyr Gly Tyr Gly Arg Lys Lys Arg Arg Gln
            20                  25                  30

Arg Arg

<210> SEQ ID NO 301
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Cys Arg Gly Trp Glu Val Leu Lys Tyr Trp Trp Asn Leu Leu Gln Tyr
1               5                   10                  15

<210> SEQ ID NO 302
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Cys Arg Gly Trp Glu Val Leu Lys Tyr Trp Trp Asn Leu Leu Gln Tyr
1               5                   10                  15

Tyr Gly Arg Lys Lys Arg Arg Gln Arg Arg
            20                  25

<210> SEQ ID NO 303
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Cys Gly Leu Phe Gly Ala Ile Ala Gly Phe Ile Glu Asn Gly Trp Glu
1               5                   10                  15

Gly Met Ile Asp Gly Trp Tyr Gly Phe Arg Tyr Gly Arg Lys Lys Arg
            20                  25                  30

Arg Gln Arg Arg
        35

<210> SEQ ID NO 304
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 305
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Cys Gly Leu Leu Glu Ala Leu Glu Gly Leu Leu Glu Asn Gly Trp Glu
1               5                   10                  15

Gly Leu Leu Glu Ala Trp Tyr Gly Tyr Gly Arg Lys Lys Arg Arg Gln
            20                  25                  30

Arg Arg

<210> SEQ ID NO 306
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Cys Leu Arg His Leu Leu Arg His Leu Leu Arg His Leu Arg His Leu
1               5                   10                  15

Leu Arg His Leu Arg His Leu Leu Arg His Leu Leu Arg His
            20                  25                  30

<210> SEQ ID NO 307
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(29)
<223> OTHER INFORMATION: Ornithine

<400> SEQUENCE: 307

Cys Gly Ile Phe Glu Ala Ile Glu Gly Phe Ile Glu Asn Gly Trp Glu
1               5                   10                  15

Gly Ile Ile Asp Gly Trp Tyr Gly Tyr Gly Arg Xaa Xaa Arg Arg Gln
            20                  25                  30

Arg Arg

<210> SEQ ID NO 308
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Cys Gly Ile Gly Ala Val Leu Lys Val Leu Thr Thr Gly Leu Pro Ala
1               5                   10                  15

Leu Ile Ser Trp Ile Lys Arg Lys Arg Gln Gln
            20                  25

<210> SEQ ID NO 309
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Cys Gly Ile Gly Ala Val Leu Lys Val Leu Thr Thr Gly Leu Pro Ala
1               5                   10                  15

Leu Ile Ser Trp Ile His His His His Gln Gln
            20                  25

<210> SEQ ID NO 310
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Cys Gly Ala Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 311
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Leu His Leu Leu His His Leu His His Leu His His Leu Leu His
1               5                   10                  15

His Leu Leu His Leu Leu His His Leu Leu His His Leu Arg Arg Arg
            20                  25                  30

Arg Arg

<210> SEQ ID NO 312
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Cys Gly Leu Phe Gly Ala Ile Trp Gly Phe Ile Glu Asn Trp Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 313
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Cys Gly Leu Phe Gly Ala Ile Glu Gly Phe Ile Glu Asn Gly Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 314
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Cys Gly Leu Phe Glu Ala Ile Ala Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 315
<211> LENGTH: 34

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Gly Leu Phe Glu Ala Ile Glu Gly Phe Ile Glu Asn Gly Trp Lys Gly
1               5                   10                  15

Leu Ile Asp Trp Trp Tyr Gly Tyr Gly Arg Lys Lys Arg Arg Gln Arg
            20                  25                  30

Arg Cys

<210> SEQ ID NO 316
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Tyr Gly Arg Lys Lys Arg Arg Gln Arg Gly Leu Phe Glu Ala Ile
1               5                   10                  15

Glu Gly Phe Ile Glu Asn Gly Trp Lys Gly Leu Ile Asp Ala Trp Tyr
            20                  25                  30

Gly Cys

<210> SEQ ID NO 317
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Tyr Gly Arg Lys Lys Arg Arg Gln Arg Gly Leu Phe Glu Ala Ile
1               5                   10                  15

Glu Gly Phe Ile Glu Asn Gly Trp Lys Gly Leu Ile Asp Trp Trp Tyr
            20                  25                  30

Gly Cys

<210> SEQ ID NO 318
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Cys Gly Leu Phe His Ala Ile His Gly Phe Ile Glu Asn Gly Trp His
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 319
<211> LENGTH: 35
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 319

Cys Gly Leu Phe Glu Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg Lys
        35

<210> SEQ ID NO 320
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Cys Gly Leu Phe Lys Ala Leu Leu Lys Leu Leu Lys Ser Leu Trp Lys
1               5                   10                  15

Leu Leu Leu Lys Ala Trp Tyr Gly Tyr Gly His Lys Lys His His Gln
            20                  25                  30

His Arg

<210> SEQ ID NO 321
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Cys Gly Leu Phe Lys Ala Leu Leu Lys Leu Leu Lys Ser Leu Trp Lys
1               5                   10                  15

Gly Leu Leu Lys Ala Trp Tyr Gly Tyr Gly His Lys Lys His His Gln
            20                  25                  30

His Arg

<210> SEQ ID NO 322
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Cys Gly Leu Ala Lys Ala Leu Leu Lys Leu Leu Lys Ser Leu Trp Lys
1               5                   10                  15

Gly Leu Ile Glu Ala Trp Tyr Gly Tyr Gly Arg Lys Lys Arg Arg Gln
            20                  25                  30

Arg Arg

<210> SEQ ID NO 323
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 323

Cys Gly Ile Phe Gly Ala Ile Ala Gly Phe Ile Lys Asn Ile Trp
1               5                   10                  15

<210> SEQ ID NO 324
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Cys Ile Phe Gly Ala Ile Ala Gly Phe Ile Lys Asn Ile Trp Glu Gly
1               5                   10                  15

Leu Ile Asp Gly Trp Tyr Gly Tyr Gly Arg Lys Lys Arg Arg Gln Arg
            20                  25                  30

Arg

<210> SEQ ID NO 325
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Cys Gly Ile Phe Gly Ala Ile Ala Gly Phe Ile Lys Asn Ile Trp Glu
1               5                   10                  15

Gly Leu Ile Asp Gly Tyr Gly Arg Lys Lys Arg Arg Gln Arg Arg
            20                  25                  30

<210> SEQ ID NO 326
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Cys Gly Ile Phe Gly Ala Ile Ala Gly Phe Ile Lys Asn Ile Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 327
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Cys Ile Phe Gly Ala Ile Ala Gly Phe Ile Lys Asn Ile Trp Lys Gly
1               5                   10                  15

Leu Ile Asp Trp Trp Tyr Gly Tyr Gly Arg Lys Lys Arg Arg Gln Arg
            20                  25                  30

Arg

<210> SEQ ID NO 328
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Cys Leu Phe Gly Ala Ile Ala Gly Phe Ile Lys Asn Ile Trp
1               5                   10

<210> SEQ ID NO 329
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Cys Gly Leu Arg Arg Arg Arg Glu Ala Ile Glu Gly Phe Ser Ser
1               5                   10                  15

Ser Ser Ser Ser Ser Ser Glu Asn Gly Trp Glu Gly Met Ile Asp Gly
            20                  25                  30

Trp Tyr Gly Tyr Gly Arg Lys Lys Arg Arg Gln Arg Arg
        35                  40                  45

<210> SEQ ID NO 330
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Cys Gly Leu Phe Glu Ala Ser Ser Ser Ser Glu Gly Phe Ser Ser
1               5                   10                  15

Ser Ser Ser Glu Asn Gly Trp Glu Gly Met Ile Asp Gly Trp Tyr Gly
            20                  25                  30

Tyr Gly Arg Lys Lys Arg Arg Gln Arg Arg
        35                  40

<210> SEQ ID NO 331
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Cys Gly Leu Phe Glu Ala Ile Glu Gly Phe Ile Glu Asn Gly Trp Glu
1               5                   10                  15

Gly Ala Ile Asp Gly Trp Tyr Gly Tyr Gly Arg Lys Lys Arg Arg Gln
            20                  25                  30

Arg Arg

<210> SEQ ID NO 332
<211> LENGTH: 34
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 332

Cys Gly Leu Phe Glu Ala Ile Glu Gly Phe Ile Glu Asn Gly Trp Glu
1               5                   10                  15

Gly Glu Ile Asp Gly Trp Tyr Gly Tyr Gly Arg Lys Lys Arg Arg Gln
            20                  25                  30

Arg Arg

<210> SEQ ID NO 333
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Cys Gly Ile Phe Gly Ala Ile Ala Gly Phe Ile Lys Asn Gly Trp Glu
1               5                   10                  15

Gly Met Val Asp Trp Tyr Gly Tyr Gly Arg Lys Lys Arg Arg Gln Arg
            20                  25                  30

Arg

<210> SEQ ID NO 334
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Cys Gly Leu Phe Glu Ala Ile Ala Gly Phe Ile Glu Asn Gly Trp Glu
1               5                   10                  15

Gly Met Ile Asp Gly Trp Tyr Gly Phe Tyr Gly Arg Lys Lys Arg Arg
            20                  25                  30

Gln Arg Arg
        35

<210> SEQ ID NO 335
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Cys Gly Ile Phe Gly Ala Ile Ala Gly Phe Ile Lys Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 336
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 336

Cys Ile Phe Gly Ala Ile Ala Gly Phe Ile Lys Asn Ile Trp
1               5                   10

<210> SEQ ID NO 337
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Cys Ile Phe Gly Ala Ile Ala Gly Phe Ile Lys Asn Ile Trp Tyr Gly
1               5                   10                  15

Arg Lys Lys Arg Arg Gln Arg Arg
            20

<210> SEQ ID NO 338
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Cys Gly Ile Phe Gly Ala Ile Ala Gly Phe Ile Lys Asn Ile Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 339
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Cys Gly Leu Phe Glu Ala Ile Glu Gly Phe Ile Glu Asn Gly Trp Glu
1               5                   10                  15

Gly Leu Ile Glu Ala Tyr Gly Arg Lys Lys Arg Arg Gln Arg Arg
            20                  25                  30

<210> SEQ ID NO 340
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Cys Gly Leu Phe Glu Ala Leu Leu Gly Phe Ile Glu Asn Gly Trp Glu
1               5                   10                  15

Gly Leu Ile Asp Gly Tyr Gly Arg Lys Lys Arg Arg Gln Arg Arg
            20                  25                  30

<210> SEQ ID NO 341

```
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Cys Gly Leu Phe Gly Ala Ile Glu Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg Arg
        35

<210> SEQ ID NO 342
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Cys Glu Leu Phe Gly Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg Arg
        35

<210> SEQ ID NO 343
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly His Lys Lys His His Gln
            20                  25                  30

His Arg

<210> SEQ ID NO 344
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Cys Gly Leu Phe Gly Ala Ile Glu Gly Phe Ile Glu Gly Gly Trp Pro
1               5                   10                  15

Gly Leu Ile Asn Gly Trp Tyr Gly Tyr Gly Arg Lys Lys Arg Arg Gln
            20                  25                  30

Arg Arg Arg
        35

<210> SEQ ID NO 345
```

```
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Cys Gly Leu Phe Lys Ala Leu Leu Lys Leu Leu Lys Ser Leu Trp Lys
1               5                   10                  15
Leu Leu Leu Lys Ala Tyr Gly Arg Lys Lys Arg Arg Gln Arg Arg
            20                  25                  30

<210> SEQ ID NO 346
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Cys Gly Leu Phe Lys Ala Leu Leu Lys Leu Leu Lys Ser Leu Trp Lys
1               5                   10                  15
Leu Leu Leu Lys Ala Trp Tyr Gly Tyr Gly Arg Lys Lys Arg Arg Gln
            20                  25                  30
Arg Arg

<210> SEQ ID NO 347
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Cys Gly Leu Phe Arg Ala Leu Leu Arg Leu Leu Arg Ser Leu Trp Arg
1               5                   10                  15
Leu Leu Leu Arg Ala Tyr Gly Arg Lys Lys Arg Arg Gln Arg Arg
            20                  25                  30

<210> SEQ ID NO 348
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Cys Gly Leu Phe Glu Ala Ile Leu Gly Phe Ile Glu Asn Gly Trp Glu
1               5                   10                  15
Gly Leu Ile Asp Gly Trp Tyr Gly Tyr Gly Arg Lys Lys Arg Arg Gln
            20                  25                  30
Arg Arg

<210> SEQ ID NO 349
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 349

Cys Gly Leu Phe Glu Ala Ile Trp Glu Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 350
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Cys Gly Leu Phe Glu Ala Ile Glu Gly Phe Ile Glu Asn Gly Trp Glu
1               5                   10                  15

Gly Met Ile Asp Gly Trp Tyr Gly Gly Gly Leu His Leu Leu His
            20                  25                  30

His Leu Leu His His Leu His His Leu Leu His His Leu Leu His Leu
        35                  40                  45

<210> SEQ ID NO 351
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Cys Gly Pro Val Glu Asp Ala Ile Thr Ala Ala Ile Gly Arg Val Ala
1               5                   10                  15

Asp Thr Val Gly Thr Tyr Gly Arg Lys Lys Arg Arg Gln Arg Arg
            20                  25                  30

<210> SEQ ID NO 352
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Cys Met Asp Gly Thr Leu Phe Pro Gly Asp Asp Leu Ala Ile Pro
1               5                   10                  15

Ala Thr Glu Phe Phe Ser Thr Lys Ala
            20                  25

<210> SEQ ID NO 353
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Cys Gly Leu Phe Glu Ala Leu Glu Glu Phe Ile Glu Gly Gly Trp Glu
1               5                   10                  15

Gly Leu Leu Glu Ala Trp Tyr Gly Tyr Gly Arg Lys Lys Arg Arg Gln

```
                20                  25                  30

Arg Arg

<210> SEQ ID NO 354
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Cys Gly Leu Phe Glu Ala Leu Glu Glu Phe Ile Glu Asn Gly Trp Glu
1               5                   10                  15

Gly Leu Leu Glu Ala Trp Tyr Gly Tyr Gly Arg Lys Lys Arg Arg Gln
                20                  25                  30

Arg Arg

<210> SEQ ID NO 355
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Cys Glu Leu Phe Gly Ala Ile Trp Glu Phe Ile Glu Gly Gly Trp Glu
1               5                   10                  15

Gly Leu Ile Glu Ala Tyr Gly Arg Lys Lys Arg Arg Gln Arg Arg
                20                  25                  30

<210> SEQ ID NO 356
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Cys Gly Leu Phe Glu Ala Ile Glu Gly Phe Ile Glu Glu Gly Trp Glu
1               5                   10                  15

Gly Met Ile Asp Gly Trp Tyr Gly Tyr Gly Arg Lys Lys Arg Arg Gln
                20                  25                  30

Arg Arg

<210> SEQ ID NO 357
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Cys Gly Leu Phe Glu Ala Ile Ala Glu Phe Ile Glu Asn Gly Trp Glu
1               5                   10                  15

Gly Met Ile Asp Gly Trp Tyr Gly Tyr Gly Arg Lys Lys Arg Arg Gln
                20                  25                  30

Arg Arg
```

```
<210> SEQ ID NO 358
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Cys Gly Leu Phe Glu Ala Ile Ala Glu Phe Ile Glu Gly Leu Trp Glu
1               5                   10                  15

Gly Leu Ile Glu Gly Trp Tyr Gly Tyr Gly Arg Lys Lys Arg Arg Gln
            20                  25                  30

Arg Arg

<210> SEQ ID NO 359
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Cys Gly Leu Leu Glu Ala Leu Glu Gly Leu Leu Glu Ser Leu Trp Glu
1               5                   10                  15

Gly Leu Leu Glu Ala Trp Tyr Gly Tyr Gly Arg Lys Lys Arg Arg Gln
            20                  25                  30

Arg Arg

<210> SEQ ID NO 360
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Cys Gly Leu Phe Glu Ala Ile Glu Gly Phe Ile Glu Asn Gly Trp Glu
1               5                   10                  15

Gly Met Ile Asp Ile Trp Tyr Gly Tyr Gly Arg Lys Lys Arg Arg Gln
            20                  25                  30

Arg Arg

<210> SEQ ID NO 361
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Cys Gly Leu Phe Glu Ala Ile Glu Gly Phe Ile Glu Asn Gly Trp Arg
1               5                   10                  15

Gly Met Ile Asp Gly Trp Tyr Gly Tyr Gly Arg Lys Lys Arg Arg Gln
            20                  25                  30

Arg Arg

<210> SEQ ID NO 362
<211> LENGTH: 34
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 362

Cys Gly Leu Phe Glu Ala Ile Glu Gly Phe Ile Glu Asn Gly Trp Asp
1               5                   10                  15

Gly Met Ile Asp Gly Trp Tyr Gly Tyr Gly Arg Lys Lys Arg Arg Gln
            20                  25                  30

Arg Arg

<210> SEQ ID NO 363
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Cys Gly Leu Phe Glu Ala Ile Glu Gly Phe Ile Glu Asn His Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 364
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Cys Gly Leu Phe Glu Ala Ile Glu Gly Phe Ile Glu Asn Trp Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 365
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Gly Leu Phe Glu Ala Ile Glu Gly Phe Ile Glu Asn Gly Trp Lys Gly
1               5                   10                  15

Leu Ile Asp Ala Trp Tyr Gly Tyr Gly Arg Lys Lys Arg Arg Gln Arg
            20                  25                  30

Arg Cys

<210> SEQ ID NO 366
<211> LENGTH: 34
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 366

Cys Gly Leu Phe Glu Ala Ile Glu Gly Phe Ile Glu Asn Gly Trp Lys
1               5                   10                  15

Gly Met Ile Asp Ala Trp Tyr Gly Tyr Gly Arg Lys Lys Arg Arg Gln
            20                  25                  30

Arg Arg

<210> SEQ ID NO 367
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Cys Gly Leu Phe Glu Ala Ile Glu Gly Phe Ile Glu Asn Gly Trp Lys
1               5                   10                  15

Gly Met Ile Asp Trp Trp Tyr Gly Tyr Gly Arg Lys Lys Arg Arg Gln
            20                  25                  30

Arg Arg

<210> SEQ ID NO 368
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Cys Gly Leu Ala Glu Ala Ile Glu Gly Phe Ile Glu Asn Gly Leu Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 369
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: D-amino acid

<400> SEQUENCE: 369

Arg Arg Gln Arg Arg Lys Lys Arg Gly Tyr Gly Tyr Trp Gly Asp Ile
1               5                   10                  15

Leu Gly Glu Trp Gly Asn Glu Ile Phe Gly Glu Ile Ala Glu Phe Leu
            20                  25                  30

Gly Cys

<210> SEQ ID NO 370
<211> LENGTH: 34
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: D-amino acid

<400> SEQUENCE: 370

Cys Arg Arg Gln Arg Arg Lys Lys Arg Gly Tyr Gly Tyr Trp Gly Asp
1               5                   10                  15

Ile Leu Gly Glu Trp Gly Asn Glu Ile Phe Gly Glu Ile Ala Glu Phe
            20                  25                  30

Leu Gly

<210> SEQ ID NO 371
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Cys Gly Leu Phe Glu Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 372
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Cys Gly Phe Phe Glu Ala Ile Glu Gly Phe Ile Glu Asn Gly Leu Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 373
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Cys Gly Leu Phe Glu Ala Ile Glu Gly Phe Ile Glu Asn Gly Leu Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 374
<211> LENGTH: 34
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 374

Cys Glu Leu Phe Gly Ala Ile Glu Gly Phe Ile Glu Asn Gly Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 375
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Cys Gly Leu Phe Lys Ala Ile Lys Gly Phe Ile Lys Asn Gly Trp Lys
1               5                   10                  15

Gly Leu Ile Lys Ala Trp Tyr Gly Tyr Gly Arg Lys Lys Arg Arg Gln
            20                  25                  30

Arg Arg

<210> SEQ ID NO 376
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Cys Gly Leu Ala Glu Ala Leu Leu Glu Leu Leu Glu Ser Leu Trp Lys
1               5                   10                  15

Gly Leu Ile Glu Ala Tyr Gly Arg Lys Lys Arg Arg Gln Arg Arg
            20                  25                  30

<210> SEQ ID NO 377
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Cys Gly Ile Phe Gly Ala Ile Glu Gly Phe Ile Glu Asn Gly Trp Lys
1               5                   10                  15

Gly Leu Ile Asp Ala Trp Tyr Gly Tyr Gly Arg Lys Lys Arg Arg Gln
            20                  25                  30

Arg Arg

<210> SEQ ID NO 378
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378
```

```
Cys Gly Ile Ala Gly Ala Ile Ala Gly Phe Ile Lys Asn Ile Trp Glu
1               5                   10                  15

Gly Leu Ile Asp Trp Trp Tyr Gly Tyr Gly Arg Lys Lys Arg Arg Gln
            20                  25                  30

Arg Arg
```

<210> SEQ ID NO 379
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

```
Cys Gly Ile Ala Gly Ala Ile Ala Gly Phe Ile Lys Asn Ile Trp Lys
1               5                   10                  15

Gly Leu Ile Asp Ala Trp Tyr Gly Tyr Gly Arg Lys Lys Arg Arg Gln
            20                  25                  30

Arg Arg
```

<210> SEQ ID NO 380
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

```
Cys Gly Ile Phe Gly Ala Ile Ala Gly Phe Ile Lys Asn Ile Trp Glu
1               5                   10                  15

Gly Leu Ile Asp Gly Trp Tyr Gly Lys Lys Lys Lys Lys Lys Lys
            20                  25                  30

Lys
```

<210> SEQ ID NO 381
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

```
Cys Gly Arg Arg Arg Arg Arg Phe Glu Ala Ile Glu Gly Ser Ser Ser
1               5                   10                  15

Ser Ser Ser Ser Ser Ile Glu Asn Gly Trp Glu Gly Met Ile Asp Gly
            20                  25                  30

Trp Tyr Gly Tyr Gly Arg Lys Lys Arg Arg Gln Arg Arg
            35                  40                  45
```

<210> SEQ ID NO 382
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

```
Cys Gly Leu Phe Glu Ala Ile Glu Gly Phe Arg Arg Arg Arg Arg Glu
```

```
1               5                   10                  15
Asn Gly Trp Glu Gly Ser Ser Ser Ser Ser Ser Ser Ile Asp Gly
            20                  25                  30

Trp Tyr Gly Tyr Gly Arg Lys Lys Arg Arg Gln Arg Arg
            35                  40                  45
```

<210> SEQ ID NO 383
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383

```
Gly Leu Phe Glu Ala Ile Glu Gly Phe Ile Glu Asn Gly Trp Glu Gly
1               5                   10                  15

Met Ile Asp Gly Trp Tyr Gly Cys Tyr Gly Arg Lys Lys Arg Arg Gln
            20                  25                  30

Arg Arg
```

<210> SEQ ID NO 384
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

```
Gly Leu Phe Glu Ala Ile Glu Gly Phe Ile Glu Asn Gly Trp Glu Gly
1               5                   10                  15

Met Ile Asp Gly Trp Tyr Gly Gly Cys Gly Tyr Gly Arg Lys Lys Arg
            20                  25                  30

Arg Gln Arg Arg
        35
```

<210> SEQ ID NO 385
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

```
Gly Leu Leu Glu Ala Leu Glu Gly Leu Leu Glu Asn Gly Trp Glu Gly
1               5                   10                  15

Leu Leu Asp Gly Trp Tyr Gly Tyr Gly Arg Lys Lys Arg Arg Gln Arg
            20                  25                  30

Arg
```

<210> SEQ ID NO 386
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

```
Cys Phe Phe Gly Ala Ile Trp Glu Phe Ile Arg Asn Ile Leu
1               5                   10
```

<210> SEQ ID NO 387
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 387

Cys Ile Phe Gly Ala Ile Ala Gly Phe Ile Arg Ser Ile Leu
1               5                   10

<210> SEQ ID NO 388
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 388

Cys Gly Leu Phe Glu Glu Ile Glu Glu Phe Ile Glu Asn Gly Trp Glu
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 389
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 389

Cys Gly Phe Phe Gly Ala Ile Trp Glu Phe Ile Lys Ser Ile Leu
1               5                   10                  15

<210> SEQ ID NO 390
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 390

Gly Phe Phe Gly Ala Ile Trp Glu Phe Ile Lys Ser Ile Leu Cys
1               5                   10                  15

<210> SEQ ID NO 391
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (28)..(29)
<223> OTHER INFORMATION: Ornithine

<400> SEQUENCE: 391

Cys Gly Leu Phe Glu Ala Leu Glu Gly Phe Ile Glu Asn Gly Trp Glu
1               5                   10                  15

Gly Leu Leu Asp Gly Trp Tyr Gly Tyr Gly Arg Xaa Xaa Arg Arg Gln
            20                  25                  30

Arg Arg

<210> SEQ ID NO 392
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Cys Gly Leu Phe Glu Ala Leu Leu Glu Leu Leu Glu Asn Gly Trp Glu
1               5                   10                  15

Leu Leu Leu Glu Ala Trp Tyr Gly Tyr Gly Arg Lys Lys Arg Arg Gln
            20                  25                  30

Arg Arg

<210> SEQ ID NO 393
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Cys Gly Leu Phe Glu Ala Leu Leu Glu Leu Leu Glu Asn Gly Trp Glu
1               5                   10                  15

Leu Leu Leu Asp Gly Trp Tyr Gly Tyr Gly Arg Lys Lys Arg Arg Gln
            20                  25                  30

Arg Arg

<210> SEQ ID NO 394
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

Cys Ala Leu Phe Glu Ala Ile Glu Ala Phe Ile Glu Asn Gly Trp Glu
1               5                   10                  15

Ala Met Ile Asp Ala Trp Tyr Gly Tyr Gly Arg Lys Lys Arg Arg Gln
            20                  25                  30

Arg Arg

<210> SEQ ID NO 395
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

Cys Gly Leu Phe Gly Ala Ile Trp Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 396
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Cys Gly Leu Phe Glu Ala Ile Glu Glu Leu Ile Glu Asn Leu Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 397
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Cys Gly Leu Phe Glu Glu Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 398
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Cys Gly Leu Phe Glu Glu Ile Glu Gly Phe Ile Glu Asn Gly Trp Lys
1               5                   10                  15

Gly Leu Ile Asp Trp Trp Tyr Gly Tyr Gly His Lys Lys His His Gln
            20                  25                  30

His Arg

<210> SEQ ID NO 399
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Cys Phe Phe Gly Ala Ile Trp Glu Phe Ile Lys Asn Ile Leu Lys Gly
1               5                   10                  15

Leu Ile Asp Gly Trp Tyr Gly
            20

<210> SEQ ID NO 400

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Cys Gly Ile Phe Gly Ala Ile Ala Gly Phe Ile Arg Ser Ile Leu
1               5                   10                  15

<210> SEQ ID NO 401
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Cys Gly Leu Phe Glu Glu Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 402
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Cys Gly Leu Phe Glu Ala Ile Glu Gly Phe Ile Glu Asn Gly Trp Glu
1               5                   10                  15

Gly Met Ile Asp Gly Trp Asn Gly Tyr Gly Arg Lys Lys Arg Arg Gln
            20                  25                  30

Arg Arg

<210> SEQ ID NO 403
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Ala Gly Tyr Leu Leu Gly Lys Ile Asn Leu Lys Ala Leu Ala Ala Leu
1               5                   10                  15

Ala Lys Lys Ile Leu His His His His His His Lys Lys Lys Lys
            20                  25                  30

Lys Cys

<210> SEQ ID NO 404
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404
```

-continued

```
Cys Gly Leu Phe Glu Ala Ile Glu Gly Phe Ile Glu Asn Gly Trp Glu
1               5                   10                  15

Gly Met Ile Asp Trp Trp Tyr Gly Tyr Gly Arg Lys Lys Arg Arg Gln
            20                  25                  30

Arg Arg
```

<210> SEQ ID NO 405
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (24)..(25)
<223> OTHER INFORMATION: Residues at these positions separated by a
      (PEG)6 moiety

<400> SEQUENCE: 405

```
Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg
```

<210> SEQ ID NO 406
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

```
Cys Gly Ile Phe Gly Ala Ile Trp Asn Gly Ile Lys Ser Leu Phe Glu
1               5                   10                  15

Gly Leu Ile Asp Gly Trp Tyr Gly Tyr Gly Arg Lys Lys Arg Arg Gln
            20                  25                  30

Arg Arg
```

<210> SEQ ID NO 407
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

```
Cys Gly Ile Phe Gly Ala Ile Glu Gly Phe Ile Glu Asn Gly Trp Glu
1               5                   10                  15

Gly Leu Ile Asp Trp Trp Tyr Gly Tyr Gly Arg Lys Lys Arg Arg Gln
            20                  25                  30

Arg Arg
```

<210> SEQ ID NO 408
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Cys Ile Phe Gly Ala Ile Ala Gly Phe Ile Lys Asn Ile Trp Glu Gly
1               5                   10                  15

Leu Ile Asp Trp Trp Tyr Gly Tyr Gly Arg Lys Lys Arg Arg Gln Arg
                20                  25                  30

Arg

<210> SEQ ID NO 409
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Cys Gly Leu Phe Glu Ala Ile Glu Gly Phe Ile Glu Asn Gly Trp Lys
1               5                   10                  15

Gly Leu Ile Asp Gly Trp Tyr Gly Gly Leu Phe Glu Ala Ile Glu Gly
                20                  25                  30

Phe Ile Glu Asn Gly Trp Lys Gly Leu Ile Asp Trp Trp Tyr Gly
                35                  40                  45

<210> SEQ ID NO 410
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Cys Trp Glu Ala Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Tyr
                20                  25                  30

Gly Arg Lys Lys Arg Arg Gln Arg Arg Lys
        35                  40

<210> SEQ ID NO 411
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Cys Gly Leu Phe Glu Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
                20                  25                  30

Arg Arg

<210> SEQ ID NO 412
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 412

Cys Gly Leu Phe Glu Glu Leu Glu Glu Leu Leu Glu Glu Gly Trp Glu
1               5                   10                  15

Gly Leu Leu Glu Ala Tyr Gly Arg Lys Lys Arg Arg Gln Arg Arg
            20                  25                  30

<210> SEQ ID NO 413
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Cys Gly Asn Phe Glu Glu Ile Glu Glu Phe Ile Glu Glu Gly Leu Arg
1               5                   10                  15

Asn Phe Ile Asp Trp Trp Tyr Gly Tyr Gly His Lys Lys His His Gln
            20                  25                  30

His Arg

<210> SEQ ID NO 414
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Cys Phe Phe Gly Ala Ile Trp Glu Phe Ile Arg Asn Ile Leu Glu Gly
1               5                   10                  15

Leu Ile Asp Trp Trp Tyr Gly Tyr Gly Arg Lys Lys Arg Gln Arg
            20                  25                  30

Arg

<210> SEQ ID NO 415
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Cys Phe Phe Gly Ala Ile Trp Glu Phe Ile Lys Asn Ile Leu Leu His
1               5                   10                  15

Leu Leu His His Leu Leu His His Leu His His Leu Leu His His Leu
            20                  25                  30

Leu His Leu
        35

<210> SEQ ID NO 416
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: D-amino acid
```

```
<400> SEQUENCE: 416

Cys Gly Leu Phe Glu Ala Ile Glu Gly Phe Ile Glu Asn Gly Trp Glu
1               5                   10                  15

Gly Met Ile Asp Gly Trp Tyr Gly Tyr Gly Arg Lys Lys Arg Arg Gln
            20                  25                  30

Arg Arg

<210> SEQ ID NO 417
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Cys Gly Phe Phe His Ala Phe Phe His Phe Phe His Ser Phe Trp His
1               5                   10                  15

Gly Phe Phe Glu Ala
            20

<210> SEQ ID NO 418
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Cys Gly Leu Phe His Ala Leu Leu His Leu Leu His Ser Leu Trp His
1               5                   10                  15

Gly Leu Leu His Trp Trp Tyr Gly Tyr Gly His Lys Lys His His Gln
            20                  25                  30

His Arg

<210> SEQ ID NO 419
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Cys Gly Leu Phe Gly Ala Leu Leu Glu Leu Leu Glu Ser Leu Trp Glu
1               5                   10                  15

Gly Leu Leu Glu Trp Tyr Gly Arg Lys Lys Arg Arg Gln Arg Arg
            20                  25                  30

<210> SEQ ID NO 420
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Cys Gly Leu Phe Gly Ala Leu Leu Glu Leu Leu Glu Ser Leu Trp Glu
1               5                   10                  15

Gly Leu Leu Glu Trp Tyr Gly His Lys Lys His His Gln His Arg
            20                  25                  30
```

<210> SEQ ID NO 421
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Cys Gly Leu Phe His Ala Leu Leu His Leu Leu His Ser Leu Trp Lys
1               5                   10                  15

Gly Leu Leu Glu Trp Trp Tyr Gly Phe
            20                  25

<210> SEQ ID NO 422
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Cys Ile Phe Gly Ala Ile Ala Gly Phe Ile Arg Ser Ile Leu Glu Gly
1               5                   10                  15

Phe

<210> SEQ ID NO 423
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Cys Gly Ile Phe Gly Ala Ile Ala Gly Phe Ile Lys Asn Ile Trp Lys
1               5                   10                  15

Gly Leu Ile Asp Ala
            20

<210> SEQ ID NO 424
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Cys Phe Phe Glu Ala Ile Glu Glu Phe Ile Lys Asn Ile Trp Lys
1               5                   10                  15

<210> SEQ ID NO 425
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Cys Gly Leu Phe Glu Ala Ile Glu Gly Phe Ile Glu Asn Gly Trp Lys
1               5                   10                  15

-continued

Gly Leu Ile Asp Trp Leu Ala Glu Ala Leu Ala Glu Ala Leu Glu Ala
            20                  25                  30

Leu Ala Ala
        35

<210> SEQ ID NO 426
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Gly Cys Gly Ile Phe Gly Ala Ile Ala Glu Phe Ile Lys Asn Ile Trp
1               5                   10                  15

<210> SEQ ID NO 427
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Cys Ile Phe Gly Ala Ile Ala Glu Phe Ile Lys Asn Ile Trp Lys Gly
1               5                   10                  15

Leu Ile Asp Trp
            20

<210> SEQ ID NO 428
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Cys Phe Phe Gly Ala Ile Trp Glu Phe Ile Lys Ser Ile Leu Glu Leu
1               5                   10                  15

Leu Leu Glu Ala Tyr Gly His Lys Lys His His Gln His Arg Arg
            20                  25                  30

<210> SEQ ID NO 429
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Cys Trp Phe Gly Ala Ile Trp Glu Phe Ile Lys Ser Ile Leu
1               5                   10

<210> SEQ ID NO 430
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Cys Ala Phe Gly Ala Ile Trp Glu Phe Ile Lys Ser Ile Leu
1               5                   10

<210> SEQ ID NO 431
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Cys Phe Leu Gly Ala Ile Trp Glu Phe Ile Lys Ser Ile Leu
1               5                   10

<210> SEQ ID NO 432
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Cys Phe Phe Gly Ala Ile Trp Glu Phe Ile Lys Ser Ile Lys
1               5                   10

<210> SEQ ID NO 433
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: D-amino acid

<400> SEQUENCE: 433

Cys Gly Phe Ile Gly Ala Ile Ala Asn Leu Leu Ser Lys Ile Phe Glu
1               5                   10                  15

Gly Leu Ile Asp Gly Trp Tyr Gly Tyr Gly Arg Lys Lys Arg Arg Gln
            20                  25                  30

Arg Arg

<210> SEQ ID NO 434
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Cys Phe Phe Gly Ala Ile Trp Glu Phe Ile Lys Ser Ile Leu
1               5                   10

<210> SEQ ID NO 435
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(35)

<223> OTHER INFORMATION: D-amino acid

<400> SEQUENCE: 435

Cys Ile Phe Gly Ala Ile Ala Gly Phe Ile Lys Asn Ile Trp Leu His
1               5                   10                  15

Leu Leu His His Leu Leu His Leu His His Leu Leu His His Leu
            20                  25                  30

Leu His Leu
        35

<210> SEQ ID NO 436
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Cys Phe Phe Gly Ala Ile Ala Glu Phe Ile Lys Asn Ile Trp
1               5                   10

<210> SEQ ID NO 437
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Cys Ile Phe Glu Ala Ile Trp Gly Phe Ile Lys Asn Ile Trp
1               5                   10

<210> SEQ ID NO 438
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Ala Gly Tyr Leu Leu Gly Lys Ile Asn Leu Lys Ala Leu Ala Ala Leu
1               5                   10                  15

Ala Lys Lys Ile Leu His His His His His His Lys Lys Lys Lys Lys
            20                  25                  30

Lys Cys

<210> SEQ ID NO 439
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Cys Ile Phe Glu Ala Ile Ala Gly Phe Ile Lys Asn Ile Trp Lys Gly
1               5                   10                  15

Leu Ile Asp Trp Trp Tyr Gly Tyr Gly Arg Lys Lys Arg Arg Gln Arg
            20                  25                  30

Arg

-continued

<210> SEQ ID NO 440
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Cys Gly Leu Phe Glu Ala Ile Glu Gly Phe Ile Glu Asn Gly Trp Lys
1               5                   10                  15

Gly Leu Ile Asp Trp Trp Tyr Gly Gly Arg Pro Arg Glu Ser Gly Lys
            20                  25                  30

Lys Arg Lys Arg Lys Arg Leu Lys Pro
        35                  40

<210> SEQ ID NO 441
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: b-Ala

<400> SEQUENCE: 441

Cys Ala Gly Phe Gly Glu Ile Glu Gly Phe Ile Glu Asn Gly Leu Lys
1               5                   10                  15

Asn Leu Ile Asp Trp Trp Tyr Gly Tyr Gly His Lys Lys His His Gln
            20                  25                  30

His Arg

<210> SEQ ID NO 442
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: b-Ala

<400> SEQUENCE: 442

Cys Ala Gly Phe Glu Phe Ile Glu Glu Phe Ile Glu Asn Gly Leu Lys
1               5                   10                  15

Asn Leu Ile Asp Trp Trp Tyr Gly Tyr Gly Arg Lys Lys Arg Arg Gln
            20                  25                  30

Arg Arg

<210> SEQ ID NO 443
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: b-Ala -continued

<400> SEQUENCE: 443

Cys Ala Gly Phe Glu Phe Ile Glu Glu Phe Ile Glu Asn Gly Leu Lys
1               5                   10                  15

Asn Leu Ile Asp Trp Trp Tyr Gly Tyr Gly His Lys Lys His His Gln
            20                  25                  30

His Arg

<210> SEQ ID NO 444
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Cys Gly Gly Ile Glu Glu Ile Ala Gly Leu Leu Ser Lys Ile Leu Lys
1               5                   10                  15

Gly Leu Ile Asp Trp Trp Tyr Gly Tyr Gly His Lys Lys His His Gln
            20                  25                  30

His Arg

<210> SEQ ID NO 445
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

Cys Gly Phe Ile Gly Ala Ile Ala Asn Leu Leu Ser Lys Ile Phe Glu
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 446
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Cys Gly Phe Ile Gly Ala Ile Ala Glu Leu Leu Glu Lys Ile Phe Glu
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 447
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Cys Gly Phe Ile Gly Ala Ile Ala Glu Leu Leu Glu Lys Ile Phe Glu

```
                1               5                  10                  15
Gly Leu Ile Asp Trp Trp Tyr Gly Tyr Gly His Lys Lys His His Gln
                20                  25                  30

His Arg

<210> SEQ ID NO 448
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Cys Phe Phe Gly Ala Ile Trp Glu Phe Ile Arg Asn Ile Leu Glu Gly
1               5                  10                  15

Leu Ile Asp Trp Trp Tyr Gly Tyr Gly His Lys Lys His His Gln His
                20                  25                  30

Arg

<210> SEQ ID NO 449
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Cys Phe Phe Gly Ala Ile Trp Glu Phe Ile Lys Ser Ile Leu Leu His
1               5                  10                  15

Leu Leu His His Leu Leu His His Leu His His Leu Leu His His Leu
                20                  25                  30

Leu His Leu
        35

<210> SEQ ID NO 450
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Cys Phe Phe Gly Ala Ile Trp Glu Phe Ile Arg Ser Ile Leu Leu His
1               5                  10                  15

Leu Leu His His Leu Leu His His Leu His His Leu Leu His His Leu
                20                  25                  30

Leu His Leu
        35

<210> SEQ ID NO 451
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Cys Gly Phe Phe Gly Ala Ile Trp Glu Phe Ile Arg Ser Ile Leu Glu
1               5                  10                  15
```

```
Gly Phe Ile Asp Trp Trp Tyr Gly Tyr Gly Tyr Gly His Lys Lys His
            20                  25                  30

His Gln His Arg
        35

<210> SEQ ID NO 452
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Cys Gly Leu Phe Glu Ala Ile Trp Glu Phe Ile Lys Ser Ile Leu Glu
1               5                   10                  15

Gly Leu Leu Glu Ala Tyr Gly His Lys Lys His His Gln His Arg
            20                  25                  30

<210> SEQ ID NO 453
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Cys Gly Leu Phe Glu Ala Ile Trp Glu Phe Ile Lys Ser Ile Leu Glu
1               5                   10                  15

Gly Leu Leu Glu Ala Trp Tyr Gly Tyr Gly His Lys Lys His His Gln
            20                  25                  30

His Arg

<210> SEQ ID NO 454
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Cys Gly Ile Phe Gly Ala Ile Ala Gly Phe Ile Lys Asn Ile Trp Lys
1               5                   10                  15

Tyr Gly Arg Lys Lys Arg Arg Gln Arg Arg
            20                  25

<210> SEQ ID NO 455
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Cys Gly Leu Phe Glu Ala Leu Leu Glu Leu Leu Glu Ser Leu Trp Glu
1               5                   10                  15

Leu Leu Leu Glu Ala Trp Tyr Gly Tyr Gly His Lys Lys His His Gln
            20                  25                  30

His Arg
```

<210> SEQ ID NO 456
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Cys Ile Phe Gly Ala Ile Ala Gly Phe Ile Arg Asn Ile Trp Lys Gly
1               5                   10                  15

Leu Ile Asp Gly Trp Tyr Gly
            20

<210> SEQ ID NO 457
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Cys Gly Ile Phe Gly Ala Ile Ala Gly Phe Ile Arg Asn Ile Trp Lys
1               5                   10                  15

Gly Leu Ile Asp Gly Trp Tyr Gly
            20

<210> SEQ ID NO 458
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Cys Phe Phe Gly Ala Ile Trp Glu Phe Ile Lys Asn Ile Leu Lys Leu
1               5                   10                  15

His Leu Leu His His Leu Leu His His Leu His His Leu Leu His His
            20                  25                  30

Leu Leu His Leu
        35

<210> SEQ ID NO 459
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Cys Phe Phe Gly Ala Ile Trp Glu Phe Ile Arg Asn Ile Leu Leu His
1               5                   10                  15

Leu Leu His His Leu Leu His His Leu His His Leu Leu His His Leu
            20                  25                  30

Leu His Leu
        35

<210> SEQ ID NO 460
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 460

Cys Phe Phe Gly Lys Ile Trp Glu Phe Ile Lys Ser Ile Leu
1               5                   10

<210> SEQ ID NO 461
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Cys Tyr Gly Arg Lys Lys Arg Arg Gln Arg Arg Gly Leu Phe Glu Ala
1               5                   10                  15

Leu Leu Glu Leu Leu Glu Ser Leu Trp Glu Leu Leu Leu Glu Ala
                20                  25                  30

<210> SEQ ID NO 462

<400> SEQUENCE: 462

000

<210> SEQ ID NO 463
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Cys Trp Trp Gly Ala Ile Glu Gly Phe Ile Lys Ser Ile Leu
1               5                   10

<210> SEQ ID NO 464
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Cys Phe Phe Gly Ala Ile Trp Glu Trp Ile Lys Ser Ile Leu
1               5                   10

<210> SEQ ID NO 465
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Cys Phe Phe Gly Ala Ile Trp Glu Phe Trp Lys Ser Ile Leu
1               5                   10

<210> SEQ ID NO 466
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 466

Cys Phe Phe Gly Ala Ile Trp Glu Phe Ile Lys Phe Ile Leu
1               5                   10

<210> SEQ ID NO 467
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Cys Phe Phe Gly Ala Ile Trp Glu Phe Ile Lys Lys Ile Leu
1               5                   10

<210> SEQ ID NO 468
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Cys Phe Phe Gly Ala Ile Trp Glu Phe Ile Lys Gly Ile Leu
1               5                   10

<210> SEQ ID NO 469
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Cys Phe Phe Gly Ala Ile Trp Glu Phe Ile Lys Leu Ile Leu
1               5                   10

<210> SEQ ID NO 470
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Cys Phe Phe Gly Ala Ile Trp Glu Phe Ile Lys Trp Ile Leu
1               5                   10

<210> SEQ ID NO 471
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Cys Phe Phe Gly Ala Ile Trp Glu Phe Ile Lys Ser Phe Leu
1               5                   10
```

```
<210> SEQ ID NO 472
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Cys Phe Phe Gly Ala Ile Trp Glu Phe Ile Lys Ser Lys Leu
1               5                   10

<210> SEQ ID NO 473
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Cys Phe Phe Gly Phe Ile Trp Glu Phe Ile Lys Ser Ile Leu
1               5                   10

<210> SEQ ID NO 474
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Cys Ile Phe Gly Ala Ile Ala Gly Phe Ile Lys Asn Ile Leu Lys Gly
1               5                   10                  15

Leu Ile Asp Ala Phe
            20

<210> SEQ ID NO 475
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Cys Phe Phe Gly Lys Ile Trp Glu Leu Trp Glu Trp Ile Leu
1               5                   10

<210> SEQ ID NO 476
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Cys Phe Phe Gly Ala Ile Trp Glu Phe Ala Lys Ser Ile Leu
1               5                   10

<210> SEQ ID NO 477
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 477

Cys Phe Phe Gly Ala Ile Trp Glu Phe Ile Lys Ser Ala Leu
1               5                   10

<210> SEQ ID NO 478
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Cys Phe Phe Gly Ala Ile Trp Glu Phe Ile Lys Ser Trp Leu
1               5                   10

<210> SEQ ID NO 479
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Cys Phe Phe Gly Ala Ile Trp Glu Phe Ile Lys Ser Ile Leu Lys
1               5                   10                  15

<210> SEQ ID NO 480
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Cys Phe Phe Gly Ala Ile Trp Glu Phe Ile Lys Ser Ile Leu Glu
1               5                   10                  15

<210> SEQ ID NO 481
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Cys Phe Phe Lys Ala Ile Trp Glu Phe Ile Lys Ser Ile Leu
1               5                   10

<210> SEQ ID NO 482
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Cys Phe Phe Asn Ala Ile Trp Glu Phe Ile Lys Ser Ile Leu
1               5                   10
```

<210> SEQ ID NO 483
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Cys Phe Phe Gly Gly Ile Trp Glu Phe Ile Lys Ser Ile Leu
1               5                   10

<210> SEQ ID NO 484
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Cys Phe Phe Gly Asn Ile Trp Glu Phe Ile Lys Ser Ile Leu
1               5                   10

<210> SEQ ID NO 485
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Cys Phe Phe Gly Ala Leu Trp Glu Phe Ile Lys Ser Ile Leu
1               5                   10

<210> SEQ ID NO 486
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Cys Phe Phe Gly Ala Ala Trp Glu Phe Ile Lys Ser Ile Leu
1               5                   10

<210> SEQ ID NO 487
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Cys Gly Leu Phe His Ala Leu Leu His Leu His Ser Leu Trp His
1               5                   10                  15

Gly Leu Leu Asp Gly
            20

<210> SEQ ID NO 488
<211> LENGTH: 21
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 488

Cys Gly Leu Phe His Ala Leu Leu His Leu Leu His Ser Leu Trp His
1               5                   10                  15

Gly Leu Leu Glu Trp
            20

<210> SEQ ID NO 489
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Cys Gly Leu Phe His Ala Leu Leu His Leu Leu His Ser Leu Trp His
1               5                   10                  15

Leu Leu Leu Glu Ala
            20

<210> SEQ ID NO 490
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Cys Gly Leu Phe His Ala Leu Leu His Leu Leu His Ser Leu Trp Lys
1               5                   10                  15

Leu Leu Leu Glu Trp
            20

<210> SEQ ID NO 491
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Cys Lys Phe Gly Ala Ile Trp Glu Phe Ile Lys Ser Ile Leu
1               5                   10

<210> SEQ ID NO 492
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Cys Phe Lys Gly Ala Ile Trp Glu Phe Ile Lys Ser Ile Leu
1               5                   10

<210> SEQ ID NO 493
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 493

Cys Phe Phe Gly Ala Ile Trp Lys Phe Ile Lys Ser Ile Leu
1               5                   10

<210> SEQ ID NO 494
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Cys Phe Phe Gly Ala Ile Trp Ala Phe Ile Lys Ser Ile Leu
1               5                   10

<210> SEQ ID NO 495
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Cys Phe Phe Gly Ala Ile Trp Leu Phe Ile Lys Ser Ile Leu
1               5                   10

<210> SEQ ID NO 496
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Cys Phe Phe Gly Ala Ile Trp Phe Phe Ile Lys Ser Ile Leu
1               5                   10

<210> SEQ ID NO 497
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Cys Phe Phe Gly Ala Ile Trp Asn Phe Ile Lys Ser Ile Leu
1               5                   10

<210> SEQ ID NO 498
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Cys Phe Phe Gly Ala Ile Trp Glu Leu Ile Lys Ser Ile Leu
1               5                   10

```
<210> SEQ ID NO 499
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Cys Phe Phe Gly Ala Ile Trp Glu Ala Ile Lys Ser Ile Leu
1               5                   10

<210> SEQ ID NO 500
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Cys Gly Leu Phe Glu Ala Ile Glu Gly Phe Ile Glu Asn Gly Trp Glu
1               5                   10                  15

Gly Leu Ala Glu Ala Leu Ala Glu Ala Leu Glu Ala Leu Ala Ala Tyr
            20                  25                  30

Gly Arg Lys Lys Arg Arg Gln Arg Arg
        35                  40

<210> SEQ ID NO 501
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Cys Ile Phe Gly Ala Ile Ala Gly Phe Ile Lys Asn Ile Trp Glu Gly
1               5                   10                  15

Met Ile Asp Gly Trp Tyr Gly Tyr Gly Arg Lys Lys Arg Arg Gln Arg
            20                  25                  30

Arg

<210> SEQ ID NO 502
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

Cys Ile Phe Gly Ala Ile Ala Gly Phe Ile Lys Asn Ile Trp Glu Gly
1               5                   10                  15

Leu Ile Asp Ala Trp Tyr Gly Tyr Gly Arg Lys Lys Arg Arg Gln Arg
            20                  25                  30

Arg

<210> SEQ ID NO 503
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 503

Cys Ile Phe Gly Ala Ile Ala Gly Phe Ile Lys Asn Ile Trp Lys Gly
1               5                   10                  15

Leu Ile Asp Ala Trp Tyr Gly Tyr Gly Arg Lys Lys Arg Arg Gln Arg
            20                  25                  30

Arg

<210> SEQ ID NO 504
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

Cys Ile Phe Gly Ala Ile Ala Gly Phe Ile Lys Asn Ile Trp Ile Phe
1               5                   10                  15

Gly Ala Ile Ala Gly Phe Ile Lys Asn Ile Trp Trp Tyr Gly Tyr Gly
            20                  25                  30

Arg Lys Lys Arg Arg Gln Arg Arg
            35                  40

<210> SEQ ID NO 505
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Cys Gly Leu Phe Gly Ala Ile Ala Gly Phe Ile Glu Asn Gly Trp Glu
1               5                   10                  15

Gly Leu Ile Glu Gly Trp Tyr Gly
            20

<210> SEQ ID NO 506
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(31)
<223> OTHER INFORMATION: Ornithine

<400> SEQUENCE: 506

Cys Gly Leu Phe Glu Ala Ile Glu Gly Phe Ile Glu Asn Gly Trp Glu
1               5                   10                  15

Gly Leu Ile Asp Gly Trp Tyr Gly Tyr Gly Xaa Xaa Xaa Xaa Xaa Gln
            20                  25                  30

Arg Arg

<210> SEQ ID NO 507
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Cys Gly Leu Phe Glu Ala Ile Glu Gly Phe Ile Glu Asn Gly Trp Lys
1               5                   10                  15

Gly Leu Ile Asp Trp Trp Tyr Gly Tyr Gly Arg Lys Lys Arg Arg Gln
            20                  25                  30

Arg Arg

<210> SEQ ID NO 508
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

Cys Gly Leu Phe Glu Ala Ile Glu Gly Phe Ile Glu Asn Gly Trp Glu
1               5                   10                  15

Gly Leu Ile Asp Gly Trp Tyr Gly Tyr Gly Arg Lys Lys Arg Arg Gln
            20                  25                  30

Arg Arg Lys
        35

<210> SEQ ID NO 509
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

Cys Tyr Gly His Lys Lys His His Gln His Arg Gly Leu Phe Glu Ala
1               5                   10                  15

Ile Glu Gly Phe Ile Glu Asn Gly Trp Lys Gly Leu Ile Asp Trp Trp
            20                  25                  30

Tyr Gly

<210> SEQ ID NO 510
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Cys Tyr Gly His Lys Lys His His Gln His Arg Gly Leu Phe Glu Ala
1               5                   10                  15

Ile Glu Glu Phe Ile Glu Asn Gly Trp Glu Gly Leu Ile Asp Gly Trp
            20                  25                  30

Tyr Gly

<210> SEQ ID NO 511
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

```
Cys Gly Leu Phe Glu Ala Ile Glu Gly Phe Ile Glu Asn Gly Trp Lys
1               5                   10                  15

Gly Leu Ile Asp Gly Trp Tyr Gly Tyr Gly Arg Lys Lys Arg Arg Gln
            20                  25                  30

Arg Arg Lys
        35

<210> SEQ ID NO 512
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 512

Cys Gly Leu Phe Glu Ala Ile Glu Gly Phe Ile Glu Asn Gly Trp His
1               5                   10                  15

Gly Met Ile Asp Gly Trp Tyr Gly Tyr Gly Arg Lys Lys Arg Arg Gln
            20                  25                  30

Arg Arg

<210> SEQ ID NO 513
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513

Ile Phe Gly Ile Asp Asp Leu Ile Ile Gly Leu Leu Phe Val Ala Ile
1               5                   10                  15

Val Glu Ala Gly Ile Gly Gly Tyr Leu Leu Gly Ser Tyr Gly Arg Lys
            20                  25                  30

Lys Arg Arg Gln Arg Arg Cys
        35

<210> SEQ ID NO 514
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Cys Gly Phe Phe Gly Glu Ile Ala Glu Leu Ile Glu Glu Gly Leu Lys
1               5                   10                  15

Gly Leu Ile Asp Trp Trp Asn Gly
            20

<210> SEQ ID NO 515
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Cys Gly Leu Phe Gly Glu Ile Glu Glu Leu Ile Glu Glu Gly Leu Glu
1               5                   10                  15
```

```
Asn Leu Ile Asp Trp Trp Asn Gly
            20

<210> SEQ ID NO 516
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(14)
<223> OTHER INFORMATION: D-amino acid

<400> SEQUENCE: 516

Cys Phe Phe Gly Ala Ile Trp Glu Phe Ile His Ser Ile Leu
1               5                   10

<210> SEQ ID NO 517
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Cys Phe Phe Gly Ala Ile Trp Glu Phe Ile His Asn Ile Leu
1               5                   10

<210> SEQ ID NO 518
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Cys Phe Phe Gly Ala Ile Trp Glu Phe Ile His Ser Ile Phe Lys
1               5                   10                  15

<210> SEQ ID NO 519
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Cys Gly Ile Phe Glu Ala Ile Ala Gly Leu Leu Lys Trp Ile Phe Lys
1               5                   10                  15

<210> SEQ ID NO 520
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Cys Gly Ile Phe Glu Leu Ile Ala Gly Leu Leu Lys Asn Ile Phe Lys
1               5                   10                  15
```

```
<210> SEQ ID NO 521
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Cys Gly Ile Phe Glu Ala Ile Ala Gly Leu Leu Lys Ser Ile Leu Lys
1               5                   10                  15

Lys

<210> SEQ ID NO 522
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Cys Gly Ile Phe Gly Ala Ile Ala Gly Leu Leu Lys Ser Ile Leu Lys
1               5                   10                  15

Lys

<210> SEQ ID NO 523
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(17)
<223> OTHER INFORMATION: D-amino acid

<400> SEQUENCE: 523

Cys Ile Phe Gly Ala Ile Ala Gly Phe Ile Lys Asn Ile Leu Lys Gly
1               5                   10                  15

Leu

<210> SEQ ID NO 524
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Cys Ile Phe Gly Ala Ile Ala Gly Phe Ile Lys Asn Ile Leu Lys Gly
1               5                   10                  15

Leu Ile Asp Gly Trp Trp Tyr Gly
            20

<210> SEQ ID NO 525
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525
```

```
Cys Ile Phe Gly Ala Ile Ala Gly Phe Ile Lys Asn Ile Trp His Gly
1               5                   10                  15

Leu Ile

<210> SEQ ID NO 526
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Cys Ile Phe Gly Ala Ile Ala Gly Phe Ile Lys Asn Ile Leu Lys Gly
1               5                   10                  15

Leu Lys

<210> SEQ ID NO 527
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(18)
<223> OTHER INFORMATION: D-amino acid

<400> SEQUENCE: 527

Gly Leu Gly Lys Leu Ile Asn Lys Ile Phe Gly Ala Ile Ala Gly Phe
1               5                   10                  15

Ile Cys

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Arg Lys Lys Arg Arg Gln Arg Arg Arg
1               5

<210> SEQ ID NO 529
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Gly Gly
1

<210> SEQ ID NO 530
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530
```

```
Gly Gly Gly Gly Ser
1               5

<210> SEQ ID NO 531
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Gly Gly Gly Gly Ser Asn
1               5

<210> SEQ ID NO 532
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Gly Lys Ser Ser Gly Ser Gly Ser Glu Ser Lys Ser
1               5                   10

<210> SEQ ID NO 533
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Gly Ser Thr Ser Gly Ser Gly Lys Ser Ser Glu Gly Lys Gly
1               5                   10

<210> SEQ ID NO 534
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Gly Ser Thr Ser Gly Ser Gly Lys Ser Ser Glu Gly Ser Gly Ser Thr
1               5                   10                  15

Lys Gly

<210> SEQ ID NO 535
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Gly Ser Thr Ser Gly Ser Gly Lys Pro Gly Ser Gly Glu Gly Ser Thr
1               5                   10                  15

Lys Gly
```

```
<210> SEQ ID NO 536
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Glu Gly Lys Ser Ser Gly Ser Gly Ser Glu Ser Lys Glu Phe
1               5                   10

<210> SEQ ID NO 537
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(15)
<223> OTHER INFORMATION: May or may not be present

<400> SEQUENCE: 537

Arg Arg Arg Arg Arg Arg Arg Arg Arg Arg Arg Arg Arg Arg Arg
1               5                   10                  15

<210> SEQ ID NO 538
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 538

His His His His His His
1               5

<210> SEQ ID NO 539
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Val Val Val Pro Pro
1               5

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
cuuuaacaau uccugaaaut t                                                    21

<210> SEQ ID NO 541
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
cuuuaacaau uccugaaaut t                                              21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
acaacagacu uuaauguaat t                                              21

<210> SEQ ID NO 543
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
cuguuggauu gauucgaaau u                                              21

<210> SEQ ID NO 544
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
cuuuaacaau uccugaaauu u                                              21

<210> SEQ ID NO 545
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
auuucaggaa uuguuaaagu u                                              21

<210> SEQ ID NO 546
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
auuucaggaa uuguuaaagu u                                              21
```

<210> SEQ ID NO 547
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 547
uuacauuaaa gucuguuguu u                                              21

<210> SEQ ID NO 548
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 548
uuucgaauca auccaacagu u                                              21

<210> SEQ ID NO 549
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 549
uuucgaauca auccaacagu u                                              21

<210> SEQ ID NO 550
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 550
auuucaggaa uuguuaaagu u                                              21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 551
autucaggaa uuguuaaagu u                                              21